US008754054B2

(12) United States Patent
Carr et al.

(10) Patent No.: US 8,754,054 B2
(45) Date of Patent: Jun. 17, 2014

(54) ANTIBACTERIAL COMPOUNDS, METHODS OF MAKING THEM, AND USES THEREOF

(75) Inventors: Grant J. Carr, Woodinville, WA (US); David D. Manning, Duanesburg, NY (US); Zhicai Yang, Schenectady, NY (US); Cheng Guo, Schenectady, NY (US); Jun-Ho Maeng, Cohoes, NY (US); Peter C. Michels, Voorheesville, NY (US); Matthew W. Chase, East Berne, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 12/884,650

(22) Filed: Sep. 17, 2010

(65) Prior Publication Data

US 2012/0010163 A1    Jan. 12, 2012
US 2013/0237490 A2    Sep. 12, 2013

Related U.S. Application Data

(60) Provisional application No. 61/363,087, filed on Jul. 9, 2010.

(51) Int. Cl.
*A61K 31/70* (2006.01)
*C07H 19/00* (2006.01)
*C12P 19/28* (2006.01)

(52) U.S. Cl.
USPC .............................. 514/42; 536/22.1; 435/85

(58) Field of Classification Search
USPC ................................... 536/22.1; 435/85, 22.1
See application file for complete search history.

(56) References Cited

U.S. PATENT DOCUMENTS

| 3,769,403 | A | 10/1973 | Hara et al. |
| 4,375,542 | A | 3/1983 | Waitz et al. |
| 6,780,616 | B1 * | 8/2004 | Takeuchi et al. ............... 435/74 |
| 7,745,644 | B2 | 6/2010 | Basilio et al. |
| 2002/0039723 | A1 | 4/2002 | Fox et al. |

FOREIGN PATENT DOCUMENTS

| JP | 63154695 A | 6/1988 |
| JP | 01096189 A | 4/1989 |
| WO | 89/02741 A1 | 4/1989 |
| WO | 2008079339 A2 | 7/2008 |
| WO | 2009061847 A2 | 5/2009 |

OTHER PUBLICATIONS

Asolkar et al., "Arenimycin, An Antibiotic Effective Against Rifampin- and Methicillin-Resistant *Staphylococcus aureus* from the Marine Actinomycete *Salinispora arenicola*," J. Antibiot (Tokyo) 63(1):1-10 (2010).
Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem. 43:2664-2674 (2000).
Selvam et al., "Highly Efficient Nitration of Phenolic Compounds by Zirconyl Nitrate," Tetrahedron Letters 47:2507-2509 (2006).
Mullen et al., "(-)-Spiro[1-azabicyclo[2.2.2]octane-3,5'-oxazolidin-2'one], a Conformationally Restricted Analogue of Acetylcholine, is a Highly Selective Full Agonist at the Alpha7 Nicotinic Acetylcholine Receptor," J. Med. Chem. 43:4045-4050 (2000).
Boons et al., "Organic Synthesis with Carbohydrates," ISBN 1-85075-913-8, Sheffield Academic Press, pp. 26-40 (2000).
Takeda et al., "SF2446, New Benzo[a]naphthacene Quinone Antibiotics," The Journal of Antibiotics 41(4):417-424 (1988).
Issaq et al., "Thin-Layer Chromatographic Classification of Antibiotics Exhibiting Antitumor Properties," Journal of Chromatography 133:291-301 (1977).
Gomi et al., "SF2446, New Benzo[a]naphthacene Quinone Antibiotics. II. The Structural Elucidation," J. Antibiotics 41 (4):425-432 (1988).
Kondo et al., "Structure of Ericamycin Having a 2-Azahexaphene Ring System," J. Antibiotics 51(2):232-234 (1998).
Martin et al., "Collinone, A New Recombinant Angular Polyketide Antibiotic made by an Engineered Streptomyces Strain," J. Antibiotics 54(3):239-249 (2001).
Misiek et al., "Mycorhodin, A New Antibiotic," Antibiotics and Chemotherapy 9:280-285 (1959).
Blinov et al., "Classification of Antibiotics-Quinones of the Actinomycetic Origin," Institute of Chemistry of Natural Izvestiya Akademii Nauk SSSR, Seriya Biologicheskaya, 3:357-373 (1967) (English Abstract).
International Search Report for PCT/US11/43028 (Dec. 5, 2011).
Written Opinion for PCT/US11/43028 (Dec. 5, 2011).
Katoh et al., "WNT Signaling Pathway and Stem Cell Signaling Network," Clin. Cancer Res. 13(14):4042-4045 (2007.
Lepourcelet et al, "Small-Molecule Antagonists of the Oncogenic Tcf/Beta-Catenin Protein Complex," Cancer Cell 5(1):91-102 (2004).
Colson, Kimberly Lynn, "Structure Elucidation Studies of Antibiotics Isolated From Streptomyces and Determination of Thermodynamic and Kinetic Parameters by NMR Spectroscopy," Dissertation, Pennsylvania State University (1986).

\* cited by examiner

*Primary Examiner* — Elli Peselev
(74) *Attorney, Agent, or Firm* — LeClairRyan, a Professional Corporation

(57) ABSTRACT

The present invention relates to novel therapeutics with antibacterial activity, processes for their preparation, and pharmaceutical, veterinary and nutritional compositions containing them as active ingredients. The present invention also relates to uses of the novel therapeutics, for example, as medicants or food additives in the treatment of bacterial infections or to aid body mass gain in a subject.

67 Claims, No Drawings

ANTIBACTERIAL COMPOUNDS, METHODS OF MAKING THEM, AND USES THEREOF

This application claims benefit of U.S. Provisional Patent Application Ser. No. 61/363,087, filed Jul. 9, 2010, which is hereby incorporated by reference in its entirety.

FIELD OF THE INVENTION

The present invention relates to novel therapeutics which demonstrate antibacterial activity, processes for their preparation, pharmaceutical, veterinary, and nutritional compositions containing them as active ingredients, and their use, for example, as medicants or food additives in the treatment of bacterial infections or to aid body mass gain in a subject.

BACKGROUND OF THE INVENTION

Natural products have been the single most productive source of leads for the development of drugs. Ninety five percent of the antibiotics described to date originate from leads discovered by screening natural product extracts or fractions. Many marketed antibacterial drugs are semisynthetic congeners of natural products, and are obtained from the chemical refinement of fermentation products (e.g., oritavancin, tigecyclin, telithromycin, rifampicin). Although a robust pipeline of natural-product based antibiotics recently existed, an unrelenting antimicrobial resistance to these medicines has eroded the physician's arsenal with which to treat infectious disease.

Over the past several decades, the frequency of antimicrobial resistance and its association with serious infectious diseases has increased at alarming rates. The increasing resistance to the current arsenal of antibiotics is of growing concern. A release by the National Institute of Allergy and Infectious Diseases (April 2006) reported that:

Nearly two million patients in the United States get an infection in the hospital each year. Of those patients, about 90,000 die each year as a result of their infection. This is up from 13,300 patient deaths in 1992.

In 2003, epidemiologists reported in the New England Journal of Medicine that 5 to 10 percent of patients admitted to hospitals acquire an infection during their stay, and that the risk for a hospital-acquired infection has risen steadily in recent decades.

More than 70 percent of the bacteria that cause hospital-acquired infections are resistant to at least one of the drugs most commonly used to treat them.

Strains of *S. aureus* resistant to methicillin (MRSA) are endemic in hospitals and are increasing in non-hospital settings such as locker rooms.

A number of cases of community-associated MRSA have also been reported, including cases in patients without established risk factors.

The first *S. aureus* infections resistant to vancomycin (VRSA) emerged in the United States in 2002.

Increasing reliance on vancomycin has led to the emergence of vancomycin-resistant enterococci infections.

Now that vancomycin resistance has been established in *S. aureus*, it is expected to increase at rates similar to those witnessed for vancomycin resistant enterococci, becoming endemic in United States hospitals by 2015. To maintain our current level of therapeutic efficacy, new antibiotics, with new mechanisms of action and chemotypes need to be developed.

The present invention is directed to overcoming these and other deficiencies in the prior art.

SUMMARY OF THE INVENTION

The present invention relates to a therapeutic having a structure comprising formula I as follows:

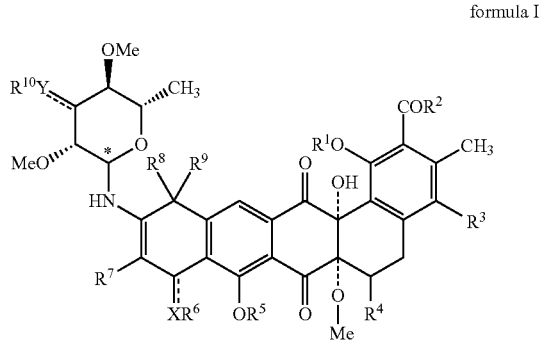

formula I wherein:
the carbohydrate anomeric carbon designated * is in the R or S configuration;
$R^1$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, arylalkyl, heteroarylalkyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, or —$NR^{12}R^{13}$
$R^2$ is selected from the group consisting of H, —$OR^{12}$, —$NR^{12}R^{13}$, —$(CH_2)_nC(O)R^{11}$, —$(CH_2)_nC(O)NR^{12}R^{13}$, —$(CH_2)_nOC(O)NR^{12}R^{13}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, phenyl, benzyl, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;
$R^3$ is selected from the group consisting of H, halogen, —$OR^{12}$, —$NR^{12}R^{13}$, —$NR^{12}C(O)R^{13}$, —$NR^{12}C(O)_2R^{13}$, —$NR^{12}C(O)NR^{12}R^{13}$, $S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^4$ is selected from the group consisting of H, halogen, —$OR^{12}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, —$(CH_2)_nOC(O)NR^{12}R^{13}$, phenyl, benzyl, =$NOR^{14}$, =$NR^{14}$, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^5$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, phenyl, benzyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^6$ is optionally present and, if present, is selected from the group consisting of H, —$OR^{12}$, —$NR^{12}R^{13}$, —$(CH_2)_n(O)R^{11}$, —$(CH_2)_nC(O)NR^{12}R^{13}$, $C_1$-$C_6$ alkyl, $C_1$-$C_6$ haloalkyl, phenyl, benzyl, a benzyl ether moiety, a carbamate moiety, an =$NR^{14}$ moiety, and a carbonate moiety, wherein each of —$(CH_2)_n(O)R^{11}$, —$(CH_2)_nC(O)NR^{12}R^{13}$, $C_1$-$C_6$ alkyl, $C_1$-$C_6$ haloalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

or $R^5$ and $R^6$ can combine to form a heterocycle group containing from 1 to 5 heteroatoms selected from the group consisting of oxygen, nitrogen, and sulfur and optionally substituted 1 to 3 times with halogen, oxo, cyano, $C_1$-$C_4$ alkyl, $C_1$-$C_4$ haloalkyl, or $C_1$-$C_4$ alkoxy;

$R^7$ is selected from the group consisting of H, halogen, —$OR^{12}$, —$NR^{12}R^{13}$, —$NR^{12}C(O)R^{13}$, —$NR^{12}C(O)_2R^{13}$, —$NR^{12}C(O)NR^{12}R^{13}$, $S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^8$ and $R^9$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$OR^{12}$, phenyl, benzyl, a benzyl ether moiety, a carbamate moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^8$ and $R^9$ can combine to form an oxo, thio, imine, or an =$NR^{14}$ moiety;

$R^{10}$ is optionally present and, if present, is selected from the group consisting of H, —$OR^{12}$, —$(CH_2)_nC(O)R^{11}$, —$(CH_2)_nC(O)NR^{12}R^{13}$, $C_1$-$C_6$ alkyl, $C_1$-$C_6$ haloalkyl, benzyl, a carbohydrate, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_1$-$C_6$ haloalkyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^{11}$ is H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$C(O)R^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{12}$ and $R^{13}$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nNR^{16}R^{17}$, —$(CH_2)_nC(O)R^{11}$, —$(CH_2)_nOC(O)R^{11}$, —$(CH_2)_nC(O)_2R^{11}$, —$(CH_2)_nC(O)NR^{16}R^{17}$, —$(CH_2)_nOC(O)NR^{16}R^{17}$, —$(CH_2)_nNR^{16}C(O)OR^{17}$, —$(CH_2)_nNC(O)NR^{16}R^{17}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —$(CH_2)_nNR^{16}R^{17}$, —$(CH_2)_nC(O)R^{11}$, —$(CH_2)_nOC(O)R^{11}$, —$(CH_2)_nC(O)_2R^{11}$, —$(CH_2)_nC(O)NR^{16}R^{17}$, —$(CH_2)_nOC(O)NR^{16}R^{17}$, —$(CH_2)_nNR^{16}C(O)OR^{17}$, —$(CH_2)_nNC(O)NR^{16}R^{17}$, aryl, heteroaryl, arylalkyl, and heteroarylalkyl is optionally substituted 1 to 3 times with halogen, cyano, $C_1$-$C_4$ alkyl, $C_1$-$C_4$ haloalkyl, OH, $C_1$-$C_4$ alkoxy, an amino acid group, or [$NR^{11}C(O)(CH_2)_n]_m$ $NR^{16}R^{17}$, which is optionally substituted 1 to 3 times with halogen, cyano, $C_1$-$C_4$ alkyl, $C_1$-$C_4$ haloalkyl, or $C_1$-$C_4$ alkoxy, aryl alkyl, wherein the $C_1$-$C_4$ alkyl and the aryl alkyl substituents are optionally substituted 1 to 3 times with halogen, alkyl, OH, $NH_2$, —$CO_2H$, —$C(O)NH_2$, —NHC(O)$NH_2$, —NHC(NH)$NH_2$, imidazole, pyrrolidine, SMe, SH, or SeH;

or $R^{12}$ and $R^{13}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

$R^{14}$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, $S(O)_qR^{12}$, $(CH_2)_nNR^{12}R^{13}$, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$(CH_2)_nNR^{11}C(O)OR^{12}$, —$(CH_2)_nNC(O)NR^{12}R^{13}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$(CH_2)_nNR^{11}C(O)OR^{12}$, —$(CH_2)_nNC(O)NR^{12}R^{13}$, aryl, heteroaryl, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, —$NR^{12}R^{13}$, or an amino acid group;

$R^{15}$ is H, $C_1$-$C_4$ alkyl, arylalkyl, heteroarylalkyl $C_1$-$C_4$ haloalkyl, or phenyl, wherein each of $C_1$-$C_4$ alkyl, arylalkyl, heteroarylalkyl $C_1$-$C_4$ haloalkyl, and phenyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{16}$ and $R^{17}$ are each independently H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —C(O)$R^{15}$, —C(O)O$R^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^{16}$ and $R^{17}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

X is O or N;
Y is O or N;
m is 0, 1, 2, or 3;
n is 0 to 5;
q is 0, 1, or 2; and
$\dashv\dashv\dashv$ represents an optional double bond;

with the provisos: (1) if $R^1$ is H, $R^2$ is $OCH_3$, $R^3$ is H, $R^4$ is OH, $R^5$ is H, $R^7$ is H, $R^8$ and $R^9$ are combined to form an oxo, $R^{10}$ is H, and X and Y are O, then at least one of $R^1$ to $R^{10}$ is a benzyl ether moiety, a carbamate moiety, an =$NR^{14}$ moiety, or a carbonate moiety; and (2) that X, $R^6$, $R^8$, and $R^9$ can form a dihydroquinone ring;

or an oxide thereof, a pharmaceutically acceptable salt thereof, or a solvate thereof.

Another aspect of the present invention relates to a therapeutic having a structure comprising formula I as follows:

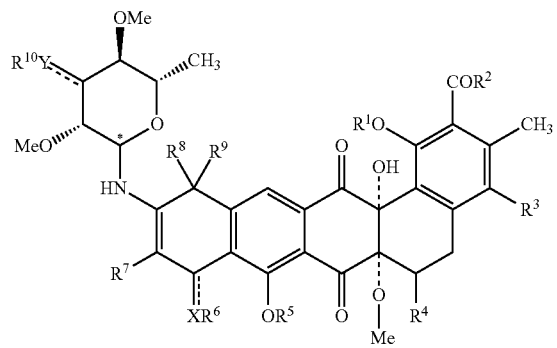

formula I wherein:
the carbohydrate anomeric carbon designated * is in the R or S configuration;

$R^1$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$ arylalkyl, heteroarylalkyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, or —$NR^{12}R^{13}$;

$R^2$ is selected from the group consisting of H, —$OR^{12}$, —$NR^{12}R^{13}$, —$(CH_2)_nC(O)R^{11}$, —$(CH_2)_nC(O)NR^{12}R^{13}$, —$(CH_2)_nOC(O)NR^{12}R^{13}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, phenyl, benzyl, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^3$ is selected from the group consisting of H, halogen, —$OR^{12}$, —$NR^{12}R^{13}$, —$NR^{12}C(O)R^{13}$, —$NR^{12}C(O)_2R^{13}$, —$NR^{12}C(O)NR^{12}R^{13}$, $S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^4$ is selected from the group consisting of H, halogen, —$OR^{12}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, —$(CH_2)_nOC(O)NR^{12}R^{13}$, phenyl, benzyl, =$NOR^{14}$, =$NR^{14}$, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^5$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, phenyl, benzyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^6$ is optionally present and, if present, is selected from the group consisting of H, —$OR^{12}$, —$NR^{12}R^{13}$, —$(CH_2)_n(O)R^{11}$, —$(CH_2)_nC(O)NR^{12}R^{13}$, $C_1$-$C_6$ alkyl, $C_1$-$C_6$ haloalkyl, phenyl, benzyl, a benzyl ether moiety, a carbamate moiety, an =$NR^{14}$ moiety, and a carbonate moiety, wherein each of —$(CH_2)_n(O)R^{11}$, —$(CH_2)_nC(O)NR^{12}R^{13}$, $C_1$-$C_6$ alkyl, $C_1$-$C_6$ haloalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

or $R^5$ and $R^6$ can combine to form a heterocycle group containing from 1 to 5 heteroatoms selected from the group consisting of oxygen, nitrogen, and sulfur and optionally substituted 1 to 3 times with halogen, oxo, cyano, $C_1$-$C_4$ alkyl, $C_1$-$C_4$ haloalkyl, or $C_1$-$C_4$ alkoxy;

$R^7$ is selected from the group consisting of H, halogen, —$OR^{12}$, —$NR^{12}R^{13}$, —$NR^{12}C(O)R^{13}$, —$NR^{12}C(O)_2R^{13}$, —$NR^{12}C(O)NR^{12}R^{13}$, $S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^8$ and $R^9$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$OR^{12}$, phenyl, benzyl, a benzyl ether moiety, a carbamate moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^8$ and $R^9$ can combine to form an oxo, thio, imine, or an =$NR^{14}$ moiety;

$R^{10}$ is optionally present and, if present, is selected from the group consisting of H, —$OR^{12}$, —$(CH_2)_nC(O)R^{11}$, —$(CH_2)_nC(O)NR^{12}R^{13}$, $C_1$-$C_6$ alkyl, $C_1$-$C_6$ haloalkyl, benzyl, a carbohydrate, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_1$-$C_6$ haloalkyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

or $R^1$, $R^2$, $R^3$, $R^4$, $R^5$, $R^6$, $R^7$, $R^8$, $R^9$, and $R^{10}$ are each, independently, an O-glycosidic bond, an N-glycosidic bond, a C-glycosidic bond, or a peptide bond;

$R^{11}$ is H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$C(O)R^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{12}$ and $R^{13}$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nNR^{16}R^{17}$, —$(CH_2)_nC(O)R^{11}$, —$(CH_2)_nOC(O)R^{11}$, —$(CH_2)_nC(O)_2R^{11}$, —$(CH_2)_nC(O)NR^{16}R^{17}$, —$(CH_2)_nOC(O)NR^{16}R^{17}$, —$(CH_2)_nNR^{16}C(O)OR^{17}$, —$(CH_2)_nNC(O)NR^{16}R^{17}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —$(CH_2)_nNR^{16}R^{17}$, —$(CH_2)_nC(O)R^{11}$, —$(CH_2)_nOC(O)R^{11}$, —$(CH_2)_nC(O)_2R^{11}$, —$(CH_2)_nC(O)NR^{16}R^{17}$, —$(CH_2)_nOC(O)NR^{16}R^{17}$, —$(CH_2)_nNR^{16}C(O)OR^{17}$, —$(CH_2)_nNC(O)NR^{16}R^{17}$, aryl, heteroaryl, arylalkyl, and heteroarylalkyl is optionally substituted 1 to 3 times with halogen, cyano, $C_1$-$C_4$ alkyl, $C_1$-$C_4$ haloalkyl, OH, $C_1$-$C_4$ alkoxy, an amino acid group, or [$NR^{11}C(O)(CH_2)_n]_m NR^{16}R^{17}$, which is optionally substituted 1 to 3 times with halogen, cyano, $C_1$-$C_4$ alkyl, $C_1$-$C_4$ haloalkyl, or $C_1$-$C_4$ alkoxy, aryl alkyl, wherein the $C_1$-$C_4$ alkyl and the aryl alkyl substituents are optionally substituted 1 to 3 times with halogen, alkyl, OH, $NH_2$, —$CO_2H$, —$C(O)NH_2$, —$NHC(O)NH_2$, —$NHC(NH)NH_2$, imidazole, pyrrolidine, SMe, SH, or SeH;

or $R^{12}$ and $R^{13}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

$R^{14}$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, $S(O)_qR^{12}$, $(CH_2)_nNR^{12}R^{13}$, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$(CH_2)_nNR^{11}C(O)OR^{12}$, —$(CH_2)_nNC(O)NR^{12}R^{13}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$(CH_2)_nNR^{11}C(O)OR^{12}$, —$(CH_2)_nNC(O)NR^{12}R^{13}$, aryl, heteroaryl, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, —$NR^{12}R^{13}$, or an amino acid group;

$R^{15}$ is H, $C_1$-$C_4$ alkyl, arylalkyl, heteroarylalkyl $C_1$-$C_4$ haloalkyl, or phenyl, wherein each of $C_1$-$C_4$ alkyl, arylalkyl, heteroarylalkyl $C_1$-$C_4$ haloalkyl, and phenyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{16}$ and $R^{17}$ are each independently H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$C(O)R^{15}$, —$C(O)OR^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^{16}$ and $R^{17}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

X is O or N;

Y is O or N;

m is 0, 1, 2, or 3;

n is 0 to 5;

q is 0, 1, or 2; and

╌╌╌ represents an optional double bond;

with the provisos: (1) if $R^1$ is H, $R^2$ is $OCH_3$, $R^3$ is H, $R^4$ is OH, $R^5$ is H, $R^7$ is H, $R^8$ and $R^9$ are combined to form an oxo, $R^{10}$ is H, and X and Y are O, then at least one of $R^1$ to $R^{10}$ is an O-glycosidic bond, an N-glycosidic bond, a C-glycosidic bond, or a peptide bond; and (2) that X, $R^6$, $R^8$, and $R^9$ can form a dihydroquinone ring;

or an oxide thereof, a pharmaceutically acceptable salt thereof, or a solvate thereof.

The present invention also relates to pharmaceutical compositions, cosmetic compositions, veterinary compositions, methods of treating or preventing a bacterial infection in a subject including administering a therapeutic having a structure comprising formula I to the subject, and methods of enhancing growth in a subject including administering a therapeutic including a structure of formula I to the subject.

Yet another aspect of the present invention relates to a method for making a product compound having the formula:

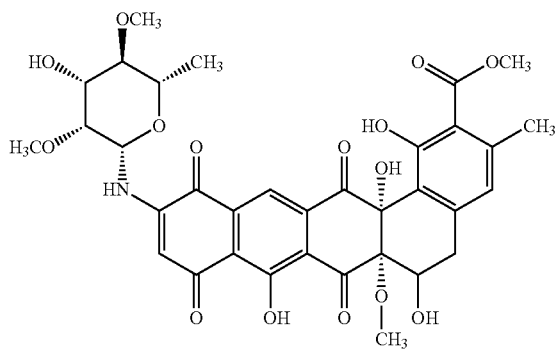 [SMILES: COC(=O)c1c(C)cc2c(c1O)[C@]1(O)C(=O)c3cc4c(c(O)c3C(=O)[C@]1(OC)C(O)C2)C(=O)C=C(N[C@H]1O[C@@H](C)[C@H](OC)[C@@H](O)[C@H]1OC)C4=O]

said method including fermenting a culture medium including *Streptomyces* strain AMRI-7957 (ATCC Accession No. PTA-11098) under conditions effective to produce a fermentation broth comprising the product compound, and isolating the product compound.

A further aspect of the present invention relates to a *Streptomyces* strain AMRI-7957 having ATCC Accession No. PTA-11098.

An additional aspect of the present invention relates to a method for making a product compound having the formula:

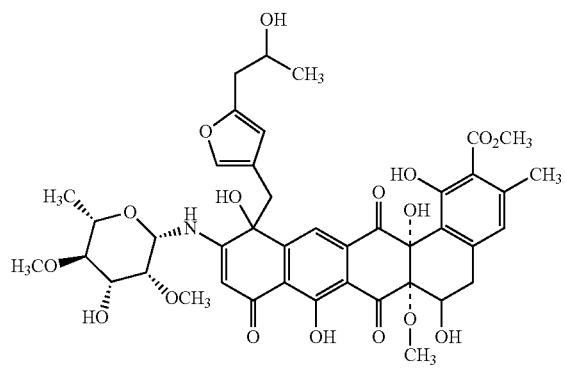 [SMILES: COC(=O)c1c(C)cc2c(c1O)[C@]1(O)C(=O)c3cc4c(c(O)c3C(=O)[C@]1(OC)C(O)C2)C(=O)C=C(N[C@H]1O[C@@H](C)[C@H](OC)[C@@H](O)[C@H]1OC)C4(O)Cc1coc(CC(C)O)c1]

said method including culturing a culture medium including *Streptomyces* strain AMRI-45379 under conditions effective to produce a suspension comprising the product compound, and isolating the product compound.

A further aspect of the present invention relates to a *Streptomyces* strain AMRI-45379 having ATCC Accession No. PTA-11097.

Yet another aspect of the present invention relates to methods of making the compounds of formula I of the present invention.

The continuing development of resistance to antibiotics, including those more recently introduced to the clinic (Seedat et al., "Rapid Emergence of Resistance to Linezolid During Linezolid Therapy of an *Enterococcus faecium* Infection," *Antimicrob. Agents Chemotherapy*, 50(12):4217-4219 (2006) and Hayden et al., "Development of Daptomycin Resistance In Vivo in Methicillin-Resistant *Staphylococcus aureus*," *J. Clin. Microbiol.*, 43(10):5285-5287 (2005), which are hereby incorporated by reference in their entirety), necessitates the development of new antibiotics that are able to overcome existing mechanisms of resistance for the treatment of bacterial infection, including those associated with multi-drug resistance organisms. The present invention provides compounds which can be used to treat multi-drug resistant strains.

DETAILED DESCRIPTION OF THE INVENTION

The present invention relates to a therapeutic having a structure comprising formula I as follows:

formula I

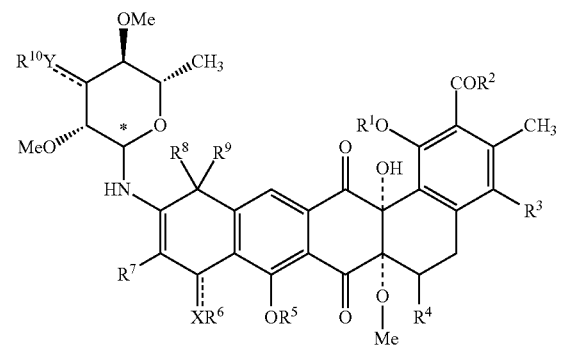

wherein:
the carbohydrate anomeric carbon designated * is in the R or S configuration;

$R^1$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, arylalkyl, heteroarylalkyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, or —$NR^{12}R^{13}$;

$R^2$ is selected from the group consisting of H, —$OR^{12}$, —$NR^{12}R^{13}$, —$(CH_2)_nC(O)R^{11}$, —$(CH_2)_nC(O)NR^{12}R^{13}$, —$(CH_2)_nOC(O)NR^{12}R^{13}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, phenyl, benzyl, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^3$ is selected from the group consisting of H, halogen, —$OR^{12}$, —$NR^{12}R^{13}$, —$NR^{12}C(O)R^{13}$, —$NR^{12}C(O)_2R^{13}$, —$NR^{12}C(O)NR^{12}R^{13}$, $S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^4$ is selected from the group consisting of H, halogen, —$OR^{12}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, —$(CH_2)_nOC(O)NR^{12}R^{13}$, phenyl, benzyl, =$NOR^{14}$, =$NR^{14}$, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^5$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, phenyl, benzyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^6$ is optionally present and, if present, is selected from the group consisting of H, —$OR^{12}$, —$NR^{12}R^{13}$, —$(CH_2)_n(O)R^{11}$, —$(CH_2)_nC(O)NR^{12}R^{13}$, $C_1$-$C_6$ alkyl, $C_1$-$C_6$ haloalkyl, phenyl, benzyl, a benzyl ether moiety, a carbamate moiety, an =$NR^{14}$ moiety, and a carbonate moiety, wherein each of —$(CH_2)_n(O)R^{11}$, —$(CH_2)_nC(O)NR^{12}R^{13}$, $C_1$-$C_6$ alkyl, $C_1$-$C_6$ haloalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

or $R^5$ and $R^6$ can combine to form a heterocycle group containing from 1 to 5 heteroatoms selected from the group consisting of oxygen, nitrogen, and sulfur and optionally substituted 1 to 3 times with halogen, oxo, cyano, $C_1$-$C_4$ alkyl, $C_1$-$C_4$ haloalkyl, or $C_1$-$C_4$ alkoxy;

$R^7$ is selected from the group consisting of H, halogen, —$OR^{12}$, —$NR^{12}R^{13}$, —$NR^{12}C(O)R^{13}$, —$NR^{12}C(O)_2R^{13}$, —$NR^{12}C(O)NR^{12}R^{13}$, $S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^8$ and $R^9$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$OR^{12}$, phenyl, benzyl, a benzyl ether moiety, a carbamate moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^8$ and $R^9$ can combine to form an oxo, thio, imine, or an =$NR^{14}$ moiety;

$R^{10}$ is optionally present and, if present, is selected from the group consisting of H, —$OR^{12}$, —$(CH_2)_nC(O)R^{11}$, —$(CH_2)_nC(O)NR^{12}R^{13}$, $C_1$-$C_6$ alkyl, $C_1$-$C_6$ haloalkyl, benzyl, a carbohydrate, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_1$-$C_6$ haloalkyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^{11}$ is H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$C(O)R^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{12}$ and $R^{13}$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_n$NR$^{16}$R$^{17}$, —$(CH_2)_n$C(O)R$^{11}$, —$(CH_2)_n$OC(O)R$^{11}$, —$(CH_2)_n$C(O)$_2$R$^{11}$, —$(CH_2)_n$C(O)NR$^{16}$R$^{17}$, —$(CH_2)_n$OC(O)NR$^{16}$R$^{17}$, —$(CH_2)_n$NR$^{16}$C(O)OR$^{17}$, —$(CH_2)_n$NC(O)NR$^{16}$R$^{17}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —$(CH_2)_n$NR$^{16}$R$^{17}$, —$(CH_2)_n$C(O)R$^{11}$, —$(CH_2)_n$OC(O)R$^{11}$, —$(CH_2)_n$C(O)$_2$R$^{11}$, —$(CH_2)_n$C(O)NR$^{16}$R$^{17}$, —$(CH_2)_n$OC(O)NR$^{16}$R$^{17}$, —$(CH_2)_n$NR$^{16}$C(O)OR$^{17}$, —$(CH_2)_n$NC(O)NR$^{16}$R$^{17}$, aryl, heteroaryl, arylalkyl, and heteroarylalkyl is optionally substituted 1 to 3 times with halogen, cyano, $C_1$-$C_4$ alkyl, $C_1$-$C_4$ haloalkyl, OH, $C_1$-$C_4$ alkoxy, an amino acid group, or [NR$^{11}$C(O)(CH$_2$)$_n$]$_m$NR$^{16}$R$^{17}$, which is optionally substituted 1 to 3 times with halogen, cyano, $C_1$-$C_4$ alkyl, $C_1$-$C_4$ haloalkyl, or $C_1$-$C_4$ alkoxy, aryl alkyl, wherein the $C_1$-$C_4$ alkyl and the aryl alkyl substituents are optionally substituted 1 to 3 times with halogen, alkyl, OH, NH$_2$, —CO$_2$H, —C(O)NH$_2$, —NHC(O)NH$_2$, —NHC(NH)NH$_2$, imidazole, pyrrolidine, SMe, SH, or SeH;

or $R^{12}$ and $R^{13}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

$R^{14}$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, S(O)$_q$R$^{12}$, (CH$_2$)$_n$NR$^{12}$R$^{13}$, —$(CH_2)_n$C(O)R$^{11}$, —$(CH_2)_n$OC(O)R$^{11}$, —$(CH_2)_n$C(O)$_2$R$^{11}$, —$(CH_2)_n$C(O)NR$^{12}$R$^{13}$, —$(CH_2)_n$OC(O)NR$^{12}$R$^{13}$, —$(CH_2)_n$NR$^{11}$C(O)OR$^{12}$, —$(CH_2)_n$NC(O)NR$^{12}$R$^{13}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —$(CH_2)_n$C(O)R$^{11}$, —$(CH_2)_n$OC(O)R$^{11}$, —$(CH_2)_n$C(O)$_2$R$^{11}$, —$(CH_2)_n$C(O)NR$^{12}$R$^{13}$, —$(CH_2)_n$OC(O)NR$^{12}$R$^{13}$, —$(CH_2)_n$NR$^{11}$C(O)OR$^{12}$, —$(CH_2)_n$NC(O)NR$^{12}$R$^{13}$, aryl, heteroaryl, arylalkyl, and heteroarylalkyl is optionally substituted with from 1 to 3 substituents independently selected at each occurrence thereof from $C_1$-$C_3$ alkyl, halogen, —CN, —OR$^{12}$, —NR$^{12}$R$^{13}$, and phenyl which is optionally substituted 1-3 times with halogen, $C_1$-$C_4$ alkyl, $C_1$-$C_4$ haloalkyl, $C_1$-$C_4$ alkoxy, —CN, —NO$_2$, —OR$^{12}$, —NR$^{12}$R$^{13}$, or an amino acid group;

$R^{15}$ is H, $C_1$-$C_4$ alkyl, arylalkyl, heteroarylalkyl $C_1$-$C_4$ haloalkyl, or phenyl, wherein each of $C_1$-$C_4$ alkyl, arylalkyl, heteroarylalkyl $C_1$-$C_4$ haloalkyl, and phenyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{16}$ and $R^{17}$ are each independently H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —C(O)R$^{15}$, —C(O)OR$^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^{16}$ and $R^{17}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

X is O or N;
Y is O or N;
m is 0, 1, 2, or 3;
n is 0 to 5;
q is 0, 1, or 2; and
⁝⁝⁝⁝ represents an optional double bond;

with the provisos: (1) if $R^1$ is H, $R^2$ is OCH$_3$, $R^3$ is H, $R^4$ is OH, $R^5$ is H, $R^7$ is H, $R^8$ and $R^9$ are combined to form an oxo, $R^{10}$ is H, and X and Y are O, then at least one of $R^1$ to $R^{10}$ is a benzyl ether moiety, a carbamate moiety, an =NR$^{14}$ moiety, or a carbonate moiety; and (2) that X, $R^6$, $R^8$, and $R^9$ can form a dihydroquinone ring;

or an oxide thereof, a pharmaceutically acceptable salt thereof, or a solvate thereof.

Another aspect of the present invention relates to a therapeutic having a structure comprising formula I as follows:

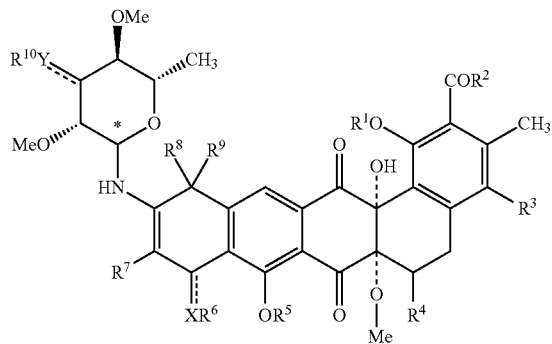

formula I wherein:
the carbohydrate anomeric carbon designated * is in the R or S configuration;

$R^1$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_n$C(O)R$^{11}$, —$(CH_2)_n$OC(O)R$^{11}$, —$(CH_2)_n$C(O)$_2$R$^{11}$, (CH$_2$)$_n$C(O)NR$^{12}$R$^{13}$, —$(CH_2)_n$OC(O)NR$^{12}$R$^{13}$, arylalkyl, heteroarylalkyl, a benzyl ether moiety, a carbamate moiety, an =NR$^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_n$C(O)R$^{11}$, —$(CH_2)_n$OC(O)R$^{11}$, —$(CH_2)_n$C(O)$_2$R$^{11}$, —$(CH_2)_n$C(O)NR$^{12}$R$^{13}$, —$(CH_2)_n$OC(O)NR$^{12}$R$^{13}$, arylalkyl, and heteroarylalkyl is optionally substituted with from 1 to 3 substituents independently selected at each occurrence thereof from $C_1$-$C_3$ alkyl, halogen, —CN, —OR$^{12}$, —NR$^{12}$R$^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —NO$_2$, —OR$^{12}$, or —NR$^{12}$R$^{13}$;

$R^2$ is selected from the group consisting of H, —OR$^{12}$, —NR$^{12}$R$^{13}$, —$(CH_2)_n$C(O)R$^{11}$, —$(CH_2)_n$C(O)NR$^{12}$R$^{13}$, —$(CH_2)_n$OC(O)NR$^{12}$R$^{13}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, phenyl, benzyl, a benzyl ether moiety, a carbamate moiety, an =NR$^{14}$ moiety, and a carbonate moiety, wherein each of —$(CH_2)_n$C(O)R$^{11}$, —$(CH_2)_n$C(O)NR$^{12}$R$^{13}$, $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, —NO$_2$, —NR$^{12}$R$^{13}$, —OR$^{12}$, C$_1$-C$_4$ alkyl, C$_1$-C$_4$ haloalkyl, C$_1$-C$_4$ alkoxy, or an amino acid group;

R$^3$ is selected from the group consisting of H, halogen, —OR$^{12}$, —NR$^{12}$R$^{13}$, —NR$^{12}$C(O)R$^{13}$, —NR$^{12}$C(O)$_2$R$^{13}$, —NR$^{12}$C(O)NR$^{12}$R$^{13}$, S(O)$_q$R$^{12}$, —CN, —NO$_2$, —(CH$_2$)$_n$C(O)R$^{11}$, —(CH$_2$)$_n$C(O)$_2$R$^{11}$, —(CH$_2$)$_n$C(O)NR$^{12}$R$^{13}$, —(CH$_2$)$_n$OC(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, heteroaryl, a benzyl ether moiety, a carbamate moiety, an =NR$^{14}$ moiety, and a carbonate moiety, wherein each of —(CH$_2$)$_n$C(O)R$^{11}$, —(CH$_2$)$_n$C(O)$_2$R$^{11}$, —(CH$_2$)$_n$C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{12}$, —NR$^{12}$R$^{13}$, an amino acid group, and phenyl which is optionally substituted 1-3 times with halogen, C$_1$-C$_4$ alkyl, C$_1$-C$_4$ haloalkyl, C$_1$-C$_4$ alkoxy, —CN, —OR$^{12}$, or —NR$^{12}$R$^{13}$;

R$^4$ is selected from the group consisting of H, halogen, —OR$^{12}$, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$C(O)R$^{11}$, —(CH$_2$)$_n$C(O)NR$^{12}$R$^{13}$, —(CH$_2$)$_n$OC(O)NR$^{12}$R$^{13}$, phenyl, benzyl, =NOR$^{14}$, =NR$^{14}$, a benzyl ether moiety, a carbamate moiety, an =NR$^{14}$ moiety, and a carbonate moiety, wherein each of —(CH$_2$)$_n$C(O)R$^{11}$, —(CH$_2$)$_n$C(O)NR$^{12}$R$^{13}$, C$_1$-C$_6$ alkyl, C$_3$-C$_6$ cycloalkyl, C$_4$-C$_7$ cycloalkylalkyl, phenyl, and benzyl is optionally substituted with from 1 to 3 substituents independently selected at each occurrence thereof from C$_1$-C$_3$ alkyl, halogen, —CN, —OR$^{12}$, —NR$^{12}$R$^{13}$, an amino acid group, and phenyl which is optionally substituted 1-3 times with halogen, C$_1$-C$_4$ alkyl, C$_1$-C$_4$ haloalkyl, C$_1$-C$_4$ alkoxy, —CN, —OR$^{12}$, or —NR$^{12}$R$^{13}$;

R$^5$ is selected from the group consisting of H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$C(O)R$^{11}$, —(CH$_2$)$_n$C(O)NR$^{12}$R$^{13}$, phenyl, benzyl, a benzyl ether moiety, a carbamate moiety, an =NR$^{14}$ moiety, and a carbonate moiety, wherein each of C$_1$-C$_6$ alkyl, C$_3$-C$_6$ cycloalkyl, C$_4$-C$_7$ cycloalkylalkyl, —(CH$_2$)$_n$C(O)R$^{11}$, —(CH$_2$)$_n$C(O)NR$^{12}$R$^{13}$, phenyl, and benzyl is optionally substituted 1 to 3 times with halogen, cyano, —NO$_2$, —NR$^{12}$R$^{13}$, —OR$^{12}$, C$_1$-C$_4$ alkyl, C$_1$-C$_4$ haloalkyl, C$_1$-C$_4$ alkoxy, or an amino acid group;

R$^6$ is optionally present and, if present, is selected from the group consisting of H, —OR$^{12}$, —NR$^{12}$R$^{13}$, —(CH$_2$)$_n$(O)R$^{11}$, —(CH$_2$)$_n$C(O)NR$^{12}$R$^{13}$, C$_1$-C$_6$ alkyl, C$_1$-C$_6$ haloalkyl, phenyl, benzyl, a benzyl ether moiety, a carbamate moiety, an =NR$^{14}$ moiety, and a carbonate moiety, wherein each of —(CH$_2$)$_n$(O)R$^{11}$, —(CH$_2$)$_n$C(O)NR$^{12}$R$^{13}$, C$_1$-C$_6$ alkyl, C$_1$-C$_6$ haloalkyl, phenyl, and benzyl is optionally substituted 1 to 3 times with halogen, cyano, —NO$_2$, —NR$^{12}$R$^{13}$, —OR$^{12}$, C$_1$-C$_4$ alkyl, C$_1$-C$_4$ haloalkyl, C$_1$-C$_4$ alkoxy, or an amino acid group;

or R$^5$ and R$^6$ can combine to form a heterocycle group containing from 1 to 5 heteroatoms selected from the group consisting of oxygen, nitrogen, and sulfur and optionally substituted 1 to 3 times with halogen, oxo, cyano, C$_1$-C$_4$ alkyl, C$_1$-C$_4$ haloalkyl, or C$_1$-C$_4$ alkoxy;

R$^7$ is selected from the group consisting of H, halogen, —OR$^{12}$, —NR$^{12}$R$^{13}$, —NR$^{12}$C(O)R$^{13}$, —NR$^{12}$C(O)$_2$R$^{13}$, —NR$^{12}$C(O)NR$^{12}$R$^{13}$, S(O)$_q$R$^{12}$, —CN, —NO$_2$, —(CH$_2$)$_n$C(O)R$^{11}$, —(CH$_2$)$_n$C(O)$_2$R$^{11}$, —(CH$_2$)$_n$C(O)NR$^{12}$R$^{13}$, —(CH$_2$)$_n$OC(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, heteroaryl, a benzyl ether moiety, a carbamate moiety, an =NR$^{14}$ moiety, and a carbonate moiety, wherein each of —(CH$_2$)$_n$C(O)R$^{11}$, —(CH$_2$)$_n$C(O)$_2$R$^{11}$, —(CH$_2$)$_n$C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{12}$, —NR$^{12}$R$^{13}$, an amino acid group, and phenyl which is optionally substituted 1-3 times with halogen, C$_1$-C$_4$ alkyl, C$_1$-C$_4$ haloalkyl, C$_1$-C$_4$ alkoxy, —CN, —OR$^{12}$, or —NR$^{12}$R$^{13}$;

R$^8$ and R$^9$ are each independently selected from the group consisting of H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$C(O)R$^{11}$, —(CH$_2$)$_n$C(O)$_2$R$^{11}$, —(CH$_2$)$_n$C(O)NR$^{12}$R$^{13}$, —(CH$_2$)$_n$OC(O)NR$^{12}$R$^{13}$, —OR$^{12}$, phenyl, benzyl, a benzyl ether moiety, a carbamate moiety, and a carbonate moiety, wherein each of C$_1$-C$_6$ alkyl, C$_3$-C$_6$ cycloalkyl, C$_4$-C$_7$ cycloalkylalkyl, —(CH$_2$)$_n$C(O)R$^{11}$, —(CH$_2$)$_n$C(O)$_2$R$^{11}$, —(CH$_2$)$_n$C(O)NR$^{12}$R$^{13}$, phenyl, and benzyl is optionally substituted from 1 to 3 times with a substituent selected independently at each occurrence thereof from the group consisting of halogen, cyano, C$_1$-C$_4$ alkyl, C$_1$-C$_4$ haloalkyl, C$_1$-C$_4$ alkoxy, and an amino acid group;

or R$^8$ and R$^9$ can combine to form an oxo, thio, imine, or an =NR$^{14}$ moiety;

R$^{10}$ is optionally present and, if present, is selected from the group consisting of H, —OR$^{12}$, —(CH$_2$)$_n$C(O)R$^{11}$, —(CH$_2$)$_n$C(O)NR$^{12}$R$^{13}$, C$_1$-C$_6$ alkyl, C$_1$-C$_6$ haloalkyl, benzyl, a carbohydrate, a benzyl ether moiety, a carbamate moiety, an =NR$^{14}$ moiety, and a carbonate moiety, wherein each of —(CH$_2$)$_n$C(O)R$^{11}$, —(CH$_2$)$_n$C(O)NR$^{12}$R$^{13}$, C$_1$-C$_6$ alkyl, C$_1$-C$_6$ haloalkyl, and benzyl is optionally substituted 1 to 3 times with halogen, cyano, —NO$_2$, —NR$^{12}$R$^{13}$, —OR$^{12}$, C$_1$-C$_4$ alkyl, C$_1$-C$_4$ haloalkyl, C$_1$-C$_4$ alkoxy, or an amino acid group;

or R$^1$, R$^2$, R$^3$, R$^4$, R$^5$, R$^6$, R$^7$, R$^8$, R$^9$, and R$^{10}$ are each, independently, an O-glycosidic bond, an N-glycosidic bond, a C-glycosidic bond, or a peptide bond;

R$^{11}$ is H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —C(O)R$^{15}$, phenyl, or benzyl, wherein each of C$_1$-C$_6$ alkyl, C$_3$-C$_6$ cycloalkyl, C$_4$-C$_7$ cycloalkylalkyl, phenyl, and benzyl is optionally substituted 1 to 3 times with halogen, cyano, C$_1$-C$_4$ alkyl, C$_1$-C$_4$ haloalkyl, C$_1$-C$_4$ alkoxy, or an amino acid group;

R$^{12}$ and R$^{13}$ are each independently selected from the group consisting of H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$NR$^{16}$R$^{17}$, —(CH$_2$)$_n$C(O)R$^6$, —(CH$_2$)$_n$OC(O)R$^{11}$, —(CH$_2$)$_n$C(O)$_2$R$^{11}$, —(CH$_2$)$_n$C(O)NR$^{16}$R$^{17}$, —(CH$_2$)$_n$OC(O)NR$^{16}$R$^{17}$, —(CH$_2$)$_n$NR$^{16}$C(O)OR$^7$, —(CH$_2$)$_n$NC(O)NR$^{16}$R$^{17}$, aryl, heteroaryl, arylalkyl, and heteroarylalkyl, wherein each of C$_1$-C$_6$ alkyl, C$_3$-C$_6$ cycloalkyl, C$_4$-C$_7$ cycloalkylalkyl, —(CH$_2$)$_n$NR$^{16}$R$^{17}$, —(CH$_2$)$_n$C(O)R$^{11}$, —(CH$_2$)$_n$OC(O)R$^{11}$, —(CH$_2$)$_n$C(O)$_2$R$^{11}$, —(CH$_2$)$_n$C(O)NR$^{16}$R$^{17}$, —(CH$_2$)$_n$OC(O)NR$^{16}$R$^{17}$, —(CH$_2$)$_n$NR$^{16}$C(O)OR$^{17}$, —(CH$_2$)$_n$NC(O)NR$^{16}$R$^{17}$, aryl, heteroaryl, arylalkyl, and heteroarylalkyl is optionally substituted 1 to 3 times with halogen, cyano, C$_1$-C$_4$ alkyl, C$_1$-C$_4$ haloalkyl, OH, C$_1$-C$_4$ alkoxy, an amino acid group, or [NR$^{11}$C(O)(CH$_2$)$_n$]$_m$NR$^{16}$R$^{17}$, which is optionally substituted 1 to 3 times with halogen, cyano, C$_1$-C$_4$ alkyl, C$_1$-C$_4$ haloalkyl, or C$_1$-C$_4$ alkoxy, aryl alkyl, wherein the C$_1$-C$_4$ alkyl and the aryl alkyl substituents are optionally substituted 1 to 3 times with halogen, alkyl, OH, NH$_2$, —CO$_2$H, —C(O)NH$_2$, —NHC(O)NH$_2$, —NHC(NH)NH$_2$, imidazole, pyrrolidine, SMe, SH, or SeH;

or $R^{12}$ and $R^{13}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

$R^{14}$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, $S(O)_q R^{12}$, $(CH_2)_n NR^{12}R^{13}$, $—(CH_2)_n C(O)R^{11}$, $—(CH_2)_n OC(O)R^{11}$, $—(CH_2)_n C(O)_2 R^{11}$, $—(CH_2)_n C(O)NR^{12}R^{13}$, $—(CH_2)_n OC(O)NR^{12}R^{13}$, $—(CH_2)_n NR^{11}C(O)OR^{12}$, $—(CH_2)_n NC(O)NR^{12}R^{13}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, $—(CH_2)_n C(O)R^{11}$, $—(CH_2)_n OC(O)R^{11}$, $—(CH_2)_n C(O)_2 R^{11}$, $—(CH_2)_n C(O)NR^{12}R^{13}$, $—(CH_2)_n OC(O)NR^{12}R^{13}$, $—(CH_2)_n NR^{11}C(O)OR^{12}$, $—(CH_2)_n NC(O)NR^{12}R^{13}$, aryl, heteroaryl, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, —$NR^{12}R^{13}$, or an amino acid group;

$R^{15}$ is H, $C_1$-$C_4$ alkyl, arylalkyl, heteroarylalkyl $C_1$-$C_4$ haloalkyl, or phenyl, wherein each of $C_1$-$C_4$ alkyl, arylalkyl, heteroarylalkyl $C_1$-$C_4$ haloalkyl, and phenyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{16}$ and $R^{17}$ are each independently H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$C(O)R^{15}$, —$C(O)OR^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^{16}$ and $R^{17}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

X is O or N;
Y is O or N;
m is 0, 1, 2, or 3;
n is 0 to 5;
q is 0, 1, or 2; and
---- represents an optional double bond;

with the provisos: (1) if $R^1$ is H, $R^2$ is $OCH_3$, $R^3$ is H, $R^4$ is OH, $R^5$ is H, $R^7$ is H, $R^8$ and $R^9$ are combined to form an oxo, $R^{10}$ is H, and X and Y are O, then at least one of $R^1$ to $R^{10}$ is an O-glycosidic bond, an N-glycosidic bond, a C-glycosidic bond, or a peptide bond; and (2) that X, $R^6$, $R^8$, and $R^9$ can form a dihydroquinone ring;

or an oxide thereof, a pharmaceutically acceptable salt thereof, or a solvate thereof.

As used above, and throughout the description of the invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, and the like.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. In the present invention, the term "alkenyl" may also refer to a hydrocarbon chain having 2 to 6 carbons containing at least one double bond and at least one triple bond.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

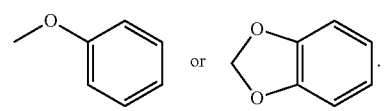

The term "alkoxyalkyl" means an alkyl residue attached to an alkoxy group, as herein described.

The term "amino acid group" means a side chain including an alpha-amino acid with the general formula $H_2NCHRCOOH$, where R is an organic substituent.

The term "aryl" means an aromatic monocyclic or multicyclic (polycyclic) ring system of 6 to about 19 carbon atoms, preferably of 6 to about 10 carbon atoms, and includes arylalkyl groups. The ring system of the aryl group may be optionally substituted. Representative aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" means an alkyl residue attached to an aryl ring. Examples are benzyl, phenethyl, and the like. Attachment can be through the alkyl or aryl residue.

The term "benzyl ether moiety" means a pendant group within the compound of formula I which includes a benzyl ether group. The benzyl ether group may be present within the benzyl ether moiety as a terminal group or as a non-terminal group. Other moieties and functional groups may be present in the benzyl ether moiety provided that the descriptive moiety is still present.

The term "carbamate moiety" means a pendant group within the compound of formula I which includes a carbamate group. The carbamate group may be present within the carbamate moiety as a terminal group or as a non-terminal group. Other moieties and functional groups may be present in the carbamate moiety provided that the descriptive moiety is still present.

The term "carbonate moiety" means a pendant group within the compound of formula I which includes a carbonate group. The carbonate group may be present within the carbonate moiety as a terminal group or as a non-terminal group. Other moieties and functional groups may be present in the carbonate moiety provided that the descriptive moiety is still present.

The term "compounds of the invention", and equivalent expressions, are meant to embrace compounds of general formula I as hereinbefore described, which expression includes the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio. Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. Thus, in accordance with some embodiments of the invention, a compound as described herein, including in the contexts of pharmaceutical compositions, methods of treatment, and compounds per se, is provided as the salt form. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "cycloalkyl" means a non-aromatic, saturated or unsaturated, mono- or multi-cyclic ring system of about 3 to about 7 carbon atoms, preferably of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "cycloalkylalkyl" means an cycloalkyl-alkyl-group in which the cycloalkyl and alkyl are as defined herein. Exemplary cycloalkylalkyl groups include cyclopropylmethyl and cyclopentylmethyl. The alkyl radical and the cycloalkyl radical may be optionally substituted as defined herein.

The term "functional group" means a specific atom or group of atoms within a molecule that is responsible for the characteristic chemical reactions of those molecules. The same functional group will undergo the same or similar chemical reaction(s) regardless of the size of the molecule it is a part of. However, its relative reactivity can be modified by nearby functional groups.

The term "haloalkyl" means both branched and straight-chain alkyl substituted with one or more halogen, wherein the alkyl group is as herein described.

The term "halogen" means fluorine, chlorine, bromine, or iodine.

The term "heteroaryl" means an aromatic monocyclic or multi-cyclic ring system of about 5 to about 19 ring atoms, preferably about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

The term "heteroarylalkyl" means an alkyl residue attached to a heteroaryl ring. Examples are 3-picolyl, 1-(furan-2-yl)propan-2-ol, and the like.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this invention, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, 2-oxooxazolidinyl, 3-oxomorpholino, 1,1-dioxothiomorpholino, tetrahydro-2H-oxazinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "hydrogen" means all isotopes, including protium, deuterium, and tritium.

The term "method of treating" means amelioration or relief from the symptoms and/or effects associated with the disorders described herein.

The term "monocyclic" used herein indicates a molecular structure having one ring.

The term "multiple drug resistance" or "multi-drug resistance" used herein indicates a condition enabling a disease-causing organism to resist distinct drugs or chemicals of a wide variety (National Library of Medicine Medica Subject Headings 2009, http://www.nlm.nih.gov/cgi/mesh/2009/MB_cgi?mode=&term=DRUG+RESISTANCE,+MULTIPLE,+BACTERIAL, which is hereby incorporated by reference in its entirety). In clinical practice, an organism is considered multi-drug resistant when it is able to resist the activities of two or more distinct varieties of structure that are effective against non-resistant strains. For example, multi-drug resistant Tuberculosis is defined as resistant to isoniazid and rifampicin whether there is resistance to other drugs or not (Davies, Multi-Drug Resistant Tuberculosis, http://priory.com/cmol/TBMultid.htm, which is hereby incorporated by reference in its entirety). Microorganisms that can display multi-drug resistance include pathological bacteria and fungi. Microorganisms develop resistance to antimicrobial agents via spontaneous mutation and DNA transfer (Walsh, "Antibiotics. Actions, Origins, Resistance," American Society for Microbiology (2003) and Bennett, *British Journal of Pharmacology*, 153(Suppl. 1):S347-S357 (2008), which are hereby incorporated by reference in their entirety). These processes allow pathological bacteria to become resistant to antibiotics used in the clinic and community, rendering the antibiotics ineffective (Walsh, "Antibiotics. Actions, Origins, Resistance," American Society for Microbiology (2003), which is hereby incorporated by reference in its entirety). Microorganisms employ several mechanisms in attaining multi-drug resistance including: (1) enzymatic deactiviation of antibiotics through destruction or modification; (2) replacement or modification of the antibiotic target; (3) use of efflux pumps to keep intracellular antibiotic concentrations below lethal levels (Li et al., "Efflux-mediated Drug Resistance in Bacteria: An Update," *Drug*, 69(12): 1555-1623 (2009) which is hereby incorporated by reference in its entirety); and (4) an increased mutation rate as a response to stress (Stix, "An Antibiotic Resistance Fighter," *Scientific American*, 294(4):81-83 (2006), which is hereby incorporated by reference in its entirety). Many different bacteria now exhibit multi-drug resistance, including staphylococci, enterococci, gonococci, streptococci, *salmonella*, pseudomonas, *Mycobacterium tuberculosis*, and others. In addition, some resistant bacteria are able to transfer copies of DNA that codes for a mechanism of resistance to other bacteria, thereby conferring resistance to their neighbors, which then are also able to pass on the resistant gene (Bennett, *British Journal of Pharmacology*, 153(Suppl. 1):S347-S357 (2008), which is hereby incorporated by reference in its entirety).

The term "=$NR^{14}$ moiety" means a pendant group within the compound of formula I which includes an =$NR^{14}$ group. The =$NR^{14}$ group may be present within the =$NR^{14}$ moiety as a terminal group or as a non-terminal group. Other moieties and functional groups may be present in the =$NR^{14}$ moiety provided that the descriptive moiety is still present. Suitable =$NR^{14}$ moieties include, but are not limited to, hydrazone moieties and acyl hydrazide moieties.

The term "pharmaceutical composition" means a composition comprising a therapeutic including a structure of formula I and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Various antibacterial and antifungal agents can be included, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Commonly, the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); Methods in Enzymology, K. Widder et al, Ed., Academic Press, 42, p. 309-396 (1985); A Textbook of Drug Design and Development, Krogsgaard-Larsen and H. Bundgaard, ed., Chapter 5; "Design and Applications of Prodrugs," p. 113-191 (1991); Advanced Drug Delivery Reviews, H. Bundgaard, 8, p. 1-38 (1992); *Journal of Pharmaceutical Sciences,* 77:285 (1988); Nakeya et al, *Chem. Pharm. Bull.,* 32:692 (1984); Higuchi et al., "Prodrugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "pharmaceutically acceptable salt" refers to salts prepared from pharmaceutically acceptable non-toxic acids or bases including inorganic acids and bases and organic acids and bases. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine. Pharmaceutically acceptable salts include, but are not limited to, amine salts, such as but not limited to N,N'dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methyl-benzimidazole, diethylamine and other alkylamines, piperazine, and tris (hydroxymethyl)aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C═C(OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C═C(OC(O)R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

The term "polycyclic" or "multi-cyclic" used herein indicates a molecular structure having two or more rings, including, but not limited to, fused, bridged, or spiro rings.

Terminology related to "protecting," "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The term "substituted" or "substitution" of an atom means that one or more hydrogen on the designated atom is replaced with a selection from the indicated group, provided that the designated atom's normal valency is not exceeded.

The term "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amount" is meant to describe an amount of compound of the present invention effective in producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

In accordance with one embodiment of the present invention, $R^1$ is selected from the group consisting of H, $C_1$-$C_6$ alkyl, $—(CH_2)_nC(O)_2R^{11}$, $—(CH_2)_nC(O)NR^{12}R^{13}$, arylalkyl, and heteroarylalkyl, wherein n is 1.

In accordance with another embodiment of the present invention, $R^2$ is $—OR^{14}$ or $—NR^{12}R^{13}$.

In accordance with another embodiment of the present invention, $R^3$ is selected from the group consisting of H, halogen, $—NR^{12}R^{13}$, and $—NO_2$.

In accordance with another embodiment of the present invention, $R^4$ is OH.

In accordance with another embodiment of the present invention, $R^4$ is =NOH.

In accordance with another embodiment of the present invention, $R^5$ is H or $C_1$-$C_6$ alkyl.

In accordance with another embodiment of the present invention, $R^6$ is selected from the group consisting of H, $—OR^{12}$, and $—(CH_2)_n(O)R^{11}$.

In accordance with another embodiment of the present invention, $R^7$ is H or halogen.

In accordance with another embodiment of the present invention, $R^8$ is $C_1$-$C_6$ alkyl or phenyl, wherein phenyl is optionally substituted from 1 to 3 times with halogen.

In accordance with another embodiment of the present invention, $R^9$ is OH.

In accordance with another embodiment of the present invention, $R^8$ and $R^9$ are combined to form an oxo group.

In accordance with another embodiment of the present invention, $R^{10}$ is H or $—OR^{12}$.

In accordance with another embodiment of the present invention, X is O.

In accordance with another embodiment of the present invention, X is N.

In accordance with another embodiment of the present invention, Y is O.

In accordance with another embodiment of the present invention, Y is N.

In accordance with another embodiment of the present invention, X is N, $R^6$ is $—NR^{12}R^{13}$, and $R^{12}$ is H.

In accordance with another embodiment of the present invention, X, $R^6$, $R^8$, and $R^9$ form a dihydroquinone ring, as follows:

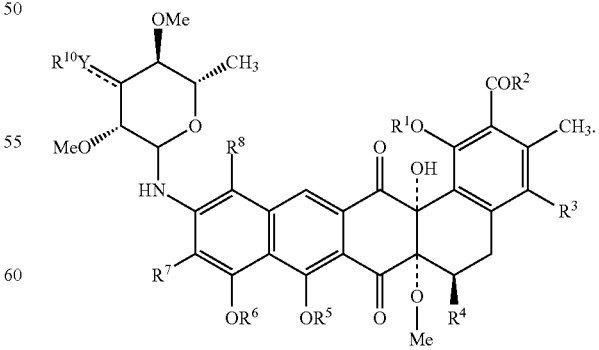

In accordance with another embodiment of the present invention, at least one of $R^1$ to $R^{10}$ is a benzyl ether moiety, a carbamate moiety, an =$NR^{14}$ moiety, or a carbonate moiety within the compound of formula I. An example of a compound of formula I including a benzyl ether moiety is (6R,6aS,14aR)-methyl 1-(benzyloxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (see Example 7). An example of a compound of formula I including a carbamate moiety is (6R,6aS,14aR)-methyl 1,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-6-(methylcarbamoyloxy)-7,9,12,14-tetraoxo-5,6,6a,7,9,12,14,14a-octahydrobenzo[a]tetracene-2-carboxylate. An example of a compound of formula I including a carbonate moiety is (6R,6aS,14aR)-methyl 1,8,14a-trihydroxy-11-((2S,3R,4R,5R,6S)-4-hydroxy-3,5-dimethoxy-6-methyltetrahydro-2H-pyran-2-ylamino)-6a-methoxy-6-(methoxycarbonyloxy)-3-methyl-7,9,12,14-tetraoxo-5,6,6a,7,9,12,14,14a-octahydrobenzo[a]tetracene-2-carboxylate. An example of a compound of formula I including an =NR$^{14}$ moiety, wherein the =NR$^{14}$ moiety is a hydrazone moiety is (6R,6aS,14aR)-methyl 11-((2S,3R,5R,6S,Z)-3,5-dimethoxy-6-methyl-4-(2-propylhydrazono)tetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate. An example of a compound of formula I including an =NR$^{14}$ moiety, wherein the =NR$^{14}$ moiety is an acyl hydrazide moiety is (6R,6aS,14aR,E)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,12,14-trioxo-9-(2-propionylhydrazono)-5,6,6a,7,9,12,14,14a-octahydrobenzo[a]tetracene-2-carboxylate.

Exemplary compounds of the present invention including benzyl ether moieties further include, but are not limited to:

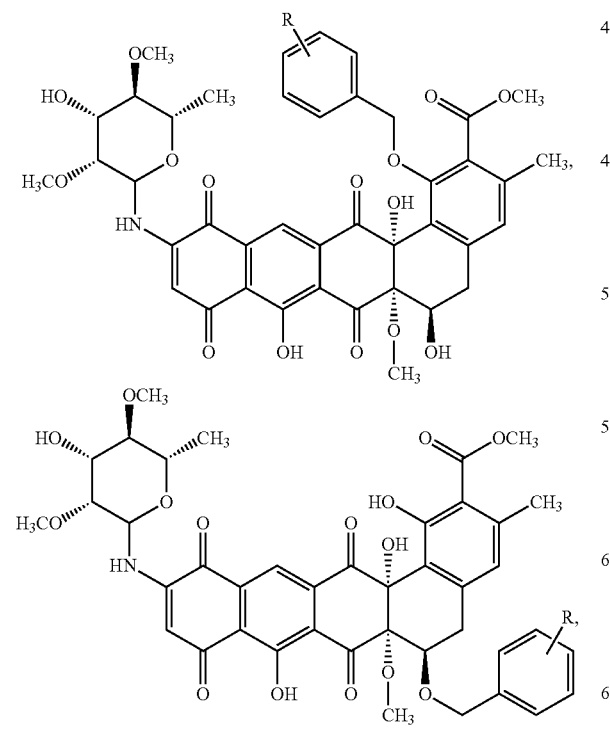

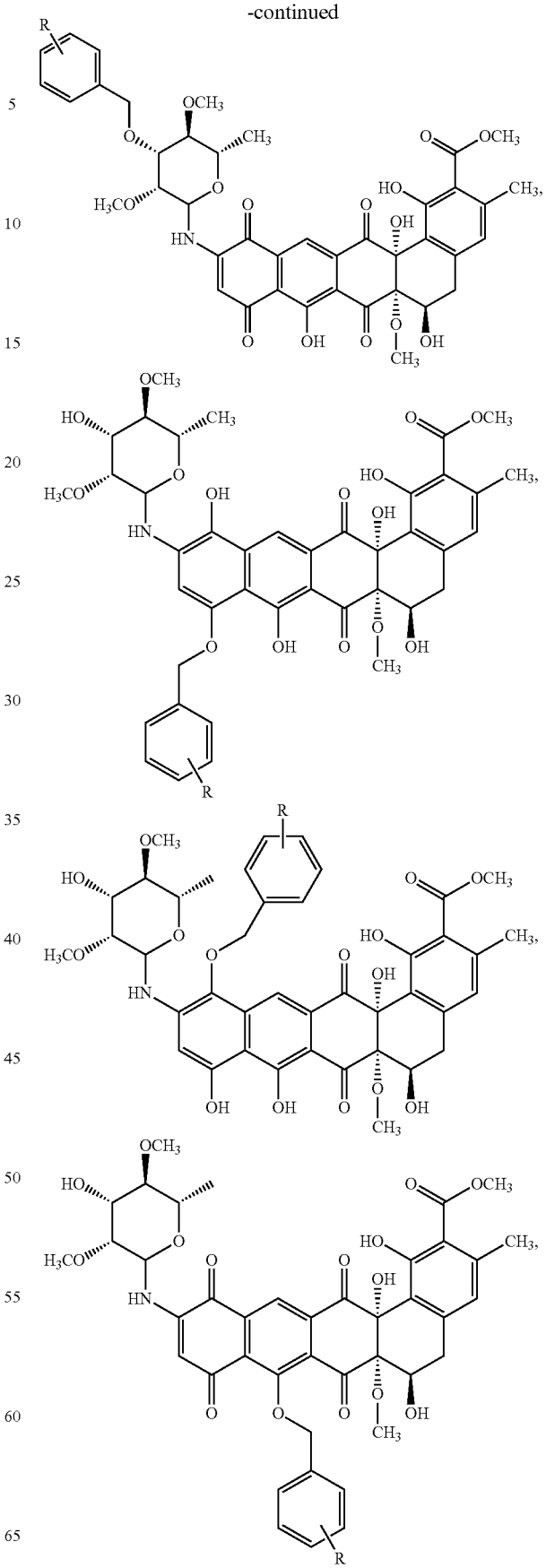

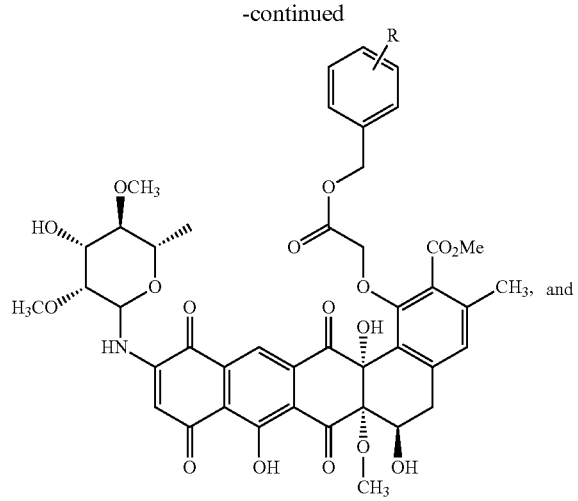
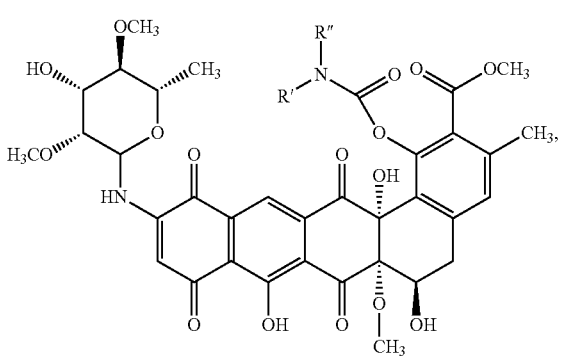
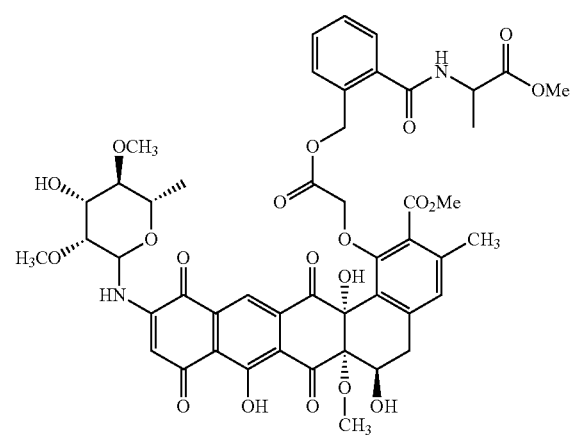
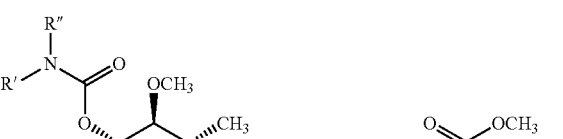
where R is defined as any of $R^1$ to $R^{17}$.
Additional exemplary compounds of the present invention including carbamate moieties further include, but are not limited to:
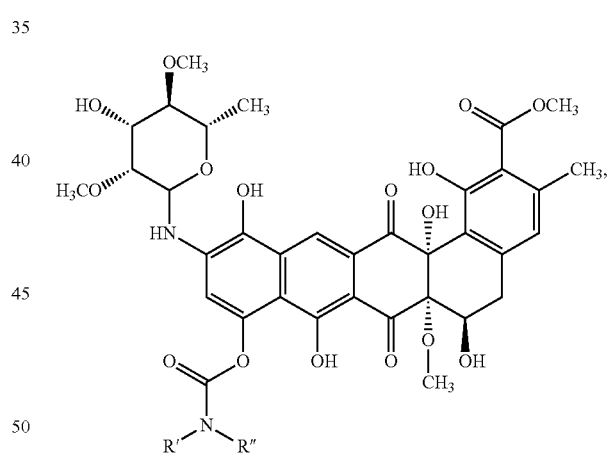
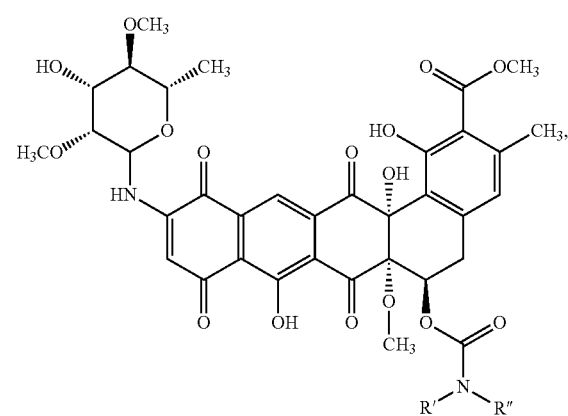
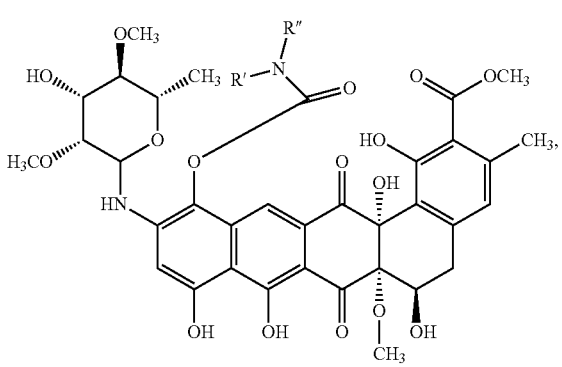

31
-continued
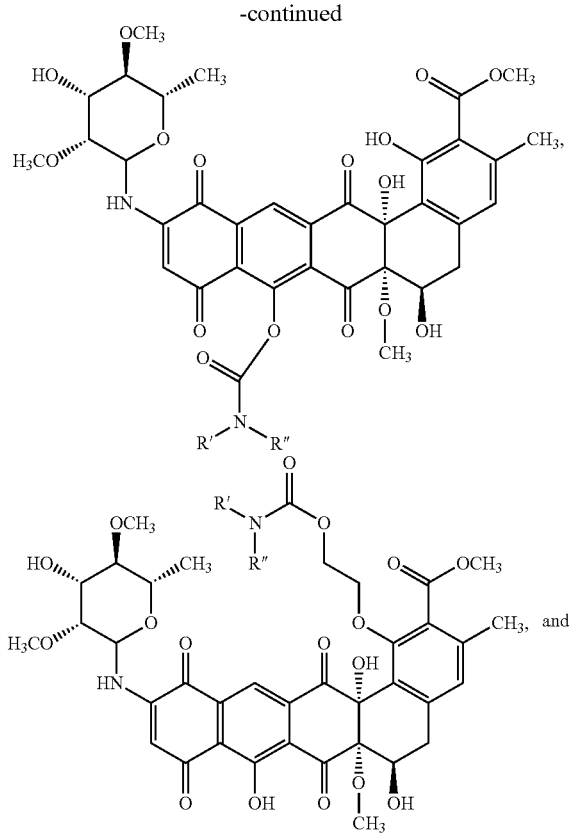
32
-continued
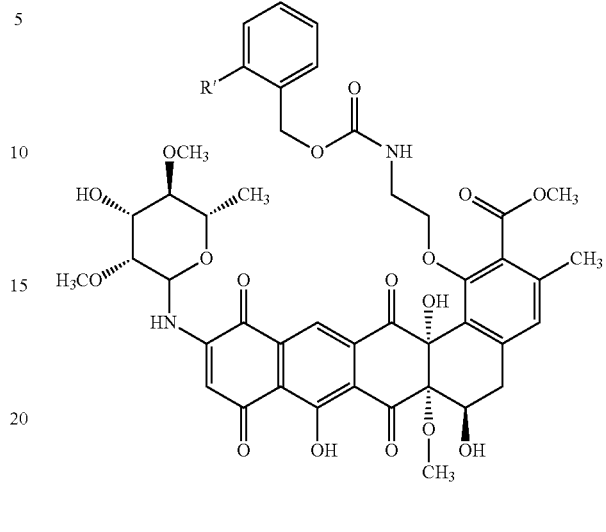
where R' and R" are defined as any of $R^1$ to $R^{17}$.
Additional exemplary compounds of the present invention including carbonate moieties further include, but are not limited to:
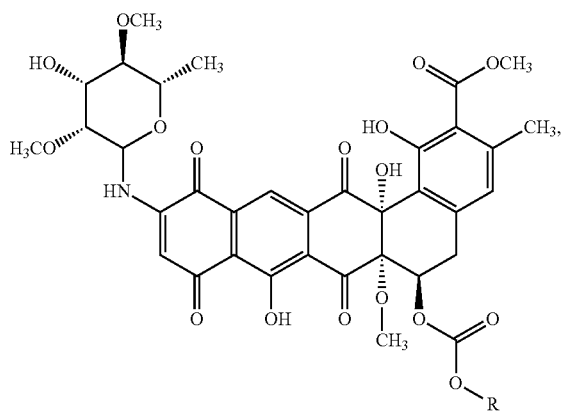
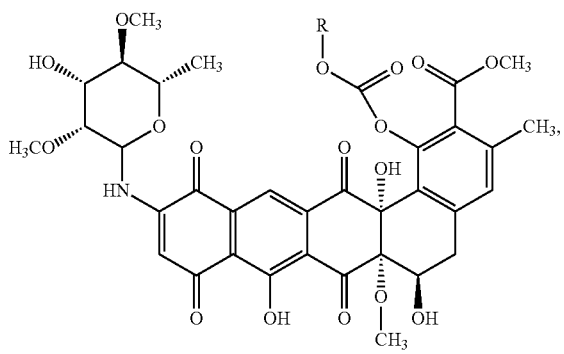
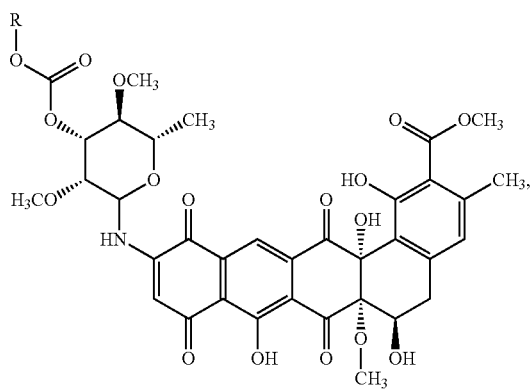
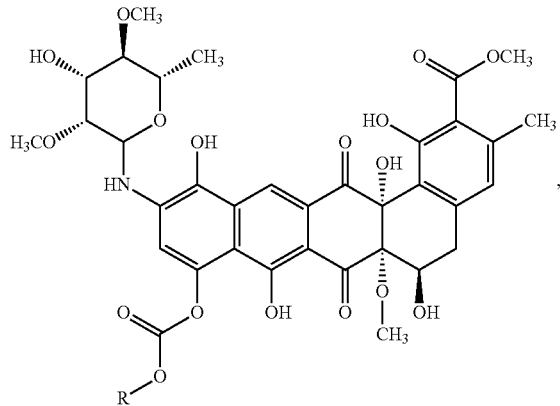

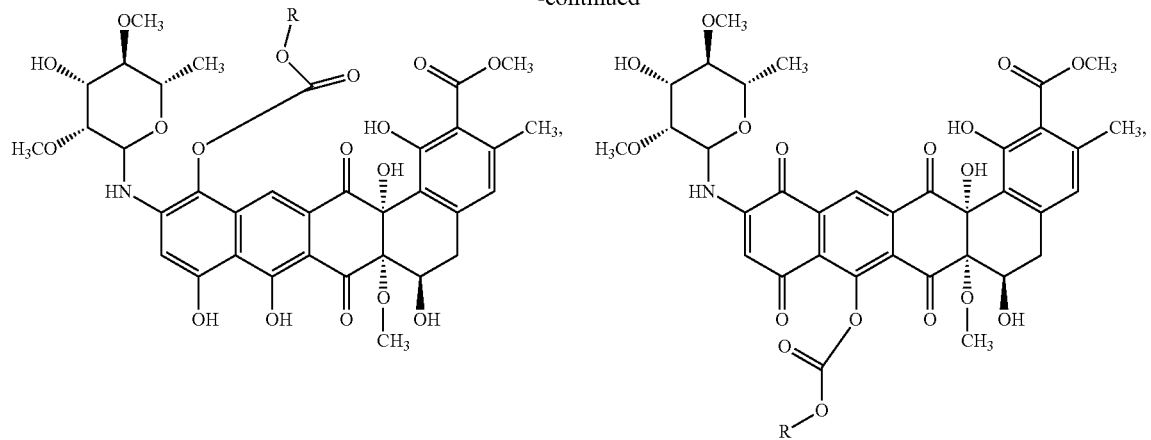
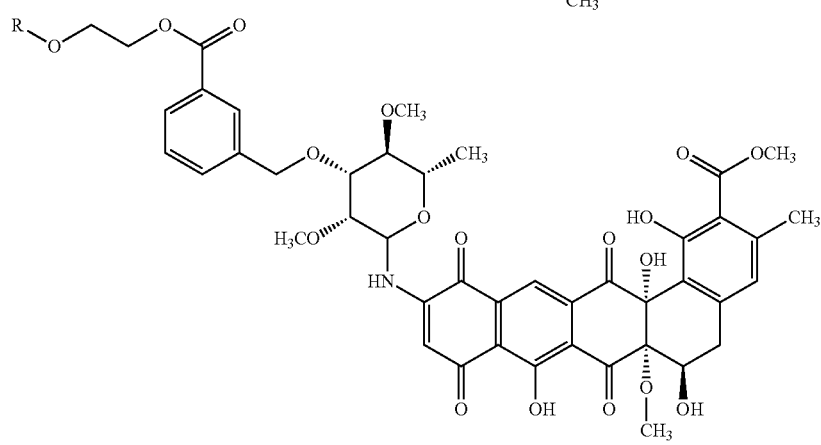
Further exemplary compounds of the present invention including =NR[14] moieties include, but are not limited to:
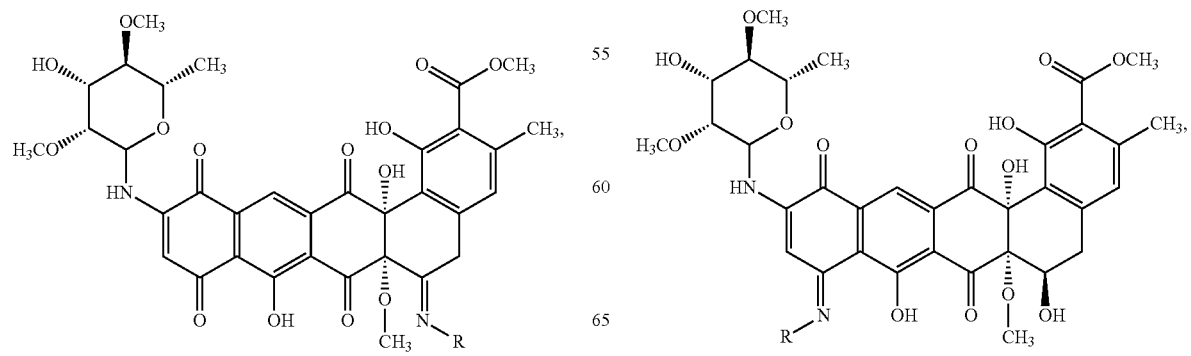

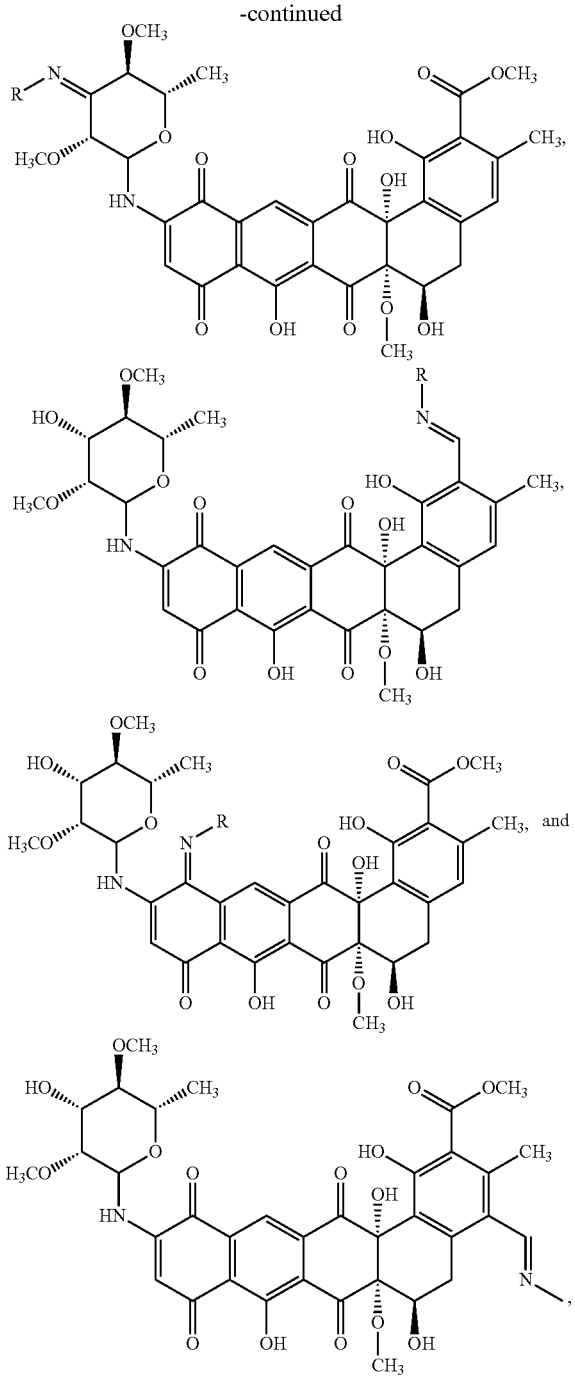

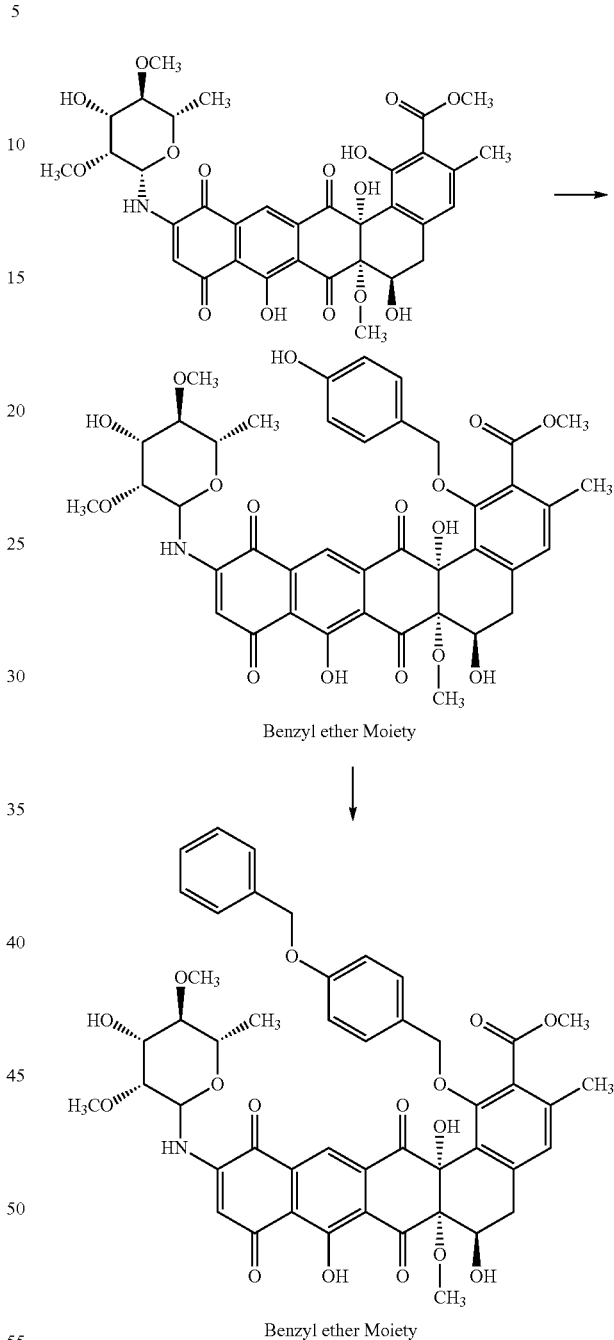

Benzyl ether Moiety tion of such moiety is intended to be inclusive in the definition of moiety provided that the descriptive moiety is still present in the product. An example of preparation of a compound of formula I including a benzyl ether moiety is shown below:

Benzyl ether Moiety

"Moieties" described herein (e.g., benzyl ether moiety, carbamate moiety, carbonate moiety, or =NR$^{14}$ moiety) may be prepared directly by transforming (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate or (6R,6aS,14aR)-methyl 1,6,8,14a-tetrahydroxy-11-((2R,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate or by reaction of derivatives to yield a new product with a covalent attachment. Subsequent transforma- Either primary transformation or secondary transformation of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate results in a "benzyl ether moiety". (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene- 2-carboxylate does not bear a benzyl ether attachment at any of the specified positions and is therefore not a benzyl ether moiety.

Specific compounds of the present invention include, but are not limited to:

(6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-1,6a-dimethoxy-3-methyl-7,9,12,14-tetraoxo-5,6,6a,7,9,12,14,14a-octahydrobenzo[a]tetracene-2-carboxylate;

(6R,6aS,14aR)-Methyl 6,14a-dihydroxy-11-((3R,4R,5R,6S)-4-hydroxy-3,5-dimethoxy-6-methyltetrahydro-2H-pyran-2-ylamino)-1,6a,8-trimethoxy-3-methyl-7,9,12,14-tetraoxo-5,6,6a,7,9,12,14,14a-octahydrobenzo[a]tetracene-2-carboxylate;

(6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-1-(2-methoxy-2-oxoethoxy)-3-methyl-7,9,12,14-tetraoxo-5,6,6a,7,9,12,14,14a-octahydrobenzo[a]tetracene-2-carboxylate;

(6R,6aS,14aR)-Methyl 1-(benzyloxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 1-(2-(benzyloxy)-2-oxoethoxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

2-((6R,6aS,14aR)-6,8,14a-Trihydroxy-11-((3R,4R,5R,6S)-4-hydroxy-3,5-dimethoxy-6-methyltetrahydro-2H-pyran-2-ylamino)-6a-methoxy-2-(methoxycarbonyl)-3-methyl-7,9,12,14-tetraoxo-5,6,6a,7,9,12,14,14a-octahydrobenzo[a]tetracene-1-yloxy)acetic acid;

(6R,6aS,14aR)-Methyl 1-(2-amino-2-oxoethoxy)-6,8,14a-trihydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-1-(pyridin-3-ylmethoxy)-5,6,6a,7,9,12,14,14a-octahydrobenzo[a]tetracene-2-carboxylate hydrochloride;

(6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-1-(2-oxo-2-(piperidin-1-yl)ethoxy)-5,6,6a,7,9,12,14,14a-octahydrobenzo[a]tetracene-2-carboxylate;

(6R,6aS,14aR)-1,6,8,14a-Tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-phenyl-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-2-(4-phenylpiperazine-1-carbonyl)-6,6a-dihydrobenzo[a]tetracene-7,9,12,14(5H,14aH)-tetraone hydrochloride;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-N,N,3-trimethyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(pyridin-3-ylmethyl)-5,6,6a,7,9,12,14,14a-octahydrobenzo[a]tetracene-2-carboxamide hydrochloride;

(6R,6aS,14aR)—N-Cyclohexyl-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-N,3-dimethyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-2-(piperidine-1-carbonyl)-6,6a-dihydrobenzo[a]tetracene-7,9,12,14(5H,14aH)-tetraone;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-2-(pyrrolidine-1-carbonyl)-6,6a-dihydrobenzo[a]tetracene-7,9,12,14(5H,14aH)-tetraone;

(6R,6aS,14aR)—N-(Biphenyl-4-yl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-N-(2-hydroxyethyl)-6a-methoxy-3-methyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(3-phenylpropyl)-5,6,6a,7,9,12,14,14a-octahydrobenzo[a]tetracene-2-carboxamide;

(6R,6aS,14aR)—N-(4-Fluorobenzyl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide;

(6R,6aS,14aR)—N-(4-Chlorobenzyl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-N-(4-methoxybenzyl)-3-methyl-7,9-12-14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-

(pyridin-3-yl)-5,6,6a,7,9,12,14,14a-octahydrobenzo[a]tetracene-2-carboxamide Hydrochloride;

(6R,6aS,14aR)—N-Benzyl-1,6,8,14-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide;

(6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-N-isopropyl-6a-methoxy-3-methyl-7,9,12,14-tetraoxo-5,6,6a,7,9,12,14,14a-octahydrobenzo[a]tetracene-2-carboxamide;

Benzyl 2-((6R,6aS,14aR)-1,6,8,14-tetrahydroxy-11-((3R,4R,5R,6S)-4-hydroxy-3,5-dimethoxy-6-methyltetrahydro-2H-pyran-2-ylamino)-6a-methoxy-N,3-dimethyl-7,9,12,14-tetraoxo-5,6,6a,7,9,12,14,14a-octahydrobenzo[a]tetracene-2-carboxamido)acetate;

(6R,6aS,14aR)-3-Phenylpropyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Ethyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-2-Morpholinoethyl 1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Isobutyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide;

(6R,6aS,14aR)-Benzyl 1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 11-((2S,3R,4R,5S,6S)-3,5-dimethoxy-6-methyl-4-((2S,3R,4S,5S,6R)-3,4,5-trihydroxy-6-(hydroxymethyl)tetrahydro-2H-pyran-2-yloxy)tetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 4-bromo-1,6,8,14a-tetrahydroxy-11-(4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 4,10-dibromo-1,6,8,14a-tetrahydroxy-11-(4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 10-chloro-1,6,8,14a-tetrahydroxy-11-(4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6S,6aS,14aR)-Methyl 4,10-dichloro-1,6,8,14a-tetrahydroxy-11-(4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 1,6,8,14a-tetrahydroxy-11-(4-hydroxy-3,5-dimethoxy-6-methyltetrahydro-2H-pyran-2-ylamino)-6a-methoxy-3-methyl-4-nitro-7,9,12,14-tetraoxo-5,6,6a,7,9,12,14,14a-octahydrobenzo[a]tetracene-2-carboxylate;

(6R,6aS,14aR)-Methyl 4-amino-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate 2,2,2-trifluoroacetate;

(6R,6aS,14aR)-Methyl 1,6,8,14a-tetrahydroxy-11-(4-hydroxy-3,5-dimethoxy-6-methyltetrahydro-2H-pyran-2-ylamino)-9-imino-6a-methoxy-3-methyl-7,12,14-trioxo-5,6,6a,7,9,12,14,14a-octahydrobenzo[a]tetracene-2-carboxylate;

(6R,6aS,14aR,E)-Methyl 1,6,8,14a-tetrahydroxy-11-(4-hydroxy-3,5-dimethoxy-6-methyltetrahydro-2H-pyran-2-ylamino)-6a-methoxy-3-methyl-9-(methylimino)-7,12,14-trioxo-5,6,6a,7,9,12,14,14a-octahydrobenzo[a]tetracene-2-carboxylate;

(6R,6aS,14aR,E)-Methyl 1,6,8,14a-tetrahydroxy-11-(4-hydroxy-3,5-dimethoxy-6-methyltetrahydro-2H-pyran-2-ylamino)-9-(hydroxyimino)-6a-methoxy-3-methyl-7,12,14-trioxo-5,6,6a,7,9,12,14,14a-octahydrobenzo[a]tetracene-2-carboxylate;

(6R,6aS,14aR,E)-Methyl 1,6,8,14a-tetrahydroxy-11-(4-hydroxy-3,5-dimethoxy-6-methyltetrahydro-2H-pyran-2-ylamino)-6a-methoxy-9-(2-methoxyethylimino)-3-methyl-7,12,14-trioxo-5,6,6a,7,9,12,14,14a-octahydrobenzo[a]tetracene-2-carboxylate;

(6R,6aS,14aR,E)-Methyl 1,6,8,14a-tetrahydroxy-11-(4-hydroxy-3,5-dimethoxy-6-methyltetrahydro-2H-pyran-2-ylamino)-6a-methoxy-9-(3-methoxypropylimino)-3-methyl-7,12,14-trioxo-5,6,6a,7,9,12,14,14a-octahydrobenzo[a]tetracene-2-carboxylate;

(6R,6aS,14aR,E)-Methyl 1,6,8,14a-tetrahydroxy-11-(4-hydroxy-3,5-dimethoxy-6-methyltetrahydro-2H-pyran-2-ylamino)-9-(3-hydroxypropylimino)-6a-methoxy-3-methyl-7,12,14-trioxo-5,6,6a,7,9,12,14,14a-octahydrobenzo[a]tetracene-2-carboxylate;

(6R,6aS,14aR)-Methyl 1,6,8,14a-tetrahydroxy-11-(4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 11-(Z)-3,5-dimethoxy-4-(methoxyimino)-6-methyltetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate;

2-{(Z)-3,5-Dimethoxy-2-methyl-6-[(6R,6aS,14aR)-1,6,8,14a-tetrahydroxy-6a-methoxy-2-(methoxycarbonyl)-3-methyl-7,9,12,14-tetraoxo-5,6,6a,7,9,12,14,14a-octahydrobenzo[a]tetracene-11-ylamino]-2H-pyran-4(3H,5H,6H)-ylideneaminooxy}acetic acid;

(6R,6aS,14aR)-Methyl 11-[(Z)-4-(2-aminoethoxyimino)-3,5-dimethoxy-6-methyltetrahydro-2H-pyran-2-ylamino]-1,6,8,14a-tetrahydroxy-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 1,8,14a-trihydroxy-6-(hydroxyimino)-11-[(Z)-4-(hydroxyimino)-3,5-dimethoxy-6-methyltetrahydro-2H-pyran-2-ylamino]-6a-methoxy-3-methyl-7,9,12,14-tetraoxo-5,6,6a,7,9,12,14,14a-octahydrobenzo[a]tetracene-2-carboxylate;

(6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3,12-dimethyl-7,9,14-trioxo-5,6,6a,7,9,12,14,14a-octahydrobenzo[a]tetracene-2-carboxylate;

(6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-12-phenyl-5,6,6a,7,9,12,14,14a-octahydrobenzo[a]tetracene-2-carboxylate;

(6R,6aS,14aR)-Methyl 12-ethyl-1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-5,6,6a,7,9,12,14,14a-octahydrobenzo[a]tetracene-2-carboxylate;

(6R,6aS,14aR)-Methyl 12-(4-fluorophenyl)-1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-5,6,6a,7,9,12,14,14a-octahydrobenzo[a]tetracene-2-carboxylate; and (6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-12-((5-(2-hydroxypropyl)furan-3-yl)methyl)-6a-methoxy-3-methyl-7,9,14-trioxo-5,6,6a,7,9,12,14,14a-octahydrobenzo[a]tetracene-2-carboxylate.

One embodiment of the present invention relates to pharmaceutically acceptable salts, or non-salt forms, of any of the compounds of formula I described herein. In one embodiment, the salt is a HCl salt.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present invention also includes compounds of formula I, wherein one or more of the atoms, e.g., C or H, are replaced by the corresponding radioactive isotopes of that atom (e.g., C replaced by $^{14}$C and H replaced by $^{3}$H), or a stable isotope of that atom (e.g., C replaced by $^{13}$C or H replaced by $^{2}$H). Radioisotopes of hydrogen, carbon, phosphorous, fluorine, iodine and chlorine include $^{3}$H, $^{14}$C, $^{35}$S, $^{18}$F, $^{32}$P, $^{33}$P, $^{125}$I, and $^{36}$Cl, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Such compounds have a variety of potential uses, e.g., as standards and reagents in determining the ability of a potential pharmaceutical to bind to neurotransmitter proteins. In addition, in the case of stable isotopes, such compounds may have the potential to favorably modify the biological properties, e.g., pharmacological and/or pharmacokinetic properties, of compound of formula I. The details concerning selection of suitable sites for incorporating radioactive isotopes into the compounds are known to those skilled in the art.

Therapeutics of the present invention as described herein are useful as antibacterials, which includes activity against multi-drug resistant strains. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a compound aspect, is all therapeutics including structures of formula I, except those that are in the public's possession.

While it may be possible for compounds of formula I to be administered as the raw chemical, it will often be preferable to present them as part of a pharmaceutical composition. Accordingly, another aspect of the present invention is a pharmaceutical composition containing a therapeutically effective amount of a therapeutic including a structure of formula I, or a pharmaceutically acceptable salt or solvate thereof, and a pharmaceutically acceptable carrier. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

Solid carriers suitable for use in the composition of the invention include one or more substances which may also act as flavoring agents, lubricants, solubilizers, suspending agents, fillers, glidants, compression aides, binders, tablet-disintegrating agents, or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

In one embodiment of the present invention, the pharmaceutical composition further comprises one or more other therapeutic adjuncts, e.g., other compounds effective in treating bacterial infections or enhancing growth (body mass), that are known to persons of skill in the art. Such other therapeutic adjuncts are described below.

Another aspect of the present invention relates to a method of treating a a bacterial infection. This method involves selecting a subject with a bacterial infection and administering to the subject a therapeutically effective amount of a therapeutic including a structure of formula I.

Suitable subjects include, for example, fish, amphibians, reptiles, birds, and mammals. The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

Bacterial infections which are susceptible to treatment with a therapeutic in accordance with the present invention include Gram positive bacterial infections, Gram negative bacterial infections, and multi-drug resistant bacterial infections (which may be Gram positive or Gram negative). In particular, bacterial infections in accordance with the present invention include, but are not limited to, epidermal infection, acne, complicated skin and soft tissue bacterial infection, and bacterial pneumonia.

In one embodiment, the bacterial infection is a multi-drug resistant bacterial infection of a strain of *Staphylococcus aureus, Streptococcus pneumoniae,* or *Enterococci.*

In another embodiment of the present invention, the above method further involves administering a therapeutically effective amount of one or more therapeutic adjuncts. Suitable therapeutic adjuncts include, but are not limited to, antibiotic compounds, such as penicillins, cephalosporins, azetreonam, glycopeptides (e.g., vancomycin), bacitracin, carbacephem, carbapenems, aminoglycosides, tetracyclines, macrolides, chloramphenicol, clindamycin, quinolones, and sulfonamides.

The present invention also relates to a method of preventing a bacterial infection in a subject. This method involves selecting a subject susceptible to bacterial infection and administering to the subject a therapeutic including a structure of formula I under conditions effective to prevent a bacterial infection.

This method further involves administering an adjunct, if desired, as described above.

Yet another aspect of the present invention relates to a method of enhancing growth in a subject. This method involves selecting a subject and administering to the subject a therapeutically effective amount of a therapeutic including a structure of formula I or a pharmaceutically acceptable salt thereof under conditions effective to enhance growth.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Yet another aspect of the present invention relates to a method for making a product compound having the formula:

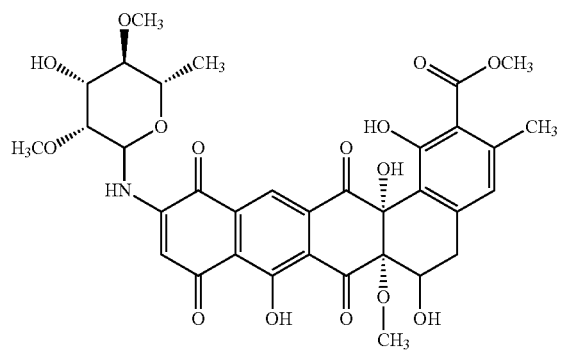

said method including fermenting a culture medium including *Streptomyces* strain AMRI-7957 (ATCC Accession No. PTA-11098) under conditions effective to produce a fermentation broth comprising the product compound, and isolating the product compound.

Methods of fermenting are known in the art and are described in detail in the Examples below and include culturing a suspension including the producing *Streptomyces* strain AMRI-7957 (ATCC Accession No. PTA-11098), and inoculating the culture into a fermentor.

Once the target compound has accumulated in the fermentor, it can be isolated. In accordance with the present invention, the product compound can be isolated from both the biomass fraction and the supernatant fraction of the fermentation broth. Accordingly, the biomass fraction and the supernatant fraction can be separated and the product compound can be extracted from each fraction.

A further aspect of the present invention relates to a *Streptomyces* strain AMRI-7957 having ATCC Accession No. PTA-11098.

Yet another aspect of the present invention relates to a method of making a product compound having the formula:

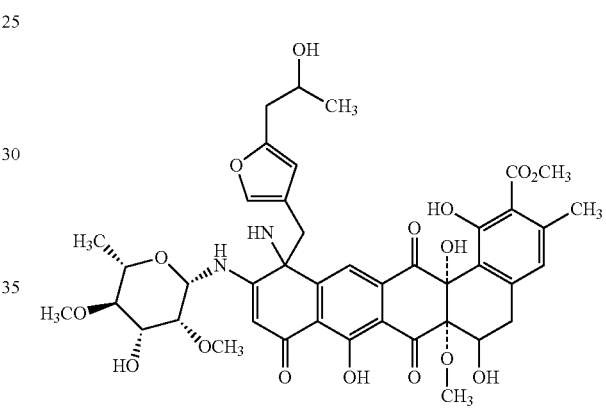

said method including culturing a culture medium including *Streptomyces* strain AMRI-45379 under conditions effective to produce a suspension comprising the product compound, and isolating the product compound.

Suitable conditions for producing a suspensing comprising the product compound include microbial transformation techniques. Such microbial transformation techniques include, for example, adding intermediate (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a, 7,9,12,14,14a-octahydrobenzo[a]tetracene-2-carboxylate to the culture medium and incubating under conditions effective to allow formation of the product compound (see, e.g., Example 62).

A further aspect of the present invention relates to a *Streptomyces* strain AMRI-45379 having ATCC Accession No. PTA-11097.

Another aspect of the present invention relates to a method of making a product compound of formula I. This method involves treating a first intermediate compound having the structure:

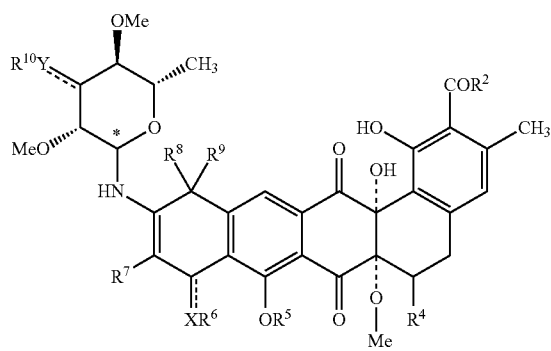

under conditions effective to form the product compound.

In one embodiment, treating comprises reacting the first intermediate with $R^1Z^1$, wherein $Z^1$ is a halide and $R^1$ is as defined above.

A further aspect of the present invention relates to a method of making a product compound of formula I which involves treating a first intermediate compound having the structure:

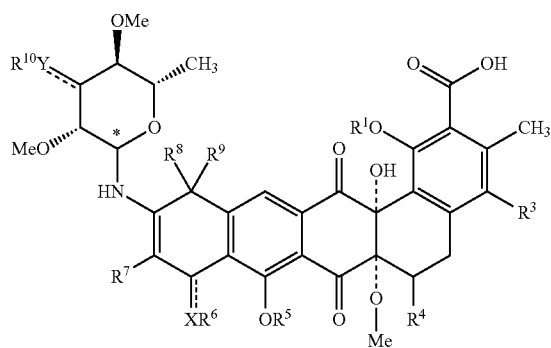

under conditions effective to form the product compound.

In one embodiment, treating comprises reacting the first intermediate with $R^2Z^2$, wherein $Z^2$ is a halide or H and $R^2$ is as defined above.

Another aspect of the present invention relates to a method of making a product compound of formula I which involves treating a first intermediate compound having the structure:

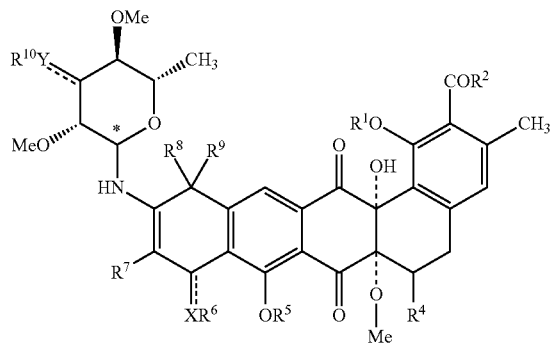

under conditions effective to form the product compound.

In one embodiment, treating comprises reacting the first intermediate compound with N—$R^3$-succinimide, wherein $R^3$ is as defined above.

In another embodiment, wherein $R^3$ is —$NO_2$, treating comprises reacting the first intermediate with a nitration agent. Suitable nitration agents include, for example, zirconyl (IV) nitrate hydrate. In another embodiment, the method further includes reacting the compound of formula I, wherein $R^3$ is —$NO_2$, with a reducing agent.

Yet another aspect of the present invention relates to a method of making a product compound of formula I which involves treating a first intermediate having the structure:

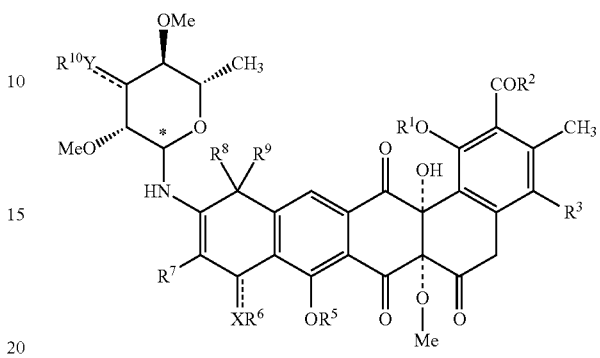

under conditions effective to form the product compound.

In one embodiment, wherein $R^4$ is =$NR^{14}$, treating comprises reacting the first intermediate with $NH_2R^{14}$.

A further aspect of the present invention relates to a method of making a product compound of formula I which involves treating a first intermediate having the structure:

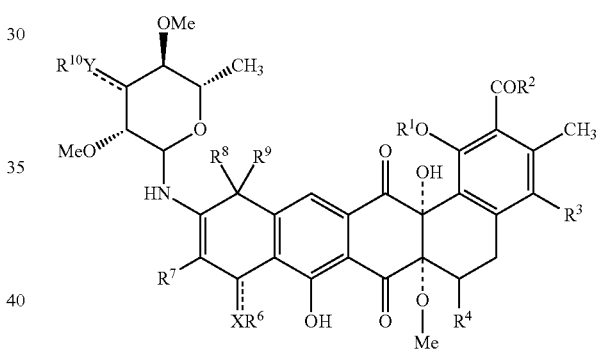

under conditions effective to form the product compound.

In one embodiment, treating comprises reacting the first intermediate compound with $R^5Z^1$, wherein $Z^1$ is a halide and $R^5$ is as defined above.

Another aspect of the present invention relates to a method of making a product compound of formula I which involves treating a first intermediate having the structure:

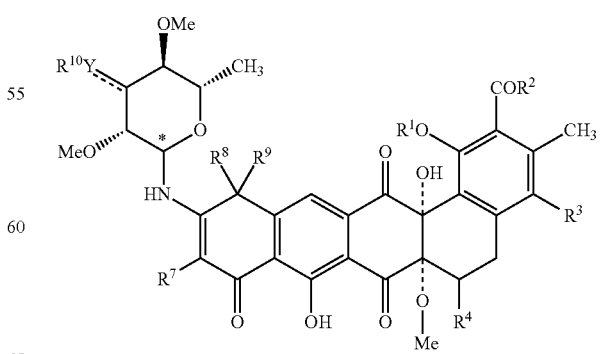

under conditions effective to form the product compound.

In one embodiment, wherein X is N, treating comprises reacting the first intermediate with $NH_2R^6$, wherein $R^6$ is as defined above.

In another embodiment, the method further includes reacting the product compound with a coupling agent such that $R^5$ and $R^6$ combine to form a heterocycle group containing from 1 to 5 heteroatoms selected from the group consisting of oxygen, nitrogen, and sulfur and optionally substituted 1 to 3 times with halogen, oxo, cyano, $C_1$-$C_4$ alkyl, $C_1$-$C_4$ haloalkyl, or $C_1$-$C_4$ alkoxy.

Suitable coupling agents include, for example, carbonyldiimidazole.

Another aspect of the present invention relates to a method of making a product compound of formula I which involves treating a first intermediate having the structure:

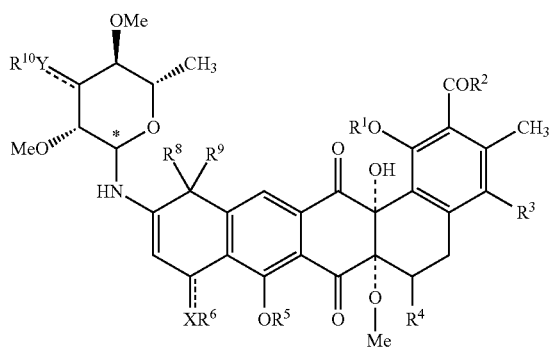

under conditions effective to form the product compound.

In one embodiment, treating comprises reacting the first intermediate compound with N—$R^7$-succinimide, wherein $R^7$ is as defined above.

In another embodiment, wherein $R^7$ is —$NO_2$, treating comprises reacting the first intermediate with a nitration agent. Suitable nitration agents include, for example, zirconyl (IV) nitrate hydrate. In another embodiment, the method further includes reacting the compound of formula I, wherein $R^7$ is —$NO_2$, with a reducing agent.

Another aspect of the present invention relates to a method of making a product compound of formula I which involves treating a first intermediate having the structure:

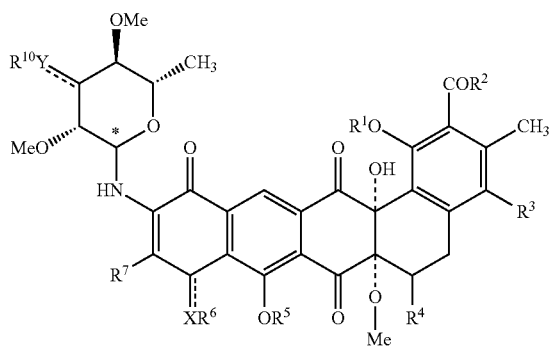

under conditions effective to form the product compound.

In one embodiment, treating comprises reacting the first intermediate with $R^8$-M-L, wherein M is a metal and L is a halide. In another embodiment, treating comprises reacting the first intermediate with $R^9$-M-L, wherein M is a metal and L is a halide.

Another aspect of the present invention relates to a method of making a product compound of formula I which involves treating a first intermediate having the structure:

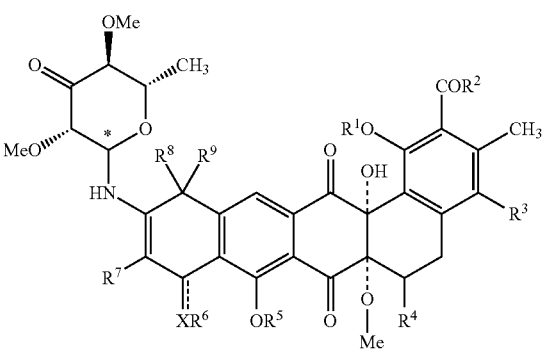

under conditions effective to form the product compound.

In one embodiment, wherein Y is N, treating comprises reacting the first intermediate with $NH_2R^{10}$, wherein $R^{10}$ is as defined above.

Another aspect of the present invention relates to a method of making a product compound of formula I which involves treating a first intermediate having the structure:

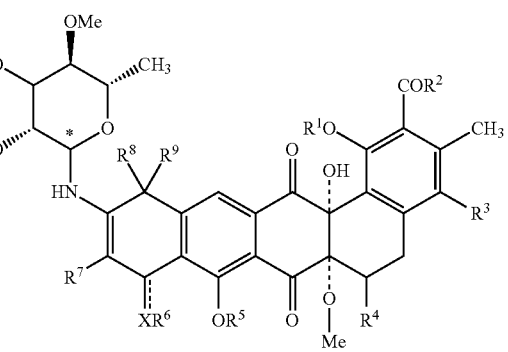

under conditions effective to form the product compound.

In one embodiment, treating comprises reacting the first intermediate with an imidate having a formula:

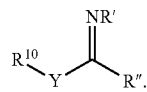

Suitable imidates include, but are not limited to,

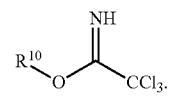

Compounds according to the invention, for example, starting materials, intermediates, or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice and as described above.

The novel compounds of formula I of this invention can be prepared by the methods illustrated in the general reaction schemes as, for example, described below, or by modifications thereof, using readily available starting materials, reagents, and conventional synthesis procedures. Reagent 1 may be prepared by the methods described herein. In these reactions, it is also possible to make use of variants that are known in the art but are not mentioned here. Although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Scheme 1

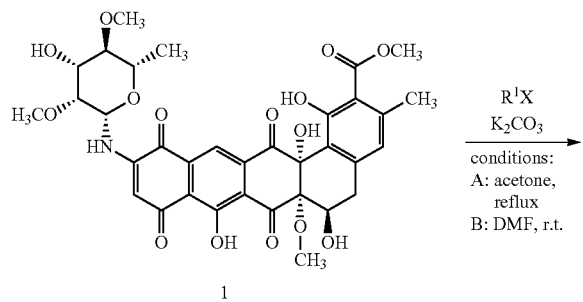

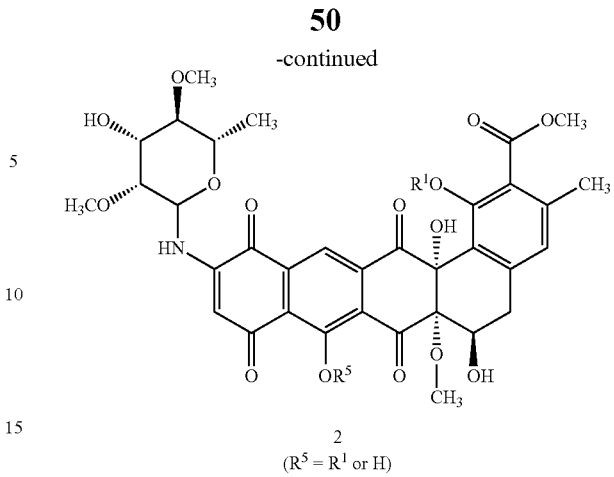

The compounds of formula 2 may be prepared from a mixture of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate, potassium carbonate, and alkyl halide ($R^1X$). The reaction is carried out in a solvent, e.g., acetone, and heated under reflux until completion. Alternatively, the compounds of formula 2 may be prepared with the mixture described above in DMF at room temperature until completion. The completion is reached as shown by LC-MS or TLC analysis. The product 2 may be purified by preparative TLC or preparative HPLC or normal phase chromatography.

Examples of compounds produced in accordance with Scheme 1 are shown in Table 1, below:

TABLE 1

| Example # | $R^1X$ | $R^1$ | $R^5$ | Conditions |
|---|---|---|---|---|
| 4 | $CH_3I$ | $CH_3$ | H | A |
| 5 | $CH_3I$ | $CH_3$ | $CH_3$ | A |
| 6 | Br-CH₂-C(O)-O-CH₃ | -CH₂-C(O)-O-CH₃ | H | A |
| 7 | PhCH₂Br | PhCH₂- | H | A |
| 8 | Br-CH₂-C(O)-O-CH₂-Ph | -CH₂-C(O)-O-CH₂-Ph | H | A |
| 10 | $BrCH_2CONH_2$ | $CH_2CONH_2$ | H | A |
| 11 | 3-pyridyl-CH₂Cl·HCl | 3-pyridyl-CH₂- | H | B |

TABLE 1-continued

| Example # | R¹X | R¹ | R⁵ | Conditions |
|---|---|---|---|---|
| 12 |  |  | H | B |

Scheme 2

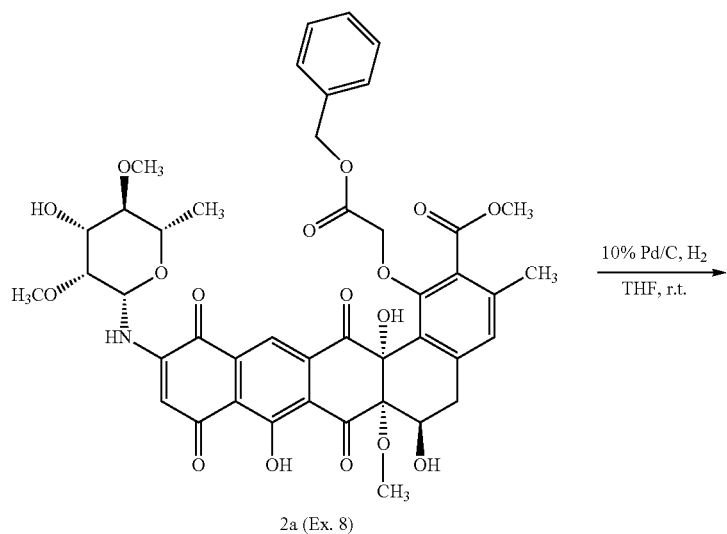

2a (Ex. 8)

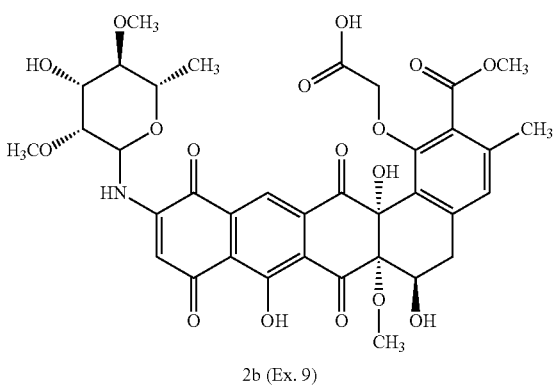

2b (Ex. 9)

The compound of formula 2b may be prepared from a mixture of 2a and 10% Pd/C in THF or appropriate solvent stirred under hydrogen (1 atm) at room temperature. The reaction mixture is filtered and concentrated. The residue is purified by by routine chromatography such as preparative TLC or preparative HPLC or normal phase chromatography to produce the compound of formula 2b.

Scheme 3

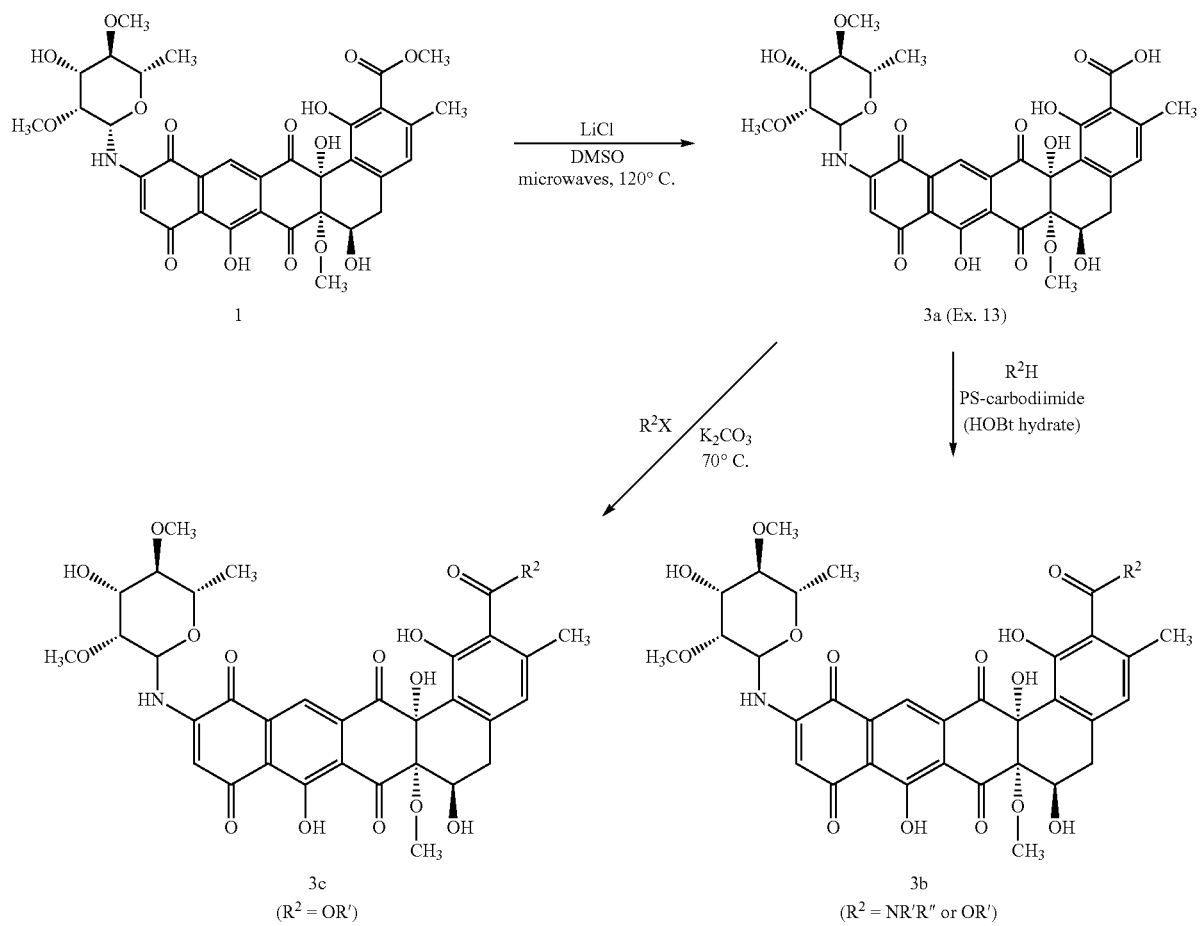

The compounds of formula 3a may be prepared from a mixture of (6R,6aS,14aR)-methyl 1,6,8,14a-tetrahydroxy-11-(4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate in DMSO and lithium chloride. The reaction mixture is irradiated with microwaves at elevated temperature (e.g. 120° C.). The crude material is purified by chromatography such as (e.g. 120° C.). The crude material is purified by routine chromatography such as preparative TLC or preparative HPLC or normal phase chromatography to obtain the compounds of formula 3a.

Polystyrene-carbodiimide (PS-carbodiimide), 1-hydroxybenzotriazole hydrate (HOBt hydrate), and $R^2H$ may be added to the compounds of formula 3a in THF or appropriate solvent (e.g., methylene chloride). The reaction mixture is stirred at room temperature or slightly heated (e.g., 40° C.) under nitrogen or argon. A catalytic amount of 4-pyrrolidinopyridine may be added to the reaction mixture. Before the step of adding PS-carbodiimide, HOBt hydrate and $R^2H$, palladium on carbon (e.g. 10% Pd/C) may be add to the compounds of formula 3a in THF and the reaction mixture is stirred at room temperature under hydrogen atmosphere. The crude material is purified by routine chromatography such as preparative TLC or preparative HPLC or normal phase chromatography to produce the compounds of formula 3b.

Alternatively, potassium carbonate, alkyl halide (e.g. $R^2X$), and a catalytic amount of potassium iodide may be added to the compounds of formula 3a, and then the reaction heated (e.g. to 70° C.) under nitrogen. The reaction mixture may then be concentrated under reduced pressure and the crude product purified by routine chromatography such as preparative TLC or preparative HPLC or normal phase chromatography. The resulting product may be lyophilized from acetonitrile and water to yield the compounds of formula 3c.

Examples of compounds produced in accordance with Scheme 3 are shown in Table 2, below:

TABLE 2

| Example # | $R^2$ |
|---|---|
| Compound 3b | |
| 14 | ⸾—NH—C₆H₅ |
| 15 | ⸾—N(piperazine)N—C₆H₅ |
| 16 | $(CH_3)_2N$ |

TABLE 2-continued
| Example # | R² |
|---|---|
| 17 | ⸺NH–CH₂–(pyridin-3-yl) |
| 18 | ⸺NH–cyclohexyl |
| 19 | NHCH₃ |
| 20 | NH₂ |
| 21 | ⸺N(piperidinyl) |
| 22 | ⸺N(pyrrolidinyl) |
| 23 | ⸺NH–(4-phenylphenyl) |
| 24 | NH(CH₂)₂OH |
| 25 | NH(CH₂)₃Ph |
| 26 | ⸺NH–CH₂–(4-F-C₆H₄) |
| 27 | ⸺NH–CH₂–(4-Cl-C₆H₄) |
TABLE 2-continued
| Example # | R² |
|---|---|
| 28 | ⸺NH–CH₂–(4-OCH₃-C₆H₄) |
| 29 | ⸺NH–(pyridin-3-yl)·HCl |
| 30 | ⸺NH–CH₂–Ph |
| 31 | NHCH(CH₃)₂ |
| 32 | ⸺N(CH₃)–CH₂–C(=O)–O–CH₂–Ph |
| 34 | OEt |
| 35 | ⸺O–CH₂CH₂–(morpholin-4-yl) |
| 36 | OCH₂CH(CH₃)₂ |
| 37 | ⸺O–CH₂–Ph |
Compound 3c
| 33 | O(CH₂)₃Ph |
Scheme 4
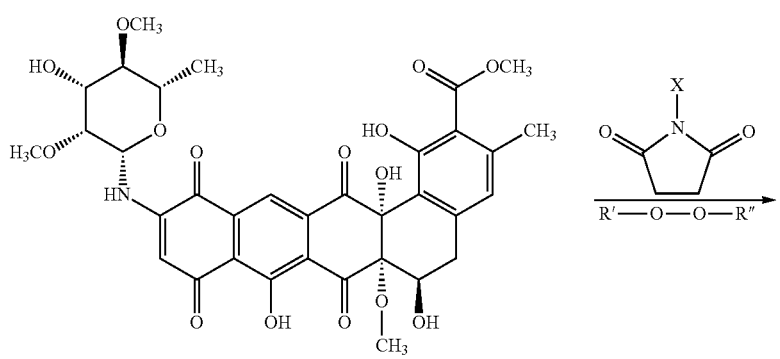

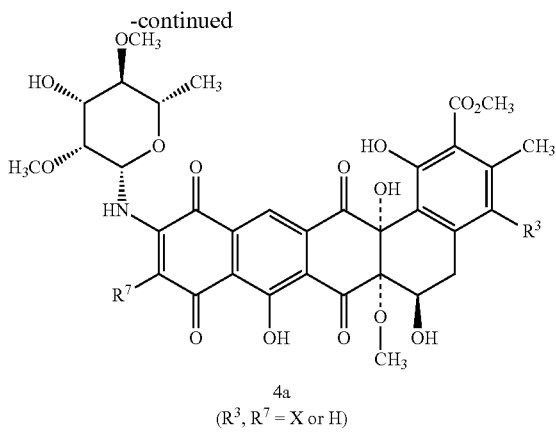

4a
(R³, R⁷ = X or H)

The compounds of formula 4a may be produced by mixing compound 1 in chloroform with N—X-succinimide (e.g. N-chlorosuccinimide), followed by R'—O—O—R" (e.g., benzoyl peroxide). The reaction mixture is heated (e.g. 75° C.). The N—X-succinimide may then be re-charged and reaction mixture heated again. After cooling to room temperature, the reaction mixture is diluted with chloroform and washed with saturated sodium bicarbonate. The aqueous layer may be further extracted with chloroform. The combined organics are dried ($Na_2SO_4$), filtered, and concentrated. The crude material is purified by routine chromatography such as preparative TLC or preparative HPLC or normal phase chromatography to produce compounds of formula 4a.

Examples of compounds produced in accordance with Scheme 4 are shown in Table 3, below:

TABLE 3

| Example # | R⁷ | R³ |
|---|---|---|
| 38 | H | Br |
| 39 | Br | Br |
| 40 | Cl | H |
| 40 | Cl | Cl |

Scheme 5

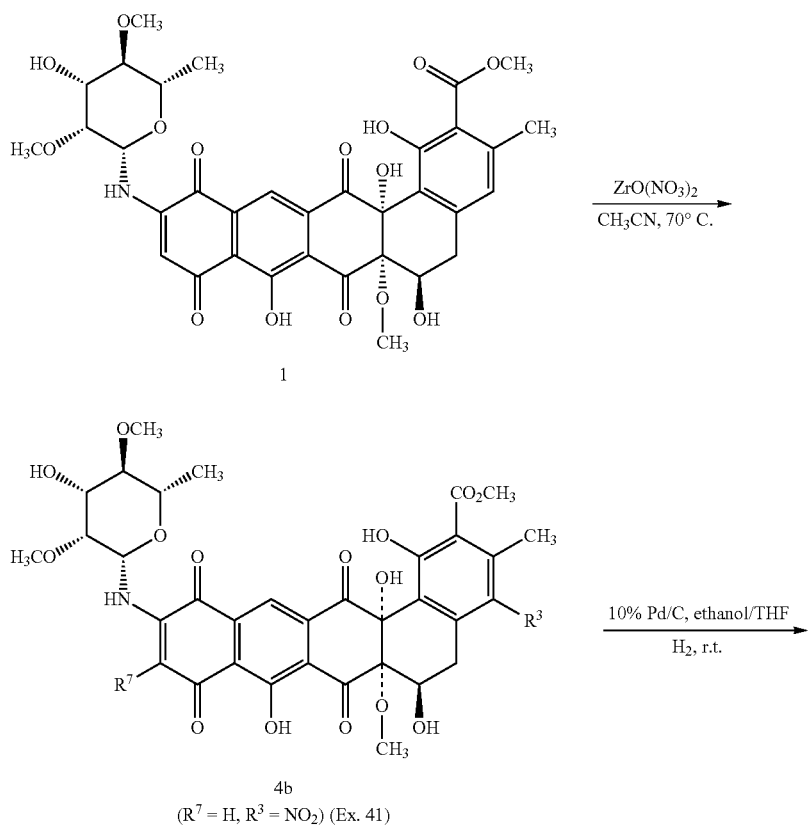

4b
(R⁷ = H, R³ = NO₂) (Ex. 41)

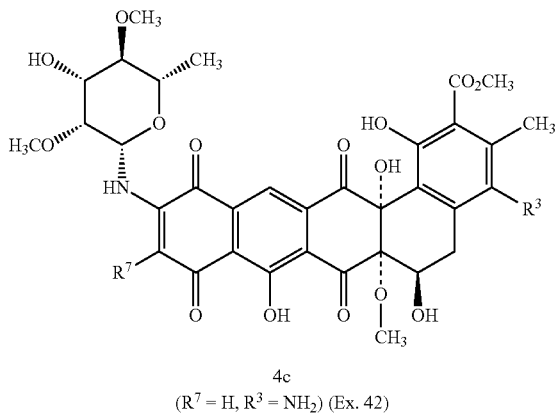

4c
(R⁷ = H, R³ = NH₂) (Ex. 42)

The compound of formula 4b may be produced from a mixture of compound 1 and zirconyl(IV) nitrate hydrate in an appropriate solvent (e.g., acetonitrile). The reaction mixture is heated (e.g. to 70° C.) and, after cooling to room temperature, the reaction mixture is filtered and the filtrate concentrated under reduced pressure. The crude material may be purified by routine chromatography such as preparative TLC or preparative HPLC or normal phase chromatography 4b.

Palladium on carbon (e.g. 10% Pd/C) may be added to a solution of 4b in ethanol and THF and the reaction mixture shaked under a hydrogen atmosphere at 45 psi at ambient temperature. The reaction mixture may be filtered through diatomaceous earth and the filtrate concentrated under reduced pressure. The crude material may be purified by routine chromatography such as preparative TLC or preparative HPLC or normal phase chromatography to produce compound 4c.

Scheme 6

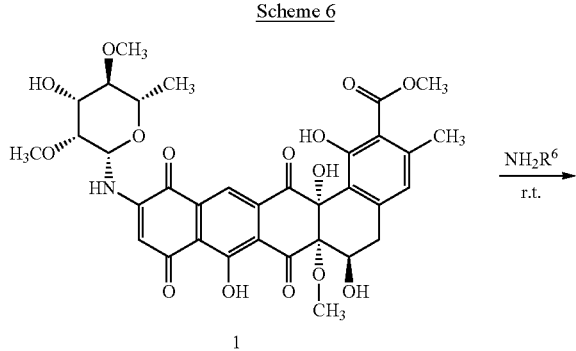

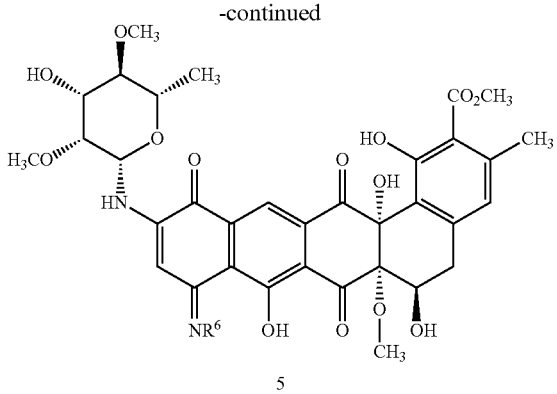

5

To produce compounds 5, $NH_2R^6$ may be added to a solution of compound 1 in alcoholic solvent (e.g. methanol and/or pyridine) at room temperature, and the mixture stirred under inert atmosphere. The reaction mixture may be quenched with a saturated solution of ammonium chloride and extracted with chloroform. The extract may be washed (e.g., with brine or 1N HCl and brine or water), dried, filtered, and concentrated. The residue may be purified by routine chromatography such as preparative TLC or preparative HPLC or normal phase chromatography to produce the compounds of formula 5.

Examples of compounds produced in accordance with Scheme 6 are shown in Table 4, below:

TABLE 4

| Example # | $R^6$ |
|---|---|
| 43 | H |
| 45 | OH |
| 44 | $CH_3$ |
| 48 | $(CH_2)_3OH$ |
| 46 | $(CH_2)_2OCH_3$ |
| 47 | $(CH_2)_3OCH_3$ |

Scheme 7

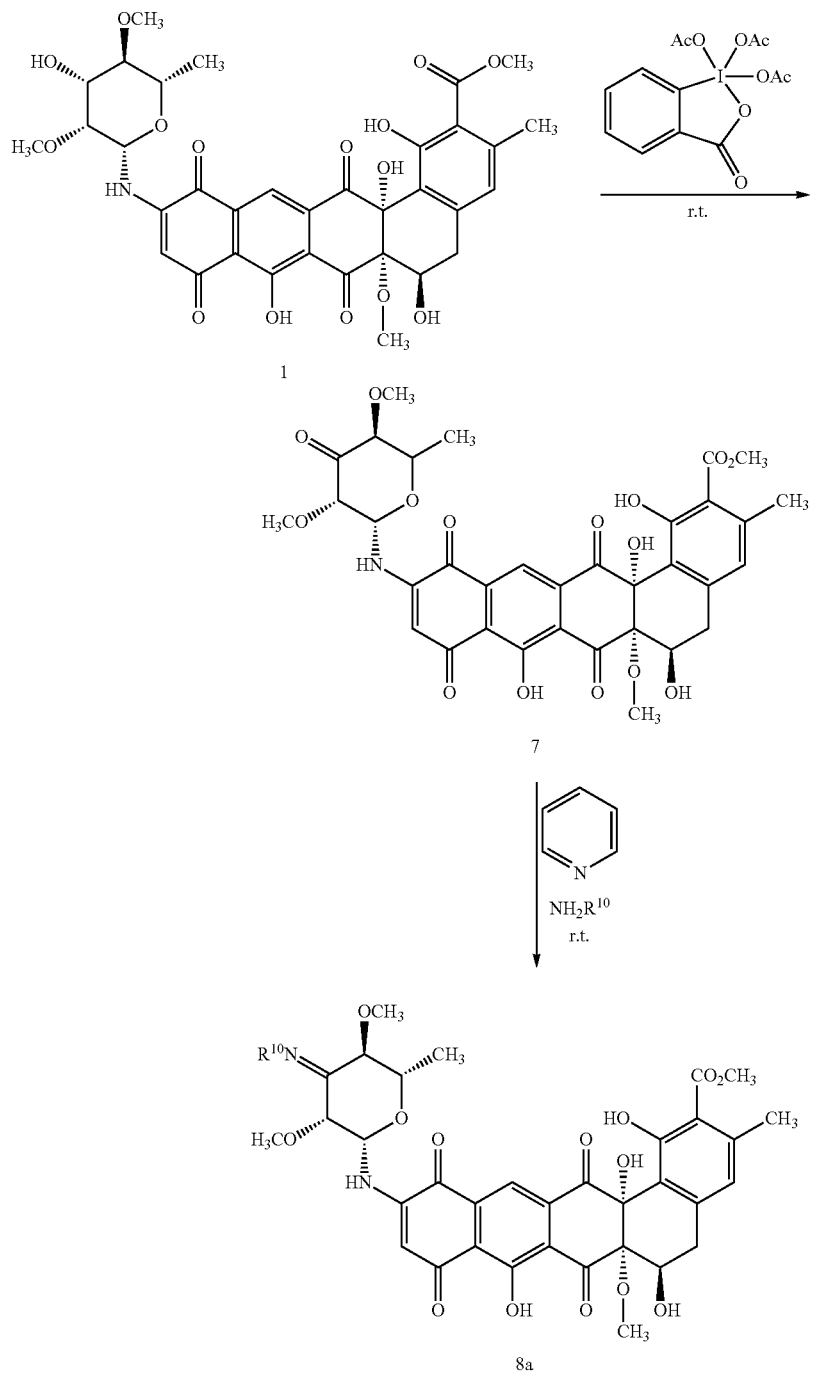

The compounds of formula 7 may be produced from a mixture of compound I in methylene chloride and Dess-Martin periodinane at room temperature, stirred under nitrogen atmosphere. The reaction mixture may be quenched with a saturated solution of sodium bicarbonate and extracted with ethyl acetate. The combined extracts may be washed with brine, dried, filtered, and concentrated to afford a ketone (compound 7). $NH_2R^{10}$ and pyridine is added to a solution of the compound 7 in methanol at room temperature. The mixture is stirred under nitrogen and the reaction mixture quenched with 1N HCl and extracted with ethyl acetate. The combined extracts may be washed with brine, dried, filtered, and concentrated. The residue may be purified by routine chromatography such as preparative TLC or preparative HPLC or normal phase chromatography to produce compounds of formula 8a.

Examples of compounds produced in accordance with Scheme 7 are shown in Table 5, below:

TABLE 5
| Example # | $R^{10}$ | $R^4$ |
|---|---|---|
| 49 | OH (isomer A) | OH |
| 49 | OH (isomer B) | OH |
| 50 | $OCH_3$ | OH |
TABLE 5-continued
| Example # | $R^{10}$ | $R^4$ |
|---|---|---|
| 51 | $OCH_2CO_2H$ | OH |
| 52 | $O(CH_2)_2NH_2$ | OH |
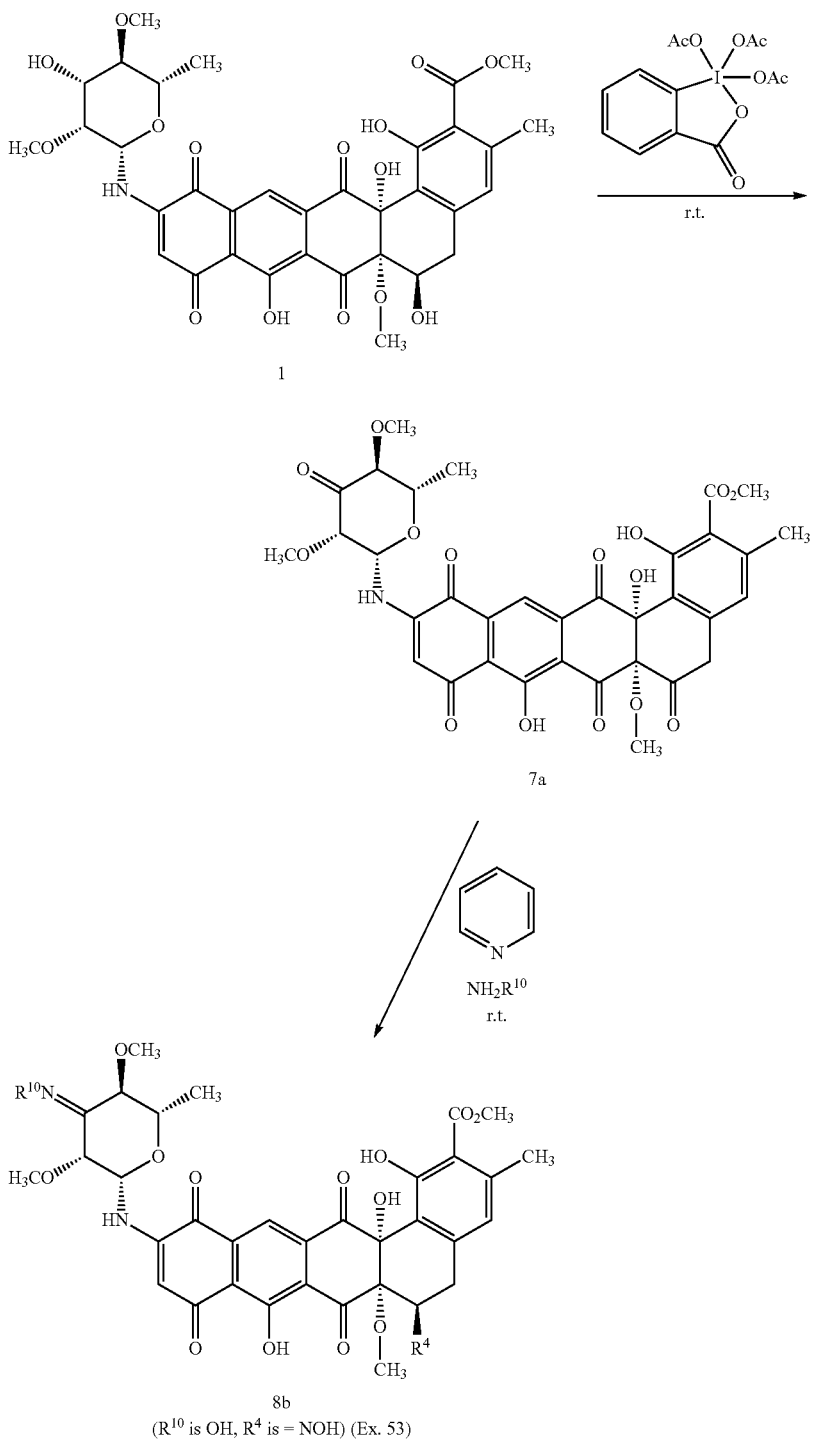

In Scheme 8, a diketone (compound 7a) is produced following the procedure of Scheme 7. $NH_2R^{10}$ and pyridine is added to a solution of compound 7a in methanol at room temperature. The mixture is stirred under nitrogen and the reaction mixture quenched with 1N HCl and extracted with ethyl acetate. The combined extracts may be washed with brine, dried, filtered, and concentrated. The residue may be purified by preparative TLC to produce compound 8a.

Scheme 9

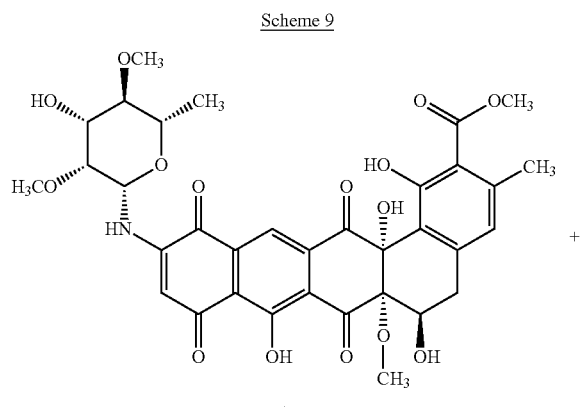

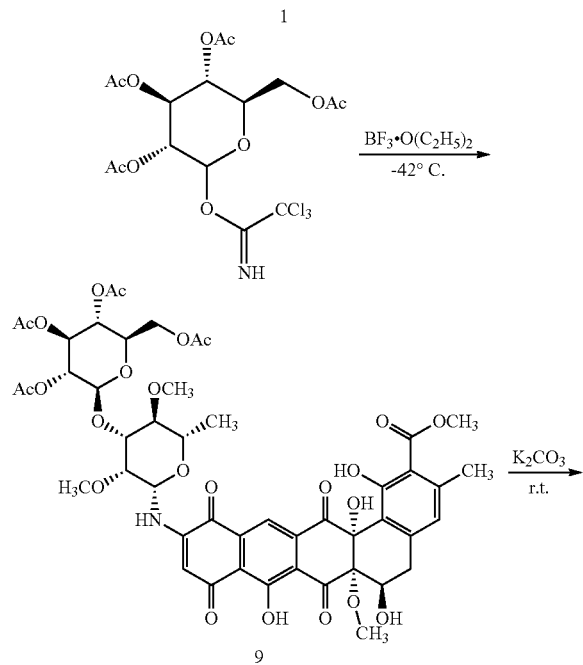

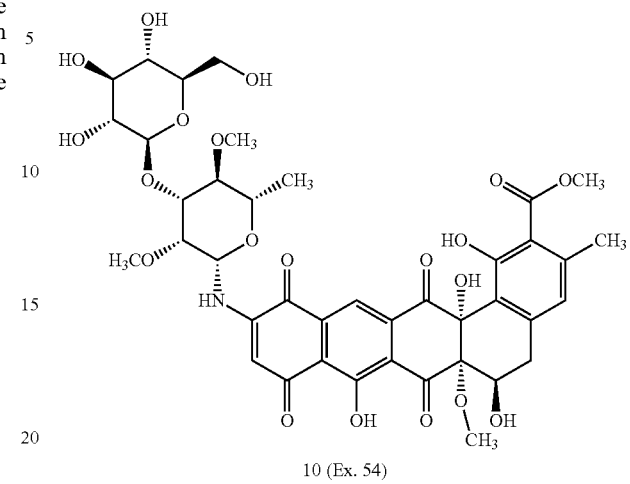

10 (Ex. 54)

In Scheme 9, a mixture of compound 1, (2R,3R,4S,5R)-2-(acetoxymethyl)-6-(2,2,2-trichloro-1-iminoethoxy)-tetrahydro-2H-pyran-3,4,5-triyl triacetate, and 4 Å molecular sieves in dichloromethane is stirred at room temperature under nitrogen. Then borontrifluoride diethyl etherate is added at −40° C. Upon completion (TLC analysis), the reaction is quenched with sodium bicarbonate, filtered through diatomaceous earth, and concentrated. The crude product may be purified by routine chromatography such as preparative TLC or preparative HPLC or normal phase chromatography to produce compound 9. A mixture of compound 9 and potassium carbonate in methanol is stirred at room temperature under nitrogen. The reaction mixture is concentrated under reduced pressure and the crude product purified by routine chromatography such as preparative TLC or preparative HPLC or normal phase chromatography to produce compound 10.

Scheme 10

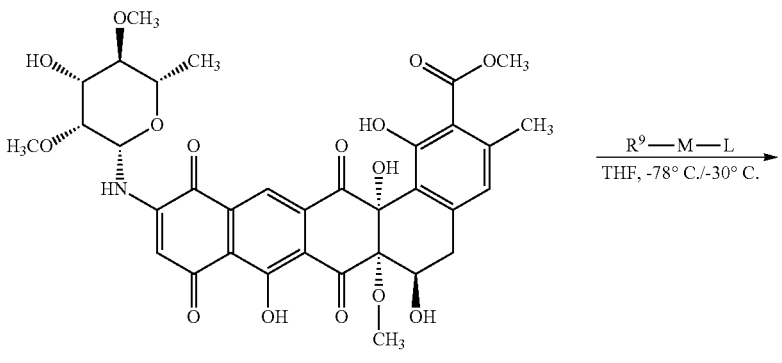

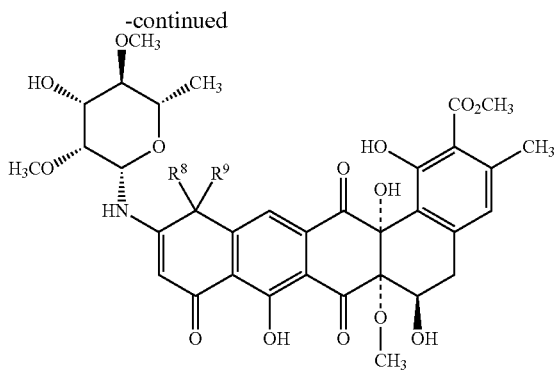

11 (R[8] = OH)
L = halogen

The compounds of formula 11 may be produced from a solution of compound I in THF to which is added a solution of R[9]-M-L (e.g. phenyl magnesium bromide) dropwise. The reaction mixture is stirred at low temperature (e.g. −78° C. to −30° C.), and then subsequently quenched with, for example, a saturated solution of ammonium chloride or water. The mixture is extracted and the combined organics are dried (Na$_2$SO$_4$), filtered, and concentrated. Suitable techniques for extraction include the use of chloroform or dichloromethane. The crude product may be purified by routine chromatography such as preparative TLC or preparative HPLC or normal phase chromatography to afford the compounds of formula 11.

Examples of compounds produced in accordance with Scheme 10 are shown in Table 6, below:

TABLE 6

| Example # | R[9] | R[8] |
|---|---|---|
| 55 | CH$_3$ (Diastereomer A) | OH |
| 55 | CH$_3$ (Diastereomer B) | OH |
| 56 | Ph (Diastereomer A) | OH |
| 56 | Ph (Diastereomer B) | OH |
| 57 | Et (Diastereomer A) | OH |
| 57 | Et (Diastereomer B) | OH |
| 58 | p-F—Ph (Diastereomer A) | OH |

Scheme 11

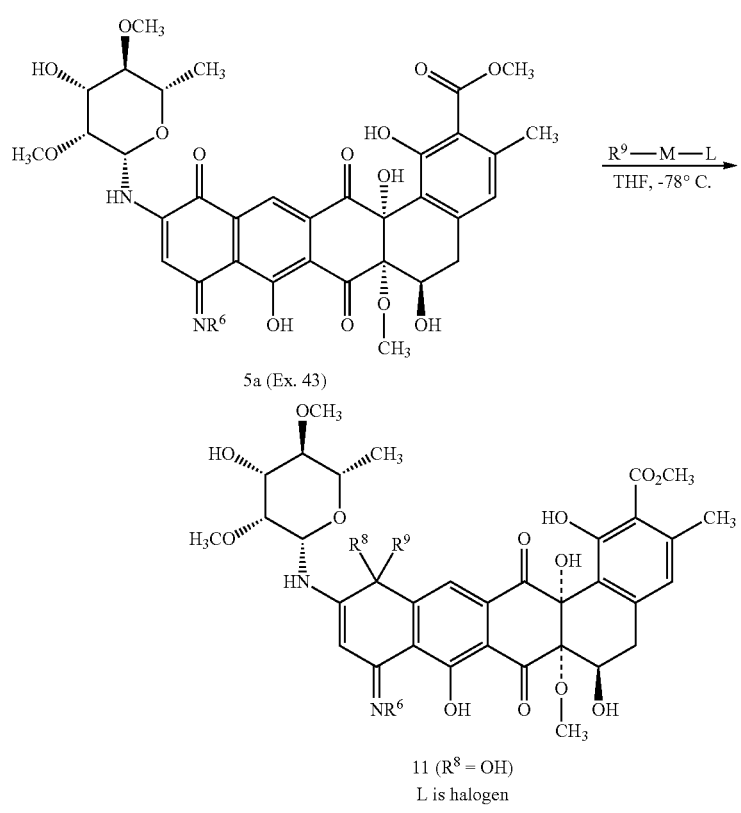

11 (R[8] = OH)
L is halogen

The compound of formula 11 where NR$^6$ is NH is produced from a mixture of compound 5a (Example 43) and R$^9$-M-L (e.g. 3-ethoxy-3-oxopropylzinc bromide) in THF. The reaction mixture is stirred at low temperature (−78° C.), and then subsequently quenched with, for example, a saturated solution of ammonium chloride. The mixture is extracted (e.g., with chloroform), and the combined organics are dried (Na$_2$SO$_4$), filtered, and concentrated. The crude product may be purified by routine chromatography such as preparative TLC or preparative HPLC or normal phase chromatography to produce compound II where NR$^6$ is NH.

Examples of compounds produced in accordance with Scheme 11 are shown in Table 7, below:

TABLE 7

| Example # | R$^9$ | R$^8$ |
|---|---|---|
| 59 | ～～～CH$_2$CH$_2$C(O)OCH$_2$CH$_3$ | OH |

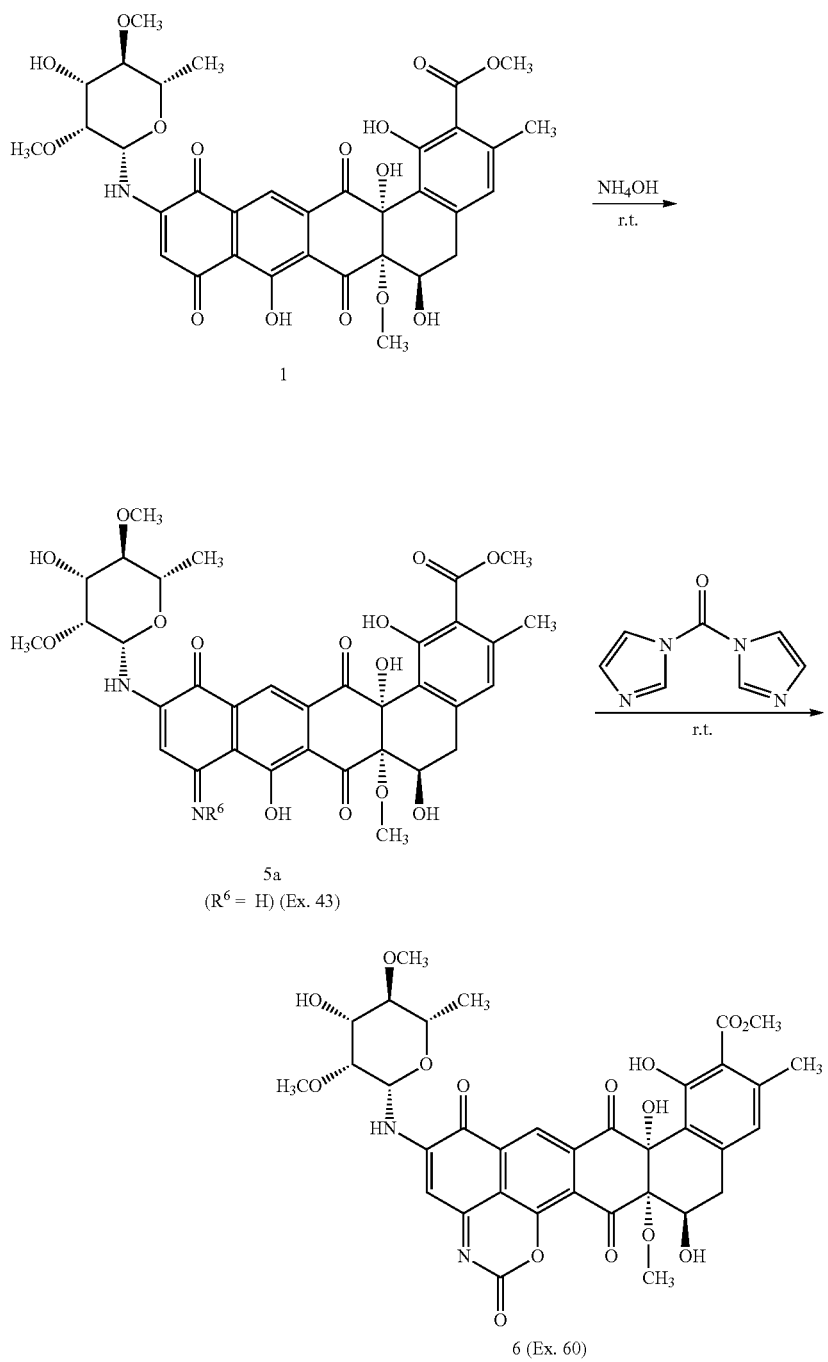

Scheme 12

The compound of formula 5a may be produced from a mixture of compound I and NH$_4$OH (0.1 mL) at room temperature, stirred under nitrogen. The NH$_4$OH may be refilled and the mixture stirred again. The reaction mixture is quenched with a saturated solution of ammonium chloride and extracted with chloroform. The combined extracts may be washed with brine, dried, filtered, and concentrated. The residue may be purified by preparative TLC to produce compound 5a. A coupling agent (e.g., carbonyldiimidazole) is added to a solution of compound 5a in THF at room temperature, and the mixture stirred under nitrogen. The reaction mixture is quenched with a saturated solution of ammonium chloride and extracted. The combined extracts are washed with brine, dried, filtered, and concentrated. The residue may be purified by preparative TLC to afford compound 6.

Compounds of formula (I) may be obtained in enantiomerically enriched (R) and (S) form by crystallization with chiral salts as well known to one skilled in the art, or alternatively, may be isolated through chiral HPLC employing commercially available chiral columns.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallization techniques, or they are separately prepared from the appropriate isomers of their intermediates.

The present invention provides compositions containing the compounds described herein, including, in particular, pharmaceutical compositions comprising therapeutically effective amounts of the compounds and pharmaceutically acceptable carriers and cosmetic compositions comprising the compounds of the present invention.

In addition, the compounds or compositions of the present invention can be used as a food or beverage additive for human or animal consumption It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining one or more active ingredients useful in treating the infection. A kit may provide (alone or in combination with a pharmaceutically acceptable diluent or carrier) the compounds of formula I and an additional active ingredient (alone or in combination with diluent or carrier), as described above.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The formulations of compounds of formula I include those suitable for oral, parenteral (including subcutaneous, intradermal, intramuscular, intraperitoneal, intravenous, and intraarticular), rectal, colonic, and topical (including dermal, buccal, nasal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques. "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.001 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The amount of active ingredient that may be combined with the carrier materials to produce a single dosage form will vary depending upon the host treated and the particular mode of administration. For example, a formulation intended for the oral administration of humans may vary from about 5 to about 95% of the total composition.

A dosage unit (e.g. an oral dosage unit) can include from, for example, 0.01 to 0.1 mg, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 0.01 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

For additional information about pharmaceutical compositions and their formulation, see, for example, Remington, *The Science and Practice of Pharmacy,* 20$^{th}$ Edition (2000), which is hereby incorporated by reference in its entirety.

The compounds of formula I can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The compounds of formula I can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. PCT Publication No. WO 97/11682, which is hereby incorporated by reference in its entirety) via a liposomal formulation (see, e.g., European Patent EP 736299 and PCT Publication Nos. WO 99/59550 and WO 97/13500, which are hereby incorporated by reference in their entirety), via formulations described in PCT Publication No. WO 03/094886, which is hereby incorporated by reference in its entirety, or in some other form. The compounds of formula I can also be administered transdermally (i.e. via reservoir-type or matrix-type patches, microneedles, thermal poration, hypodermic needles, iontophoresis, electro-poration, ultrasound or other forms of sonophoresis, jet injection, or a combination of any of the preceding methods (Prausnitz et al., *Nature Reviews Drug Discovery* 3:115 (2004), which is hereby incorporated by reference in its entirety)). The compounds can be administered locally, for example, at the site of injury to an injured blood vessel. The compounds can be coated on a stent.

The compounds can be administered using high-velocity transdermal particle injection techniques using the hydrogel particle formulation described in U.S. Patent Publication No. 20020061336, which is hereby incorporated by reference in its entirety. Additional particle formulations are described in PCT Publication Nos. WO 00/45792, WO 00/53160, and WO 02/19989, which are hereby incorporated by reference in their entirety. An example of a transdermal formulation containing plaster and the absorption promoter dimethylisosorbide can be found in PCT Publication No. WO 89/04179, which is hereby incorporated by reference in its entirety. PCT Publication No. WO 96/11705, which is hereby incorporated by reference in its entirety, provides formulations suitable for transdermal administration.

The compounds can be administered in the form a suppository or by other vaginal or rectal means. The compounds can be administered in a transmembrane formulation as described in PCT Publication No. WO 90/07923, which is hereby incorporated by reference in its entirety. The compounds can be administered non-invasively via the dehydrated particles described in U.S. Pat. No. 6,485,706, which is hereby incorporated by reference in its entirety. The compound can be administered in an enteric-coated drug formulation as described in PCT Publication No. WO 02/49621, which is hereby incorporated by reference in its entirety. The compounds can be administered intranasaly using the formulation described in U.S. Pat. No. 5,179,079, which is hereby incorporated by reference in its entirety. Formulations suitable for parenteral injection are described in PCT Publication No. WO 00/62759, which is hereby incorporated by reference in its entirety. The compounds can be administered using the casein formulation described in U.S. Patent Publication No. 20030206939 and PCT Publication No. WO 00/06108, which are hereby incorporated by reference in their entirety. The compounds can be administered using the particulate formulations described in U.S. Patent Application Publication No. 20020034536, which is hereby incorporated by reference in its entirety.

The compounds, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion.

Pulmonary formulations may also include surfactants which include but are not limited to bile salts and those described in U.S. Pat. No. 6,524,557 and references therein, which is hereby incorporated by reference in its entirety. The surfactants described in U.S. Pat. No. 6,524,557, which is hereby incorporated by reference in its entirety, e.g., a $C_8$-$C_{16}$ fatty acid salt, a bile salt, a phospholipid, or alkyl saccharide are advantageous in that some of them also reportedly enhance absorption of the compound in the formulation.

Also suitable in the invention are dry powder formulations comprising a therapeutically effective amount of active compound blended with an appropriate carrier and adapted for use in connection with a dry-powder inhaler. Absorption enhancers that can be added to dry powder formulations of the present invention include those described in U.S. Pat. No. 6,632,456, which is hereby incorporated by reference in its entirety. PCT Publication No. WO 02/080884, which is hereby incorporated by reference in its entirety, describes new methods for the surface modification of powders. Aerosol formulations may include U.S. Pat. No. 5,230,884, U.S. Pat. No. 5,292,499, PCT Publication No. WO 017/8694, PCT Publication No. WO 01/78696, U.S. Patent Application Publication No. 2003019437, U.S. Patent Application Publication No. 20030165436, and PCT Publication No. WO 96/40089 (which includes vegetable oil), which are hereby incorporated by reference in their entirety. Sustained release formulations suitable for inhalation are described in U.S. Patent Application Publication Nos. 20010036481A1, 20030232019A1, and 20040018243A1 as well as in PCT Publication Nos. WO 01/13891, WO 02/067902, WO 03/072080, and WO 03/079885, which are hereby incorporated by reference in their entirety.

Pulmonary formulations containing microparticles are described in PCT Publication No. WO 03/015750, U.S. Patent Application Publication No. 20030008013, and PCT Publication No. WO 00/00176, which are hereby incorporated by reference in their entirety. Pulmonary formulations containing stable glassy state powder are described in U.S. Patent Application Publication No. 20020141945 and U.S. Pat. No. 6,309,671, which are hereby incorporated by reference in their entirety. Other aerosol formulations are described in EP 1338272A1, PCT Publication No. WO 90/09781, U.S. Pat. No. 5,348,730, U.S. Pat. No. 6,436,367, PCT Publication No. WO 91/04011, and U.S. Pat. No. 6,294,153, which are hereby incorporated by reference in their entirety, and U.S. Pat. No. 6,290,987, which is hereby incorporated by reference in its entirety, describes a liposomal based formulation that can be administered via aerosol or other means.

Powder formulations for inhalation are described in U.S. Patent Application Publication No. 20030053960 and PCT Publication No. WO 01/60341, which are hereby incorporated by reference in their entirety. The compounds can be administered intranasally as described in U.S. Patent Application Publication No. 20010038824, which is hereby incorporated by reference in its entirety.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy, which are hereby incorporated by reference in their entirety.

Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington, which are hereby incorporated by reference in their entirety.

Compounds of formula I can be incorporated into a liposome to improve half-life. Compounds of formula I can also be conjugated to polyethylene glycol (PEG) chains. Methods for pegylation and additional formulations containing PEG-conjugates (i.e. PEG-based hydrogels, PEG modified liposomes) can be found in Harris et al., *Nature Reviews Drug Discovery*, 2:214-221 (2003) and the references therein, which are hereby incorporated by reference in their entirety. Compounds of formula I can also be administered via a nanocochleate or cochleate delivery vehicle (BioDelivery Sciences International, Raleigh, N.C.). Compounds of formula I can also be delivered using nanoemulsion formulations.

EXAMPLES

The Examples set forth below are for illustrative purposes only and are not intended to limit, in any way, the scope of the present invention.

Example 1

Analytical Methods and Materials

Unless otherwise noted, reagents and solvents were used as received from commercial suppliers. Proton nuclear magnetic resonance (NMR) spectra were obtained on Bruker spectrometers at 300, 400, or 500 MHz. Spectra are given in ppm (δ) and coupling constants, J, are reported in Hertz. Tetramethylsilane (TMS) was used as an internal standard. Mass spectra were collected using either a Finnigan LCQ Duo LC-MS ion trap electrospray ionization (ESI) or a mass Varian 1200L single quadrapole mass spectrometer (ESI). High performance liquid chromatograph (HPLC) analyses were obtained using a Luna C18(2) column (250×4.6 mm, Phenomenex, Torrance, Calif.) with UV detection at 223 nm using a standard solvent gradient program (Method A or Method B).

Method A:

| Time (min) | Flow (mL/min) | % A | % B |
|---|---|---|---|
| 0 | 1.0 | 100 | 0 |
| 25 | 1.0 | 0 | 100 |
| 30 | 1.0 | 0 | 100 |
| 35 | 1.0 | 100 | 0 |

A = Water with 0.05% Trifluoroacetic Acid
B = Acetonitrile with 0.05% Trifluoroacetic Acid Method B:

| Time (min) | Flow (mL/min) | % A | % B |
|---|---|---|---|
| 0 | 1.0 | 90 | 10 |
| 15 | 1.0 | 10 | 90 |
| 25 | 1.0 | 10 | 90 |
| 30 | 1.0 | 90 | 10 |

A = Water with 0.05% Trifluoroacetic Acid
B = Acetonitrile with 0.05% Trifluoroacetic Acid Example 2

Preparation of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate is a natural product derived from the fermentation of an *actinomyces* strain, *Streptomyces* sp. AMRI-7957, deposited in an international depositary authority (IDA) collection according to the Budapest Treaty. The strain AMRI-7957 was mailed on Jun. 22, 2010 to the ATCC Patent Collection by Federal Express Priority Overnight Mail with Tracking Number 793661147245. The strain AMRI-7957 was received by ATCC on Jun. 23, 2010 and assigned ATCC Accession No. PTA-11098.

a) Production of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate via Fermentation Typical methods for production of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate via fermentation of *Streptomyces* sp. AMRI-7957 are exemplified as follows:

The inoculum for a 500 L pilot scale production fermentation was prepared in three stages. A frozen spore suspension of the producing organism was initially cultured in a 250 ml shaking flask containing 50 ml of an aqueous medium consisting of (per liter): 11.0 g glucose, 20.0 g soluble starch, 5.0 g NZ amine, 5.0 g yeast extract and 1.0 g of $CaCO_3$. The culture was grown for 45-50 hours at 28° C. and a shaking speed of 250 rpm. This stage I culture was then transferred to a secondary seed culture in a 2.8 L flask containing 600 ml of the same medium and grown for another 45-50 hours under the same conditions. The stage 11 flask culture was then transferred to a final 20 L stage III seed fermentor containing 15 liters of the same growth medium. Operating parameters for the stage III seed fermentor were as follows: temperature (28° C.), agitation (300-350 rpm), airflow (6 liters/min) and back-pressure (10 psig). After approximately 45-50 hours the stage III seed culture was used to inoculate a 650 liter fermentor containing 450 liters of a production medium consisting of (per liter); 10.5 g alpha-lactose monohydrate, 30.0 g starch, 10.0 g Nutrisoy 7B, 6.0 g $CaSO_4.2H_2O$, 5.0 g $CaCO_3$ and 0.2 ml of antifoam (MAZU). The operating conditions for the production fermentor were as follow: temperature (28° C.), agitation (80 rpm), airflow (50 L/min) and back-pressure (10 psig). Sterile glucose was fed during the fermentation to maintain a glucose concentration of 2-10 g/L. In addition, 1-2 liters of sterile soybean oil was feed over the first 48 hours of the fermentation. The target product, (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate, accumulated over the course of 10-12 days, achieving titers of 250-275 mg/L.

b) Recovery and Purification of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate from Fermentation The product (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate was detected both in solution (20%) and associated with the biomass (80%). For maximum recovery of the product, these two fractions were processed separately in the primary recovery steps, as exemplified below. The fermentation broth was first cooled to 20° C. and then passed through a continuous centrifuge resulting in about 50 Kg of cell solids and 400 liters of supernatant.

c) Recovery of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate from Fermentation Supernatant 5 Kg (wet weight) of hydrated HP20 adsorbent resin was added to the 400 L of supernatant and agitated for 12-16 hours during which time the product was almost entirely bound to the resin. The resin was recovered by sieving (50 mesh). The resin was sequentially washed in a column format with 8 column volumes of water, 4 column volumes of 15% acetonitrile and 4 column volumes of 20% acetonitrile with only minimal product losses in the washes. The product was then eluted in approximately 1-2 column volumes of either 100% acetone or 100% acetonitrile. Elution fractions containing the bulk of the product were pooled and evaporate under vacuum to a thick reddish brown slurry. This slurry was then dissolved in a minimum volume (approximately 3-5 liters) of ethyl acetate. The ethyl acetate extract was washed with an equal volume of water followed by a equal volume of saturated solution of NaCl. The ethyl acetate extract was further dewatered by passing over a bed of anhydrous sodium sulfate. Substantially pure (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate was then crystallized out of the ethyl acetate by chilling to 4° C., reducing under vacuum and/or the addition of incremental volumes of hexane and then recovered by filtration.

d) Recovery of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate from Fermentation Biomass To the fermentation cell solids recovered as described in step b), eight liters of acetonitrile was first added to 50 kg of biomass and allowed to contact for 30 minutes. 25-30 liters of ethyl acetate was then added to the biomass/acetonitrile and agitated for 12-16 hours. The liquid containing ethyl acetate, acetonitrile and some water was siphoned away from the biomass and concentrated under vacuum to about $\frac{1}{3}^{rd}$ the starting volume. The aqueous layer was removed in a separatory funnel. The organic layer was washed twice with equal volumes of water to pull away any acetonitrile and then washed a $3^{rd}$ time with saturated solution of NaCl. The washed ethyl acetate extract was then further dewatered with anhydrous sodium sulfate and the product is crystallized out and recovery in a manner identical to the ethyl acetate extract from the HP20 resin as described in step c). Additional material may be recovered with repeated extractions of the biomass.

e) Genotypic and Phenotypic Analysis

Strain AMRI-7957, the producer of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate, was characterized genotypically to determine its taxonomic position. Using a 1088 bp fragment of the 16S rDNA gene, AMRI-7957 was compared to the NCBI database via a BLAST search. The results of this search placed AMRI-7957 in the genus *Streptomyces*, with the closest match being *Streptomyces scabrisporus*. A representative of *Streptomyces scabrisporus*, NRRL B-24202, was obtained from the USDA Agricultural Research Service Culture Collection.

Because the structure of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate is consistent with that of SF2446A1 (Japanese Patent Nos. JP 01096189 A and JP 63154695 A and Takeda et al., J. Antibiotics, 41(4): 417-424 (1988), which are hereby incorporated by reference in their entirety) and that of mycorhodin, phenotypic tests were used to compare AMRI-7957, with SF2446 and ATCC 12644, the producers of SF2446A1 and mycorhodin, respectively. *Streptomyces* scabrisporus NRRL B-24202 was also included in the phenotypic comparison because of its close relationship to AMRI-7957. Strain SF2446 was not available, so the phenotypic tests carried out as described herein were performed on the other three strains and the results compared.

Morphological observations of strains AMRI-7957, ATCC 12644, and NRRL B-24202 were made on cultures grown at 28° C. for 21 days on inorganic salts-starch agar (ISP medium 4), using a 40× long-working distance objective. Vegetative mycelium was well-developed and branched, with no fragmentation for all cultures. Strain AMRI-7957 produced aerial mycelium with long (>50 spores), branching, flexuous spore chains, usually terminating in loose spirals. While the morphological description of SF2446 and the observed morphology of ATCC 12644 were similar to AMRI-7957, the morphology of NRRL B-24202 was distinctly different, with long, flexous, branching spore chains arising directly from the substrate, with no observed hooks or coils. The production of a brown (melanoid) pigment on tyrosine agar, oatmeal agar, yeast-malt extract agar, and Bennett's agar is one feature that clearly distinguishes strain AMRI-7957 from SF2446 and NRRL B-24202, neither of which produced any pigments. ATCC 12644 produced melanoid pigments on the same four media as AMRI-7957 and three additional characterization media. Other cultural characteristics also varied from medium to medium for the four strains, including level of growth and aerial mycelium color and quantity. Additional tests also gave variable results between the four strains. Notably, AMRI-7957 and the other three strains differ in both the growth temperature range (32° C. maximum vs. ≥35° C. maximum) and NaCl tolerance (AMRI-7957 is more sensitive to NaCl than any of the other strains, with growth totally inhibited in the presence of 4% NaCl). Although the carbon utilization profile for AMRI-7957 is very similar to that of SF2446, with only two carbon sources (glucose and glycerol) utilized well, the other two strains had very different profiles, with NRRL-B-24202 utilizing seven of the eleven carbon sources and ATCC 12644 utilizing all eleven carbon sources tested.

Example 3

General Procedure for Alkylation of 1-Hydroxyl Group in (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

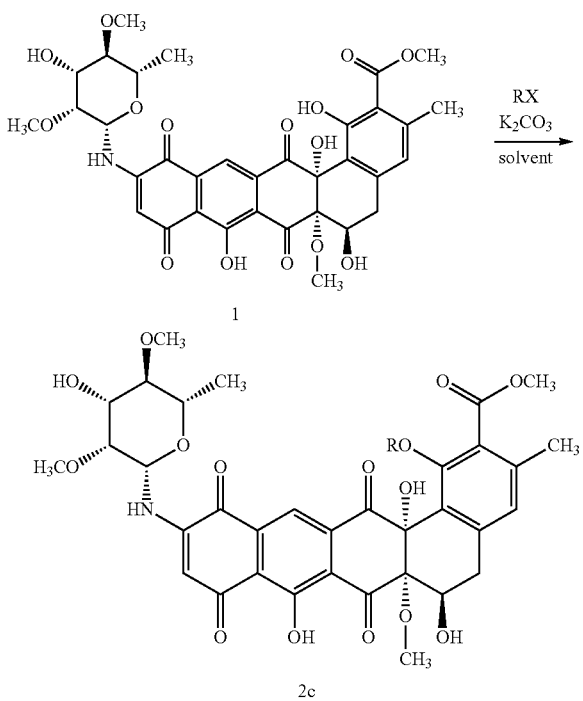

Method A: A mixture of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol), potassium carbonate (21 mg, 0.15 mmol) and RX (0.15 mmol) in acetone (1 mL) was heated under reflux until completion. The completion was reached as shown by LC-MS or TLC analysis. The reaction mixture was cooled to room temperature and the product 2c was purified by preparative TLC. In some cases re-purification by semi-preparative HPLC was necessary.

Method B: A mixture of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.05 mmol), potassium carbonate (21 mg, 0.15 mmol) and RX (0.15 mmol) in DMF (1 mL) was stirred at room temperature until completion. The completion was reached as shown by LC-MS or TLC analysis. The reaction mixture was quenched with water (5 mL) and extracted with ethyl acetate (3×). The combined extracts were dried over sodium sulfate and concentrated. The product 2c was then purified by preparative TLC. In some cases re-purification by semi-preparative HPLC was necessary.

Example 4

Preparation of (6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-1,6a-dimethoxy-3-methyl-7,9,12,14-tetraoxo-5,6,6a,7,9,12,14,14a-octahydrobenzo[a]tetracene-2-carboxylate

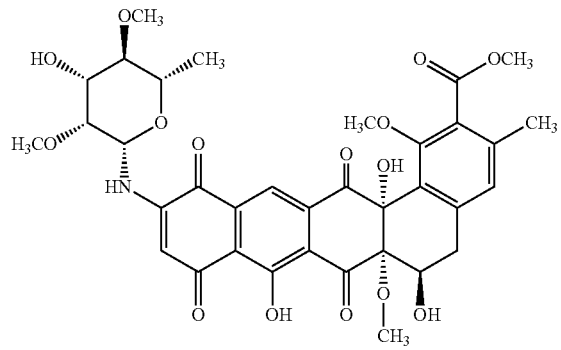 [SMILES: COC(=O)c1c(C)cc2c(c1OC)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O)[C@H]1OC)C4=O]

Following General Procedure: Method A using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (25 mg, 0.035 mmol), potassium carbonate (15 mg, 0.11 mmol) and iodomethane (7 μL, 0.11 mmol), the product was purified by preparative TLC (silica gel, 95:5 dichloromethane/methanol) to afford (6R,6aS,14aR)-methyl 6,8,14a-trihydroxy-11-((2S,3R,4R,5R,6S)-4-hydroxy-3,5-dimethoxy-6-methyltetrahydro-2H-pyran-2-ylamino)-1,6a-dimethoxy-3-methyl-7,9,12,14-tetraoxo-5,6,6a,7,9,12,14,14a-octahydrobenzo[a]tetracene-2-carboxylate (12 mg, 48%) as a brown solid: $^1$H NMR (500 MHz, CDCl$_3$) δ 14.15 (s, 1H), 8.11 (s, 1H), 6.84 (d, J=9.0 Hz, 1H), 6.81 (s, 1H), 5.88 (s, 1H), 5.04 (br s, 1H), 4.96 (dd, J=10.3, 6.6 Hz, 1H), 4.69 (d, J=8.9 Hz, 1H), 4.54 (d, J=10.6 Hz, 1H), 3.80 (s, 3H), 3.79 (s, 3H), 3.74-3.71 (m, 1H), 3.69 (dd, J=3.1, 1.2 Hz, 1H), 3.60 (s, 3H), 3.59 (s, 3H), 3.61-3.56 (m, 1H), 3.40 (s, 3H), 3.39-3.33 (m, 2H), 3.12 (t, J=9.2 Hz, 1H), 2.47 (d, J=4.6 Hz, 1H), 2.18 (s, 3H), 1.36 (d, J=6.2 Hz, 3H); MS (ESI+) m/z 712 (M+H); HPLC 95.9% (AUC), $t_R$ 12.66 min.

Example 5

Preparation of (6R,6aS,14aR)-Methyl 6,14a-dihydroxy-11-((3R,4R,5R,6S)-4-hydroxy-3,5-dimethoxy-6-methyltetrahydro-2H-pyran-2-ylamino)-1,6a,8-trimethoxy-3-methyl-7,9,12,14-tetraoxo-5,6,6a,7,9,12,14,14a-octahydrobenzo[a]tetracene-2-carboxylate

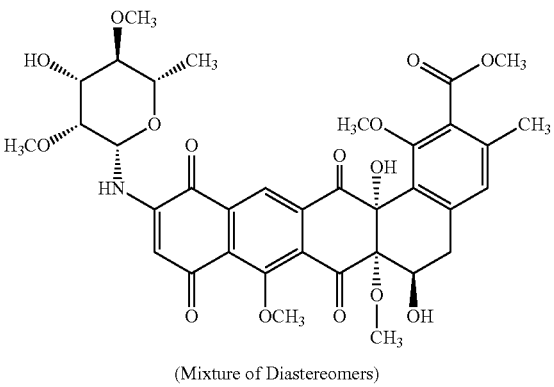 [SMILES: COC(=O)c1c(C)cc2c(c1OC)[C@]1(O)C(=O)c3cc4c(c(OC)c3C(=O)[C@]1(OC)[C@H](O)C2)C(=O)C=C(N[C@H]1O[C@@H](C)[C@H](OC)[C@@H](O)[C@H]1OC)C4=O]

(Mixture of Diastereomers)

Following General Procedure: Method A using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol), potassium carbonate (42 mg, 0.30 mmol) and iodomethane (14 μL, 0.15 mmol), the product was purified by preparative TLC (silica gel, 95:5 dichloromethane/methanol) followed by semi-preparative HPLC (45:55 acetonitrile/water with 0.05% TFA) to afford (6R,6aS,14aR)-methyl 6,14a-dihydroxy-11-((3R,4R,5R,6S)-4-hydroxy-3,5-dimethoxy-6-methyltetrahydro-2H-pyran-2-ylamino)-1,6a,8-trimethoxy-3-methyl-7,9,12,14-tetraoxo-5,6,6a,7,9,12,14,14a-octahydrobenzo[a]tetracene-2-carboxylate (8 mg, 23%) as an orange-yellow solid: $^1$H NMR (500 MHz, CDCl$_3$) δ 8.49 (s, 0.3H), 8.45 (s, 0.7H), 6.83 (s, 0.3H), 6.82 (s, 0.7H), 6.52 (d, J=9.1 Hz, 0.7H), 5.90 (d, J=6.0 Hz, 0.3H), 6.23 (s, 0.3H), 5.96 (s, 0.7H), 4.96 (d, J=6.4 Hz, 1H), 4.66 (d, J=8.3 Hz, 1H), 4.23 (br s, 1H), 3.96-3.91 (m, 0.7H), 3.85-3.83 (m, 0.3H), 3.85 (s, 0.9H), 3.84 (s, 2.1H), 3.82 (s, 0.9H), 3.81 (s, 2.1H), 3.79 (s, 3H), 3.74 (dd, J=9.4, 3.2 Hz, 1H), 3.70-3.69 (m, 1H), 3.64-3.63 (m, 1H), 3.61 (s, 2.1H), 3.60 (s, 2.1H), 3.56 (s, 0.9H), 3.55 (s, 0.9H), 3.38 (s, 2.1H), 3.37 (s, 0.9H), 3.40-3.33 (m, 3H), 3.14-3.10 (m, 1H), 2.20 (s, 0.9H), 2.19 (s, 2.1H), 1.35 (d, J=6.1 Hz, 2.1H), 1.28 (d, J=6.2 Hz, 0.9H); MS (ESI+) m/z 726 (M+H); HPLC 93.4% (AUC), $t_R$ 14.84, 15.04 min.

Example 6

Preparation of (6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-1-(2-methoxy-2-oxoethoxy)-3-methyl-7,9,12,14-tetraoxo-5,6,6a,7,9,12,14,14a-octahydrobenzo[a]tetracene-2-carboxylate

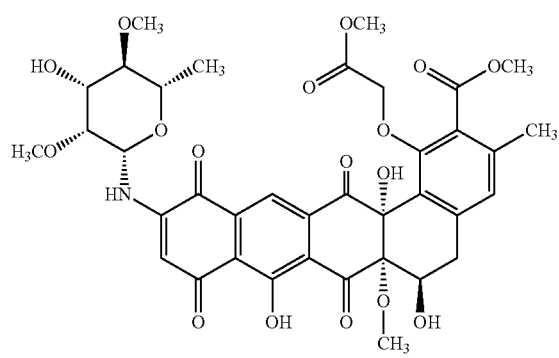 [SMILES: COC(=O)COc1c(C(=O)OC)c(C)cc2c1[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O)[C@H]1OC)C4=O]

Following General Procedure: Method A using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (50 mg, 0.072 mmol), potassium carbonate (30 mg, 0.22 mmol) and methyl bromoacetate (20 µL, 0.22 mmol), the product was purified by preparative TLC (silica gel, 95:5 dichloromethane/methanol) and semi-preparative HPLC (45:55 acetonitrile/water with 0.05% TFA) to afford (6R,6aS,14aR)-methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-1-(2-methoxy-2-oxoethoxy)-3-methyl-7,9,12,14-tetraoxo-5,6,6a,7,9,12,14,14a-octahydrobenzo[a]tetracene-2-carboxylate (10 mg, 20%) as a red solid: $^1$H NMR (500 MHz, CDCl$_3$) δ 14.19 (s, 1H), 8.27 (s, 1H), 6.89 (d, J=9.0 Hz, 1H), 6.86 (s, 1H), 5.88 (s, 1H), 4.96 (d, J=6.6 Hz, 1H), 4.69 (d, J=8.7 Hz, 1H), 4.54 (d, J=15.1 Hz, 1H), 4.43 (d, J=15.1 Hz, 1H), 3.91 (br s, 3H), 3.79 (s, 3H), 3.76-3.67 (m, 3H), 3.73 (s, 3H), 3.64-3.55 (m, 1H), 3.60 (s, 3H), 3.39 (s, 3H), 3.36-3.29 (m, 3H), 3.13 (t, J=9.2 Hz, 1H), 2.60 (br s, 1H), 2.19 (s, 3H), 1.36 (d, J=6.2 Hz, 3H); MS (ESI+) m/z 770 (M+H); HPLC 96.4% (AUC), $t_R$ 15.46 min.

Example 7

Preparation of (6R,6aS,14aR)-Methyl 1-(benzyloxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

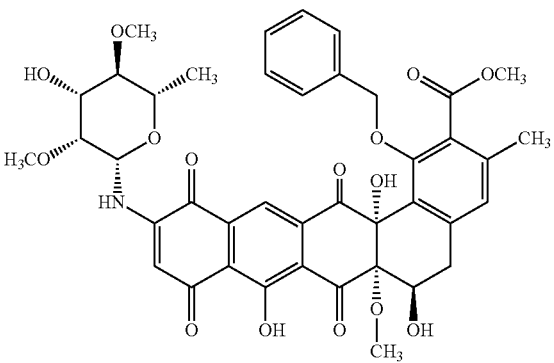 [SMILES: COC(=O)c1c(C)cc2c(c1OCc1ccccc1)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O)[C@H]1OC)C4=O]

Following General Procedure: Method A using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol), potassium carbonate (21 mg, 0.15 mmol) and benzyl bromide (18 µL, 0.15 mmol), the product was purified by preparative TLC (silica gel, 95:5 dichloromethane/methanol) to afford (6R,6aS,14aR)-methyl 1-(benzyloxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (18 mg, 45%) as a brown solid: $^1$H NMR (500 MHz, CDCl$_3$) δ 14.17 (s, 1H), 7.82 (s, 1H), 7.46-7.44 (m, 2H), 7.40-7.38 (m, 1H), 7.34-7.32 (m, 2H), 6.85 (s, 1H), 6.81 (d, J=8.6 Hz, 1H), 5.86 (s, 1H), 5.07 (br s, 1H), 4.98-4.94 (m, 1H), 4.93 (d, J=11.3 Hz, 1H), 4.82 (d, J=11.3 Hz, 1H), 4.68 (d, J=8.8 Hz, 1H), 4.54 (d, J=10.5 Hz, 1H), 3.82 (s, 3H), 3.74-3.72 (m, 2H), 3.65-3.62 (m, 1H), 3.60 (s, 3H), 3.54 (s, 3H), 3.51-3.38 (m, 1H), 3.39 (s, 3H), 3.36-3.32 (m, 1H), 3.13 (t, J=9.0 Hz, 1H), 2.48 (d, J=4.1 Hz, 1H), 2.19 (s, 3H), 1.36 (d, J=6.2 Hz, 3H); MS (ESI+) m/z 788 (M+H); HPLC 95.4% (AUC), $t_R$ 14.56 min.

85
Example 8

Preparation of (6R,6aS,14aR)-Methyl 1-(2-(benzyloxy)-2-oxoethoxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

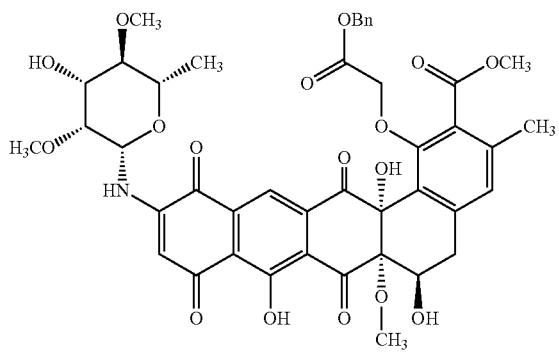 [SMILES: COC(=O)c1c(C)cc2c(c1OCC(=O)OCc1ccccc1)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O)[C@H]1OC)C4=O]

Following General Procedure: Method A using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol), potassium carbonate (21 mg, 0.15 mmol) and benzyl bromoacetate (24 μL, 0.15 mmol), the product was purified by preparative TLC (silica gel, 95:5 dichloromethane/methanol) to afford (6R,6aS,14aR)-methyl 1-(2-(benzyloxy)-2-oxoethoxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (22 mg, 51%) as a brown solid: $^1$H NMR (500 MHz, CDCl$_3$) δ 14.18 (s, 1H), 8.29 (s, 1H), 7.44-7.31 (m, 5H), 6.88 (d, J=8.7 Hz, 1H), 6.85 (s, 1H), 5.87 (s, 1H), 5.40 (d, J=12.2 Hz, 1H), 5.31 (d, J=12.2 Hz, 1H), 5.00 (s, 1H), 4.95 (dd, J=9.9, 7.3 Hz, 1H), 4.68 (d, J=8.7 Hz, 1H), 4.54 (d, J=15.2 Hz, 1H), 4.48 (br s, 1H), 4.45 (br s, 1H), 3.78 (s, 3H), 3.76-3.71 (m, 1H), 3.69 (d, J=1.6 Hz, 1H), 3.60-3.54 (m, 2H), 3.60 (s, 6H), 3.39 (s, 3H), 3.36-3.32 (m, 1H), 3.13 (t, J=9.2 Hz, 1H), 2.47 (d, J=4.5 Hz, 1H), 2.18 (s, 3H), 1.36 (d, J=6.2 Hz, 3H); MS (ESI+) m/z 846 (M+H); HPLC 94.4% (AUC), $t_R$ 18.76 min.

86
Example 9

Preparation of 2-((6R,6aS,14aR)-6,8,14a-Trihydroxy-11-((3R,4R,5R,6S)-4-hydroxy-3,5-dimethoxy-6-methyltetrahydro-2H-pyran-2-ylamino)-6a-methoxy-2-(methoxycarbonyl)-3-methyl-7,9,12,14-tetraoxo-5,6,6a,7,9,12,14,14a-octahydrobenzo[a]tetracen-1-yloxy)acetic acid

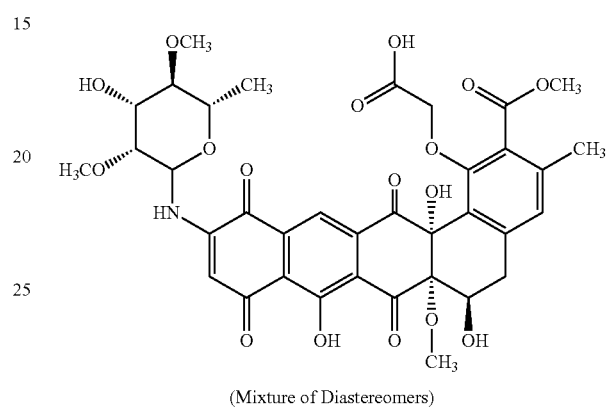

(Mixture of Diastereomers)

A mixture of (6R,6aS,14aR)-methyl 1-(2-(benzyloxy)-2-oxoethoxy)-6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (22 mg, 0.024 mmol) and 10% Pd/C (10 mg) in THF (1 mL) was stirred under hydrogen (1 atm) at room temperature for 1 h. The reaction mixture was filtered and concentrated. The residue was purified by semi-preparative HPLC (45:55 acetonitrile/water with 0.05% TFA) to afford 2-((6R,6aS,14aR)-6,8,14a-trihydroxy-11-((3R,4R,5R,6S)-4-hydroxy-3,5-dimethoxy-6-methyltetrahydro-2H-pyran-2-ylamino)-6a-methoxy-2-(methoxycarbonyl)-3-methyl-7,9,12,14-tetraoxo-5,6,6a,7,9,12,14,14a-octahydrobenzo[a]tetracen-1-yloxy)acetic acid (13 mg, 66%) as an orange solid and as a mixture of diastereomers: $^1$H NMR (500 MHz, acetone-d$_6$) δ 14.30 (br s, 1H), 8.21 (s, 0.5H), 8.17 (s, 0.5H), 7.19 (d, J=9.0 Hz, 0.5H), 7.08 (d, J=5.7 Hz, 0.5H), 6.99 (s, 0.5H), 6.91 (s, 0.5H), 6.17 (s, 0.5H), 6.00 (s, 0.5H), 5.30 (br s, 1H), 5.11 (d, J=4.8 Hz, 0.5H), 5.06 (d, J=4.8 Hz, 0.5H), 4.92-4.85 (m, 0.5H), 4.76-4.72 (m, 0.5H), 4.62 (br s, 0.5H), 4.60 (br s, 0.5H), 4.50-4.41 (m, 1H), 4.04 (d, J=5.1 Hz, 1H), 3.91-3.83 (m, 1H), 3.76 (s, 1.5H), 3.75 (s, 1.5H), 3.74 (br s, 3H), 3.54 (br s, 3H), 3.52 (s, 1.5H), 3.50 (s, 1.5H), 3.32-3.30 (m, 1H), 3.09-3.05 (m, 1H), 2.19 (s, 1.5H), 2.17 (s, 1.5H), 1.25 (d, J=6.2 Hz, 1.5H), 1.21 (d, J=6.3 Hz, 1.5H); MS (ESI+) m/z 756 (M+H); HPLC 98.5% (AUC), $t_R$ 11.48, 11.45 min.

Example 10

Preparation of (6R,6aS,14aR)-Methyl 1-(2-amino-2-oxoethoxy)-6,8,14a-trihydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

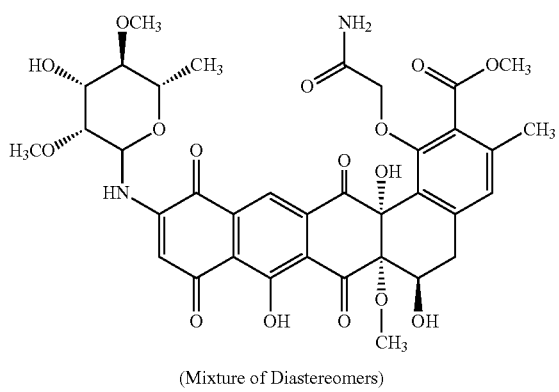 [SMILES: COC(=O)c1c(C)cc2c(c1OCC(N)=O)[C@]1(O)C(=O)c3cc4c(c(O)c3C(=O)[C@]1(OC)[C@H](O)C2)C(=O)C=C(NC1O[C@@H](C)[C@H](OC)[C@@H](O)[C@H]1OC)C4=O]

(Mixture of Diastereomers)

Following General Procedure: Method A using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol), potassium carbonate (21 mg, 0.15 mmol) and bromoacetamide (21 mg, 0.15 mmol), the product was purified by preparative TLC (silica gel, 95:5 dichloromethane/methanol) and preparative HPLC (45:55 acetonitrile/water with 0.05% TFA) to afford (6R,6aS,14aR)-methyl 1-(2-amino-2-oxoethoxy)-6,8,14a-trihydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (6 mg, 15%) as an orange-red solid and as a mixture of diastereomers: $^1$H NMR (500 MHz, CDCl$_3$) δ 14.27 (s, 0.3H), 14.21 (s, 0.7H), 8.12 (s, 0.3H), 8.11 (s, 0.7H), 6.90 (br s, 1H), 6.22 (br s, 1H), 5.94 (br s, 1H), 5.91 (s, 0.7H), 5.90 (s, 0.3H), 5.14 (d, J=4.5 Hz, 0.3H), 4.97 (d, J=6.7 Hz, 0.7H), 4.75 (d, J=14.7 Hz, 0.3H), 4.48 (d, J=14.7 Hz, 0.7H), 4.70 (br s, 1H), 4.21 (d, J=14.7 Hz, 1H), 3.81-3.80 (m, 1H), 3.81 (s, 3H), 3.78 (br s, 2H), 3.74-3.70 (m, 2H), 3.65-3.56 (m, 1H), 3.61 (s, 3H), 3.40 (s, 3H), 3.36 (s, 3H), 3.13 (t, J=9.2 Hz, 1H), 2.21 (s, 3H), 1.36 (d, J=6.1 Hz, 3H); MS (ESI+) m/z 755 (M+H); HPLC >99% (AUC), t$_R$ 13.72 min.

Example 11

Preparation of (6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-1-(pyridin-3-ylmethoxy)-5,6,6a,7,9,12,14,14a-octahydrobenzo[a]tetracene-2-carboxylate hydrochloride

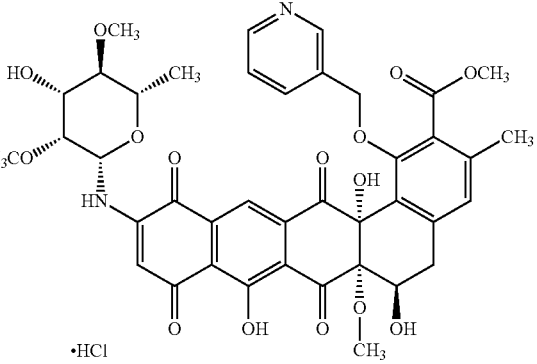

Following General Procedure: Method B using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol), potassium carbonate (21 mg, 0.15 mmol) and 3-picolyl chloride hydrochloride (25 mg, 0.15 mmol), the product was purified by preparative TLC (silica gel, 95:5 dichloromethane/methanol) and converted to hydrochloride to afford (6R,6aS,14aR)-methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-1-(pyridin-3-ylmethoxy)-5,6,6a,7,9,12,14,14a-octahydrobenzo[a]tetracene-2-carboxylate hydrochloride (13 mg, 31%) as an orange-red solid: $^1$H NMR (500 MHz, CDCl$_3$) δ 14.21 (s, 1H), 8.79 (br s, 2H), 8.26 (d, J=4.1 Hz, 1H), 7.87 (br s, 1H), 7.41 (s, 1H), 6.92 (s, 1H), 6.89 (br s, 1H), 5.85 (s, 1H), 5.12 (d, J=11.2 Hz, 1H), 5.05 (d, J=11.3 Hz, 1H), 4.98 (br s, 1H), 4.66 (br s, 1H), 4.39 (br s, 1H), 3.85 (s, 3H), 3.81-3.74 (m, 1H), 3.72 (s, 3H), 3.65 (dd, J=19.3, 7.3 Hz, 1H), 3.60 (s, 3H), 3.43 (s, 1H), 3.40 (s, 3H), 3.36-3.31 (m, 1H), 3.14 (t, J=9.0 Hz, 1H), 2.51 (br s, 1H), 2.24 (s, 3H), 1.36 (d, J=6.1 Hz, 3H); MS (ESI+) m/z 789 (M+H); HPLC >99% (AUC), t$_R$ 12.34 min.

Example 12

Preparation of (6R,6aS,14aR)-Methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-1-(2-oxo-2-(piperidin-1-yl)ethoxy)-5,6,6a,7,9,12,14,14a-octahydrobenzo[a]tetracene-2-carboxylate

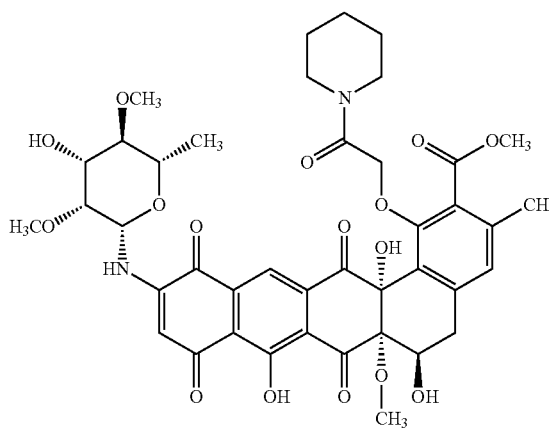

Following General Procedure: Method B using (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol), potassium carbonate (21 mg, 0.15 mmol) and 2-bromo-1-(piperidin-1-yl)ethanone (31 mg, 0.15 mmol), the product was purified by preparative TLC (silica gel, 95:5 dichloromethane/methanol) to afford (6R,6aS,14aR)-methyl 6,8,14a-trihydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-1-(2-oxo-2-(piperidin-1-yl)ethoxy)-5,6,6a,7,9,12,14,14a-octahydrobenzo[a]tetracene-2-carboxylate (31 mg, 75%) as a brown solid: $^1$H NMR (500 MHz, CDCl$_3$) δ 14.17 (s, 1H), 8.28 (s, 1H), 6.85 (d, J=9.0 Hz, 1H), 6.81 (s, 1H), 5.87 (s, 1H), 5.82 (d, J=7.3 Hz, 1H), 4.95 (s, 1H), 4.68 (d, J=8.6 Hz, 1H), 4.59-4.50 (m, 2H), 4.00-3.74 (m, 2H), 3.78 (s, 3H), 3.74 (s, 3H), 3.69 (s, 1H), 3.60 (s, 6H), 3.40 (s, 3H), 3.35-3.25 (m, 4H), 3.12 (t, J=9.2 Hz, 1H), 2.54 (br s, 1H), 2.16 (s, 3H), 1.68 (br s, 2H), 1.62 (br s, 4H), 1.36 (d, J=6.1 Hz, 3H); MS (ESI+) m/z 823 (M+H); HPLC 98.7% (AUC), $t_R$ 16.81 min.

Example 13

Preparation of (6R,6aS,14aR)-1,6,8,14a-Tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid

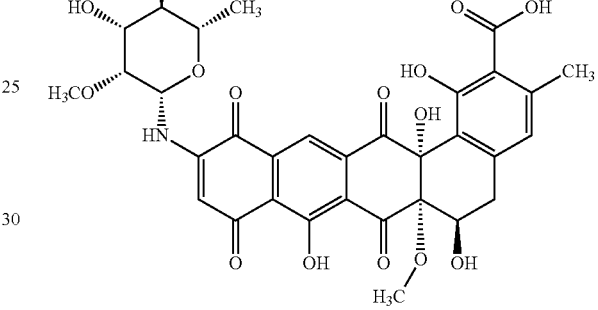

To a solution of (6R,6aS,14aR)-methyl 1,6,8,14a-tetrahydroxy-11-(4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in DMSO (1 mL) was added lithium chloride (121 mg, 2.87 mmol). The reaction mixture was irradiated with microwaves at 120° C. for 21 min. The crude material was purified by preparative HPLC (10:90 acetonitrile/water to 100% acetonitrile with 0.05% TFA over 50 min) to afford (6R,6aS,14aR)-1,6,8,14a-tetrahydroxy-11-(2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (12.0 mg, 12.5%) as a dark orange-red solid: $^1$H NMR (500 MHz, acetone-d$_6$) δ 14.27 (s, 1H), 8.06 (s, 1H), 6.91 (d, J=8.0 Hz, 1H), 6.62 (s, 1H), 6.00 (s, 2H), 5.09-5.05 (m, 1H), 4.90-4.83 (m, 1H), 4.78-4.71 (m, 1H), 4.55-4.43 (m, 1H), 3.86-3.82 (m, 1H), 3.74 (s, 3H), 3.73-3.70 (m, 1H), 3.54 (s, 3H), 3.53-3.45 (m, 2H), 3.32 (s, 3H), 3.30-3.20 (m, 2H), 3.06 (t, J=9.1 Hz, 2H), 2.43 (s, 3H), 1.19 (d, J=6.0 Hz, 3H); MS (ESI+) m/z 684 (M+H); HPLC 93.4% (AUC), $t_R$ 11.84 min.

Example 14

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-phenyl-5,6,6a,7,9,12,14,14a-octahydrobenzo[a]tetracene-2-carboxamide

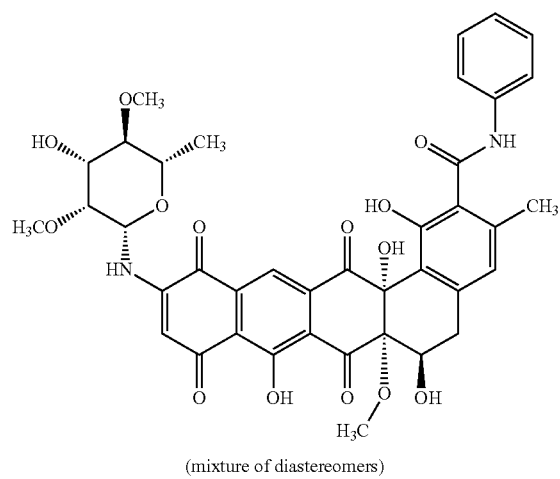 [SMILES: CO[C@@H]1[C@@H](O)[C@@H](OC)[C@@H](NC2=CC(=O)c3c(cc4c(c3O)C(=O)[C@]3(OC)[C@H](O)Cc5cc(C)c(C(=O)Nc6ccccc6)c(O)c5[C@]3(O)C4=O)C2=O)O[C@H]1C]

(mixture of diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (100 mg, 0.14 mmol) in THF (3 mL) was added polystyrene-carbodiimide (261 mg, 0.29 mmol), 1-hydroxybenzotriazole hydrate (39 mg, 0.29 mmol) and aniline (127 mg, 1.43 mmol). The reaction mixture was stirred at room temperature under nitrogen for 6 h. The reaction was filtered through a micro filter. The crude material was purified by preparative TLC (silica gel, 90:10 chloroform/methanol) and preparative HPLC (10:90 acetonitrile/water to 100% acetonitrile with 0.05% TFA over 50 min) to afford (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-phenyl-5,6,6a,7,9,12,14,14a-octahydrobenzo[a]tetracene-2-carboxamide as a mixture of diastereomers (5.0 mg, 4%) and as a red solid: $^1$H NMR (500 MHz, CDCl$_3$) δ 14.25 (s, 0.3H), 14.19 (s, 0.7H), 11.64 (br s, 1H), 8.28 (s, 0.3H), 8.24 (s, 0.7H), 7.50-7.42 (m, 3H), 7.38-7.32 (m, 3H), 7.16 (t, J=14.0 Hz, 2H), 6.91 (d, J=8.5 Hz, 0.3H), 6.86 (d, J=8.5 Hz, 0.7H), 6.54 (s, 1H), 6.20 (s, 0.3H), 6.18 (s, 0.7H), 5.85 (s, 1H), 5.18-5.13 (m, 1H), 4.98 (d, J=8.5 Hz, 1H), 4.67-4.62 (m, 1H), 3.81 (s, 3H), 3.79 (s, 2H), 3.60 (s, 3H), 3.56-3.51 (m, 2H), 3.44 (s, 2H), 3.38 (s, 1H), 3.15-3.10 (m, 1H), 2.51 (s, 3H), 1.37 (d, J=6.0 Hz, 3H); MS (ESI−) m/z 757 (M−H); HPLC 97.0% (AUC), t$_R$ 12.95 min.

Example 15

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-2-(4-phenylpiperazine-1-carbonyl)-6,6a-dihydrobenzo[a]tetracene-7,9,12,14(5H,14aH)-tetraone hydrochloride

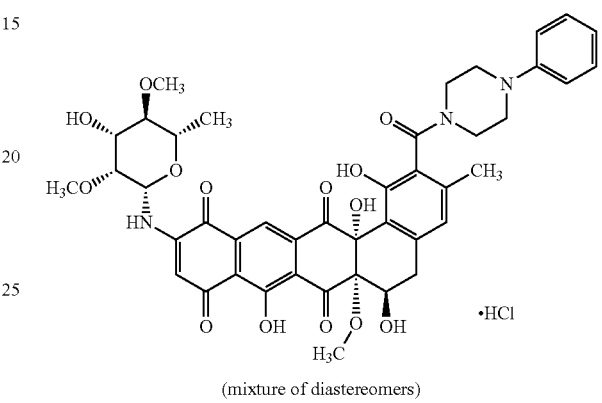

(mixture of diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (60 mg, 0.09 mmol) in THF (2 mL) was added polystyrene-carbodiimide (156 mg, 0.18 mmol), 1-hydroxybenzotriazole hydrate (24 mg, 0.18 mmol) and 1-phenylpiperazine (21 mg, 0.13 mmol). The reaction mixture was stirred at room temperature under nitrogen for 5 h. The reaction was filtered through a micro filter and concentrated. The crude material was purified by preparative TLC (silica gel, 90:10 dichloromethane/methanol) to afford a dark red solid. The solid was dissolved in methanol (1 mL) and treated with HCl (1.25 M solution in methanol, 0.5 mL) at 0° C. The solution was concentrated and triturated with diethyl ether to afford (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-2-(4-phenylpiperazine-1-carbonyl)-6,6a-dihydrobenzo[a]tetracene-7,9,12,14(5H,14aH)-tetraone hydrochloride as a mixture of diastereomers (9.0 mg, 25%) and as a red solid: $^1$H NMR (500 MHz, CD$_3$OD) δ 8.10 (s, 1H), 7.60-7.20 (m, 5H), 6.70 (s, 1H), 6.20-6.10 (m, 0.3H), 6.04-5.95 (m, 0.7H), 5.49 (s, 1H), 4.96-4.85 (m, 1H), 4.18-4.08 (m, 1H), 4.05-3.89 (m, 1H), 3.78-3.62 (m, 7H), 3.54 (s, 3H), 3.61-3.52 (m, 2H), 3.51-3.41 (m, 7H), 3.27-3.16 (m, 1H), 3.09-2.90 (m, 1H), 3.16 (s, 3H), 1.30-1.20 (m, 3H); MS (ESI−) m/z 826 (M−H); HPLC 94.2% (AUC), t$_R$ 11.89 min.

Example 16

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-N,N,3-trimethyl-7,9,12,14-tetraoxo-5,6,6a,7,9,12,14,14a-octahydrobenzo[a]tetracene-2-carboxamide

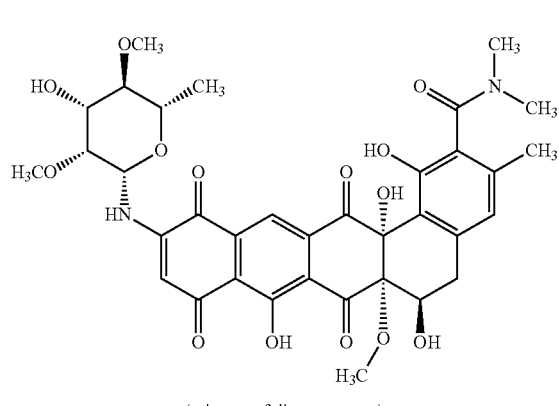

(mixture of diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (60 mg, 0.09 mmol) in THF (2 mL) was added polystyrene-carbodiimide (156 mg, 0.18 mmol), 1-hydroxybenzotriazole hydrate (18 mg, 0.13 mmol) and dimethylamine (0.09 mL, 0.13 mmol). The reaction mixture was stirred at room temperature under nitrogen for 4 h. The reaction was filtered through a micro filter and concentrated. The crude material was purified by preparative TLC (9:1, methylene chloride/methanol) to afford (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-N,N,3-trimethyl-7,9,12,14-tetraoxo-5,6,6a,7,9,12,14,14a-octahydrobenzo[a]tetracene-2-carboxamide as a mixture of diastereomers (8.0 mg, 13%) and as a red solid: $^1$H NMR (500 MHz, CDCl$_3$) δ 14.18 (s, 1H), 8.16 (s, 1H), 6.85 (d, J=9.0 Hz, 0.8H), 6.57 (s, 1H), 6.28-6.24 (m, 0.2H), 6.20 (s, 0.2H), 5.87 (s, 0.8H), 5.14-5.08 (m, 1H), 5.00-4.94 (m, 1H), 4.71-4.66 (m, 1H), 4.62-4.56 (m, 1H), 3.79 (s, 3H), 3.75-3.68 (m. 2H), 3.61 (s, 3H), 3.59-3.52 (m, 3H), 3.41 (s, 3H), 3.38-3.28 (m, 2H), 3.13 (t, J=9.0 Hz, 1H), 2.92 (s, 6H), 2.14 (s, 3H), 3.14 (d, J=6.0 Hz, 3H); MS (ESI−) m/z 709 (M−H); HPLC 95.6% (AUC), $t_R$ 11.51 min.

Example 17

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(pyridin-3-ylmethyl)-5,6,6a,7,9,12,14,14a-octahydrobenzo[a]tetracene-2-carboxamide hydrochloride

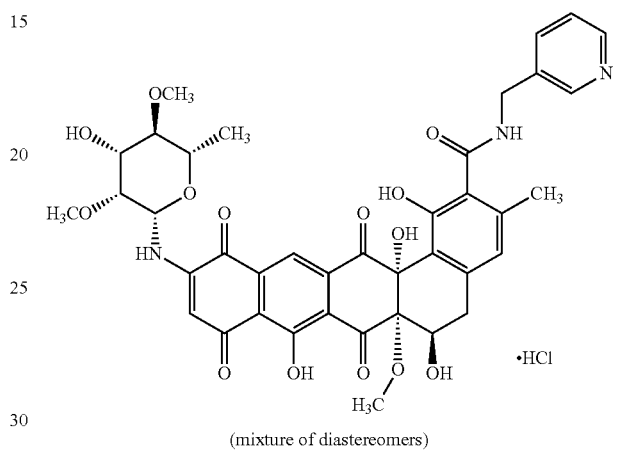

(mixture of diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (60 mg, 0.09 mmol) in THF (2 mL) was added polystyrene-carbodiimide (156 mg, 0.18 mmol), 1-hydroxybenzotriazole hydrate (24 mg, 0.18 mmol) and 3-(aminomethyl)pyridine (11 mg, 0.10 mmol). The reaction mixture was stirred at room temperature under nitrogen for 7 h. The reaction was filtered through a micro filter and concentrated. The crude material was purified by preparative HPLC (10:90 acetonitrile/water to 60:40 acetonitrile/water with 0.05% TFA over 10 min, then isocratic) to afford a dark red solid. The solid was dissolved in methanol (2 mL) and treated with HCl (0.20 mL, 1.25 M solution in methanol) at 0° C. The solution was concentrated and triturated with diethyl ether to afford 6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(pyridin-3-ylmethyl)-5,6,6a,7,9,12,14,14a-octahydrobenzo[a]tetracene-2-carboxamide hydrochloride as a mixture of diastereomers (12 mg, 21%) and as a red solid: $^1$H NMR (500 MHz, CD$_3$OD) δ 8.84-8.80 (m, 1H), 8.80-8.65 (m, 1H), 8.64-8.58 (m, 1H), 8.10 (s, 1H), 8.09-8.06 (m, 1H), 6.63 (s, 1H), 6.16 (s, 0.3H), 6.01 (s, 0.7H), 5.20 (s, 0.3H), 4.95 (s, 0.7H), 4.67 (br s, 1H), 3.92-3.89 (m, 1H), 3.75 (s, 3H), 3.70-3.67 (m, 0.3H), 3.64-3.62 (m, 0.7H), 3.57 (s, 3H), 3.54 (s, 1H), 3.50 (s, 1H), 3.49-3.37 (m, 5H), 3.24-3.17 (m, 1H), 3.10-3.02 (m, 1H), 2.23 (s, 3H), 1.28 (d, J=6.5 Hz, 2H), 1.23 (d, J=6.5 Hz, 1H); MS (ESI−) m/z 772 (M−H); HPLC 96.7% (AUC), $t_R$ 10.53 min.

Example 18

Preparation of (6R,6aS,14aR)—N-Cyclohexyl-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide

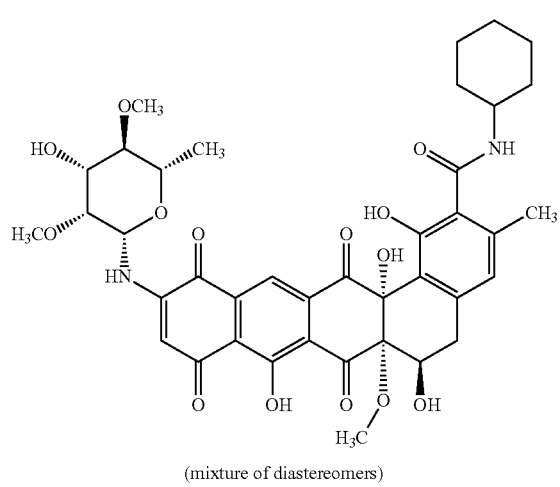 [SMILES: CO[C@@H]1[C@@H](O)[C@@H](OC)[C@@H](NC2=CC(=O)c3c(cc4c(c3O)C(=O)[C@]3(OC)[C@H](O)Cc5cc(C)c(C(=O)NC6CCCCC6)c(O)c5[C@]3(O)C4=O)C2=O)O[C@H]1C]

(mixture of diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (60 mg, 0.09 mmol) in THF (2 mL) was added polystyrene-carbodiimide (156 mg, 0.18 mmol), 1-hydroxybenzotriazole hydrate (24 mg, 0.18 mmol) and cyclohexylamine (10 mg, 0.13 mmol). The reaction mixture was stirred at room temperature under nitrogen for 4 h. The reaction was filtered through a micro filter and concentrated. The crude material was purified by preparative HPLC (10:90 acetonitrile/water to 60:40 acetonitrile/water with 0.05% TFA over 10 min, then isocratic) to afford (6R,6aS,14aR)—N-cyclohexyl-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide as a mixture of diastereomers (14 mg, 20%) and as a dark red solid: $^1$H NMR (500 MHz, CD$_3$OD) δ 8.10 (s, 1H), 6.59 (s, 1H), 6.15 (s, 0.3H), 6.00 (s, 0.7H), 5.19 (s, 0.3H), 4.95 (s, 0.7H), 4.89 (br s, 1H), 3.95-3.90 (m, 1H), 3.75 (s, 3H), 3.74-3.71 (m, 0.7H), 3.70-3.68 (m, 0.3H), 3.67-3.64 (m, 1H), 3.58 (s, 3H), 3.53 (s, 1H), 3.50 (s, 2H), 3.48-3.35 (m, 5H), 3.27-3.20 (m, 1H), 3.09-3.02 (m, 1H), 2.22 (s, 3H), 1.93-1.81 (m, 2H), 1.80-1.69 (m, 2H), 1.66-1.57 (m, 1H), 1.40-1.33 (m, 2H), 1.27 (d, J=6.5 Hz, 2H), 1.22 (d, J=6.5 Hz, 1H), 1.19-1.15 (m, 2H); MS (ESI+) m/z 765 (M+H); HPLC 95.4% (AUC), $t_R$ 13.79 min.

Example 19

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-N,3-dimethyl-7,9,12,14-tetraoxo-5,6,6a,7,9,12,14,14a-octahydrobenzo[a]tetracene-2-carboxamide

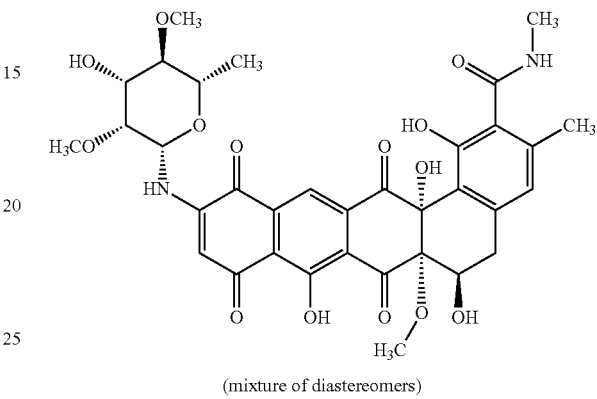

(mixture of diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (100 mg, 0.15 mmol) in THF (2 mL) was added 10% Pd/C and the reaction mixture was stirred at room temperature under hydrogen atmosphere for 4 h. The reaction mixture was filtered without exposure to air into another flask containing polystyrene-carbodiimide (260 mg, 0.29 mmol) and the mixture was stirred for 10 min. A solution of 1-hydroxybenzotriazole hydrate (40 mg, 22 mmol) in THF (1 mL) and methylamine (0.08 mL, 2.0 M solution in THF, 0.16 mmol) were added and the reaction mixture was stirred at room temperature under nitrogen for 4 h. The reaction was filtered through a micro filter and concentrated. The crude material was purified by preparative HPLC (10:90 acetonitrile/water to 60:40 acetonitrile/water with 0.05% TFA over 10 min, then isocratic) to afford (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-N,3-dimethyl-7,9,12,14-tetraoxo-5,6,6a,7,9,12,14,14a-octahydrobenzo[a]tetracene-2-carboxamide as a mixture of diastereomers (7.5 mg, 7%) and as a dark red solid: $^1$H NMR (500 MHz, CD$_3$OD) δ 8.11 (s, 1H), 6.59 (s, 1H), 6.15 (s, 0.3H), 5.99 (s, 0.7H), 5.19-5.17 (m, 0.3H), 4.94 (s, 0.7H), 3.75 (s, 3H), 3.57 (s, 3H), 3.54 (s, 1H), 3.51 (s, 1H), 3.48-3.35 (m, 6H), 3.26-3.21 (m, 1H), 3.08 (t, J=9.0 Hz, 0.3H), 3.04 (t, J=9.0 Hz, 0.7H), 2.78 (s, 3H), 2.22 (s, 3H), 1.27 (d, J=9.0 Hz, 2H), 1.22 (d, J=6.5 Hz, 1H); MS (ESI+) m/z 697 (M+H); HPLC >99% (AUC), $t_R$ 10.63 min.

Example 20

Preparation of (6R,6aS,14aR)-1,6,8,14a-Tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide

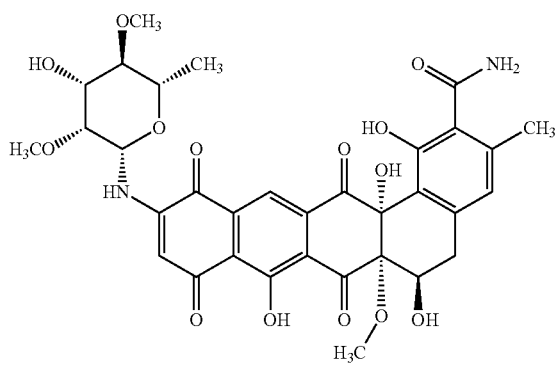

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (100 mg, 0.15 mmol) in THF (2 mL) was added 10% Pd/C and the reaction mixture was stirred at room temperature under hydrogen at 1 atmosphere for 4 h. The reaction mixture was filtered without exposure to air into another flask containing polystyrene-carbodiimide (260 mg, 0.29 mmol) and the mixture was stirred for 10 min. A solution of 1-hydroxybenzotriazole hydrate (40 mg, 22 mmol) in THF (1 mL) and ammonia (0.22 mL, 2.0 M solution in THF, 0.16 mmol) were added and the reaction mixture was stirred at room temperature under nitrogen for 4 h. The reaction was filtered through a micro filter and concentrated. The crude material was purified by preparative HPLC (10:90 acetonitrile/water to 60:40 acetonitrile/water with 0.05% TFA over 10 min, then isocratic) to afford 6R,6aS,14aR)-1,6,8,14a-tetrahydroxy-11-((2S,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide (12 mg, 15%) as a dark red solid: $^1$H NMR (500 MHz, CDCl$_3$) δ 14.19 (s, 1H), 12.89 (s, 1H), 8.22 (s, 1H), 6.86 (d, J=8.5 Hz, 1H), 6.52 (s, 1H), 5.96 (s, 2H), 5.87 (s, 1H), 4.96 (d, J=6.0 Hz, 1H), 4.68 (d, J=9.0 Hz, 1H), 3.79 (s, 3H), 3.78-3.66 (m, 3H), 3.61 (s, 3H), 3.59-3.50 (m, 2H), 3.40 (s, 3H), 3.37-3.30 (m, 3H), 3.13 (t, J=9.5 Hz, 1H), 2.46 (s, 3H), 1.36 (s, 3H); MS (ESI+) m/z 683 (M+H); HPLC 94.3% (AUC), $t_R$ 11.64 min.

Example 21

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-2-(piperidine-1-carbonyl)-6,6a-dihydrobenzo[a]tetracene-7,9,12,14(5H,14aH)-tetraone

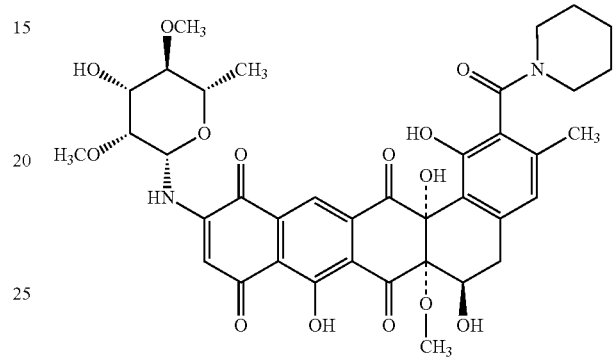

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid$^2$ (90 mg, 0.13 mmol) in THF (3 mL) was added polystyrene carbodiimide (0.24 g, 0.27 mmol) and 1-hydroxybenzotriazole hydrate (36 mg, 0.27 mmol), and then the reaction mixture was stirred at room temperature under nitrogen. After 15 min, piperidine (15 mg, 0.18 mmol) was added and the reaction mixture was stirred at room temperature under nitrogen. After 2 h, the reaction mixture was filtered and concentrated under reduced pressure. The resulting crude material was purified by preparative HPLC (10:90 acetonitrile/water to 60:40 acetonitrile/water with 0.05% TFA over 10 min, then isocratic). The resulting product was lyophilized from acetonitrile (3 mL) and water (1 mL) to yield (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-2-(piperidine-1-carbonyl)-6,6a-dihydrobenzo[a]tetracene-7,9,12,14(5H,14aH)-tetraone (10 mg, 10%) as a mixture of diastereomers and as a dark red solid: $^1$H NMR (500 MHz, CD$_3$OD) δ 8.10 (s, 1H), 6.64 (s, 0.8H), 6.63 (s, 0.2H), 6.17-6.14 (m, 0.2H), 6.02-5.97 (m, 0.8H), 5.19 (d, J=2.0 Hz, 0.2H), 4.97-4.87 (m, 2H), 4.32 (d, J=4.5 Hz, 0.8H), 3.74 (s, 3H), 3.78-3.70 (m, 4H), 3.65-3.63 (m, 1H), 3.58 (s, 3H), 3.52 (d, J=15.0 Hz, 3H), 3.45-3.39 (m, 5H), 3.36-3.33 (m, 2H), 3.23-3.21 (m, 2H), 3.16-3.02 (m, 1H), 2.46 (s, 0.6H), 2.09 (s, 2.4H), 1.89-1.86 (m, 1H), 1.27 (d, J=6.0 Hz, 2.4H), 1.22-1.21 (m, 0.6H); MS (ESI+) m/z 751 (M+H); HPLC 98.3% (AUC), $t_R$ 11.40 min.

Example 22

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-2-(pyrrolidine-1-carbonyl)-6,6a-dihydrobenzo[a]tetracene-7,9,12,14(5H,14aH)-tetraone

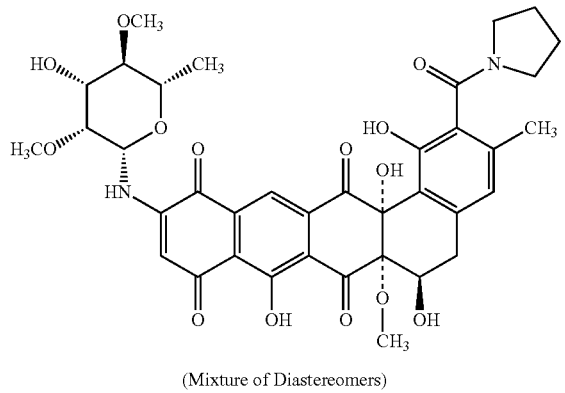 [SMILES: CO[C@@H]1[C@@H](O)[C@@H](OC)[C@@H](NC2=CC(=O)c3c(cc4c(c3O)C(=O)[C@]3(OC)[C@H](O)Cc5cc(C)c(C(=O)N6CCCC6)c(O)c5[C@]3(O)C4=O)C2=O)O[C@H]1C]

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (56 mg, 0.082 mmol) in THF (2 mL) was added polystyrene carbodiimide (0.15 mg, 0.17 mmol) and 1-hydroxybenzotriazole hydrate (22 mg, 0.16 mmol), and then the reaction mixture was stirred at room temperature under nitrogen. After 15 min, pyrrolidine (11 mg, 0.16 mmol) was added and the reaction mixture was stirred at room temperature under nitrogen. After 5 h, the reaction mixture was filtered and concentrated under reduced pressure. The crude material was purified by preparative HPLC (10:90 acetonitrile/water to 60:40 acetonitrile/water with 0.05% TFA over 10 min, then isocratic). The resulting product was lyophilized from acetonitrile (3 mL) and water (1 mL) to give (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-2-(pyrrolidine-1-carbonyl)-6,6a-dihydrobenzo[a]tetracene-7,9,12,14(5H,14aH)-tetraone (1.7 mg, 2.8%) as a mixture of diastereomers and as a dark red solid: $^1$H NMR (500 MHz, CD$_3$OD) δ 8.10 (s, 1H), 6.64 (s, 1H), 6.17 (s, 0.3H), 6.01 (s, 0.7H), 4.96-4.87 (m, 2H), 3.74 (s, 3H), 3.64 (s, 1H), 3.57 (s, 3H), 3.52 (d, J=18.0 Hz, 3H), 3.46-3.39 (m, 6H), 3.26-3.20 (m, 1H), 3.08-3.02 (m, 2H), 2.08 (s, 3H), 1.93-1.87 (m, 4H), 1.28 (d, J=6.0 Hz, 2.1H), 1.22 (d, J=6.0 Hz, 0.9H); MS (ESI+) m/z 737 (M+H); HPLC 94.4% (AUC), $t_R$ 10.71 min.

Example 23

Preparation of (6R,6aS,14aR)—N-(Biphenyl-4-yl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide

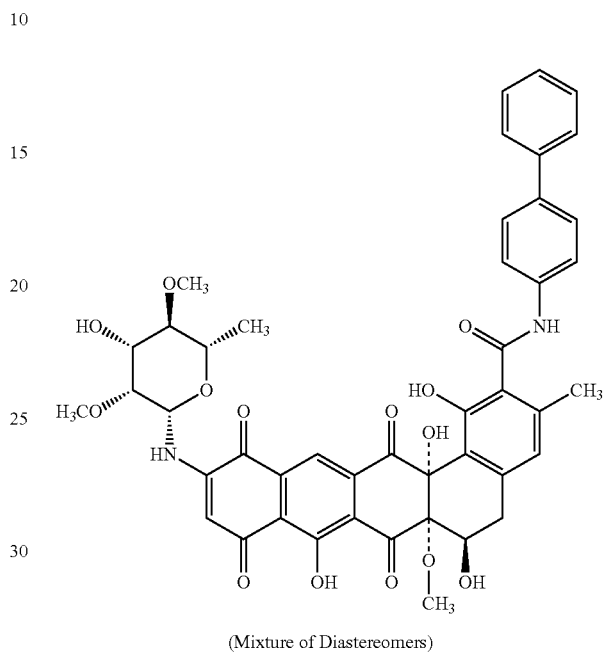

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid$^2$ (0.11 g, 0.16 mmol) in THF (2 mL) was added polystyrene carbodiimide (0.26 g, 0.32 mmol) and 1-hydroxybenzotriazole hydrate (43 mg, 0.32 mmol), and then the reaction mixture was stirred at room temperature under nitrogen. After 15 min, 4-aminobiphenyl (42 mg, 0.25 mmol) was added and the reaction mixture was stirred at room temperature under nitrogen. After 3 h, the reaction mixture was filtered and concentrated under reduced pressure. The crude material was purified by preparative TLC (95:5 chloroform/methanol) and then by semi-preparative HPLC (20:80 acetonitrile/water to 100% acetonitrile with 0.05% TFA over 40 min). The resulting product was lyophilized from acetonitrile (3 mL) and water (1 mL) to give (6R,6aS,14aR)—N-(biphenyl-4-yl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide (3.7 mg, 3.3%) as a mixture of diastereomers and as a red-orange solid: $^1$H NMR (500 MHz, CDCl$_3$) δ 14.21 (s, 1H), 11.71 (s, 0.2H), 11.64 (s, 0.8H), 8.24 (s, 0.2H), 8.21 (s, 0.8H), 7.58-7.52 (m, 7H), 7.44-7.42 (m, 2H), 7.36-7.33 (m, 1H), 6.85 (d, J=9.0 Hz, 0.8H), 6.60 (s, 1H), 6.21 (d, J=6.0 Hz, 0.2H), 6.18 (s, 0.2H), 5.86 (s, 0.8H), 5.24 (br s, 1H), 4.98 (d, J=5.5 Hz, 1H), 4.66 (d, J=9.0 Hz, 2H), 3.78 (s, 3H), 3.70 (dd, J=9.5, 3.0 Hz, 1H), 3.67 (s, 1H), 3.61 (s, 3H), 3.60-3.57 (m, 1H), 3.56 (d, J=13.5 Hz, 1H), 3.41 (s, 3H), 3.38-3.31 (m, 2H), 3.13-3.10 (m, 1H), 2.55 (s, 3H), 1.35 (d, J=6.0 Hz, 2.4H), 1.25 (d, J=5.5 Hz, 0.6H); MS (ESI+) m/z 835 (M+H); HPLC 97.9% (AUC), $t_R$ 15.37 min.

Example 24

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-N-(2-hydroxyethyl)-6a-methoxy-3-methyl-7,9,12,14-tetraoxo-5,6,6a,7,9,12,14,14a-octahydrobenzo[a]tetracene-2-carboxamide

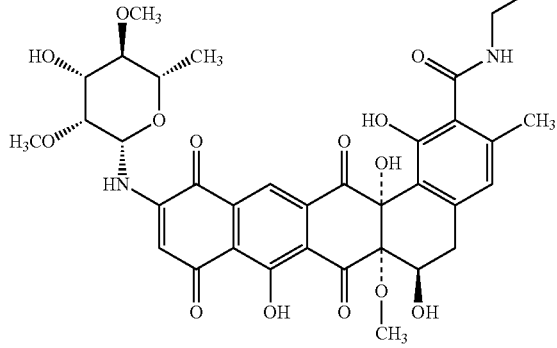

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (67 mg, 0.098 mmol) in THF (3 mL) was added 10% Pd/C (67 mg) and the reaction was stirred at room temperature under hydrogen (1 atm). After 5 h, the reaction was filtered into a round bottom flask containing polystyrene carbodiimide (0.17 g, 0.19 mmol) in THF (2 mL) without exposure to air under argon at room temperature. To the reaction mixture, 1-hydroxybenzotriazole hydrate (27 mg, 0.20 mmol) and ethanol amine (5.7 mg, 0.093 mmol) were added and the reaction was stirred at room temperature under argon. After 4 h, the reaction was filtered and concentrated under reduced pressure. The crude product was purified by preparative HPLC (10:90 acetonitrile/water to 60:40 acetonitrile/water with 0.05% TFA over 10 min, then isocratic). The resulting product was lyophilized from acetonitrile (3 mL) and water (1 mL) to yield (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-N-(2-hydroxyethyl)-6a-methoxy-3-methyl-7,9,12,14-tetraoxo-5,6,6a,7,9,12,14,14a-octahydrobenzo[a]tetracene-2-carboxamide (4.3 mg, 6.1%) as a mixture of diastereomers and as a red-orange solid: $^1$H NMR (500 MHz, CD$_3$OD) δ 8.10 (s, 1H), 6.59 (s, 1H), 6.15 (s, 0.4H), 5.99 (s, 0.6H), 4.94-4.87 (m, 2H), 3.75 (s, 3H), 3.64-3.60 (m, 3H), 3.58 (s, 3H), 3.52 (d, J=14.5 Hz, 3H), 3.48-3.34 (m, 5H), 3.27-3.19 (m, 1H), 3.09-3.03 (m, 1H), 2.45 (s, 3H), 1.27 (d, J=6.5 Hz, 1.8H), 1.22 (d, J=6.5 Hz, 1.2H); MS (ESI−) m/z 725 (M−H); HPLC 98.6% (AUC), $t_R$ 10.05 min.

Example 25

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(3-phenylpropyl)-5,6,6a,7,9,12,14,14a-octahydrobenzo[a]tetracene-2-carboxamide

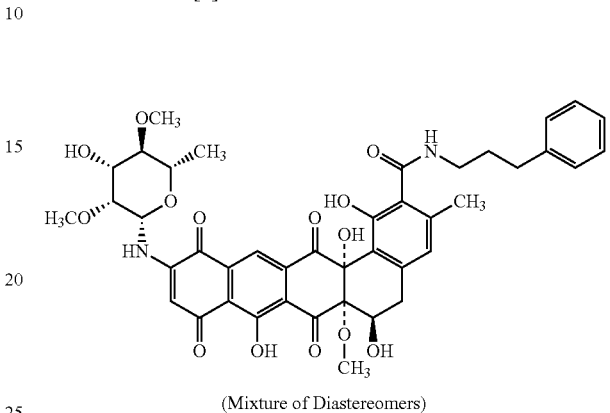

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (71 mg, 0.10 mmol) in THF (3 mL) was added 10% Pd/C (84 mg) and the reaction was stirred at room temperature under hydrogen (1 atm). After 5 h, the reaction was filtered into a round bottom flask containing polystyrene carbodiimide (0.19 g, 0.21 mmol) in THF (2 mL) without exposure to air under argon at room temperature. To the reaction mixture, 1-hydroxybenzotriazole hydrate (27 mg, 0.20 mmol) and 3-phenylpropyl amine (11 mg, 0.084 mmol) were added and the reaction was stirred at room temperature under argon. After 4 h, the reaction was filtered and concentrated under reduced pressure. The resulting crude product was purified by preparative HPLC (10:90 acetonitrile/water to 60:40 acetonitrile/water with 0.05% TFA over 10 min, then isocratic). The resulting product was lyophilized from acetonitrile (3 mL) and water (1 mL) to yield (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(3-phenylpropyl)-5,6,6a,7,9,12,14,14a-octahydrobenzo[a]tetracene-2-carboxamide (4.3 mg, 5.3%) as a mixture of diastereomers and as an orange-red solid: $^1$H NMR (500 MHz, CD$_3$OD) δ 8.11 (s, 1H), 7.26-7.20 (m, 3H), 7.16-7.11 (m, 3H), 6.61 (s, 1H), 6.14 (s, 0.3H), 5.96 (s, 0.7H), 5.18 (s, 1H), 4.90 (s, 2H), 3.74 (s, 3H), 3.57 (s, 3H), 3.52 (d, J=14.5 Hz, 3H), 3.45-3.39 (m, 3H), 3.28-3.21 (m, 1H), 3.10-3.01 (m, 1H), 2.66-2.56 (m, 2H), 2.25 (s, 3H), 1.82-1.76 (m, 2H), 1.26 (d, J=6.0 Hz, 2.1H), 1.21 (d, J=6.0 Hz, 0.9H); MS (ESI+) m/z 801 (M+H); HPLC 98.0% (AUC), $t_R$ 14.31 min.

Example 26

Preparation of (6R,6aS,14aR)—N-(4-Fluorobenzyl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide

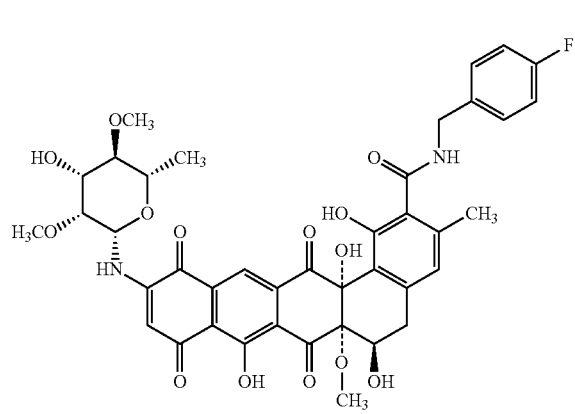

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (74 mg, 0.11 mmol) in THF (10 mL) was added 10% Pd/C (0.15 g) and the reaction was stirred at room temperature under hydrogen (1 atm). After 5 h, the reaction was filtered into a round bottom flask containing polystyrene carbodiimide (0.20 g, 0.22 mmol) in THF (2 mL) without exposure to air under argon at room temperature. To the reaction mixture, 1-hydroxybenzotriazole hydrate (27 mg, 0.20 mmol) and 4-fluorobenzyl amine (15 mg, 0.12 mmol) were added and the reaction was stirred at room temperature under argon. After 5 h, the reaction was filtered and concentrated under reduced pressure. The resulting crude product was purified by preparative HPLC (10:90 acetonitrile/water to 60:40 acetonitrile/water with 0.05% TFA over 10 min, then isocratic) and by semi-preparative HPLC (20:80 acetonitrile/water to 100% acetonitrile with 0.05% TFA over 40 min). The resulting product was lyophilized from acetonitrile (3 mL) and water (1 mL) to yield (6R,6aS,14aR)—N-(4-fluorobenzyl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide (7.3 mg, 8.5%) as a mixture of diastereomers and as an orange-red solid: $^1$H NMR (500 MHz, CD$_3$OD) δ 8.09 (s, 0.4H), 8.08 (s, 0.6H), 7.33-7.27 (m, 2H), 7.09-6.92 (m, 2H), 6.58 (s, 1H), 6.13 (s, 0.4H), 5.96 (s, 0.6H), 5.20 (s, 0.4H), 4.93 (s, 0.6H), 4.90 (s, 1H), 4.44-4.32 (m, 2H), 3.75 (s, 3H), 3.72-3.71 (m, 1H), 3.66-3.65 (m, 1H), 3.57 (s, 3H), 3.52 (d, J=10.0 Hz, 3H), 3.44-3.36 (m, 2H), 3.22 (d, J=18.5 Hz, 1H), 3.10-3.03 (m, 1H), 2.17 (s, 2H), 2.16 (s, 1H), 1.28 (d, J=6.0 Hz, 1.8H), 1.22 (d, J=6.0 Hz, 1.2H); MS (ESI+) m/z 791 (M+H); HPLC 98.8% (AUC), $t_R$ 13.31 min.

Example 27

Preparation of (6R,6aS,14aR)—N-(4-Chlorobenzyl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide

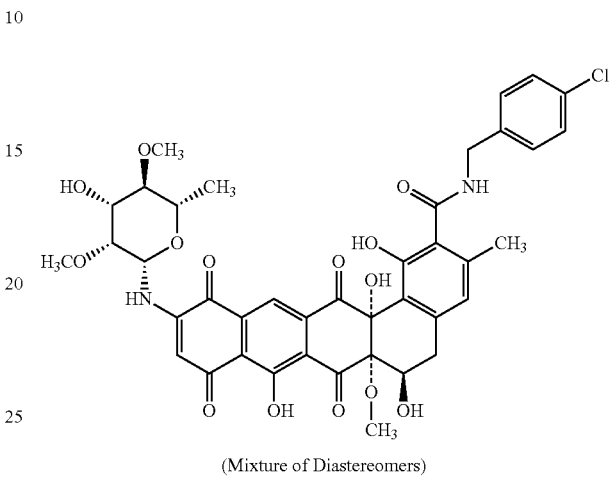

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (0.11 g, 0.17 mmol) in THF (10 mL) was added 10% Pd/C (0.21 g) and the reaction was stirred at room temperature under hydrogen (1 atm). After 5 h, the reaction was filtered into a round bottom flask containing polystyrene carbodiimide (0.30 g, 0.33 mmol) in THF (2 mL) without exposure to air under argon at room temperature. To the reaction mixture, 1-hydroxybenzotriazole hydrate (44 mg, 0.33 mmol) and 4-chlorobenzyl amine (35 mg, 0.25 mmol) were added and the reaction was stirred at room temperature under argon. After 16 h, the reaction was filtered and concentrated under reduced pressure. The resulting crude product was purified by preparative HPLC (10:90 acetonitrile/water to 60:40 acetonitrile/water with 0.05% TFA over 10 min, then isocratic). The resulting product was lyophilized from acetonitrile (3 mL) and water (1 mL) to yield (6R,6aS,14aR)—N-(4-chlorobenzyl)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide (8.8 mg, 6.4%) as a mixture of diastereomers and as an orange-red solid: $^1$H NMR (500 MHz, CD$_3$OD) δ 8.10 (s, 0.3H), 8.09 (s, 0.7H), 7.29-7.23 (m, 4H), 6.59 (s, 1H), 6.14 (s, 0.3H), 5.98 (s, 0.7H), 4.93-4.80 (m, 2H), 4.46-4.34 (m, 2H), 3.75 (s, 3H), 3.71-3.65 (m, 1H), 3.58 (s, 3H), 3.52 (d, J=13.5 Hz, 2H), 3.48-3.35 (m, 5H), 3.26 (d, J=11.5 Hz, 1H), 3.10-3.03 (m, 1H), 2.19 (s, 1.4H), 2.18 (s, 0.6H), 1.27 (d, J=6.0 Hz, 2.1H), 1.23 (d, J=6.5 Hz, 0.9H); MS (ESI+) m/z 807 (M+H); HPLC 98.2% (AUC), $t_R$ 14.03 min.

Example 28

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-N-(4-methoxybenzyl)-3-methyl-7,9-12-14-tetraoxo-5,6,6a,7,9,12,14,14a-octahydrobenzo[a]tetracene-2-carboxamide

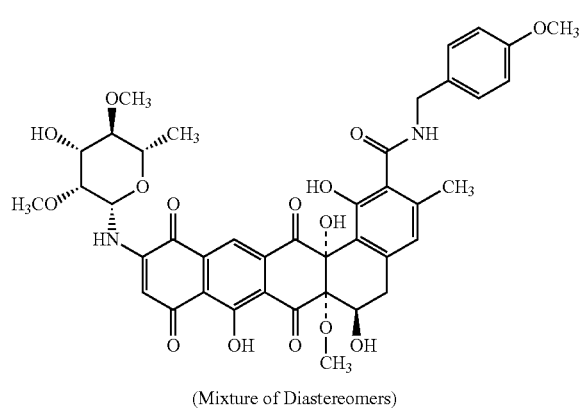 [SMILES: COc1ccc(CNC(=O)c2c(C)cc3c(c2O)[C@]2(O)C(=O)c4cc5c(c(O)c4C(=O)[C@]2(OC)[C@H](O)C3)C(=O)C=C(N[C@H]2O[C@@H](C)[C@H](OC)[C@@H](O)[C@H]2OC)C5=O)cc1]

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (0.11 g, 0.17 mmol) in THF (10 mL) was added 10% Pd/C (0.21 g) and the reaction was stirred at room temperature under hydrogen (1 atm). After 5 h, the reaction was filtered into a round bottom flask containing polystyrene carbodiimide (0.30 g, 0.33 mmol) in THF (2 mL) without exposure to air under argon at room temperature. To the reaction mixture, 1-hydroxybenzotriazole hydrate (48 mg, 0.35 mmol) and 4-methoxybenzyl amine (33 mg, 0.24 mmol) were added and the reaction was stirred at room temperature under argon. After 16 h, the reaction was filtered and concentrated under reduced pressure. The resulting crude product was purified by preparative HPLC (10:90 acetonitrile/water to 60:40 acetonitrile/water with 0.05% TFA over 10 min, then isocratic). The resulting product was lyophilized from acetonitrile (3 mL) and water (1 mL) to yield (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-N-(4-methoxybenzyl)-3-methyl-7,9-12-14-tetraoxo-5,6,6a,7,9,12,14,14a-octahydrobenzo[a]tetracene-2-carboxamide (15 mg, 11%) as a mixture of diastereomers and as a red-brown solid: $^1$H NMR (500 MHz, CD$_3$OD) δ 8.07 (s, 0.3H), 8.05 (s, 0.7H), 7.21 (d, J=8.5 Hz, 1H), 7.16 (d, J=8.0 Hz, 0.3H), 7.11 (d, J=8.0 Hz, 0.7H), 6.87 (d, J=8.5 Hz, 1H), 6.80 (d, J=8.5 Hz, 0.3H), 6.73 (d, J=8.0 Hz, 0.7H), 5.80 (s, 1H), 6.12 (s, 0.3H), 5.93 (s, 0.7H), 4.93-4.87 (m, 2H), 4.37 (s, 2H), 4.35-4.28 (m, 1H), 3.77 (s, 3H), 3.74 (s, 3H), 3.70 (s, 2H), 3.58 (s, 2H), 3.53 (d, J=10.5 Hz, 2H), 3.45-3.39 (m, 2H), 3.23 (d, J=18.5 Hz, 1H), 3.10-3.02 (m, 1H), 2.17 (s, 1.4H), 2.16 (s, 0.6H), 1.27 (d, J=6.0 Hz, 2.1H), 1.22 (d, J=6.0 Hz, 0.9H); MS (ESI+) m/z 803 (M+H); HPLC 98.5% (AUC), $t_R$ 13.14 min.

Example 29

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(pyridin-3-yl)-5,6,6a,7,9,12,14,14a-octahydrobenzo[a]tetracene-2-carboxamide Hydrochloride

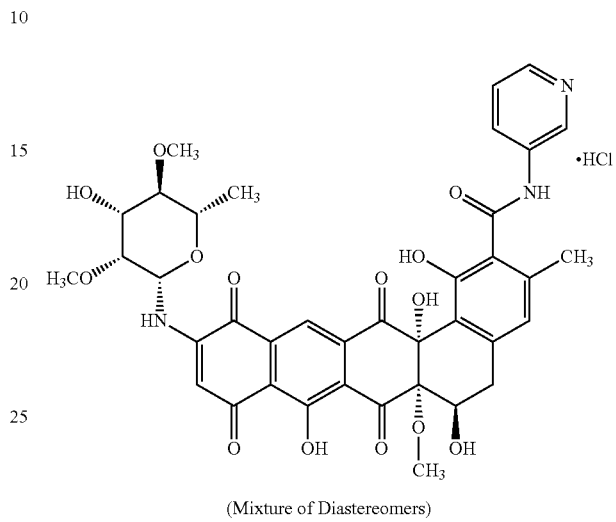

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (50 mg, 0.073 mmol) in THF (5 mL) were added 3-aminopyridine (14 mg, 0.15 mmol), polystyrene carbodiimide (130 mg, 0.147 mmol, 1.12 mmol/g), and 1-hydroxybenzotriazole hydrate (20 mg, 0.15 mmol). The reaction mixture was stirred at room temperature under nitrogen for 12 h. The reaction was quenched by adding 1N HCl solution (5 mL) and brine (25 mL). The aqueous layer was extracted with methylene chloride (2×50 mL). The organic layer was separated, dried (MgSO$_4$), filtered and concentrated to give the crude product. The crude material was purified by preparative HPLC (10:90 acetonitrile/water to 60:40 acetonitrile/water with 0.05% TFA over 10 min, then isocratic) and lyophilized to afford (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(pyridin-3-yl)-5,6,6a,7,9,12,14,14a-octahydrobenzo[a]tetracene-2-carboxamide (5 mg, 9%) as a dark red solid. To a solution of this material in anhydrous methanol at 0° C. was added 1.25 N HCl in methanol (8 μL, 0.008 mmol) and the mixture was stirred at 0° C. for 30 min. The reaction mixture was concentrated, triturated with diethyl ether, and lyophilized from acetonitrile/water to afford (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-N-(pyridin-3-yl)-5,6,6a,7,9,12,14,14a-octahydrobenzo[a]tetracene-2-carboxamide hydrochloride (5 mg, 95%) as a red-brown powder and as a mixture of diastereomers: $^1$H NMR (500 MHz, CD$_3$OD) δ 9.43 (s, 1H), 8.55 (d, J=5.0 Hz, 1H), 8.43 (t, J=8.5 Hz, 1H), 8.10 (s, 1H), 7.99 (t, J=16.5 Hz, 1H), 6.70 (s, 1H), 6.17 (s, 0.4H), 6.02 (s, 0.6H), 4.94-4.83 (m, 2H), 3.72 (s, 3H), 3.67 (t, J=3.5 Hz, 1H), 3.63-3.60 (m, 1H), 3.57 (s, 3H), 3.51 (d, J=19.5 Hz, 3H), 3.47-3.37 (m, 2H), 3.26 (d, J=19.0 Hz, 1H), 3.09-2.99 (m, 1H), 2.25 (s, 3H), 1.26 (d, J=6.0 Hz, 1.8H), 1.22 (d, J=6.0 Hz, 1.2H); MS (ESI+) m/z 760 (M+H); HPLC 90.8% (AUC), $t_R$ 11.81 min.

Example 30

Preparation of (6R,6aS,14aR)—N-Benzyl-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide

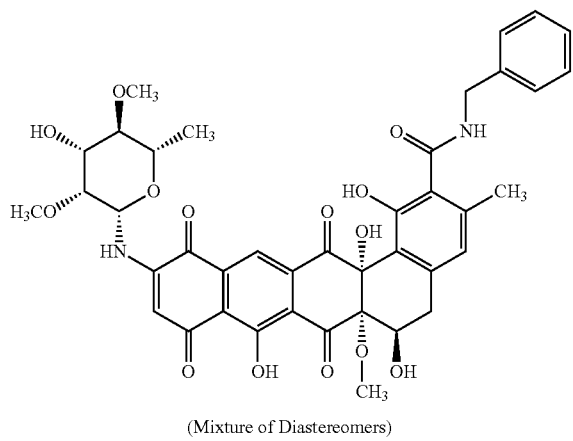 [SMILES: CO[C@@H]1[C@@H](O)[C@@H](OC)[C@@H](NC2=CC(=O)c3c(cc4c(c3O)C(=O)[C@]3(OC)[C@H](O)Cc5cc(C)c(C(=O)NCc6ccccc6)c(O)c5[C@]3(O)C4=O)C2=O)O[C@H]1C]

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (50 mg, 0.073 mmol) in THF (5 mL) was added benzyl amine (15 μL, 0.15 mmol), polystyrene carbodiimide (130 mg, 0.147 mmol, 1.12 mmol/g), and 1-hydroxybenzotriazole hydrate (20 mg, 0.15 mmol). The reaction mixture was stirred at room temperature under nitrogen for 12 h. The reaction was quenched by adding 1N HCl solution (5 mL) and brine (25 mL). The aqueous layer was extracted with methylene chloride (2×50 mL). The organic layer was separated, dried (MgSO$_4$), filtered and concentrated to give the crude product. The crude material was purified by preparative HPLC (10:90 acetonitrile/water to 60:40 acetonitrile/water with 0.05% TFA over 10 min, then isocratic) and lyophilized to afford (6R,6aS,14aR)—N-benzyl-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide (19 mg, 33%) as a red-brown powder and as a mixture of diastereomers: $^1$H NMR (500 MHz, CD$_3$OD) δ 8.12 (s, 1H) 7.32-7.21 (m, 5H), 6.61 (s, 1H), 5.99 (s, 1H), 4.96-4.87 (m, 2H), 4.53-4.33 (m, 2H), 3.75 (s, 3H), 3.75-3.72 (m, 1H), 3.64 (s, 2H), 3.57 (s, 3H), 3.47-3.38 (m, 4H), 3.25 (d, J=18.7 Hz, 1H), 3.06 (t, J=9.5 Hz, 1H), 2.19 (s, 3H), 1.27 (d, J=6.5 Hz, 3H); MS (ESI−) m/z 771 (M−H); HPLC >99% (AUC), $t_R$ 13.83 min.

Example 31

Preparation of (6R,6aS,14aR)-1,6,8,14a-Tetrahydroxy-11-((3R,4R,5R,6S)-4-hydroxy-3,5-dimethoxy-6-methyltetrahydro-2H-pyran-2-ylamino)-N-isopropyl-6a-methoxy-3-methyl-7,9,12,14-tetraoxo-5,6,6a,7,9,12,14,14a-octahydrobenzo[a]tetracene-2-carboxamide

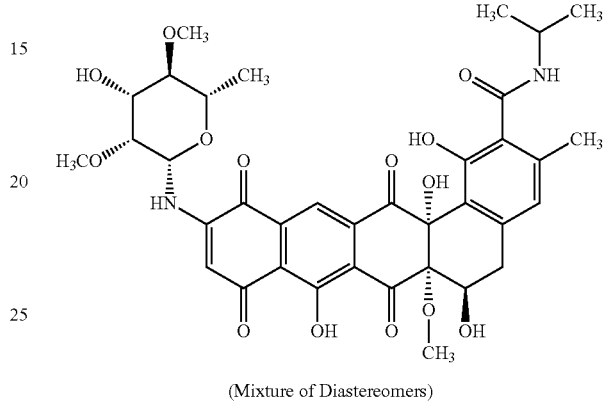

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (50 mg, 0.073 mmol) in THF (5 mL) was added 2-methylethylamine (12 μL, 0.15 mmol), polystyrene carbodiimide (130 mg, 0.147 mmol, 1.12 mmol/g), and 1-hydroxybenzotriazole hydrate (20 mg, 0.15 mmol). The reaction mixture was stirred at room temperature under nitrogen for 12 h. The reaction was quenched by adding 1N HCl solution (5 mL) and brine (25 mL). The aqueous layer was extracted with methylene chloride (2×50 mL). The organic layer was separated, dried (MgSO$_4$), filtered and concentrated to give the crude product. The crude material was purified by preparative HPLC (10:90 acetonitrile/water to 60:40 acetonitrile/water with 0.05% TFA over 10 min, then isocratic) and lyophilized to afford (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-N-isopropyl-6a-methoxy-3-methyl-7,9,12,14-tetraoxo-5,6,6a,7,9,12,14,14a-octahydrobenzo[a]tetracene-2-carboxamide (8 mg, 15%) as a red-brown powder and as a mixture of diastereomers: $^1$H NMR (500 MHz, CD$_3$OD) δ 8.11 (s, 1H) 6.59 (s, 1H), 6.19 (s, 0.2H), 5.95 (s, 0.8H), 4.97-4.89 (m, 2H), 4.10-4.03 (m, 1H), 3.75 (s, 3H), 3.73-3.69 (m, 1H), 3.64 (s, 2H), 3.59 (s, 3H), 3.57 (d, J=16.0 Hz, 3H), 3.47-3.35 (m, 1H), 3.23 (d, J=18.7 Hz, 1H), 3.09-3.02 (m, 1H), 2.22 (s, 3H), 1.27 (d, J=6.0 Hz, 2.4H), 1.23 (d, J=6.0 Hz, 0.6H), 1.14 (d, J=17.5 Hz, 6H); MS (ESI−) m/z 723 (M−H); HPLC >99% (AUC), $t_R$ 12.93 min.

Example 32

Preparation of Benzyl 2-((6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-N,3-dimethyl-7,9,12,14-tetraoxo-5,6,6a,7,9,12,14,14a-octahydrobenzo[a]tetracene-2-carboxamido)acetate

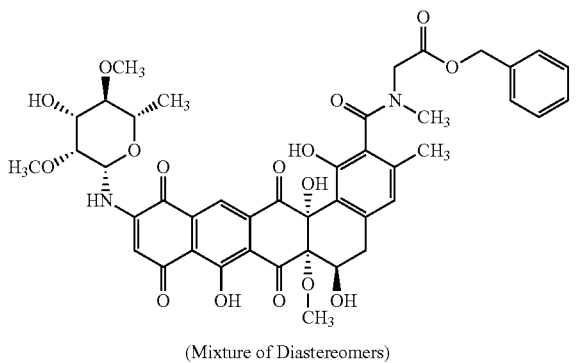 [SMILES: CO[C@@H]1[C@@H](O)[C@@H](OC)[C@@H](NC2=CC(=O)c3c(cc4c(c3O)C(=O)[C@]3(OC)[C@H](O)Cc5cc(C)c(C(=O)N(C)CC(=O)OCc6ccccc6)c(O)c5[C@]3(O)C4=O)C2=O)O[C@H]1C]

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (50 mg, 0.073 mmol) in THF (5 mL) was added benzyl 2-(methylamino)acetate (30 mg, 0.15 mmol), polystyrene carbodiimide (130 mg, 0.147 mmol, 1.12 mmol/g), and 1-hydroxybenzotriazole hydrate (20 mg, 0.15 mmol). The reaction mixture was stirred at room temperature under nitrogen for 12 h. The reaction was quenched by adding 1N HCl solution (5 mL) and brine (25 mL). The aqueous layer was extracted with methylene chloride (2×50 mL). The organic layer was separated, dried (MgSO$_4$), filtered and concentrated to give the crude product. The crude material was purified by preparative HPLC (10:90 acetonitrile/water to 60:40 acetonitrile/water with 0.05% TFA over 10 min, then isocratic) and lyophilized to afford benzyl 2-((6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-N,3-dimethyl-7,9,12,14-tetraoxo-5,6,6a,7,9,12,14,14a-octahydrobenzo[a]tetracene-2-carboxamido)acetate (17 mg, 23%) as a red-brown powder and as a mixture of diastereomers: $^1$H NMR (500 MHz, CDCl$_3$) δ 14.18 (s, 1H), 8.18 (s, 1H), 7.50-7.31 (m, 5H), 6.82 (d, J=8.0 Hz, 1H), 6.59 (s, 1H), 6.20 (s, 1H), 5.88 (s, 1H), 5.39-5.06 (m, 3H), 4.97-4.88 (m, 1H), 4.82-4.52 (m, 2H), 3.78 (s, 2H), 3.74 (s, 3H), 3.74-3.67 (m, 2H), 3.60 (s, 3H), 3.59-3.52 (m, 3H), 3.42 (s, 3H), 3.39-3.28 (m, 2H), 3.18-3.03 (m, 1H), 2.91 (s, 3H), 2.15 (s, 3H), 1.35 (d, J=6.5 Hz, 2H); MS (APCI−) m/z 843 (M−H); HPLC 97.2% (AUC), $t_R$ 12.84 min.

Example 33

Preparation of (6R,6aS,14aR)-3-Phenylpropyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

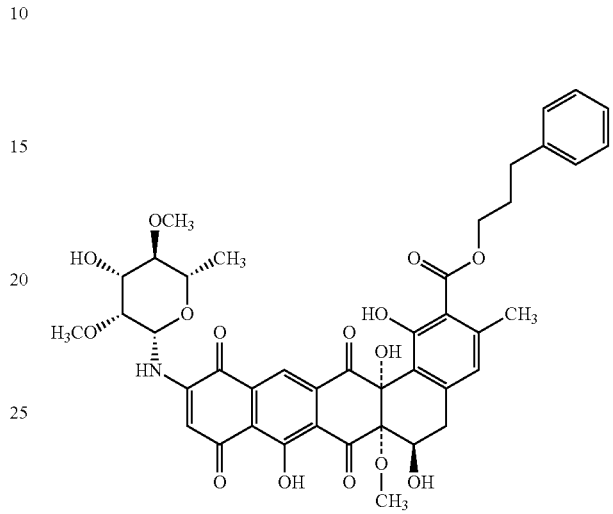

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (24 mg, 0.035 mmol) in acetone (3 mL) were added potassium carbonate (17 mg, 0.12 mmol), 3-phenylpropyl bromide (29 mg, 0.15 mmol) and a catalytic amount of potassium iodide (4 crystals), and then the reaction was heated to 70° C. under nitrogen. After 1.5 days, the reaction mixture was concentrated under reduced pressure. The crude product was purified by preparative TLC (silica gel, 95:5 chloroform/methanol) and then by semi-preparative HPLC (20:80 acetonitrile/water to 100% acetonitrile with 0.05% TFA over 40 min). The resulting product was lyophilized from acetonitrile (3 mL) and water (1 mL) to yield (6R,6aS,14aR)-3-phenylpropyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (3.8 mg, 14%) as a red-orange solid: $^1$H NMR (500 MHz, CDCl$_3$) δ 14.18 (s, 1H), 12.18 (s, 1H), 8.21 (s, 1H), 7.28-7.25 (m, 2H), 7.19-7.16 (m, 1H), 7.14-7.12 (d, J=7.5 Hz, 2H), 6.85 (d, J=9.0 Hz, 1H), 6.55 (s, 1H), 5.87 (s, 1H), 4.96 (d, J=6.0 Hz, 1H), 4.67 (d, J=6.0 Hz, 1H), 4.31-4.22 (m, 2H), 3.80 (s, 3H), 3.73-3.71 (dd, J=9.5, 3.0 Hz, 1H), 3.69 (s, 1H), 3.60 (s, 3H), 3.57 (dd, J=20.0, 6.5 Hz, 2H), 3.41 (s, 3H), 3.36-3.34 (m, 3H), 3.13 (t, J=9.5 Hz, 1H), 2.70 (t, J=7.5 Hz, 2H), 2.46 (s, 3H), 2.06-2.00 (m, 3H), 1.35 (d, J=6.0 Hz, 3H); MS (ESI+) m/z 802 (M+H); HPLC 98.8% (AUC), $t_R$ 16.81 min.

Example 34

Preparation of (6R,6aS,14aR)-Ethyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

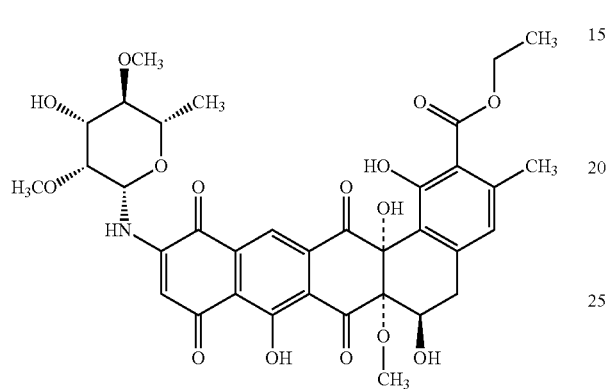

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (21 mg, 0.089 mmol) in methylene chloride (0.2 mL) at 0° C. were added polystyrene carbodiimide (45 mg, 0.050 mmol), absolute ethanol (1 mL) and a catalytic amount of 4-pyrrolidinopyridine (1 drop), and then the reaction was heated to 40° C. under nitrogen. After 4 h, the reaction mixture was filtered and concentrated under reduced pressure. The crude product was purified by preparative TLC (silica gel, 90:10 chloroform/methanol). The resulting product was lyophilized from acetonitrile (3 mL) and water (1 mL) to yield (6R,6aS,14aR)-ethyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (3.6 mg, 16%) as an orange solid: $^1$H NMR (500 MHz, CDCl$_3$) δ 14.17 (s, 1H), 12.18 (s, 1H), 8.21 (s, 1H), 6.85 (d, J=9.0 Hz, 1H), 6.53 (s, 1H), 5.87 (s, 1H), 5.20 (s, 1H), 4.96 (t, J=9.0 Hz, 1H), 4.67-4.65 (m, 2H), 4.37-4.25 (m, 2H), 3.79 (s, 3H), 3.73-3.71 (m, 2H), 3.61 (s, 3H), 3.57 (dd, J=19.5, 7.0 Hz, 1H), 3.40 (s, 3H), 3.37-3.32 (m, 2H), 3.13 (t, J=9.5 Hz, 2H), 2.42 (s, 3H), 1.37-1.32 (m, 6H); MS (ESI+) m/z 712 (M+H); HPLC 99.0% (AUC), $t_R$ 14.11 min.

Example 35

Preparation of (6R,6aS,14aR)-2-Morpholinoethyl 1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

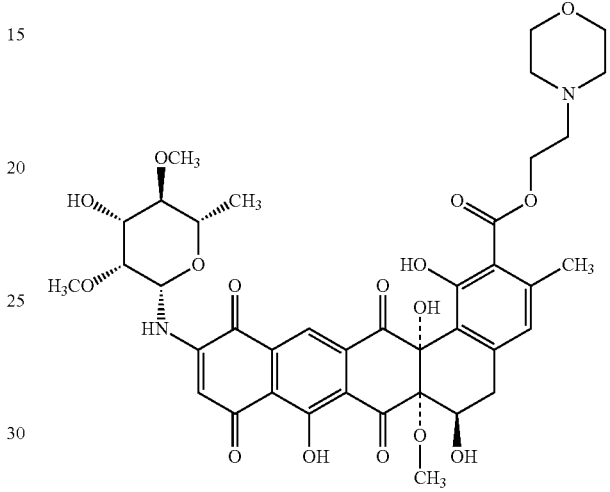

(Mixture of Diastereomers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid[2] (27 mg, 0.039 mmol) in methylene chloride (3 mL) at 0° C. were added polystyrene carbodiimide (57 mg, 0.063 mmol), 2-morpholinoethanol (0.3 mL, 2.5 mmol) and a catalytic amount of 4-pyrrolidinopyridine (1 drop) and then the reaction was heated to 40° C. under nitrogen. After 18 h, the reaction was filtered and concentrated under reduced pressure. The crude product was purified by preparative HPLC (10:90 acetonitrile/water to 60:40 acetonitrile/water with 0.05% TFA over 10 min, then isocratic). The resulting product was lyophilized from acetonitrile (3 mL) and water (1 mL) to yield (6R,6aS,14aR)-2-morpholinoethyl 1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (2.2 mg, 7.1%) as a mixture of diastereomers and as an orange solid: $^1$H NMR (500 MHz, CDCl$_3$) δ 14.21 (s, 1H), 8.18 (s, 1H), 6.84 (d, J=8.0 Hz, 0.8H), 6.54 (s, 1H), 6.22 (s, 0.2H), 6.18 (s, 0.2H), 5.87 (s, 0.8H), 5.22 (s, 1H), 4.96 (s, 1H), 4.67 (d, J=8.0 Hz, 2H), 3.79 (s, 3H), 3.73-3.70 (m, 2H), 3.60 (s, 3H), 3.58-3.49 (m, 5H), 3.40 (s, 3H), 3.36-3.32 (m, 2H), 3.13 (t, J=9.0 Hz, 1H), 2.48-2.47 (m, 2H), 2.38 (s, 3H), 1.35 (d, J=6.5 Hz, 3H), 1.33-1.25 (m, 7H); MS (ESI+) m/z 797 (M+H); HPLC 96.5% (AUC), $t_R$ 9.36 min.

Example 36

Preparation of (6R,6aS,14aR)-Isobutyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide

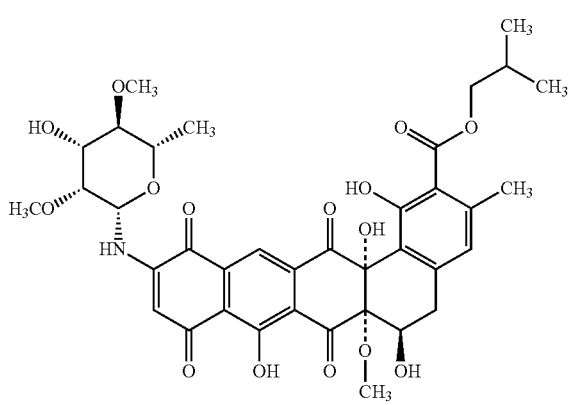 [SMILES: CO[C@@H]1[C@@H](O)[C@@H](OC)[C@@H](NC2=CC(=O)c3c(cc4c(c3O)C(=O)[C@]3(OC)[C@H](O)Cc5cc(C)c(C(=O)OCC(C)C)c(O)c5[C@]3(O)C4=O)C2=O)O[C@H]1C]

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid² (37 mg, 0.055 mmol) in methylene chloride (3 mL) at 0° C. were added polystyrene carbodiimide (74 mg, 0.083 mmol), 2-methyl propanol (1 mL, 10 mmol) and a catalytic amount of 4-pyrrolidinopyridine (2 drops) and the reaction was allowed to warm to room temperature under nitrogen. After 18 h, the reaction mixture was filtered and concentrated under reduced pressure. The crude product was purified by preparative TLC (silica gel, 90:10 chloroform/methanol). The resulting product was lyophilized from acetonitrile (3 mL) and water (1 mL) to yield (6R,6aS,14aR)-isobutyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxamide (11 mg, 26%) as an orange solid: ¹H NMR (500 MHz, CDCl₃) δ 14.17 (s, 1H), 12.26 (s, 1H), 8.21 (s, 1H), 6.85 (d, J=9.0 Hz, 1H), 6.53 (s, 1H), 5.87 (s, 1H), 5.21 (s, 1H), 4.96 (s, 1H), 4.68-4.67 (m, 2H), 4.11-4.08 (m, 1H), 4.00-3.98 (m, 1H), 3.79 (s, 3H), 3.72 (dd, J=9.5, 3.5 Hz, 1H), 3.69-3.68 (m, 1H), 3.61 (s, 3H), 3.58-3.56 (m, 2H), 3.41 (s, 3H), 3.36-3.32 (m, 2H), 3.13 (t, J=9.5 Hz, 1H), 2.44 (s, 3H), 2.05-1.97 (m, 1H), 1.35 (d, J=6.5 Hz, 3H), 0.97-0.95 (m, 6H); MS (ESI+) m/z 740 (M+H); HPLC 94.1% (AUC), $t_R$ 15.88 min.

Example 37

Preparation of (6R,6aS,14aR)-Benzyl 1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

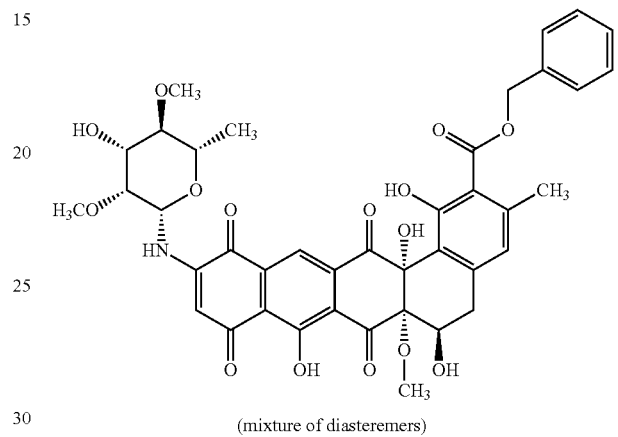

(mixture of diasteremers)

To a solution of (6R,6aS,14aR)-1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylic acid (80 mg, 0.12 mmol) in THF (1 mL) was added polystyrene-carbodiimide (208 mg, 0.24 mmol), 1-hydroxybenzotriazole hydrate (32 mg, 0.24 mmol) and benzyl alcohol (0.5 mL). The reaction mixture was stirred at room temperature under nitrogen for 17 h. The reaction was filtered through a micro filter and concentrated. The crude material was purified by preparative HPLC (10:90 acetonitrile/water to 60:40 acetonitrile/water with 0.05% TFA over 10 min, then isocratic) to afford (6R,6aS,14aR)-benzyl 1,6,8,14a-tetrahydroxy-11-((3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate as a mixture of diastereomers (14 mg, 20%) and as a dark red solid: ¹H NMR (500 MHz, CDCl₃) δ 14.26 (s, 0.3H), 14.17 (s, 0.7H), 12.09 (s, 0.3H), 12.08 (s, 0.7H), 8.32 (br s, 6H), 8.27 (s, 0.3H), 8.21 (s, 0.7H), 6.86 (d, J=8.0 Hz, 1H), 6.52 (s, 1H), 5.87 (s, 0.7H), 5.86 (s, 0.3H), 5.28 (s, 2H), 4.96 (d, J=8.0 Hz, 1H), 4.67 (d, J=8.0 Hz, 1H), 3.80 (s, 3H), 3.74-3.70 (m, 2H), 3.61 (s, 3H), 3.58-3.53 (m, 2H), 3.40 (s, 3H), 3.37-3.30 (m, 3H), 3.13 (t, J=9.0 Hz, 1H), 2.41 (s, 2H), 3.39 (s, 1H), 1.36 (d, J=6.5 Hz, 3H); MS (ESI+) m/z 774 (M+H); HPLC >99% (AUC), $t_R$ 15.52 min.

Example 38

Preparation of (6R,6aS,14aR)-Methyl 4-bromo-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

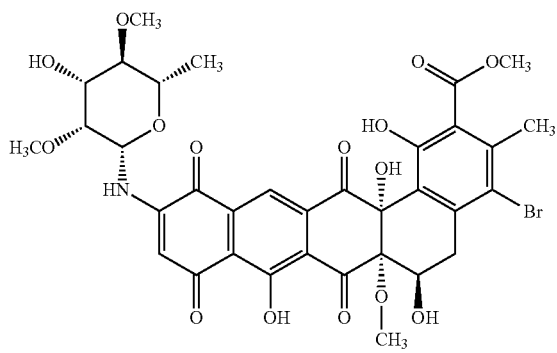

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (50 mg, 0.072 mmol) in chloroform (1 mL) was added N-bromosuccinimide (13 mg, 0.072 mmol) followed by benzoyl peroxide (1-2 mg). The reaction mixture was refluxed at 75° C. for 1 h. After cooled to room temperature, the reaction mixture was diluted with chloroform (10 mL) and washed with saturated sodium bicarbonate (5 mL). The aqueous layer was further extracted with chloroform (2×10 mL). The combined organics were dried ($Na_2SO_4$), filtered and concentrated. The crude material was purified by preparative TLC (silica gel, 95:5 chloroform/methanol) and semi-preparative HPLC to afford (6R,6aS,14aR)-methyl 4-bromo-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (20 mg, 36%) as a dark red solid: $^1$H NMR (500 MHz, $CDCl_3$) δ 14.22 (s, 1H), 11.62 (br s, 1H), 8.19 (s, 1H), 6.85 (d, J=9.0 Hz, 1H), 5.88 (s, 1H), 5.29 (s, 1H), 4.99 (s, 1H), 4.72 (s, 1H), 4.68 (d, J=8.5 Hz, 1H), 3.88 (s, 3H), 3.79 (s, 3H), 3.76-3.65 (m, 2H), 3.61 (s, 3H), 3.55 (d, J=6.5 Hz, 1H), 3.45 (d, J=20.5 Hz, 1H), 3.41 (s, 3H), 3.38-3.31 (m, 1H), 3.13 (t, J=9.5 Hz, 1H), 2.59 (s, 3H), 2.48 (d, J=4.5 Hz, 1H), 1.36 (d, J=6.0 Hz, 3H); MS (ESI+) m/z 776 (M+H); HPLC >99% (AUC), $t_R$ 14.64 min.

Example 39

Preparation of (6R,6aS,14aR)-Methyl 4,10-dibromo-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

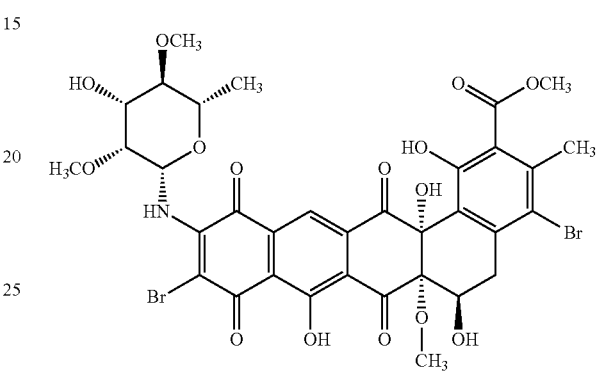

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (50 mg, 0.072 mmol) in chloroform (1 mL) was added N-bromosuccinimide (26 mg, 0.14 mmol) followed by benzoyl peroxide (1-2 mg). The reaction mixture was refluxed at 75° C. for 50 min. After cooled to room temperature, the reaction mixture was diluted with chloroform (10 mL) and washed with saturated sodium bicarbonate (5 mL). The aqueous layer was further extracted with chloroform (2×10 mL). The combined organics were dried ($Na_2SO_4$), filtered and concentrated. The crude material was purified by preparative TLC (silica gel, 95:5 chloroform/methanol) and semi-preparative HPLC to afford (6R,6aS,14aR)-methyl 4,10-dibromo-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (26 mg, 41%) as a brown-red solid: $^1$H NMR (500 MHz, $CDCl_3$) δ 13.78 (br s, 1H), 11.66 (br s, 1H), 8.19 (s, 1H), 7.11 (br s, 1H), 5.81 (d, J=9.0 Hz, 1H), 5.27 (s, 1H), 4.99 (s, 1H), 4.72 (s, 1H), 3.88 (s, 3H), 3.82 (s, 3H), 3.77-3.73 (m, 2H), 3.60 (s, 3H), 3.59-3.53 (m, 2H), 3.45 (d, J=20.5 Hz, 1H), 3.41 (s, 3H), 3.11 (t, J=9.0 Hz, 1H), 2.59 (s, 3H), 2.46 (d, J=4.0 Hz, 1H), 1.33 (d, J=6.0 Hz, 3H); MS (ESI+) m/z 854 (M+H); HPLC 91.1% (AUC), $t_R$ 16.86 min.

Example 40

Preparation of (6R,6aS,14aR)-Methyl 10-chloro-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate and (6R,6aS,14aR)-Methyl 4,10-dichloro-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

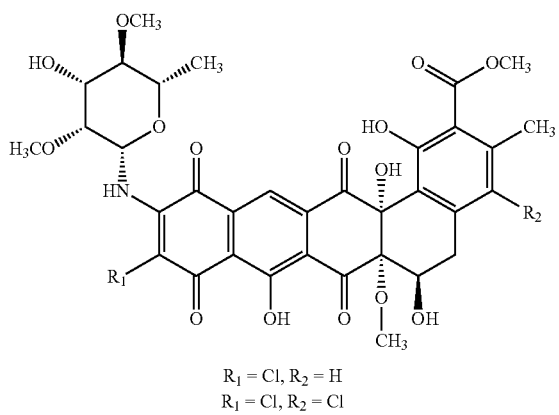

$R_1 = Cl, R_2 = H$
$R_1 = Cl, R_2 = Cl$

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in chloroform (2 mL) was added N-chlorosuccinimide (28 mg, 0.21 mmol) followed by benzoyl peroxide (1-2 mg). The reaction mixture was refluxed at 75° C. for 12 h, and then N-chlorosuccinimide (19 mg, 0.14 mmol) was refilled and the reaction mixture was refluxed for another 5 h. After cooled to room temperature, the reaction mixture was diluted with chloroform (10 mL) and washed with saturated sodium bicarbonate (5 mL). The aqueous layer was further extracted with chloroform (2×10 mL). The combined organics were dried (Na$_2$SO$_4$), filtered and concentrated. The crude material was purified by preparative TLC (silica gel, 95:5 chloroform/methanol) and semi-preparative HPLC to afford (6R,6aS,14aR)-methyl 10-chloro-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (13.3 mg, 14%) as a red solid: $^1$H NMR (500 MHz, CDCl$_3$) δ 13.72 (s, 1H), 12.11 (s, 1H), 8.22 (s, 1H), 7.11 (br s, 1H), 6.54 (s, 1H), 5.73 (s, 1H), 5.20 (s, 1H), 4.95 (s, 1H), 4.60 (s, 1H), 3.85 (s, 3H), 3.82 (s, 3H), 3.73 (s, 2H), 3.60 (s, 3H), 3.59-3.52 (m, 1H), 3.41 (s, 3H), 3.38-3.31 (m, 1H), 3.34 (d, J=19.5 Hz, 1H), 3.11 (t, J=9.5 Hz, 1H), 2.48 (br s, 1H), 2.41 (s, 3H), 1.36 (d, J=6.0 Hz, 3H); MS (ESI+) m/z 732 (M+H); HPLC 95.1% (AUC), $t_R$ 14.34 min; and (6R,6aS,14aR)-methyl 4,10-dichloro-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (3.6 mg, 3%) as a dark blue solid: $^1$H NMR (500 MHz, CDCl$_3$) δ 13.72 (s, 1H), 11.70 (br s, 1H), 8.20 (s, 1H), 7.11 (br s, 1H), 5.71 (s, 1H), 5.26 (s, 1H), 5.00 (s, 1H), 4.71 (s, 1H), 3.89 (s, 3H), 3.82 (s, 3H), 3.73 (s, 2H), 3.60 (s, 3H), 3.59-3.52 (m, 1H), 3.50-3.41 (m, 2H), 3.41 (s, 3H), 3.11 (t, J=9.0 Hz, 1H), 2.54 (s, 3H), 2.46 (s, 1H), 1.34 (d, J=6.0 Hz, 3H); MS (ESI+) m/z 766 (M+H); HPLC 92.8% (AUC), $t_R$ 15.63 min.

Example 41

Preparation of (6R,6aS,14aR)-Methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-4-nitro-7,9,12,14-tetraoxo-5,6,6a,7,9,12,14,14a-octahydrobenzo[a]tetracene-2-carboxylate

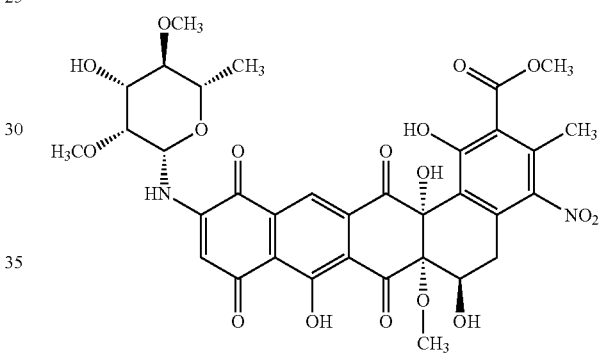

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in acetonitrile (1 mL) was added zirconyl(IV) nitrate hydrate (36 mg, 0.16 mmol). The reaction mixture was heated to 70° C. for 1 h. After cooled to room temperature, the reaction mixture was filtered through a micro filter and the filtrate was concentrated under reduced pressure. The crude material was purified by preparative TLC (silica gel, 96:4 chloroform/methanol) and semi-preparative HPLC to afford (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-4-nitro-7,9,12,14-tetraoxo-5,6,6a,7,9,12,14,14a-octahydrobenzo[a]tetracene-2-carboxylate (34 mg, 33%) as a dark red solid: $^1$H NMR (500 MHz, CDCl$_3$) δ 14.23 (s, 1H), 12.27 (br s, 1H), 8.19 (s, 1H), 6.86 (d, J=8.0 Hz, 1H), 5.89 (s, 1H), 5.31 (s, 1H), 5.19 (s, 1H), 4.69 (d, J=8.5 Hz, 1H), 4.61 (s, 1H), 3.91 (s, 3H), 3.79 (s, 3H), 3.76-3.65 (m, 2H), 3.61 (s, 3H), 3.49 (dd, J=19.5, 6.5 Hz, 1H), 3.40 (s, 3H), 3.39-3.35 (m, 1H), 3.28 (d, J=19.5 Hz, 1H), 3.13 (t, J=9.5 Hz, 1H), 2.47 (d, J=4.5 Hz, 1H), 2.40 (s, 3H), 1.36 (d, J=6.0 Hz, 3H); MS (ESI+) m/z 743 (M+H); HPLC 98.0% (AUC), $t_R$ 13.79 min.

Example 42

Preparation of (6R,6aS,14aR)-Methyl 4-amino-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate 2,2,2-trifluoroacetate

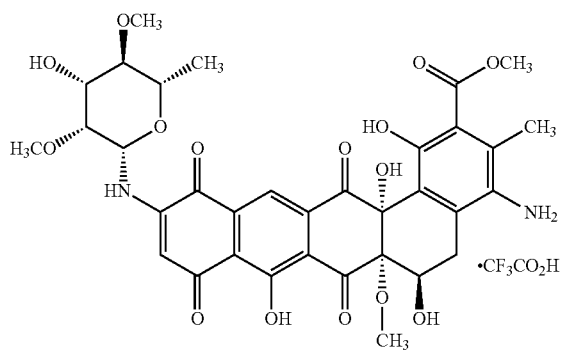

To a solution of (6R,6aS,14aR)-methyl 1,6,8,14a-tetrahydroxy-11-(4-hydroxy-3,5-dimethoxy-6-methyltetrahydro-2H-pyran-2-ylamino)-6a-methoxy-3-methyl-4-nitro-7,9,12,14-tetraoxo-5,6,6a,7,9,12,14,14a-octahydrobenzo[a]tetracene-2-carboxylate (105 mg, 0.140 mmol) in ethanol (2 mL) and THF (2 mL) was added palladium on carbon (10%, 30 mg), then the reaction mixture was shaked under a hydrogen atmosphere at 45 psi at ambient temperature for 12 h. The reaction mixture was filtered through diatomaceous earth and the pad was rinsed with chloroform. The filtrate was concentrated under reduced pressure. The crude material was purified by semi-preparative HPLC (20:80 acetonitrile/water to 100% acetonitrile with 0.05% TFA over 40 min) to afford (6R,6aS,14aR)-methyl 4-amino-1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate 2,2,2-trifluoroacetate (10 mg, 10%) as a red-brown solid: $^1$H NMR (500 MHz, CDCl$_3$) δ 14.20 (s, 1H), 10.76 (br s, 1H), 8.20 (s, 1H), 6.85 (d, J=9.0 Hz, 1H), 5.87 (s, 1H), 5.06 (d, J=6.5 Hz, 1H), 4.67 (d, J=8.0 Hz, 1H), 3.93 (s, 3H), 3.88 (s, 3H), 3.74-3.68 (m, 3H), 3.61 (s, 3H), 3.42 (s, 3H), 3.38-3.25 (m, 3H), 3.15-3.08 (m, 2H), 2.27 (s, 3H), 1.36 (d, J=6.0 Hz, 3H); MS (ESI+) m/z 713 (M+H); HPLC 96.5% (AUC), $t_R$ 12.03 min.

Example 43

Preparation of (6R,6aS,14aR)-Methyl 1,6,8,14a-tetrahydroxy-11-((2S,3R,4R,5R,6S)-4-hydroxy-3,5-dimethoxy-6-methyltetrahydro-2H-pyran-2-ylamino)-9-imino-6a-methoxy-3-methyl-7,12,14-trioxo-5,6,6a,7,9,12,14,14a-octahydrobenzo[a]tetracene-2-carboxylate

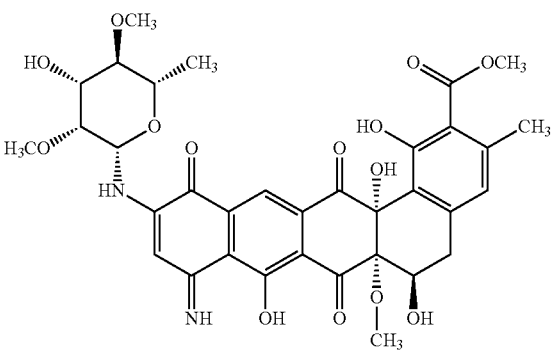 [SMILES: COC(=O)c1c(C)cc2c(c1O)[C@]1(O)C(=O)c3cc4c(c(O)c3C(=O)[C@]1(OC)[C@H](O)C2)C(=N)C=C(N[C@H]1O[C@@H](C)[C@H](OC)[C@@H](O)[C@H]1OC)C4=O]

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.143 mmol) in methanol (2 mL) was added 29.5% NH$_4$OH (0.1 mL) at room temperature, and the mixture was stirred under nitrogen for 2 h. 29.5% NH$_4$OH (0.1 mL) was refilled and the mixture was stirred for 3 h. The reaction mixture was quenched with a saturated solution of ammonium chloride and extracted with chloroform. The combined extracts were washed with brine, dried (Na$_2$SO$_4$), filtered and concentrated. The residue was purified by preparative TLC (silica gel, 90:10 chloroform/methanol) to afford (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-9-imino-6a-methoxy-3-methyl-7,12,14-trioxo-5,6,6a,7,9,12,14,14a-octahydrobenzo[a]tetracene-2-carboxylate (52 mg, 52%) as a blue solid: $^1$H NMR (500 MHz, CDCl$_3$) δ 15.80 (br s, 1H), 11.97 (s, 1H), 8.20 (br s, 1H), 7.90 (s, 1H), 6.90 (d, J=9.0 Hz, 1H), 6.49 (s, 1H), 5.27 (s, 1H), 5.00 (br s, 1H), 4.76 (br s, 1H), 4.70 (d, J=9.0 Hz, 1H), 3.84 (s, 3H), 3.79 (s, 3H), 3.75-3.67 (m, 2H), 3.60 (s, 3H), 3.58-3.54 (m, 2H), 3.40 (s, 3H), 3.32-3.28 (m, 2H), 3.12 (t, J=9.5 Hz, 1H), 2.54 (br s, 1H), 2.36 (s, 3H), 1.34 (d, J=5.5 Hz, 3H); MS (ESI+) m/z 697 (M+H); HPLC 96.6% (AUC), $t_R$ 10.34 min.

Example 44

Preparation of (6R,6aS,14aR,E)-Methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-9-(methylimino)-7,12,14-trioxo-5,6,6a,7,9,12,14,14a-octahydrobenzo[a]tetracene-2-carboxylate

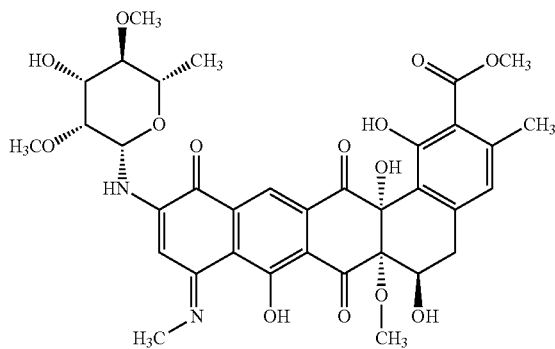 [SMILES: C/N=C1\C=C(N[C@H]2O[C@@H](C)[C@H](OC)[C@@H](O)[C@H]2OC)C(=O)c2cc3c(c(O)c21)C(=O)[C@]1(OC)[C@H](O)Cc2cc(C)c(C(=O)OC)c(O)c2[C@]1(O)C3=O]

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.143 mmol) in methanol (2 mL) was added methylamine (40% in water, 0.1 mL) at room temperature, and the mixture was stirred under nitrogen for 1 h. The reaction mixture was quenched with a saturated solution of ammonium chloride and extracted with chloroform. The combined extracts were washed with brine, dried ($Na_2SO_4$), filtered and concentrated. The residue was purified by preparative TLC (silica gel, 90:10 chloroform/methanol) to afford (6R,6aS,14aR,E)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-9-(methylimino)-7,12,14-trioxo-5,6,6a,7,9,12,14,14a-octahydrobenzo[a]tetracene-2-carboxylate (30 mg, 29%) as a blue solid: $^1$H NMR (500 MHz, $CDCl_3$) δ 11.94 (s, 1H), 7.88 (s, 1H), 7.01 (d, J=9.0 Hz, 1H), 6.49 (s, 1H), 5.91 (s, 1H), 5.26 (s, 1H), 5.00 (dd, J=10.0, 6.0 Hz, 1H), 4.75-4.72 (m, 2H), 3.82 (s, 3H), 3.79 (s, 3H), 3.75-3.68 (m, 2H), 3.61 (s, 3H), 3.57 (dd, J=19.5, 6.5 Hz, 1H), 3.40 (s, 3H), 3.39-3.36 (m, 1H), 3.34 (d, J=4.5 Hz, 3H), 3.29 (d, J=19.5 Hz, 1H), 3.15 (t, J=9.0 Hz, 1H), 2.52 (d, J=4.5 Hz, 1H), 2.36 (s, 3H), 1.38 (d, J=6.0 Hz, 3H); MS (ESI+) m/z 711 (M+H); HPLC 93.4% (AUC), $t_R$ 10.83 min.

Example 45

Preparation of (6R,6aS,14aR,E)-Methyl 1,6,8,14a-tetrahydroxy-11-((2S,3R,4R,5R,6S)-4-hydroxy-3,5-dimethoxy-6-methyltetrahydro-2H-pyran-2-ylamino)-9-(hydroxyimino)-6a-methoxy-3-methyl-7,12,14-trioxo-5,6,6a,7,9,12,14,14a-octahydrobenzo[a]tetracene-2-carboxylate

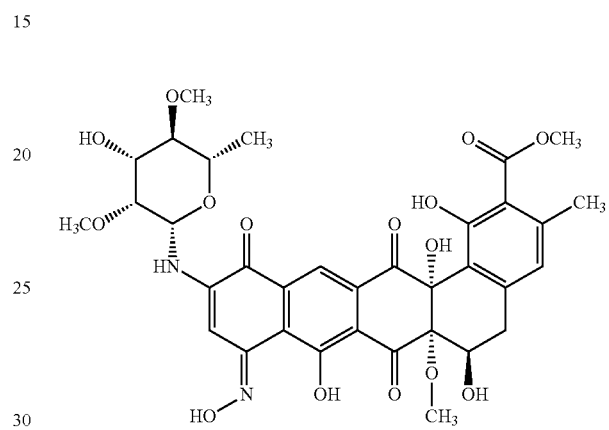

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.143 mmol) in methanol (1 mL) and pyridine (1 mL) was added hydroxylamine hydrochloride (100 mg, 1.43 mmol) at room temperature, and the mixture was stirred under nitrogen overnight. The mixture was diluted with ethyl acetate, washed with 1N HCl and brine, dried ($Na_2SO_4$), filtered and concentrated. The residue was purified by preparative TLC (silica gel, 95:5 chloroform/methanol) to afford (6R,6aS,14aR,E)-methyl 1,6,8,14a-tetrahydroxy-11-((2S,3R,4R,5R,6S)-4-hydroxy-3,5-dimethoxy-6-methyltetrahydro-2H-pyran-2-ylamino)-9-(hydroxyimino)-6a-methoxy-3-methyl-7,12,14-trioxo-5,6,6a,7,9,12,14,14a-octahydrobenzo[a]tetracene-2-carboxylate (17 mg, 16%) as an orange solid: $^1$H NMR (500 MHz, $CDCl_3$) δ 12.02 (s, 1H), 8.45 (s, 1H), 6.93 (s, 1H), 6.54 (s, 1H), 6.52 (d, J=9.0 Hz, 1H), 5.33 (br s, 1H), 5.00 (br s, 1H), 4.84-4.82 (m, 2H), 3.83 (s, 3H), 3.80 (s, 3H), 3.78-3.68 (m, 3H), 3.62 (s, 3H), 3.54 (dd, J=19.5, 6.5 Hz, 1H), 3.45-3.42 (m, 1H), 3.43 (s, 3H), 3.36 (d, J=19.5 Hz, 1H), 3.13 (t, J=9.5 Hz, 1H), 2.46 (d, J=5.0 Hz, 1H), 2.39 (s, 3H), 1.38 (d, J=6.0 Hz, 3H); MS (ESI+) m/z 713 (M+H); HPLC 95.0% (AUC), $t_R$ 12.31 min.

Example 46

Preparation of (6R,6aS,14aR,E)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-9-(2-methoxyethylimino)-3-methyl-7,12,14-trioxo-5,6,6a,7,9,12,14,14a-octahydrobenzo[a]tetracene-2-carboxylate

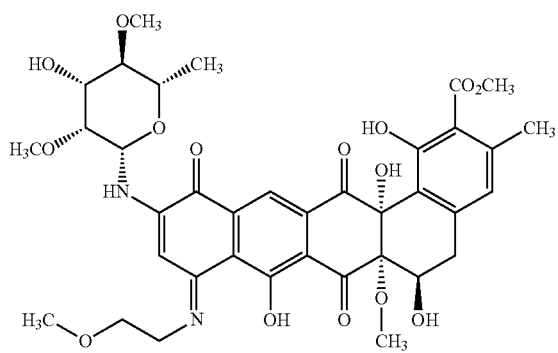 [SMILES: COCC/N=C1\C=C(N[C@H]2O[C@@H](C)[C@H](OC)[C@@H](O)[C@H]2OC)C(=O)c2cc3c(c(O)c21)C(=O)[C@]1(OC)[C@H](O)Cc2cc(C)c(C(=O)OC)c(O)c2[C@]1(O)C3=O]

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in methanol (3 mL) was added 2-methoxyethanamine (107 mg, 1.43 mmol). The reaction mixture was stirred at room temperature under nitrogen for 3 h. The reaction was quenched by adding saturated ammonium chloride solution (15 mL). Then it was extracted with chloroform (75 mL) and washed with water (2×25 mL). The organic layer was separated, dried (MgSO$_4$), filtered and concentrated to give the crude product. The crude material was purified by preparative TLC (silica gel, 90:10 chloroform/methanol) to afford (6R,6aS,14aR,E)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-9-(2-methoxyethylimino)-3-methyl-7,12,14-trioxo-5,6,6a,7,9,12,14,14a-octahydrobenzo[a]tetracene-2-carboxylate (33.8 mg, 31.2%) as a dark blue solid: $^1$H NMR (500 MHz, CDCl$_3$) δ 11.95 (s, 1H), 7.93 (s, 1H), 6.91 (d, J=8.5 Hz, 1H), 6.49 (s, 1H), 6.05 (s, 1H), 5.27 (s, 1H), 4.99 (t, J=8.0 Hz, 1H), 4.74-4.69 (m, 2H), 3.83 (s, 4H), 3.79 (s, 4H), 3.72-3.69 (m, 4H), 3.65-3.59 (m, 4H), 3.57-3.55 (m, 1H), 3.40 (s, 3H), 3.37 (s, 3H), 3.14 (t, J=9.1 Hz, 1H), 2.48 (d, J=3.8 Hz, 1H), 2.37 (s, 3H), 1.58 (br s, 1H), 1.37 (d, J=6.1 Hz, 3H); MS (ESI+) m/z 755 (M+H); HPLC 88.9% (AUC), $t_R$=11.14 min.

Example 47

Preparation of (6R,6aS,14aR,E)-Methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-9-(3-methoxypropylimino)-3-methyl-7,12,14-trioxo-5,6,6a,7,9,12,14,14a-octahydrobenzo[a]tetracene-2-carboxylate

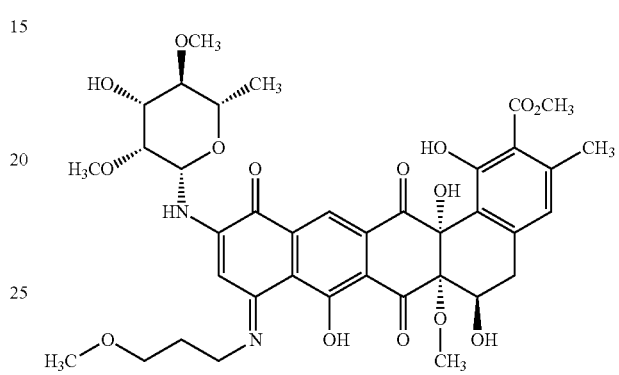

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in methanol (3 mL) was added 3-methoxypropan-1-amine (127 mg, 1.43 mmol). The reaction mixture was stirred at room temperature under nitrogen for 2 h. The reaction was quenched by adding saturated ammonium chloride solution (25 mL). Then it was extracted with chloroform (75 mL) and washed with water (2×25 mL). The organic layer was separated, dried (MgSO$_4$), filtered and concentrated to give the crude product. The crude material was purified by preparative TLC (silica gel, 90:10 chloroform/methanol) to afford (6R,6aS,14aR,E)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-9-(3-methoxypropylimino)-3-methyl-7,12,14-trioxo-5,6,6a,7,9,12,14,14a-octahydrobenzo[a]tetracene-2-carboxylate (53.3 mg, 48.3%) as a dark blue solid: $^1$H NMR (500 MHz, CDCl$_3$) δ 11.95 (s, 1H), 7.90 (s, 1H), 6.94 (d, J=8.8 Hz, 1H), 6.49 (s, 1H), 6.04 (s, 1H), 5.27 (s, 1H), 5.01-4.98 (m, 1H), 4.73 (d, J=8.6 Hz, 2H), 3.83 (s, 3H), 3.79 (s, 3H), 3.75-3.72 (m, 3H), 3.69-3.68 (m, 1H), 3.62 (s, 4H), 3.46 (t, J=6.1 Hz, 2H), 3.40 (s, 3H), 3.32 (s, 4H), 3.28 (s, 1H), 3.14 (t, J=9.2 Hz, 1H), 2.48 (d, J=4.9 Hz, 1H), 2.37 (s, 3H), 2.07-2.00 (m, 2H), 1.37 (d, J=6.2 Hz, 3H); MS (ESI+) m/z 769 (M+H); HPLC 89.1% (AUC), $t_R$=11.35 min.

Example 48

Preparation of (6R,6aS,14aR,E)-Methyl 1,6,8,14a-tetrahydroxy-11-((2S,3R,4R,5R,6S)-4-hydroxy-3,5-dimethoxy-6-methyltetrahydro-2H-pyran-2-ylamino)-9-(3-hydroxypropylimino)-6a-methoxy-3-methyl-7,12,14-trioxo-5,6,6a,7,9,12,14,14a-octahydrobenzo[a]tetracene-2-carboxylate

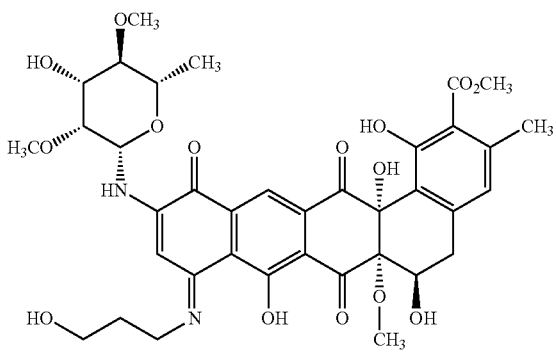

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in methanol (3 mL) was added 3-aminopropan-1-ol (107 mg, 1.43 mmol). The reaction mixture was stirred at room temperature under nitrogen for 2 h. The reaction was quenched by adding saturated ammonium chloride solution (25 mL). Then it was extracted with chloroform (75 mL) and washed with water (2×25 mL). The organic layer was separated, dried (MgSO$_4$), filtered and concentrated to give the crude product. The crude material was purified by preparative TLC (silica gel, 90:10 chloroform/methanol) to afford (6R,6aS,14aR,E)-methyl 1,6,8,14a-tetrahydroxy-11-((2S,3R,4R,5R,6S)-4-hydroxy-3,5-dimethoxy-6-methyltetrahydro-2H-pyran-2-ylamino)-9-(3-hydroxypropylimino)-6a-methoxy-3-methyl-7,12,14-trioxo-5,6,6a,7,9,12,14,14a-octahydrobenzo[a]tetracene-2-carboxylate (61.3 mg, 56.6%) as a dark blue solid: $^1$H NMR (500 MHz, CDCl$_3$) δ 11.94 (s, 1H), 7.89 (s, 1H), 6.94 (d, J=8.5 Hz, 1H), 6.48 (s, 1H), 6.12 (s, 1H), 5.27 (s, 1H), 5.02-4.99 (m, 1H), 4.74 (d, J=9.5 Hz, 2H), 4.12 (dd, J=14.2, 7.1 Hz, 2H), 3.83 (s, 3H), 3.81-3.72 (m, 9H), 3.68 (br s, 1H), 3.60 (s, 3H), 3.40 (s, 4H), 3.13 (t, J=9.1 Hz, 1H), 2.53 (s, 1H), 2.36 (s, 3H), 2.02-2.00 (m, 2H), 1.36 (d, J=6.0 Hz, 3H); MS (ESI+) m/z 755 (M+H); HPLC 97.5% (AUC), $t_R$=10.36 min.

Example 49

Preparation of (6R,6aS,14aR)-Methyl 1,6,8,14a-tetrahydroxy-11-((2S,3R,5R,6S)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate [Isomer A] and (6R,6aS,14aR)-Methyl 1,6,8,14a-tetrahydroxy-11-((2S,3R,5R,6S)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate [Isomer B]

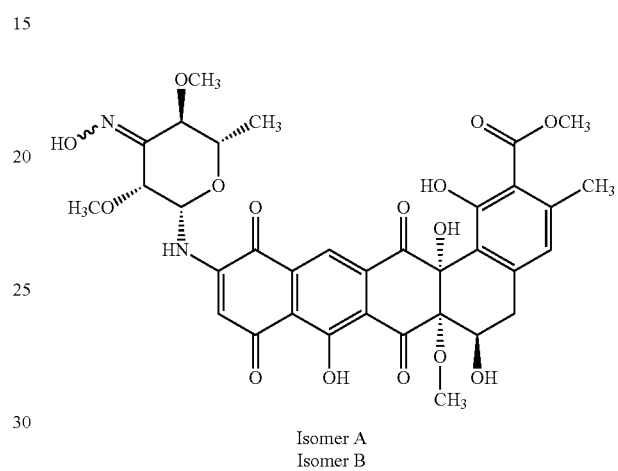

Isomer A
Isomer B

Step A: To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.143 mmol) in methylene chloride (2 mL) was added Dess-Martin periodinane (73 mg, 0.17 mmol) at room temperature, and the mixture was stirred under nitrogen for 3 h. The reaction mixture was quenched with a saturated solution of sodium bicarbonate and extracted with ethyl acetate. The combined extracts were washed with brine, dried (Na$_2$SO$_4$), filtered and concentrated to afford a ketone (83 mg, 83%) as a red solid: $^1$H NMR (500 MHz, CDCl$_3$) δ 14.05 (s, 1H), 12.10 (s, 1H), 8.22 (s, 1H), 6.99 (d, J=8.0 Hz, 1H), 6.54 (s, 1H), 5.89 (s, 1H), 5.20 (s, 1H), 4.96 (t, J=8.0 Hz, 1H), 4.81 (dd, J=8.0, 1.5 Hz, 1H), 4.66 (d, J=10.0 Hz, 1H), 3.90 (d, J=10.0 Hz, 1H), 3.84 (s, 3H), 3.77 (d, J=1.5 Hz, 1H), 3.61-3.52 (m, 2H), 3.55 (s, 3H), 3.53 (s, 3H), 3.41 (s, 3H), 3.34 (d, J=19.5 Hz, 1H), 2.40 (s, 3H), 1.46 (d, J=6.0 Hz, 3H); MS (ESI+) m/z 696 (M+H).

Step B: To a solution of the ketone from Step A (83 mg, 0.12 mmol) in methanol (1 mL) was added hydroxylamine hydrochloride (83 mg, 1.2 mmol) and pyridine (0.1 mL) at room temperature. The mixture was stirred under nitrogen for 4 h. The reaction mixture was quenched with 1N HCl and extracted with ethyl acetate. The combined extracts were washed with brine, dried (Na$_2$SO$_4$), filtered and concentrated. The residue was purified by preparative TLC (silica gel, 95:5 chloroform/methanol) to afford (6R,6aS,14aR)-methyl 1,6,8,14a-tetrahydroxy-11-((2S,3R,5R,6S)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (isomer A, 24 mg, 28%) as a red solid: $^1$H NMR (500 MHz, CDCl$_3$) δ 14.10 (s, 1H), 12.09 (s, 1H), 8.24 (s, 1H), 7.23 (d, J=8.0 Hz, 1H), 6.54 (s, 1H), 6.16 (s, 1H), 5.62 (t, J=8.0 Hz, 1H), 5.20 (s, 1H), 4.98 (d, J=7.0 Hz, 1H), 4.96 (dd, J=10.0, 7.0 Hz, 1H), 4.76-4.72 (m, 1H), 4.65 (d, J=10.0 Hz, 1H), 4.06 (d, J=7.0 Hz, 1H), 3.84 (s, 3H), 3.61 (s, 3H), 3.58 (dd, J=19.5, 6.5 Hz, 1H), 3.47 (s, 3H), 3.41 (s, 3H), 3.34 (d, J=19.5 Hz, 1H), 2.40 (s, 3H), 2.31 (d, J=3.0 Hz, 1H), 1.21 (d, J=6.0 Hz, 3H); MS (ESI+) m/z 711 (M+H); HPLC 93.1% (AUC), $t_R$ 14.01 min; and (6R,6aS,14aR)-methyl 1,6,8,14a-tetrahydroxy-11-((2S,3R,5R,6S)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (isomer B, 22 mg, 26%) as a red solid: $^1$H NMR (500 MHz, CDCl$_3$) δ 14.10 (s, 1H), 12.09 (s, 1H), 8.20 (s, 1H), 6.66 (d, J=8.0 Hz, 1H), 6.53 (s, 1H), 6.10 (s, 1H), 5.59 (dd, J=7.5, 1.0 Hz, 1H), 5.23 (s, 1H), 4.96 (dd, J=10.0, 7.0 Hz, 1H), 4.88 (d, J=1.0 Hz, 1H), 4.66 (d, J=10.0 Hz, 1H), 4.22-4.18 (m, 1H), 4.05 (d, J=7.0 Hz, 1H), 3.78 (s, 3H), 3.56 (dd, J=19.5, 6.5 Hz, 1H), 3.52 (s, 3H), 3.46 (s, 3H), 3.41 (s, 3H), 3.34 (d, J=19.5 Hz, 1H), 2.39 (s, 3H), 2.28 (d, J=3.0 Hz, 1H), 1.27 (d, J=6.0 Hz, 3H); MS (ESI+) m/z 711 (M+H); HPLC 98.8% (AUC), $t_R$ 14.16 min.

Example 50

Preparation of (6R,6aS,14aR)-Methyl 11-((2S,3R,5R,6S,Z)-3,5-dimethoxy-4-(methoxyimino)-6-methyltetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate

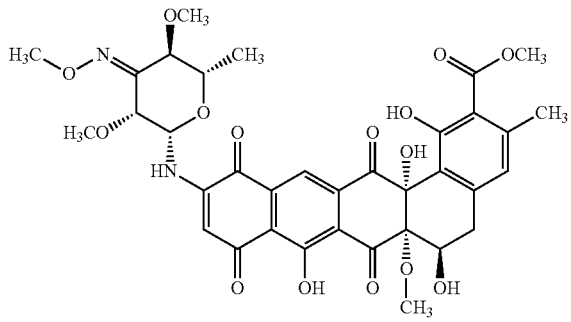

To a solution of the ketone from Step A of the preparation of (6R,6aS,14aR)-methyl 1,6,8,14a-tetrahydroxy-11-((2S,3R,5R,6S)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate [Isomer A] (Example 48) (53 mg, 0.076 mmol) in methanol (1 mL) was added methoxylamine hydrochloride (6.4 mg, 0.076 mmol) and pyridine (0.1 mL) at room temperature. The mixture was stirred under nitrogen for 2 h. The reaction mixture was quenched with 1N HCl and extracted with ethyl acetate. The combined extracts were washed with brine, dried (Na$_2$SO$_4$), filtered and concentrated. The residue was purified by preparative TLC (silica gel, 95:5 chloroform/methanol) to afford (6R,6aS,14aR)-methyl 11-((2S,3R,5R,6S,Z)-3,5-dimethoxy-4-(methoxyimino)-6-methyltetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate (30 mg, 54%) as a red solid: $^1$H NMR (500 MHz, CDCl$_3$) δ 14.15 (s, 1H), 12.09 (s, 1H), 8.20 (s, 1H), 7.00 (d, J=8.0 Hz, 1H), 6.54 (s, 1H), 5.86 (s, 1H), 5.21 (s, 1H), 4.98-4.94 (m, 2H), 4.67-4.64 (m, 2H), 3.97 (s, 3H), 3.84 (s, 3H), 3.71 (d, J=9.5 Hz, 1H), 3.59 (s, 3H), 3.57-3.52 (m, 2H), 3.47 (s, 3H), 3.40 (s, 3H), 3.34 (d, J=19.5 Hz, 1H), 2.40 (s, 3H), 1.38 (d, J=6.0 Hz, 3H); MS (ESI+) m/z 725 (M+H); HPLC 95.9% (AUC), $t_R$ 17.05 min.

Example 51

Preparation of 2-((Z)-((2S,3R,5R,6S)-3,5-Dimethoxy-2-methyl-6-((6R,6aS,14aR)-1,6,8,14a-tetrahydroxy-6a-methoxy-2-(methoxycarbonyl)-3-methyl-7,9,12,14-tetraoxo-5,6,6a,7,9,12,14,14a-octahydrobenzo[a]tetracen-11-ylamino)-2H-pyran-4(3H,5H,6H)-ylidene)aminooxy)acetic acid

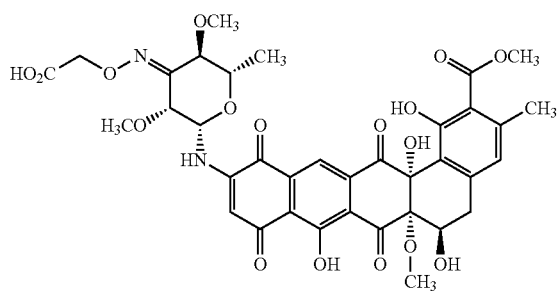 [SMILES: COC(=O)c1c(C)cc2c(c1O)[C@]1(O)C(=O)c3cc4c(c(O)c3C(=O)[C@]1(OC)[C@H](O)C2)C(=O)C=C(N[C@H]1O[C@@H](C)[C@H](OC)/C(=N/OCC(=O)O)[C@H]1OC)C4=O]

To a solution of the ketone from Step A of the preparation of (6R,6aS,14aR)-methyl 1,6,8,14a-tetrahydroxy-11-((2S,3R,5R,6S)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate [Isomer A](Example 48) (53 mg, 0.076 mmol) in methanol (1 mL) was added carboxymethoxylamine hemihydrochloride (8.3 mg, 0.076 mmol) and pyridine (0.1 mL) at room temperature. The mixture was stirred under nitrogen for 2 h. The reaction mixture was quenched with 1N HCl and extracted with ethyl acetate. The combined extracts were washed with brine, dried (Na$_2$SO$_4$), filtered and concentrated. The residue was purified by preparative TLC (silica gel, 90:10 chloroform/methanol) to afford 2-((Z)-((2S,3R,5R,6S)-3,5-dimethoxy-2-methyl-6-((6R,6aS,4aR)-1,6,8,14a-tetrahydroxy-6a-methoxy-2-(methoxycarbonyl)-3-methyl-7,9,12,14-tetraoxo-5,6,6a,7,9,12,14,14a-octahydrobenzo[a]tetracen-11-ylamino)-2H-pyran-4(3H,5H,6H)-ylidene)aminooxy)acetic acid (40 mg, 68%) as a red solid: $^1$H NMR (500 MHz, CDCl$_3$) δ 14.18 (s, 1H), 12.12 (s, 1H), 8.23 (s, 1H), 7.02 (d, J=8.0 Hz, 1H), 6.56 (s, 1H), 5.91 (s, 1H), 5.24 (br s, 1H), 5.07 (d, J=1.5 Hz, 1H), 4.99 (d, J=6.5 Hz, 1H), 4.82-4.74 (m, 3H), 4.70 (br s, 1H), 3.87 (s, 3H), 3.78 (d, J=9.5 Hz, 1H), 3.62-3.56 (m, 2H), 3.58 (s, 3H), 3.57 (s, 3H), 3.43 (s, 3H), 3.37 (d, J=19.5 Hz, 1H), 2.43 (s, 3H), 1.41 (d, J=6.0 Hz, 3H); MS (ESI+) m/z 769 (M+H); HPLC 93.9% (AUC), $t_R$ 14.32 min.

Example 52

Preparation of (6R,6aS,14aR)-Methyl 11-((2S,3R,5R,6S,Z)-4-(2-aminoethoxyimino)-3,5-dimethoxy-6-methyltetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate

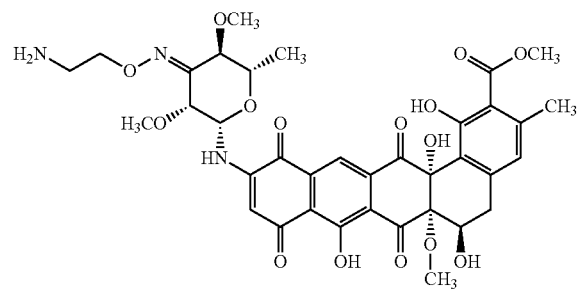 [SMILES: COC(=O)c1c(C)cc2c(c1O)[C@]1(O)C(=O)c3cc4c(c(O)c3C(=O)[C@]1(OC)[C@H](O)C2)C(=O)C=C(N[C@H]1O[C@@H](C)[C@H](OC)/C(=N/OCCN)[C@H]1OC)C4=O]

To a solution of the ketone from Step A of the preparation of (6R,6aS,14aR)-methyl 1,6,8,14a-tetrahydroxy-11-((2S,3R,5R,6S)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate [Isomer A](Example 48) (50 mg, 0.072 mmol) in methanol (1 mL) was added 2-(aminooxy)-1-ethanaminum dihydrochloride (10.7 mg, 0.072 mmol) and pyridine (0.1 mL) at room temperature. The mixture was stirred under nitrogen for 6 h. The reaction mixture was quenched with a saturated solution of sodium bicarbonate and extracted with ethyl acetate. The combined extracts were washed with brine, dried ($Na_2SO_4$), filtered and concentrated. The residue was purified by preparative TLC (silica gel, 90:10 chloroform/methanol) to afford (6R,6aS,14aR)-methyl 11-((2S,3R,5R,6S,Z)-4-(2-aminoethoxyimino)-3,5-dimethoxy-6-methyltetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate (18 mg, 33%) as a brown solid: $^1$H NMR (500 MHz, $CDCl_3$) δ 8.20 (s, 1H), 7.00 (br s, 1H), 6.53 (s, 1H), 5.93 (s, 1H), 4.98 (d, J=1.5 Hz, 1H), 4.95 (d, J=6.0 Hz, 1H), 4.87 (br s, 1H), 4.29-4.26 (m, 3H), 3.83 (s, 3H), 3.74-3.70 (m, 2H), 3.61-3.54 (m, 2H), 3.58 (s, 3H), 3.47 (s, 3H), 3.40 (s, 3H), 3.34 (d, J=19.5 Hz, 1H), 3.11-3.06 (m, 2H), 2.40 (s, 3H), 1.37 (d, J=6.0 Hz, 3H), 1.24 (t, J=7.0 Hz, 2H); MS (ESI+) m/z 754 (M+H); HPLC 95.6% (AUC), $t_R$ 10.86 min.

Example 53

Preparation of (6aS,14aR,E)-Methyl 1,8,14a-trihydroxy-6-(hydroxyimino)-11-((2S,3R,5R,6S,Z)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate

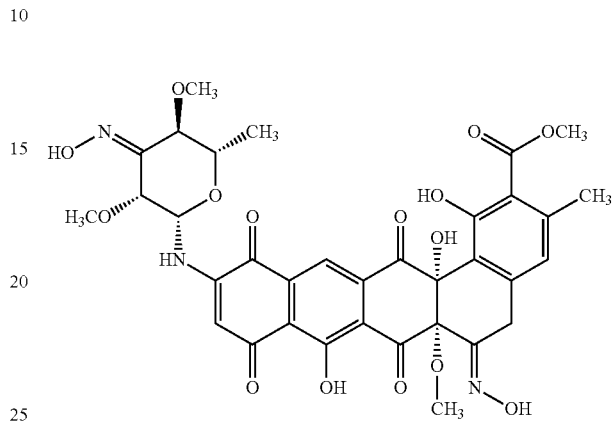

Step A: To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (200 mg, 0.287 mmol) in methylene chloride (4 mL) was added Dess-Martin periodinane (365 mg, 0.86 mmol) at room temperature, and the mixture was stirred under nitrogen for 2 h. The reaction mixture was quenched with a saturated solution of sodium bicarbonate and extracted with ethyl acetate. The combined extracts were washed with brine, dried ($Na_2SO_4$), filtered and concentrated to afford a diketone (120 mg, 60%) as a red solid: $^1$H NMR (500 MHz, $CDCl_3$) δ 14.04 (s, 1H), 12.10 (s, 1H), 8.31 (s, 1H), 7.03 (d, J=8.0 Hz, 1H), 6.58 (s, 1H), 5.91 (s, 1H), 4.83 (d, J=8.0 Hz, 1H), 3.96 (d, J=22.0 Hz, 1H), 3.91-3.50 (m, 4H), 3.86 (s, 3H), 3.85 (d, J=22.0 Hz, 1H), 3.55 (s, 3H), 3.54 (s, 3H), 3.52 (s, 3H), 2.43 (s, 3H), 1.45 (d, J=6.0 Hz, 3H); MS (ESI+) m/z 694 (M+H).

Step B: To a solution of the diketone from Step A (112 mg, 0.162 mmol) in methanol (2 mL) was added hydroxylamine hydrochloride (23 mg, 0.33 mmol) and pyridine (0.1 mL) at room temperature. The mixture was stirred under nitrogen for 4 h. The reaction mixture was quenched with 1N HCl and extracted with ethyl acetate. The combined extracts were washed with brine, dried ($Na_2SO_4$), filtered and concentrated. The residue was purified by preparative TLC (silica gel, 90:10 chloroform/methanol) to afford (6aS,14aR,E)-methyl 1,8,14a-trihydroxy-6-(hydroxyimino)-11-((2S,3R,5R,6S,Z)-4-(hydroxyimino)-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (68 mg, 58%) as a red solid: $^1$H NMR (500 MHz, $CDCl_3$) δ 14.05 (s, 1H), 12.04 (s, 1H), 8.32 (s, 1H), 7.60 (br s, 1H), 7.52 (br s, 1H), 7.04 (d, J=8.0 Hz, 1H), 6.61 (s, 1H), 5.88 (s, 1H), 5.05 (s, 1H), 4.75 (br s, 1H), 4.70 (d, J=8.0 Hz, 1H), 4.36 (d, J=22.0 Hz, 1H), 3.84 (s, 3H), 3.83 (d, J=22.0 Hz, 1H), 3.77-3.73 (m, 1H), 3.58 (s, 3H), 3.56-3.50 (m, 1H), 3.52 (s, 3H), 3.46 (s, 3H), 2.41 (s, 3H), 1.40 (d, J=6.0 Hz, 3H); MS (ESI+) m/z 724 (M+H); HPLC 97.2% (AUC), $t_R$ 13.52 min.

Example 54

Preparation of (6R,6aS,14aR)-Methyl 11-((2S,3R, 4R,5S,6S)-3,5-dimethoxy-6-methyl-4-((2S,3R,4S, 5S,6R)-3,4,5-trihydroxy-6-(hydroxymethyl)tetrahydro-2H-pyran-2-yloxy)tetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate

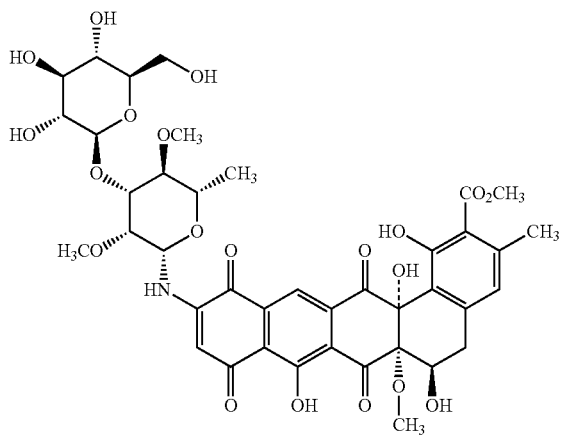 [SMILES: COC(=O)c1c(C)cc2c(c1O)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O[C@@H]2O[C@H](CO)[C@@H](O)[C@H](O)[C@H]2O)[C@H]1OC)C4=O]

Step A: A mixture of (2R,3R,4S,5R)-2-(acetoxymethyl)-6-(2,2,2-trichloro-1-iminoethoxy)-tetrahydro-2H-pyran-3,4,5-triyl triacetate (25 mg, 0.050 mmol), (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (35 mg, 0.050 mmol) and 4 Å molecular sieves (10 mg) in dichloromethane (1 mL) was stirred at room temperature under nitrogen for 1 h. Then borontrifluoride diethyl etherate (3 µL, 0.02 mmol) was added at −42° C. The reaction mixture was stirred at −42° C. for 4 h, quenched with sodium bicarbonate (20 mg), filtered through diatomaceous earth and concentrated. The crude product was purified by preparative TLC (95:5 dichloromethane/methanol) and semi-preparative HPLC (45:55 acetonitrile/water with 0.05% TFA) to afford (2R,3R,4S,5R,6R)-2-(acetoxymethyl)-6-((2S,3S,4R,5R,6S)-3,5-dimethoxy-2-methyl-6-((6R,6aS,14aR)-1,6,8,14a-tetrahydroxy-6a-methoxy-2-(methoxycarbonyl)-3-methyl-7,9,12,14-tetraoxo-5,6,6a,7,9,12,14,14a-octahydrobenzo[a]tetracen-11-ylamino)tetrahydro-2H-pyran-4-yloxy)tetrahydro-2H-pyran-3,4,5-triyl triacetate (17 mg, 32%) as a red solid: $^1$H NMR (500 MHz, CDCl$_3$) δ 14.20 (s, 1H), 12.10 (s, 1H), 8.20 (s, 1H), 6.83 (d, J=8.8 Hz, 1H), 6.53 (s, 1H), 5.85 (s, 1H), 5.23 (t, J=9.5 Hz, 1H), 5.22 (br s, 1H), 5.13 (t, J=9.7 Hz, 1H), 5.07 (dd, J=9.3, 8.2 Hz, 1H), 4.96 (d, J=6.4 Hz, 1H), 4.84 (d, J=7.9 Hz, 1H), 4.66 (br s, 1H), 4.62 (d, J=8.8 Hz, 1H), 4.20 (d, J=3.2 Hz, 2H), 3.84 (s, 3H), 3.73 (s, 3H), 3.72-3.64 (m, 3H), 3.56 (dd, J=19.7, 6.7 Hz, 1H), 3.50 (s, 3H), 3.40 (s, 3H), 3.33 (d, J=20.1 Hz, 1H), 3.30-3.25 (m, 1H), 3.17 (t, J=9.3 Hz, 1H), 2.40 (s, 3H), 2.06 (s, 3H), 2.04 (s, 3H), 2.03 (s, 3H), 2.02 (s, 3H), 1.33 (d, J=6.1 Hz, 3H); MS (ESI+) m/z 1028 (M+H); HPLC 97.7% (AUC), t$_R$ 19.30 min.

Step B: A mixture of (2R,3R,4S,5R,6R)-2-(acetoxymethyl)-6-((2S,3S,4R,5R,6S)-3,5-dimethoxy-2-methyl-6-((6R,6aS,14aR)-1,6,8,14a-tetrahydroxy-6a-methoxy-2-(methoxycarbonyl)-3-methyl-7,9,12,14-tetraoxo-5,6,6a,7,9,12,14,14a-octahydrobenzo[a]tetracen-11-ylamino)tetrahydro-2H-pyran-4-yloxy)tetrahydro-2H-pyran-3,4,5-triyl triacetate (44 mg, 0.043 mmol) and potassium carbonate (24 mg, 0.17 mmol) in methanol (4 mL) was stirred at room temperature under nitrogen for 4 h. The reaction mixture was concentrated under reduced pressure. The crude product was purified by semi-preparative HPLC (20:80 acetonitrile/water to 60:40 acetonitrile/water with 0.05% TFA over 30 min) to afford (6R,6aS,14aR)-methyl 11-((2S,3R,4R,5S,6S)-3,5-dimethoxy-6-methyl-4-((2S,3R,4S,5S,6R)-3,4,5-trihydroxy-6-(hydroxymethyl)tetrahydro-2H-pyran-2-yloxy)tetrahydro-2H-pyran-2-ylamino)-1,6,8,14a-tetrahydroxy-6a-methoxy-3-methyl-7,9,12,14-tetraoxo-5,6,6a,7,9,12,14,14a-octahydrobenzo[a]tetracene-2-carboxylate (18 mg, 49%) as an orange-red solid: $^1$H NMR (500 MHz, CD$_3$OD) δ 8.09 (s, 1H), 6.61 (s, 1H), 5.94 (s, 1H), 4.92 (s, 1H), 4.52 (d, J=8.0 Hz, 1H), 3.96-3.85 (m, 3H), 3.79 (s, 3H), 3.75 (s, 3H), 3.65-3.61 (m, 2H), 3.60 (s, 3H), 3.55-3.36 (m, 3H), 3.35 (s, 3H), 3.22-3.15 (m, 5H), 2.38 (s, 3H), 1.25 (d, J=6.0 Hz, 3H); MS (ESI+) m/z 860 (M+H); HPLC 97.6% (AUC), t$_R$ 10.95 min.

Example 55

Preparation of (6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3,12-dimethyl-7,9,14-trioxo-5, 6,6a,7,9,12,14,14a-octahydrobenzo[a]tetracene-2-carboxylate [Diastereomer A] and [Diastereomer B]

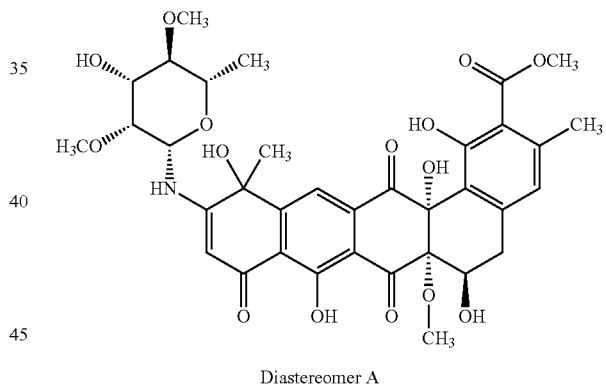

Diastereomer A
Diastereomer B

To a −78° C. solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in THF (4 mL) was added a solution of methylmagnesium bromide in diethyl ether (3 M, 0.37 mL, 1.12 mmol) dropwise. The reaction mixture was stirred at −78° C. for 5 h, and then quenched with a saturated solution of ammonium chloride. The mixture was extracted with chloroform (3×20 mL). The combined organics were dried (Na$_2$SO$_4$), filtered and concentrated. The crude was purified by preparative TLC (silica gel, 95:5 chloroform/methanol), and then the diastereomers were separated by preparative HPLC (Chiralpak AD column, 40:60 heptane/ethanol with 0.1% diethylamine) to afford (6R,6aS,14aR)-methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3,12-dimethyl-7,9,14-trioxo-5,6,6a,7,9,12,14,14a-octahydrobenzo[a]tetracene-2-carboxylate (diastereomer A, 39 mg, 39%) as a yellow solid: $^1$H NMR (500 MHz, CDCl$_3$) δ 15.20 (br s, 1H), 11.75 (br s, 1H), 7.82 (s, 1H), 6.78 (s, 1H), 6.53 (s, 1H), 5.45 (s, 1H), 5.22 (s, 1H), 4.96 (s, 1H), 4.80-4.61 (m, 2H), 3.81 (s, 3H), 3.76 (s, 3H), 3.71 (dd, J=9.0, 2.5 Hz, 1H), 3.64 (s, 1H), 3.60 (s, 3H), 3.59-3.52 (m, 1H), 3.42 (s, 3H), 3.35-3.29 (m, 2H), 3.16 (t, J=9.0 Hz, 1H), 2.95 (br s, 1H), 2.48 (br s, 1H), 2.38 (s, 3H), 1.79 (s, 3H), 1.37 (d, J=6.0 Hz, 3H); MS (ESI+) m/z 714 (M+H); HPLC >99% (AUC), $t_R$ 11.18 min; and (6R,6aS,14aR)-methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3,12-dimethyl-7,9,14-trioxo-5,6,6a,7,9,12,14,14a-octahydrobenzo[a]tetracene-2-carboxylate (diastereomer B, 13 mg, 13%) as a yellow solid: $^1$H NMR (500 MHz, CDCl$_3$) δ 15.10 (br s, 1H), 12.02 (br s, 1H), 7.84 (s, 1H), 6.73 (d, J=8.5 Hz, 1H), 6.54 (s, 1H), 5.48 (s, 1H), 5.25 (s, 1H), 4.98 (s, 1H), 4.78-4.63 (m, 2H), 3.85 (s, 3H), 3.79 (s, 3H), 3.72 (s, 2H), 3.59 (s, 5H), 3.38 (s, 4H), 3.32 (d, J=19.0 Hz, 1H), 3.10 (t, J=9.0 Hz, 1H), 2.49 (br s, 1H), 2.41 (s, 3H), 1.65 (s, 3H), 1.32 (d, J=6.0 Hz, 3H); MS (ESI+) m/z 714 (M+H); HPLC 98.1% (AUC), $t_R$ 11.45 min.

Example 56

Preparation of (6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-12-phenyl-5,6,6a,7,9,12,14,14a-octahydrobenzo[a]tetracene-2-carboxylate [Diastereomer A] and [Diastereomer B]

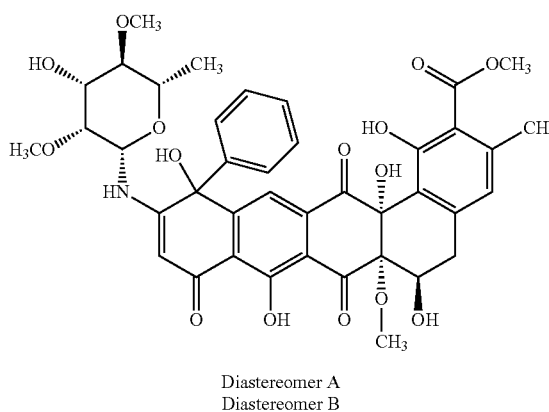 [SMILES: COC(=O)c1c(C)cc2c(c1O)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O)[C@H]1OC)C4(O)c1ccccc1]

Diastereomer A
Diastereomer B

To a −78° C. solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (50 mg, 0.072 mmol) in THF (2 mL) was added a solution of phenylmagnesium bromide in THF (1M, 0.72 mL, 0.72 mmol) dropwise. The reaction mixture was stirred at −78° C. for 3 h, and then quenched with a saturated solution of ammonium chloride. The mixture was extracted with chloroform (3×15 mL). The combined organics were dried (Na$_2$SO$_4$), filtered and concentrated. The crude was purified by preparative TLC (silica gel, 95:5 chloroform/methanol) twice to afford (6R,6aS,14aR)-methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-12-phenyl-5,6,6a,7,9,12,14,14a-octahydrobenzo[a]tetracene-2-carboxylate (diastereomer A, 8 mg, 14%) as a yellow solid: $^1$H NMR (500 MHz, CDCl$_3$) δ 15.16 (s, 1H), 11.96 (s, 1H), 7.62 (s, 1H), 7.56-7.53 (m, 2H), 7.37-7.29 (m, 3H), 6.52 (s, 1H), 6.26 (d, J=8.5 Hz, 1H), 5.66 (s, 1H), 5.19 (s, 1H), 4.94 (t, J=6.5 Hz, 1H), 4.70 (d, J=9.5 Hz, 1H), 4.64 (d, J=8.5 Hz, 1H), 3.80 (s, 3H), 3.65 (s, 4H), 3.60-3.52 (m, 2H), 3.52 (s, 3H), 3.39 (s, 3H), 3.35-3.13 (m, 3H), 3.00 (t, J=9.0 Hz, 1H), 2.48 (d, J=4.0 Hz, 1H), 2.38 (s, 3H), 1.24 (d, J=6.0 Hz, 3H); MS (ESI+) m/z 776 (M+H); HPLC 97.5% (AUC), $t_R$ 13.23 min; and (6R,6aS,14aR)-methyl 1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-12-phenyl-5,6,6a,7,9,12,14,14a-octahydrobenzo[a]tetracene-2-carboxylate (diastereomer B, 5 mg, 9%) as a yellow solid: $^1$H NMR (500 MHz, CDCl$_3$) δ 15.07 (s, 1H), 11.58 (s, 1H), 7.51 (s, 1H), 7.37-7.35 (m, 2H), 7.28-7.24 (m, 3H), 6.48 (s, 1H), 6.31 (d, J=9.0 Hz, 1H), 5.64 (s, 1H), 5.16 (s, 1H), 4.95 (t, J=6.5 Hz, 1H), 4.70-4.62 (m, 2H), 3.81 (s, 3H), 3.56 (s, 4H), 3.60-3.45 (m, 2H), 3.39 (s, 3H), 3.38 (s, 3H), 3.35-3.17 (m, 3H), 3.02 (t, J=9.0 Hz, 1H), 2.36 (s, 4H), 1.31 (d, J=6.0 Hz, 3H); MS (ESI+) m/z 776 (M+H); HPLC 93.7% (AUC), $t_R$ 12.64 min.

Example 57

Preparation of (6R,6aS,14aR)-Methyl 12-ethyl-1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-5,6,6a,7,9,12,14,14a-octahydrobenzo[a]tetracene-2-carboxylate [Diastereomer A] and [Diastereomer B]

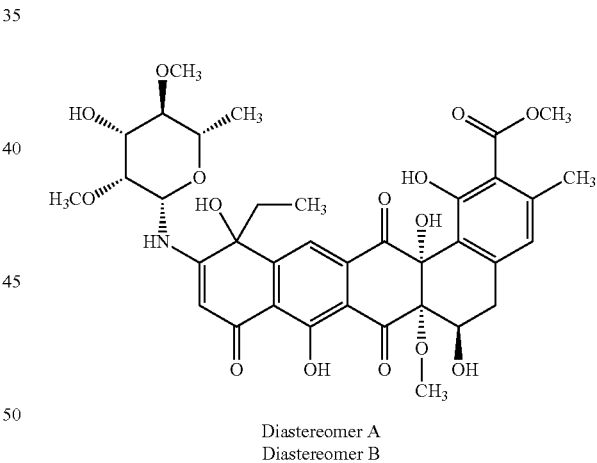

Diastereomer A
Diastereomer B

To a −78° C. solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (100 mg, 0.14 mmol) in THF (4 mL) was added a solution of ethylmagnesium bromide in THF (1M, 1.12 mL, 1.12 mmol) dropwise. The reaction mixture was stirred at −78° C. for 5 h, and then quenched with a saturated solution of ammonium chloride. The mixture was extracted with chloroform (3×20 mL). The combined organics were dried (Na$_2$SO$_4$), filtered and concentrated. The crude was purified by preparative TLC (silica gel, 95:5 chloroform/methanol), and then the diastereomers were separated by preparative HPLC (Chiralpak AD column, 40:60 heptane/ethanol with 0.1% diethylamine) to afford (6R,6aS,14aR)-methyl 12-ethyl-1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-5,6,6a,7,9,12,14,14a-octahydrobenzo[a]tetracene-2-carboxylate (diastereomer A, 29 mg, 28%) as a yellow solid: $^1$H NMR (500 MHz, CDCl$_3$) δ 7.79 (s, 1H), 6.80 (br s, 1H), 6.51 (s, 1H), 5.52 (s, 1H), 4.98 (d, J=5.0 Hz, 1H), 4.65 (s, 1H), 3.80 (s, 3H), 3.79 (s, 3H), 3.78-3.62 (m, 3H), 3.58 (s, 3H), 3.40 (s, 3H), 3.39-3.22 (m, 3H), 3.14 (t, J=9.0 Hz, 1H), 2.80 (br s, 1H), 2.36 (s, 3H), 2.12-2.01 (m, 2H), 1.35 (d, J=6.0 Hz, 3H), 0.72 (t, J=7.0 Hz, 3H); MS (ESI+) m/z 728 (M+H); HPLC 98.1% (AUC), $t_R$ 11.84 min; and (6R,6aS,14aR)-methyl 12-ethyl-1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-5,6,6a,7,9,12,14,14a-octahydrobenzo[a]tetracene-2-carboxylate (diastereomer B, 11 mg, 10%) as a yellow solid: $^1$H NMR (500 MHz, CDCl$_3$) δ 15.09 (s, 1H), 12.08 (br s, 1H), 7.75 (s, 1H), 6.75 (d, J=9.0 Hz, 1H), 6.53 (s, 1H), 5.58 (s, 1H), 5.32 (s, 1H), 4.96 (s, 1H), 4.77 (d, J=8.0 Hz, 1H), 4.76-4.62 (m, 1H), 3.84 (s, 3H), 3.77 (s, 3H), 3.72 (dd, J=9.5, 3.0 Hz, 1H), 3.69 (s, 1H), 3.55 (s, 4H), 3.42 (s, 3H), 3.31 (d, J=19.0 Hz, 1H), 3.12-3.00 (m, 3H), 2.70 (br s, 1H), 2.40 (s, 3H), 1.98-1.80 (m, 2H), 1.31 (d, J=6.0 Hz, 3H), 0.57 (t, J=7.5 Hz, 3H); MS (ESI+) m/z 728 (M+H); HPLC 98.3% (AUC), $t_R$ 11.85 min.

Example 58

Preparation of (6R,6aS,14aR)-Methyl 12-(4-fluorophenyl)-1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-5,6,6a,7,9,12,14,14a-octahydrobenzo[a]tetracene-2-carboxylate

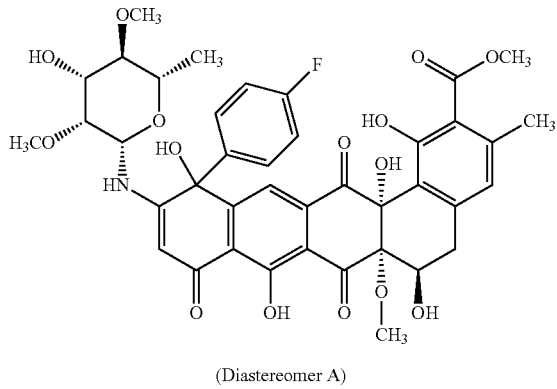 [SMILES: COC(=O)c1c(C)cc2c(c1O)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O)[C@H]1OC)C4(O)c1ccc(F)cc1]

(Diastereomer A)

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate (200 mg, 0.28 mmol) in THF (5 mL) was added 4-fluorophenylmagnesium bromide (4.30 mL, 1.0 M solution in THF, 4.30 mmol) at −30° C. The mixture was stirred under nitrogen for 30 min. The reaction mixture was quenched with water (0.30 mL), the reaction was brought to room temperature and pH was adjusted to 7 with 1N HCl. The reaction mixture was extracted with dichloromethane (3×50 mL). The combined organic phase was washed with brine, dried (Na$_2$SO$_4$), filtered and concentrated. The crude material was purified by preparative HPLC (10:90 acetonitrile/water to 60:40 acetonitrile/water with 0.05% TFA over 10 min, then isocratic) to afford (6R,6aS,14aR)-methyl 12-(4-fluorophenyl)-1,6,8,12,14a-pentahydroxy-11-((2S,3R,4R,5R,6S)-4-hydroxy-3,5-dimethoxy-6-methyltetrahydro-2H-pyran-2-ylamino)-6a-methoxy-3-methyl-7,9,14-trioxo-5,6,6a,7,9,12,14,14a-octahydrobenzo[a]tetracene-2-carboxylate as a diastereomer A (13 mg, 7%) and as a yellow solid: $^1$H NMR (500 MHz, CD$_3$OD) δ 7.58-7.55 (m, 2H), 7.53 (s, 1H), 7.13-7.07 (m, 2H), 6.60 (s, 1H), 5.69 (s, 1H), 4.93 (br s, 1H), 4.87 (s, 1H), 3.86 (s, 3H), 3.69-3.66 (m, 1H), 3.65 (s, 3H), 3.58-3.46 (m, 5H), 3.37-3.33 (m, 2H), 3.25-3.21 (m, 1H), 2.92 (t, J=9.0 Hz, 1H), 2.41 (s, 3H), 1.35-1.25 (m, 2H), 1.17 (d, J=6.5 Hz, 3H); MS (ESI+) m/z 794 (M+H); HPLC 95.4% (AUC), $t_R$ 13.49 min.

Example 59

Preparation of (6R,6aS,14aR)-methyl 12-(3-ethoxy-3-oxopropyl)-1,6,8,12,14a-pentahydroxy-11-((2S,3R,4R,5R,6S)-4-hydroxy-3,5-dimethoxy-6-methyltetrahydro-2H-pyran-2-ylamino)-9-imino-6a-methoxy-3-methyl-7,14-dioxo-5,6,6a,7,9,12,14,14a-octahydrobenzo[a]tetracene-2-carboxylate [mixture of diastereomers]

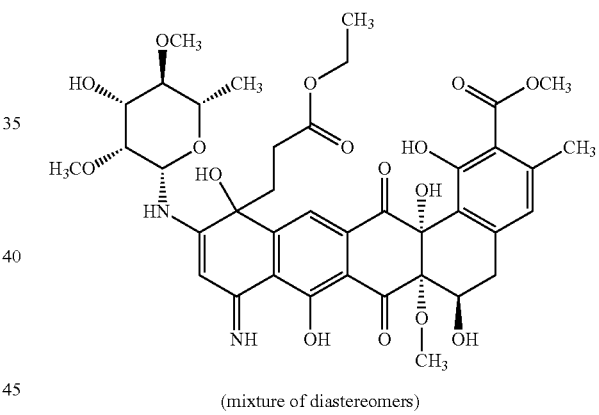

(mixture of diastereomers)

To a −78° C. solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-9-imino-6a-methoxy-3-methyl-7,12,14-trioxo-5,6,6a,7,9,12,14,14a-octahydrobenzo[a]tetracene-2-carboxylate (50 mg, 0.072 mmol) in THF (2 mL) was added a solution of 3-ethoxy-3-oxopropylzinc bromide in THF (0.5 M, 1.15 mL, 0.58 mmol) dropwise. The reaction mixture was stirred at −78° C. for 2 h, and then quenched with a saturated solution of ammonium chloride. The mixture was extracted with chloroform (3×10 mL). The combined organics were dried (Na$_2$SO$_4$), filtered and concentrated. The crude was purified by preparative TLC (silica gel, 85:15 chloroform/methanol) to afford (6R,6aS,14aR)-methyl 12-(3-ethoxy-3-oxopropyl)-1,6,8,12,14a-pentahydroxy-11-((2S,3R,4R,5R,6S)-4-hydroxy-3,5-dimethoxy-6-methyltetrahydro-2H-pyran-2-ylamino)-9-imino-6a-methoxy-3-methyl-7,14-dioxo-5,6,6a,7,9,12,14,14a-octahydrobenzo[a]tetracene-2-carboxylate (7 mg, 12%) as an orange solid and as a mixture of diastereomers: $^1$H NMR (500 MHz, CD$_3$OD) δ 7.18 (s, 1H), 6.57 (s, 1H), 5.54 (s, 1H), 4.96 (s, 1H), 4.88-4.83 (m, 2H), 3.84 (s, 3H), 3.76 (s, 3H), 3.75-3.66 (m, 3H), 3.57 (s, 3H), 3.34 (s, 3H), 3.25-3.16 (m, 2H), 3.03 (t, J=9.0 Hz, 1H), 2.39 (s, 3H), 2.15-1.85 (m, 4H), 1.45-1.26 (m, 1H), 1.25 (d, J=5.5 Hz, 3H), 1.09 (t, J=7.0 Hz, 3H); MS (ESI+) m/z 799 (M+H); HPLC >99% (AUC), $t_R$ 10.04 min.

Example 60

Preparation of (8aR,12R,12aS)-8a,12-Dihydroxy-5-((2S,3R,4R,5R,6S)-4-hydroxy-3,5-dimethoxy-6-methyltetrahydro-2H-pyran-2-ylamino)-12a-methoxy-8a,9,10,11,12,12a-hexahydro-(1-hydroxy-2-methoxycarbonyl-3-methylbenzo) [9,10-a]tetraceno[1,12-de][1,3]oxazine-2,6,8,13-tetraone

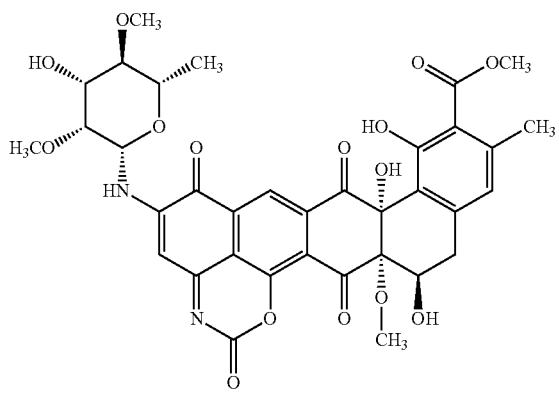 [SMILES: COC(=O)c1c(C)cc2c(c1O)[C@]1(O)C(=O)c3cc4c5c(nc(=O)oc5c3C(=O)[C@]1(OC)[C@H](O)C2)C=C(N[C@H]1O[C@@H](C)[C@H](OC)[C@@H](O)[C@H]1OC)C4=O]

To a solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-9-imino-6a-methoxy-3-methyl-7,12,14-trioxo-5,6,6a,7,9,12,14,14a-octahydrobenzo[a]tetracene-2-carboxylate (87 mg, 0.125 mmol) in THF (1 mL) was added carbonyldiimidazole (24.3 mg, 0.15 mmol) at room temperature, and the mixture was stirred under nitrogen for 4 h. The reaction mixture was quenched with a saturated solution of ammonium chloride and extracted with chloroform. The combined extracts were washed with brine, dried (Na$_2$SO$_4$), filtered and concentrated. The residue was purified by preparative TLC (silica gel, 95:5 chloroform/methanol) to afford (8aR,12R,12aS)-8a,12-Dihydroxy-5-((2S,3R,4R,5R,6S)-4-hydroxy-3,5-dimethoxy-6-methyltetrahydro-2H-pyran-2-ylamino)-12a-methoxy-8a,9,10,11,12,12a-hexahydro-(1-hydroxy-2-methoxycarbonyl-3-methylbenzo)[9,10-a]tetraceno[1,12-de][1,3]oxazine-2,6,8,13-tetraone (26 mg, 29%) as a red solid: $^1$H NMR (500 MHz, CDCl$_3$) δ 12.15 (s, 1H), 8.56 (s, 1H), 7.11 (d, J=9.0 Hz, 1H), 6.56 (s, 1H), 6.30 (s, 1H), 5.16 (br s, 1H), 4.96 (br s, 1H), 4.79 (d, J=8.5 Hz, 1H), 4.54 (br s, 1H), 3.84 (s, 3H), 3.81 (s, 3H), 3.78-3.72 (m, 3H), 3.61 (s, 3H), 3.60 (dd, J=19.5, 6.5 Hz, 1H), 3.42 (s, 3H), 3.36 (d, J=19.5 Hz, 1H), 3.14 (t, J=9.5 Hz, 1H), 2.45 (d, J=5.0 Hz, 1H), 2.41 (s, 3H), 1.37 (d, J=6.0 Hz, 3H); MS (ESI+) m/z 723 (M+H); HPLC 87.3% (AUC), $t_R$ 12.05 min.

Example 61

Preparation of (6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-12-((5-(2-hydroxypropyl)furan-3-yl)methyl)-6a-methoxy-3-methyl-7,9,14-trioxo-5,6,6a,7,9,12,14,14a-octahydrobenzo[a]tetracene-2-carboxylate

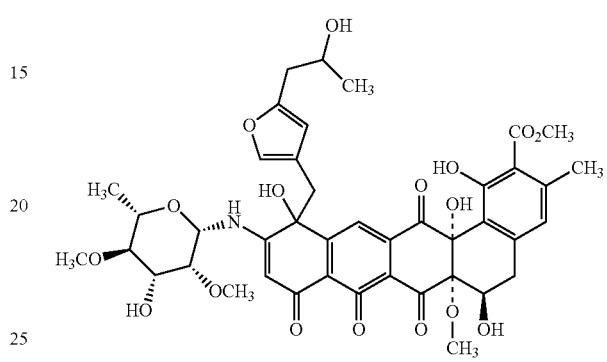

*Streptomyces* sp. AMRI-45379 is a strain isolated from environmental samples by AMRI for natural products research desposited in an international depositary authority (IDA) collection according to the Budapest Treaty. The strain AMRI-45379 was mailed on Jun. 22, 2010 to the ATCC Patent Collection by Federal Express Priority Overnight Mail with Tracking Number 793661147245. The strain AMRI-45379 was received by ATCC on Jun. 23, 2010 and assigned ATCC Accession No. PTA-11097. This strain was previously maintained on ISP 2 medium and stored as cryogenically preserved (liquid nitrogen vapor phase) stock solutions in the appropriate medium (Medium A plus 15% glycerol). ISP 2 medium is composed of (per Liter) 4.0 grams Yeast Extract, 10.0 grams Malt Extract, 4.0 grams Dextrose, and, when solidified, 20.0 grams Agar. Medium A is composed of (per Liter) 20.0 grams of soluble starch, 10.0 grams of dextrose, 5.0 grams of NZ Amine A, 5.0 grams of yeast extract, and 1.0 grams of calcium carbonate. All media were autoclaved for 30 minutes at 16 psi and 122° C. and mixed prior to dispensing into plates or flasks.

Bioconversions were carried out using cells grown according to the following protocol. Vials stored under liquid nitrogen vapor were thawed and approximately 1.0 mL of seed material was inoculated into 250 mL DeLong culture flasks containing 30 mL of Medium A. This culture was grown at 28° C., 250 RPM with a 5 cm orbit for 24 hours. The resulting culture was used to inoculate a 250 mL DeLong culture flask containing 30 mL ISP 2 at 5% (v/v). This second culture was grown at 28° C., 220 RPM with a 5 cm orbit for an additional 24 hours. Cells from this culture were recovered via centrifugation at 4,000×g for 5 minutes. These cells were subsequently resuspended in an equal volume of Mineral Salts Broth lacking a source of nitrogen and supplemented with 10 g/L sucrose and returned to the same incubation conditions. Mineral Salts Broth (MSB) was prepared essentially as described by the American Type Culture Collection (ATCC Medium 1127).

Bioconversions were initiated by the addition of (6R,6aS, 14aR)-methyl 1,6,8,14a-tetrahydroxy-11-((2S,3R,4R,5R, 6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate to the AMRI-45379 suspensions to give a 0.25 mg/mL final concentration. These additions were made from a mg/mL stock solution of (6R,6aS,14aR)-methyl 1,6,8,14a-tetrahydroxy-11-((2S,3R,4R,5R,6S)-4-hydroxy-3,5-dimethoxy-6-methyltetrahydro-2H-pyran-2-ylamino)-6a-methoxy-3-methyl-7,9,12,14-tetraoxo-5,6,6a,7,9,12,14,14a-octahydrobenzo[a]tetracene-2-carboxylate dissolved in dimethylsulfoxide. Bioconversions were allowed to proceed for 48 hours under the same incubation conditions. At the conclusion of the bioconversion, cells were removed via centrifugation and the clarified supernatant was retained.

Supernatant was extracted using High Capacity C18 Alltech SPE cartridges. Roughly, 10 grams of C18 resin were used per liter of aqueous supernatant. The C18 cartridge was conditioned as per manufacturer's general instructions using acetonitrile for solvation steps and 10% acetonitrile in distilled water for equilibration steps. Once all supernatant had been loaded onto the C18 resin, the bed was washed with 4 column volumes of 10% acetonitrile in distilled water. Approximately 2 bed volumes of 20% acetonitrile in distilled water were eluted from the cartridge under gentle vacuum achieving separation of a leading impurity band from the product band. The product was subsequently eluted using 1 to 2 bed volumes of 100% acetonitrile. The acetonitrile was removed under nitrogen. Solids were dissolved in dimethylsulfoxide, and the product was isolated via preparatory HPLC. Pure fractions containing (6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-12-((5-(2-hydroxypropyl)furan-3-yl)methyl)-6a-methoxy-3-methyl-7,9,14-trioxo-5,6,6a,7,9,12,14,14a-octahydrobenzo[a]tetracene-2-carboxylate were pooled, the acetonitrile was removed under reduced pressure, and the remaining aqueous portion was lyophilized. Overall isolated biotransformation yields were approximately 20 to 25%.

Preparatory HPLC (Shimadzu) was performed using a Waters Sun Fire™ C18 OBD 5 um 30×150 mm column with the mobile phase initially composed of 75% of solvent A (water) and 25% of solvent B [acetonitrile]. Elution was performed with a linear gradient from 25 to 70% B in 21 minutes at a flow rate of 40 mL/min. UV data were acquired at 254 nm with an injection volume of 4-5 mL of sample solution.

Analytical HPLC (Shimadzu) was performed at a controlled temperature of 40° C. using a Waters Sun Fire™ C18 3.5 um 4.6×100 mm column with the mobile phase initially composed of 80% of solvent A (0.1% formic acid in water) and 20% of solvent B [0.1% (v/v) formic acid in acetonitrile]. Elution was performed with an initial isocratic hold for 1 minute, followed by a linear gradient from 20 to 80% B in 12 minutes, and then isocratic at 80% B for 2 minutes at a flow rate of 1 mL/min. The column was re-equilibrated for 3 minutes after programming back to the starting solvent mixture over 0.5 minute. UV data were acquired using a photodiode array at 190-370 nm (extraction at 254 nm) with an injection volume of 5 µL of sample solution.

LC/MS analyses were performed on a PE SCIEX system with a PDA detector and MS system consisting of API 150 LC/MS mass spectrometer. Chromatography was accomplished using a Waters Sun Fire™ C18 3.5 um 4.6×100 mm column UV data were acquired using a photodiode array at 190-370 nm (extraction at 254 nm) with an injection volume of 5 µL of sample solution. The mass spectrometer was operated in positive ion mode with spray voltage set at 5400 V. The ion source temperature was set at 450° C. The 1.0 mL/min effluent from the HPLC column was directed to TIS ion source with ⅓ splitting after UV detection. The delay in signal response between the two detectors was less than 0.2 minutes. The retention time of (6R,6aS,14aR)-Methyl 1,6,8,12,14a-pentahydroxy-11-((2S,3R,4R,5R,6S)-4-hydroxy-3,5-dimethoxy-6-methyltetrahydro-2H-pyran-2-ylamino)-12-((5-(2-hydroxypropyl)furan-3-yl)methyl)-6a-methoxy-3-methyl-7,9,14-trioxo-5,6,6a,7,9,12,14,14a-octahydrobenzo[a]tetracene-2-carboxylate using this method is 7.47 minutes. The $[M+H]^+$ ion is m/z 838.2.

High resolution mass spectra were gathered on a Waters Premier QT of mass spectrometer running on the MassLynx software platform and equipped with an electrospray ionization source. Samples were diluted with $H_2O$:Acetonitrile (1:1) containing 0.1% formic acid and introduced via infusion using the onboard syringe pump. The samples were diluted to yield good s/n which occurred at an approximate concentration of 0.01 mg/mL. The positive electrospray ionization T of mass spectrum acquired by infusing showed an $[M+H]^+$ ion at m/z 838.2933 which was in agreement with the molecular formula $C_{42}H_{47}NO_{17}$ (calcd for $C_{42}H_{48}NO_{17}$: 838.2922, error: 1.3 ppm). Positive electrospray ionization also showed the expected $[M+Na]^+$ ion at m/z 860.2756 which was also in agreement with the molecular formula $C_{42}H_{47}NO_{17}$ (calcd for $C_{42}H_{47}NO_{17}Na$: 860.2742, error: 1.6 ppm).

$^1H$ and $^{13}C$ NMR as well as COSY, HSQC, and HMBC spectra were recorded using a Bruker DRX 500 NMR spectrometer in $CDCl_3$ at 500 MHz for $^1H$ and 125 MHz for $^{13}C$ NMR. The spectrum was referenced to the residual solvent signal ($\delta_H$ 7.24, $\delta_C$ 77.0 for $CDCl_3$). Spectra are given in ppm ($\delta$) and coupling constants, J, are reported in Hertz (Table 8).

TABLE 8

$^1H$ and $^{13}C$ NMR Data for Example 61 in $CDCl_3$

| Position | $\delta_H$ mult. (J in Hz) | $\delta_c$ |
|---|---|---|
| 1 | | 160.0 |
| 1-OH | 12.09 s | |
| 2 | | 109.9 |
| 3 | | 142.9 |
| 4 | 6.53 s | 124.4 |
| 4a | | 142.8 |
| 5 | 3.29 dd (2.5, 20.5) | 38.1 |
|   | 3.54 m | |
| 6 | 4.94 bs | 62.8 |
| 6-OH | 4.72 bs | |
| 6a | | 84.3 |
| 6a-OCH$_3$ | 3.31 s | 52.4 |
| 7 | | 189.9 |
| 7a | | 117.9 |
| 8 | | 163.0 |
| 8-OH | 15.03 s | |
| 8a | | 119.0 |
| 9 | | 187.1 |
| 10 | 5.44 s | 97.7 |
| 11 | | 166.1 |
| 11-NH | 6.73 d (8.8) | |
| 12 | | 73.5 |
| 12-OH | 4.94 s | |
| 12a | | 151.9 |
| 13 | 7.78 s | 113.6 |
| 13a | | 138.6 |
| 14 | | 197.9 |
| 14a | | 78.9 |
| 14a-OH | 5.33 s | |
| 14b | | 120.4 |
| 15 | | 172.2 |
| 15-OCH$_3$ | 3.78 s | 52.3 |
| 16 | 2.39 s | 23.9 |
| 1' | 4.64 d (8.8) | 79.4 |
| 2' | 3.51 m | 79.9 |
| 2'-OCH$_3$ | 3.68 s | 62.3 |

TABLE 8-continued $^1$H and $^{13}$C NMR Data for Example 61 in CDCl$_3$

| Position | $\delta_H$ mult. (J in Hz) | $\delta_c$ |
|---|---|---|
| 3' | 3.68 m | 75.1 |
| 3'-OH | | |
| 4' | 3.04 t (9.1) | 82.8 |
| 4'-OCH$_3$ | 3.52 s | 61.1 |
| 5' | 3.24 dd (6.3, 9.1) | 73.1 |
| 6' | 1.23 d (6.3) | 17.9 |
| 1" | 2.77 d (13.9) | 43.6 |
|  | 2.92 d (13.9) | |
| 2" | | 117.7 |
| 3" | 5.42 s | 109.3 |
| 4" | | 153.0 |
| 5" | 2.42 dd (7.6, 14.8) | 37.4 |
|  | 2.53 dd (4.1, 14.8) | |
| 6" | 3.84 m | 66.4 |
| 6"-OH | | |
| 7" | 1.06 d (6.0) | 22.9 |
| 8" | 6.66 s | 140.1 |

Example 62

Antibacterial Activity

NCCLS standards for antimicrobial susceptibility testing using the dilution method were followed. See: Performance Standards for Antimicrobial Susceptibility Testing; Fourteenth Informational Supplement. NCCLS Document M100-S14 (ISBN 1-56238-516-X), 2004. NCCLS, 940 West Valley Road, Suite 1400, Wayne, Pa. 19087-1898 USA, 2004; Methods for Dilution Antimicrobial Susceptibility Tests for Bacteria that Grow Aerobically; Approved Standard—Sixth Edition. NCCLS document M7-A6 (IBSBN 1-56238-486-4), NCCLS, 940 West Valley Road, Suite 1400, Wayne, Pa. 19087-1898 USA, 2003, which are hereby incorporated by reference in their entirety.

The results are set forth in Table 9, below:

TABLE 9

Antibacterial Activity

| Example # | MRSA 43300 MIC, μg/mL |
|---|---|
| 2 | 0.008 |
| 4 | 0.06-0.12 |
| 5$^a$ | 2 |
| 6 | 0.12 |
| 7 | 0.12 |
| 8 | 1 |
| 9$^a$ | 32 |
| 10$^a$ | 32 |
| 11 | 0.12-0.25 |
| 12 | 0.25-1 |
| 13 | 32 |
| 16$^a$ | 16 |
| 17$^a$ | 32 |
| 18$^a$ | 2 |
| 19$^a$ | 2 |
| 20 | 2 |
| 21 | 1 |
| 22$^a$ | 1 |
| 23$^a$ | 4 |
| 24$^a$ | 32 |
| 25$^a$ | 2-4 |
| 26$^a$ | 0.5 |
| 27$^a$ | 8 |
| 28$^a$ | 0.5 |
| 30$^a$ | 0.12-0.5 |
| 31$^a$ | 2 |
| 33 | 1-2 |

TABLE 9-continued

Antibacterial Activity

| Example # | MRSA 43300 MIC, μg/mL |
|---|---|
| 34 | 0.008-0.016 |
| 36 | 0.12 |
| 37$^a$ | 0.25 |
| 38 | 1 |
| 39 | 2 |
| 40 | 1 |
| 40 | 2 |
| 42 | 2-4 |
| 44 | 1-2 |
| 46 | 1 |
| 47 | 1-2 |
| 48 | 1 |
| 49 | 0.06 |
| 50 | 0.25 |
| 51 | 8 |
| 52 | 0.12-0.25 |
| 53 | 0.12 |
| 54 | 2 |
| 55 | 32 |
| 55 | 16 |
| 56 | 8 |
| 56 | 16 |
| 57 | 16 |
| 57 | 4-8 |
| 58 | 8-16 |
| 59 | 32 |
| 60 | 0.12-0.5 |
| 61 | 0.06 |

$^a$Tested as a mixture of diastereomers.

Example 63

Testing for Antibacterial Activities (In Vitro)

A compound having the formula:

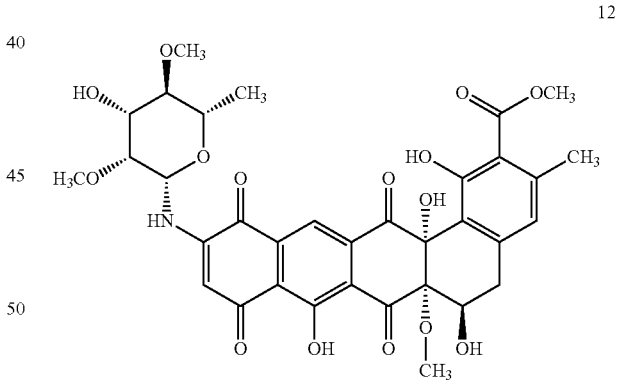

was tested for antibacterial activity, as follows:

NCCLS standards for antimicrobial susceptibility testing using the dilution method were followed. See: Performance Standards for Antimicrobial Susceptibility Testing; Fourteenth Informational Supplement. NCCLS Document M100-S14 (ISBN 1-56238-516-X), 2004. NCCLS, 940 West Valley Road, Suite 1400, Wayne, Pa. 19087-1898 USA, 2004; Methods for Dilution Antimicrobial Susceptibility Tests for Bacteria that Grow Aerobically; Approved Standard—Sixth Edition. NCCLS document M7-A6 (IBSBN 1-56238-486-4), NCCLS, 940 West Valley Road, Suite 1400, Wayne, Pa. 19087-1898 USA, 2003, which are hereby incorporated by reference in their entirety. The results are shown in Table 10, below:

TABLE 10

| Organism & Strain # | Gram +/- | Phenotype | Vancomycin | Cmpd 12 | Linezolid | Meropenem |
|---|---|---|---|---|---|---|
| S. aureus (ATCC 6538) | + | MSSA | 0.5 | 0.008 | 0.5 | |
| S. aureus (ATCC 29213) | + | MSSA | 1 | ≤0.06 | 4 | 0.12 |
| S. aureus 1137 | + | MRSA | 1 | ≤0.06 | 4 | >4 |
| S. aureus (ATCC 43300) | + | MRSA | 2 | 0.008 | 1 | |
| S. aureus 2012 | + | VISA | 8 | ≤0.06 | 1 | >4 |
| S. aureus 2018 | + | VISA | 8 | ≤0.06 | | |
| S. aureus 1725 | + | LRSA | 1 | ≤0.06 | 4 | 0.25 |
| S. aureus 1651 | + | LRSA | 1 | ≤0.06 | | |
| S. aureus 2144 | + | CA, USA 300 Strain | 1 | ≤0.06 | | |
| S. epidermidis 1597 | + | MSSE | 2 | ≤0.06 | | |
| S. epidermidis 1452 | + | MRSE | 2 | ≤0.06 | | |
| S. saprophyticus 495 | + | | 1 | ≤0.06 | | |
| E. faecalis 846 | + | VRE | >64 | ≤0.06 | | |
| E. faecium 700221 | + | VRE | >64 | 0.06 | 1 | |
| S. pneumoniae 975 | + | PSSP | 0.5 | ≤0.06 | 1 | 0.015 |
| S. pneumoniae 940 | + | PRSP | 0.25 | ≤0.06 | 0.5 | 1 |
| S. pneumoniae 376 | + | Quin-R | 0.5 | ≤0.06 | 1 | 0.015 |
| S. pneumoniae 933 | + | MDR | 0.5 | ≤0.06 | | |
| S. pyogenes 723 | + | | 0.5 | ≤0.06 | | |
| S. agalactiae 2033 | + | | 0.5 | ≤0.06 | | |
| H. influenzae 1742 | − | ampR | >64 | 4 | 8 | 0.06 |
| H. parainfluenzae 2319 (ATCC 7901) | − | | 64 | 8 | 16 | 0.03 |
| E. coli 102 (ATCC 25922) | − | QC strain | >64 | 32 | >64 | 0.03 |
| E. coli 2269 | − | ESBL-producer | >64 | 32 | >64 | 0.03 |
| K. pneumoniae 2239 | − | | >64 | 64 | >64 | 0.06 |
| K. pneumoniae 2262 | − | ampC, MDR | >64 | 64 | >64 | >4 |
| M. catarrhalis 557 | − | | >64 | 0.12 | 8 | ≤0.04 |
| S. marcescens 1635 | − | | >64 | 64 | >64 | 0.12 |
| P. aeruginosa (ATCC 27853) | − | | >64 | 32 | >64 | |

The present invention is not limited to the compounds found in the above examples, and many other compounds falling within the scope of the invention may also be prepared using the procedures set forth in the above synthetic schemes. The preparation of additional compounds of formula I using these methods will be apparent to one of ordinary skill in the chemical arts.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated therapeutic having a structure of formula I as follows:

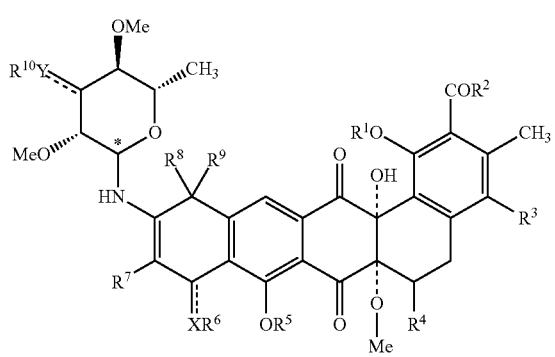

formula I wherein:
the carbohydrate anomeric carbon designated * is in the R or S configuration;

$R^1$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_n$ $OC(O)R^{11}$, —$(CH_2)_nC(O)_2R^{11}$, —$(CH_2)_nC(O)$ $NR^{12}R^{13}$, —$(CH_2)_nOC(O)NR^{12}R^{13}$, arylalkyl, heteroarylalkyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_n$ $OC(O)NR^{12}R^{13}$, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, or —$NR^{12}R^{13}$;

$R^2$ is selected from the group consisting of H, —$OR^{12}$, —$NR^{12}R^{13}$, —$(CH_2)_nC(O)R^{11}$, —$(CH_2)_nC(O)$ $NR^{12}R^{13}$, —$(CH_2)_nOC(O)NR^{12}R^{13}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, phenyl, benzyl, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^3$ is selected from the group consisting of H, halogen, —$OR^{12}$, —$NR^{12}R^{13}$, —$NR^{12}C(O)R^{13}$, —$NR^{12}C(O)_2$ $R^{13}$, —$NR^{12}C(O)NR^{12}R^{13}$, —$S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —(CH$_2$)$_n$C(O)R$^{11}$, —(CH$_2$)$_n$C(O)$_2$R$^{11}$, —(CH$_2$)$_n$C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{12}$, —NR$^{12}$R$^{13}$, an amino acid group, and phenyl which is optionally substituted 1-3 times with halogen, C$_1$-C$_4$ alkyl, C$_1$-C$_4$ haloalkyl, C$_1$-C$_4$ alkoxy, —CN, —OR$^{12}$, or —NR$^{12}$R$^{13}$;

R$^4$ is selected from the group consisting of H, halogen, —OR$^{12}$, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$C(O)R$^{11}$, —(CH$_2$)$_n$C(O)NR$^{12}$R$^{13}$, —(CH$_2$)$_n$OC(O)NR$^{12}$R$^{13}$, phenyl, benzyl, =NOR$^{14}$, =NR$^{14}$, a benzyl ether moiety, a carbamate moiety, an =NR$^{14}$ moiety, and a carbonate moiety, wherein each of —(CH$_2$)$_n$C(O)R$^{11}$, —(CH$_2$)$_n$C(O)NR$^{12}$R$^{13}$, C$_1$-C$_6$ alkyl, C$_3$-C$_6$ cycloalkyl, C$_4$-C$_7$ cycloalkylalkyl, phenyl, and benzyl is optionally substituted with from 1 to 3 substituents independently selected at each occurrence thereof from C$_1$-C$_3$ alkyl, halogen, —CN, —OR$^{12}$, —NR$^{12}$R$^{13}$, an amino acid group, and phenyl which is optionally substituted 1-3 times with halogen, C$_1$-C$_4$ alkyl, C$_1$-C$_4$ haloalkyl, C$_1$-C$_4$ alkoxy, —CN, —OR$^{12}$, or —NR$^{12}$R$^{13}$;

R$^5$ is selected from the group consisting of H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$C(O)R$^{11}$, —(CH$_2$)$_n$C(O)NR$^{12}$R$^{13}$, phenyl, benzyl, a benzyl ether moiety, a carbamate moiety, an =NR$^{14}$ moiety, and a carbonate moiety, wherein each of C$_1$-C$_6$ alkyl, C$_3$-C$_6$ cycloalkyl, C$_4$-C$_7$ cycloalkylalkyl, —(CH$_2$)$_n$C(O)R$^{11}$, —(CH$_2$)$_n$C(O)NR$^{12}$R$^{13}$, phenyl, and benzyl is optionally substituted 1 to 3 times with halogen, cyano, —NO$_2$, —NR$^{12}$R$^{13}$, —OR$^{12}$, C$_1$-C$_4$ alkyl, C$_1$-C$_4$ haloalkyl, C$_1$-C$_4$ alkoxy, or an amino acid group;

R$^6$ is optionally present and, if present, is selected from the group consisting of H, —OR$^{12}$, NR$^{12}$R$^{13}$, —(CH$_2$)$_n$(O)R$^{11}$, —(CH$_2$)$_n$C(O)NR$^{12}$R$^{13}$, C$_1$-C$_6$ alkyl, C$_1$-C$_6$ haloalkyl, phenyl, benzyl, a benzyl ether moiety, a carbamate moiety, an =NR$^{14}$ moiety, and a carbonate moiety, wherein each of —(CH$_2$)$_n$(O)R$^{11}$, —(CH$_2$)$_n$C(O)NR$^{12}$R$^{13}$, C$_1$-C$_6$ alkyl, C$_1$-C$_6$ haloalkyl, phenyl, and benzyl is optionally substituted 1 to 3 times with halogen, cyano, —NO$_2$, —NR$^{12}$R$^{13}$, —OR$^{12}$, C$_1$-C$_4$ alkyl, C$_1$-C$_4$ haloalkyl, C$_1$-C$_4$ alkoxy, or an amino acid group;

or R$^5$ and R$^6$ can combine to form a heterocycle group containing from 1 to 5 heteroatoms selected from the group consisting of oxygen, nitrogen, and sulfur and optionally substituted 1 to 3 times with halogen, oxo, cyano, C$_1$-C$_4$ alkyl, C$_1$-C$_4$ haloalkyl, or C$_1$-C$_4$ alkoxy;

R$^7$ is selected from the group consisting of H, halogen, —OR$^{12}$, —NR$^{12}$R$^{13}$, —NR$^{12}$C(O)R$^{13}$, —NR$^{12}$C(O)$_2$R$^{13}$, —NR$^{12}$C(O)NR$^{12}$R$^{13}$, —S(O)$_q$R$^{12}$, —CN, —NO$_2$, —(CH$_2$)$_n$C(O)R$^{11}$, —(CH$_2$)$_n$C(O)$_2$R$^{11}$, —(CH$_2$)$_n$C(O)NR$^{12}$R$^{13}$, —(CH$_2$)$_n$OC(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, heteroaryl, a benzyl ether moiety, a carbamate moiety, an =NR$^{14}$ moiety, and a carbonate moiety, wherein each of —(CH$_2$)$_n$C(O)R$^{11}$, —(CH$_2$)$_n$C(O)$_2$R$^{11}$, —(CH$_2$)$_n$C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, heterocyclyl, aryl, and heteroaryl is optionally substituted with from 1 to 3 substituents independently selected at each occurrence thereof from C$_1$-C$_3$ alkyl, halogen, —CN, —OR$^{12}$, —NR$^{12}$R$^{13}$, an amino acid group, and phenyl which is optionally substituted 1-3 times with halogen, C$_1$-C$_4$ alkyl, C$_1$-C$_4$ haloalkyl, C$_1$-C$_4$ alkoxy, —CN, —OR$^{12}$, or —NR$^{12}$R$^{13}$;

R$^8$ and R$^9$ are each independently selected from the group consisting of H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$C(O)R$^{11}$, —(CH$_2$)$_n$C(O)$_2$R$^{11}$, —(CH$_2$)$_n$C(O)NR$^{12}$R$^{13}$, —(CH$_2$)$_n$C(O)NR$^{12}$R$^{13}$, —OR$^{12}$, phenyl, benzyl, a benzyl ether moiety, a carbamate moiety, and a carbonate moiety, wherein each of C$_1$-C$_6$ alkyl, C$_3$-C$_6$ cycloalkyl, C$_4$-C$_7$ cycloalkylalkyl, —(CH$_2$)$_n$C(O)R$^{11}$, —(CH$_2$)$_n$C(O)$_2$R$^{11}$, —(CH$_2$)$_n$C(O)NR$^{12}$R$^{13}$, phenyl, and benzyl is optionally substituted from 1 to 3 times with a substituent selected independently at each occurrence thereof from the group consisting of halogen, cyano, C$_1$-C$_4$ alkyl, C$_1$-C$_4$ haloalkyl, C$_1$-C$_4$ alkoxy, and an amino acid group;

or R$^8$ and R$^9$ can combine to form an oxo, thio, imine, or an =NR$^{14}$ moiety;

R$^{10}$ is optionally present and, if present, is selected from the group consisting of H, —OR$^{12}$, (CH$_2$)$_n$C(O)R$^{11}$, —(CH$_2$)$_n$C(O)NR$^{12}$R$^{13}$, C$_1$-C$_6$ alkyl, C$_1$-C$_6$ haloalkyl, benzyl, a carbohydrate, a benzyl ether moiety, a carbamate moiety, an =NR$^{14}$ moiety, and a carbonate moiety, wherein each of —(CH$_2$)$_n$C(O)R$^{11}$, —(CH$_2$)$_n$C(O)NR$^{12}$R$^{13}$, C$_1$-C$_6$ alkyl, C$_1$-C$_6$ haloalkyl, and benzyl is optionally substituted 1 to 3 times with halogen, cyano, —NO$_2$, —NR$^{12}$R$^{13}$, —OR$^{12}$, C$_1$-C$_4$ alkyl, C$_1$-C$_4$ haloalkyl, C$_1$-C$_4$ alkoxy, or an amino acid group;

R$^{11}$ is H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —C(O)R$^{15}$, phenyl, or benzyl, wherein each of C$_1$-C$_6$ alkyl, C$_3$-C$_6$ cycloalkyl, C$_4$-C$_7$ cycloalkylalkyl, phenyl, and benzyl is optionally substituted 1 to 3 times with halogen, cyano, C$_1$-C$_4$ alkyl, C$_1$-C$_4$ haloalkyl, C$_1$-C$_4$ alkoxy, or an amino acid group;

R$^{12}$ and R$^{13}$ are each independently selected from the group consisting of H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —(CH$_2$)$_n$NR$^{16}$R$^{17}$, —(CH$_2$)$_n$C(O)R$^{11}$, —(CH$_2$)$_n$OC(O)R$^{11}$, —(CH$_2$)$_n$C(O)$_2$R$^{11}$, —(CH$_2$)$_n$C(O)NR$^{16}$R$^{17}$, (CH$_2$)$_n$OC(O)NR$^{16}$R$^{17}$, —(CH$_2$)$_n$NR$^{16}$C(O)OR$^{17}$, —(CH$_2$)$_n$NC(O)NR$^{16}$R$^{17}$, aryl, heteroaryl, arylalkyl, and heteroarylalkyl, wherein each of C$_1$-C$_6$ alkyl, C$_3$-C$_6$ cycloalkyl, C$_4$-C$_7$ cycloalkylalkyl, —(CH$_2$)$_n$NR$^{16}$R$^{17}$, —(CH$_2$)$_n$C(O)R$^{11}$, —(CH$_2$)$_n$OC(O)R$^{11}$, —(CH$_2$)$_n$C(O)$_2$R$^{11}$, —(CH$_2$)$_n$C(O)NR$^{16}$R$^{17}$, —(CH$_2$)$_n$OC(O)NR$^{16}$R$^{17}$, —(CH$_2$)$_n$NR$^{16}$C(O)OR$^{17}$, —(CH$_2$)$_n$NC(O)NR$^{16}$R$^{17}$, aryl, heteroaryl, arylalkyl, and heteroarylalkyl is optionally substituted 1 to 3 times with halogen, cyano, C$_1$-C$_4$ alkyl, C$_1$-C$_4$ haloalkyl, OH, C$_1$-C$_4$ alkoxy, an amino acid group, or [NR$^{11}$C(O)(CH$_2$)$_n$]$_m$NR$^{16}$R$^{17}$, which is optionally substituted 1 to 3 times with halogen, cyano, C$_1$-C$_4$ alkyl, C$_1$-C$_4$ haloalkyl, or C$_1$-C$_4$ alkoxy, aryl alkyl, wherein the C$_1$-C$_4$ alkyl and the aryl alkyl substituents are optionally substituted 1 to 3 times with halogen, alkyl, OH, NH$_2$, —CO$_2$H, —C(O)NH$_2$, —NHC(O)NH$_2$, —NHC(NH)NH$_2$, imidazole, pyrrolidine, SMe, SH, or SeH;

or R$^{12}$ and R$^{13}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, C$_1$-C$_4$ alkyl, C$_1$-C$_4$ haloalkyl, and C$_1$-C$_4$ alkoxy;

R$^{14}$ is selected from the group consisting of H, C$_1$-C$_6$ alkyl, C$_1$-C$_6$ haloalkyl, C$_1$-C$_6$ alkoxyalkyl, C$_3$-C$_6$ cycloalkyl, C$_4$-C$_7$ cycloalkylalkyl, —S(O)$_q$R$^{12}$, —(CH$_2$)$_n$NR$^{12}$R$^{13}$, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $(CH_2)_nNR^{11}C(O)OR^{12}$, —$(CH_2)_nNC(O)NR^{12}R^{13}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$(CH_2)_nNR^{11}C(O)OR^{12}$, —$(CH_2)_nNC(O)NR^{12}R^{13}$, aryl, heteroaryl, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, $OR^{12}$, —$NR^{12}R^{13}$, or an amino acid group;

$R^{15}$ is H, $C_1$-$C_4$ alkyl, arylalkyl, heteroarylalkyl $C_1$-$C_4$ haloalkyl, or phenyl, wherein each of $C_1$-$C_4$ alkyl, arylalkyl, heteroarylalkyl $C_1$-$C_4$ haloalkyl, and phenyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{16}$ and $R^{17}$ are each independently H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$C(O)R^{15}$, —$C(O)OR^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^{16}$ and $R^{17}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

X is O or N;
Y is O or N;
m is 0, 1, 2, or 3;
n is 0 to 5;
q is 0, 1, or 2; and
⋯ represents an optional double bond;
with the provisos: (1) if $R^1$ is H, $R^2$ is $OCH_3$, $R^3$ is H, $R^4$ is OH or H, $R^5$ is H, $R^7$ is H, $R^8$ and $R^9$ are combined to form an oxo, $R^{10}$ is H, and X and Y are O, then at least one of $R^1$ to $R^{10}$ is a benzyl ether moiety, a carbamate moiety, an =$NR^{14}$ moiety, or a carbonate moiety; and (2) that X, $R^6$, $R^8$, and $R^9$ can form a dihydroquinone ring;

or a pharmaceutically acceptable salt thereof.

2. The therapeutic according to claim 1, wherein $R^1$ is selected from the group consisting of H, $C_1$-$C_6$ alkyl, —$(CH_2)_nC(O)_2R^{11}$, —$(CH_2)_nC(O)NR^{12}R^{13}$, arylalkyl, and heteroarylalkyl, wherein n is 1.

3. The therapeutic according to claim 1, wherein $R^2$ is —$OR^{14}$ or —$NR^{12}R^{13}$.

4. The therapeutic according to claim 1, wherein $R^3$ is selected from the group consisting of H, halogen, —$NR^{12}R^{13}$, and —$NO_2$.

5. The therapeutic according to claim 1, wherein $R^4$ is OH.

6. The therapeutic according to claim 1, wherein $R^4$ is =NOH.

7. The therapeutic according to claim 1, wherein $R^5$ is H or $C_1$-$C_6$ alkyl.

8. The therapeutic according to claim 1, wherein $R^6$ is selected from the group consisting of H, —$OR^{14}$, and —$(CH_2)_n(O)R^{11}$.

9. The therapeutic according to claim 1, wherein $R^7$ is H or halogen.

10. The therapeutic according to claim 1, wherein $R^8$ is $C_1$-$C_6$ alkyl or phenyl, wherein phenyl is optionally substituted from 1 to 3 times with halogen.

11. The therapeutic according to claim 1, wherein $R^9$ is OH.

12. The therapeutic according to claim 1, wherein $R^8$ and $R^9$ are combined to form an oxo group.

13. The therapeutic according to claim 1, wherein $R^{10}$ is H or —$OR^{14}$.

14. The therapeutic according to claim 1, wherein X is O.

15. The therapeutic according to claim 1, wherein X is N.

16. The therapeutic according to claim 1, wherein Y is O.

17. The therapeutic according to claim 1, wherein Y is N.

18. The therapeutic according to claim 1, wherein X is N, $R^6$ is —$NR^{12}R^{13}$, and $R^{12}$ is H.

19. The therapeutic according to claim 1, wherein X, $R^6$, $R^8$ and $R^9$ form a dihydroquinone ring having the formula:

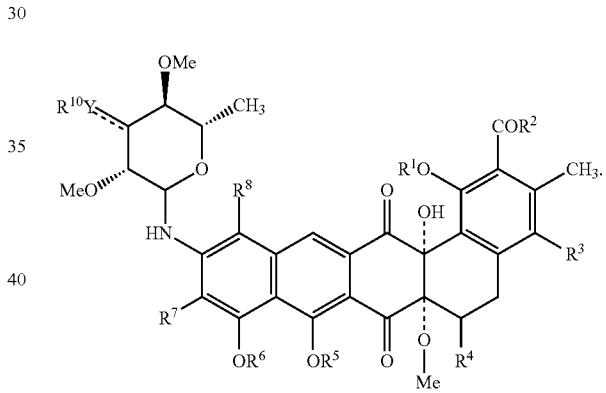

20. The therapeutic according to claim 1, wherein at least one of $R^1$ to $R^{10}$ is a benzyl ether moiety, a carbamate moiety, an =$NR^{14}$ moiety, or a carbonate moiety.

21. The therapeutic according to claim 1, wherein the structure is selected from the group consisting of:

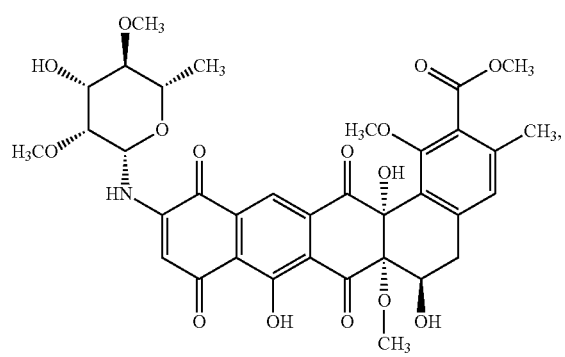 [SMILES: COC(=O)c1c(C)c(N)c2c(c1O)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O)[C@H]1OC)C4=O]

149
-continued
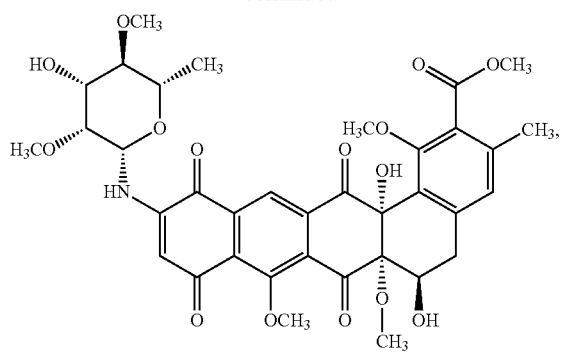
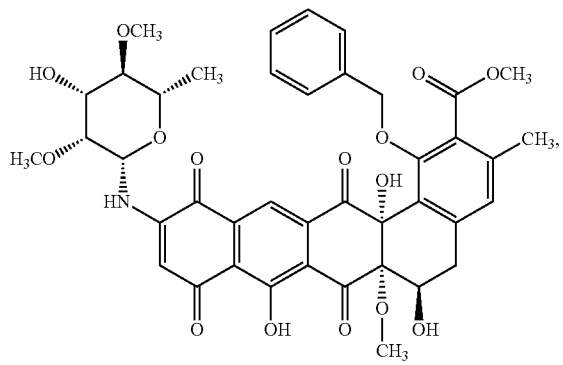
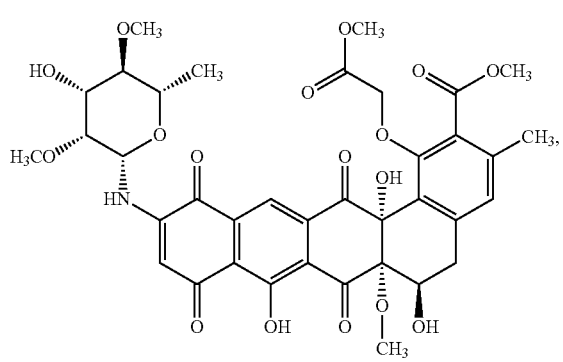
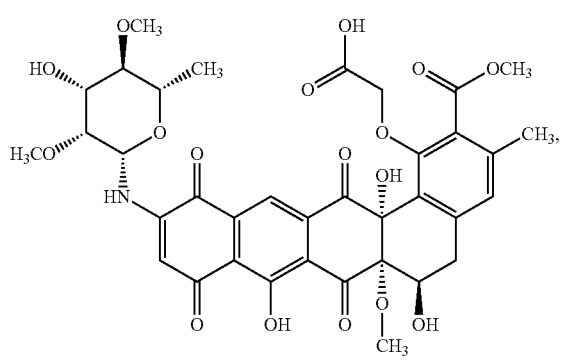
150
-continued
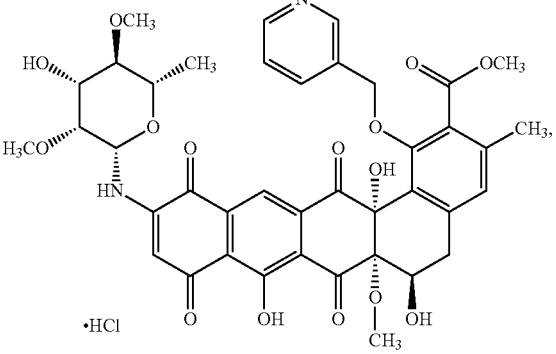
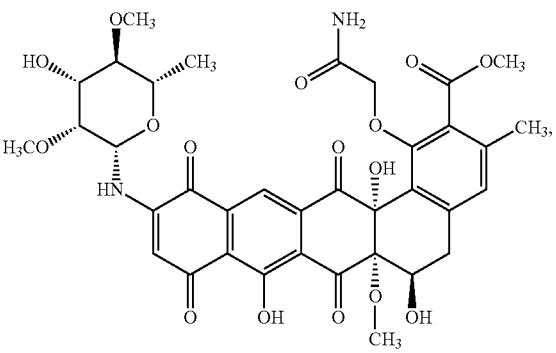
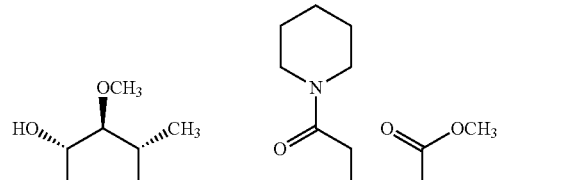
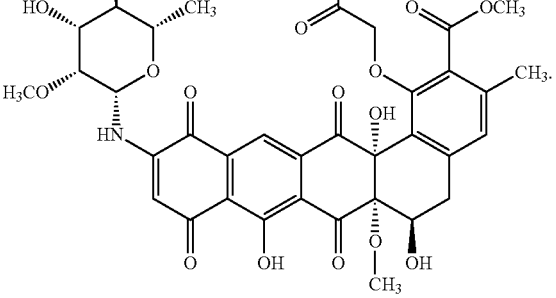
22. The therapeutic according to claim 1, wherein the structure is selected from the group consisting of:

151
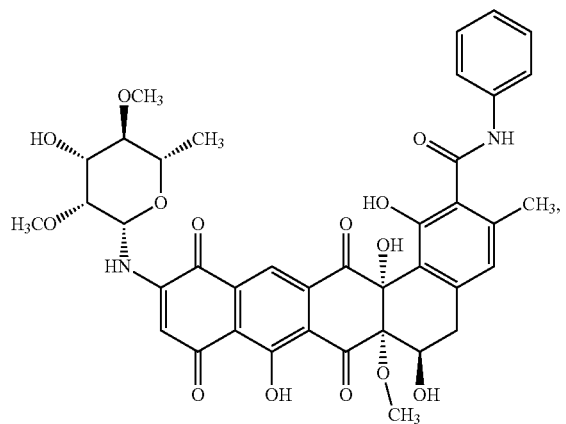
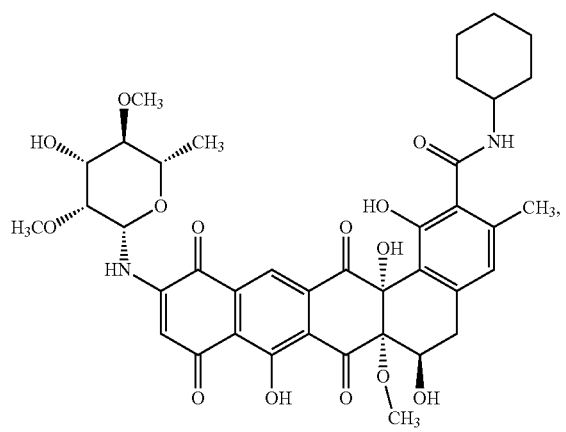
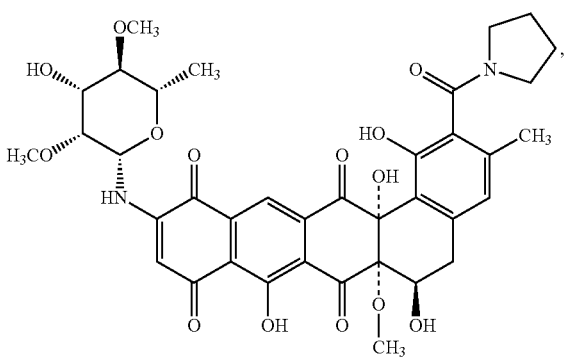
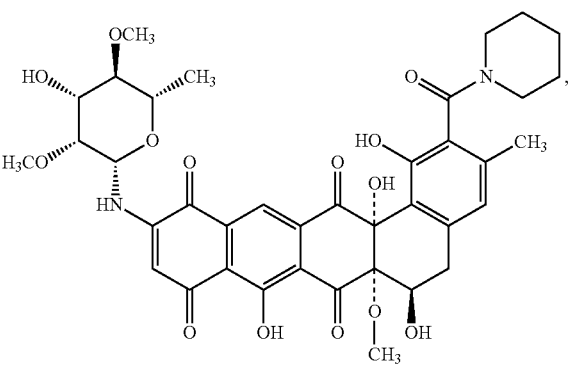
152
-continued
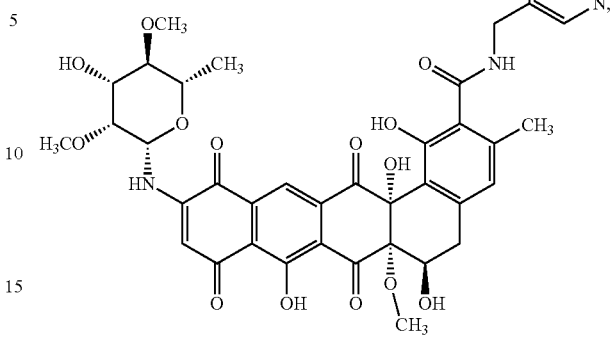
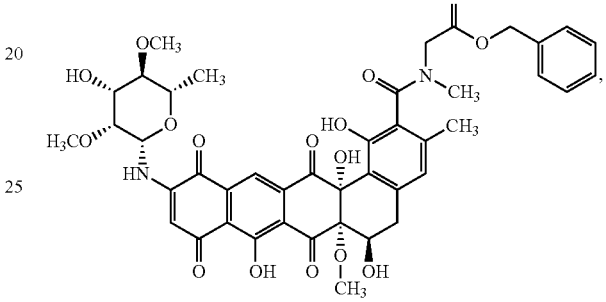
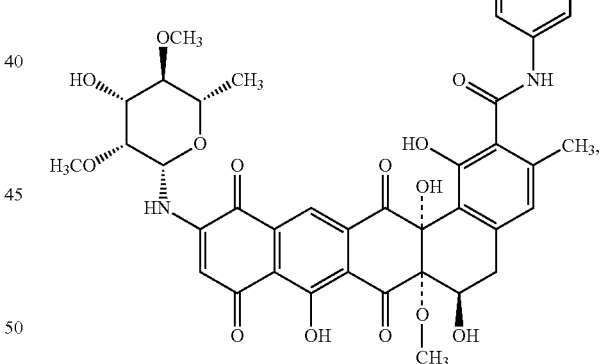
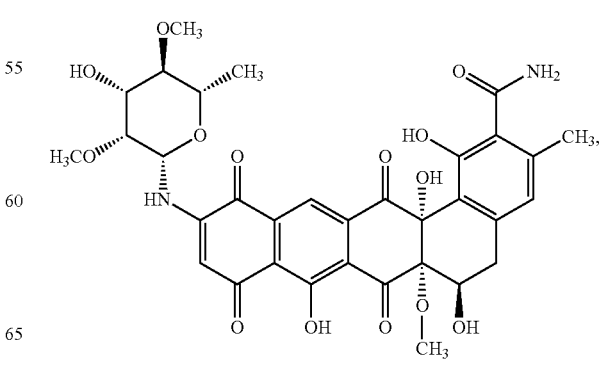

153
-continued
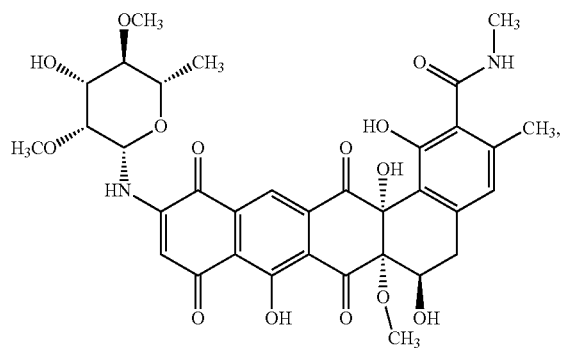
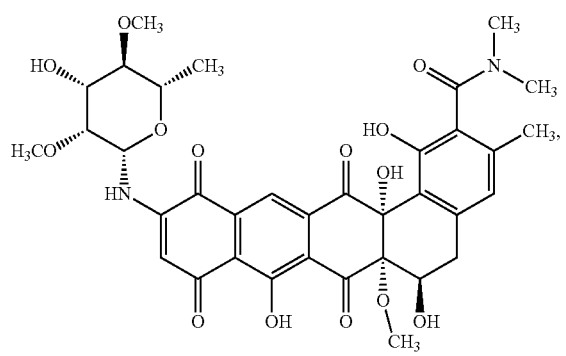
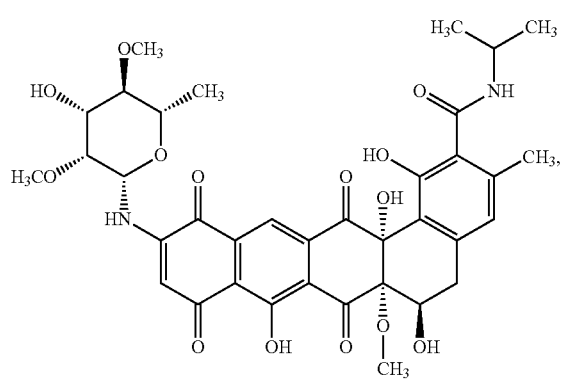
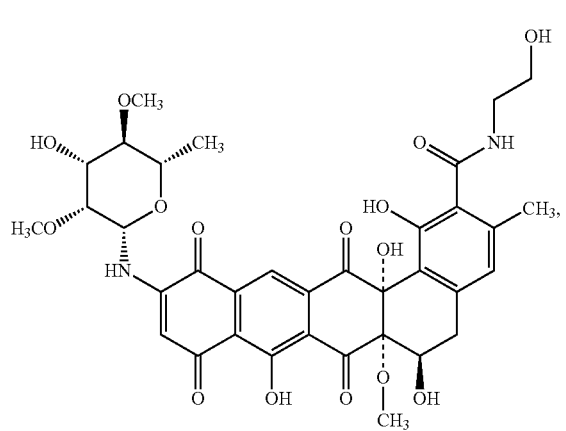
154
-continued
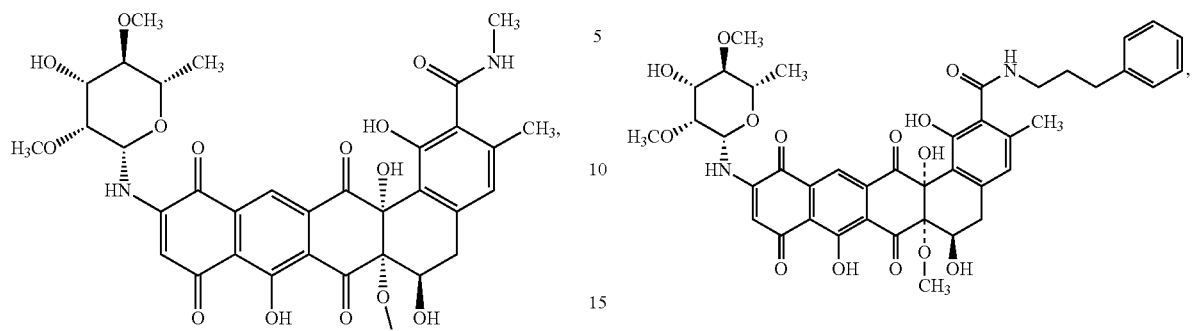
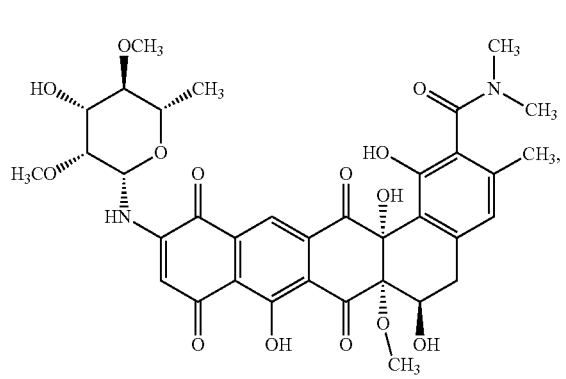
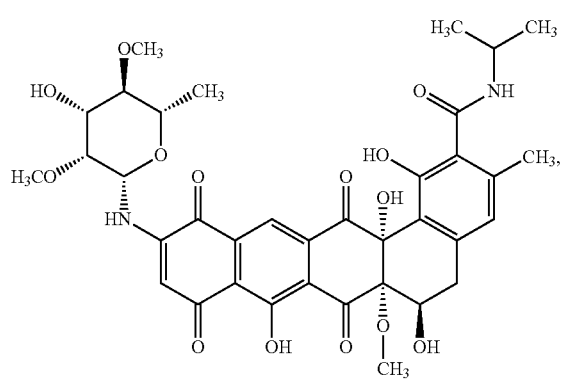
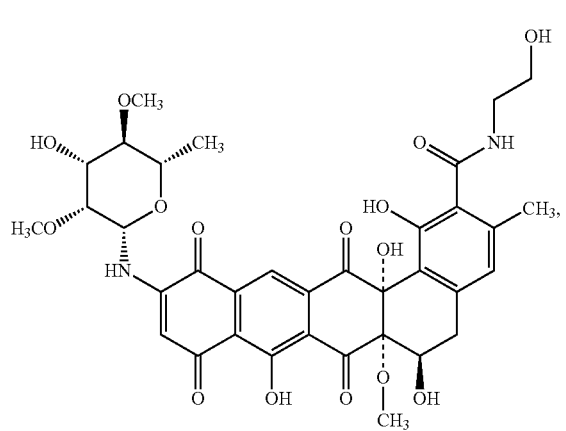

155
-continued
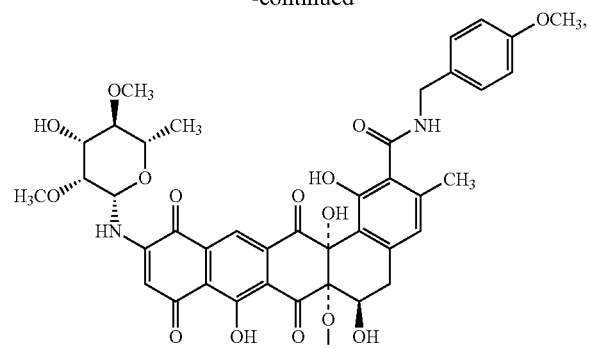
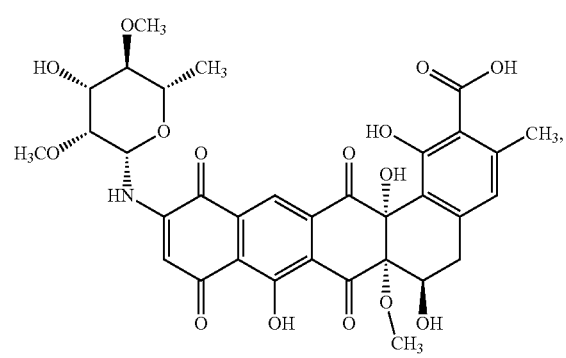
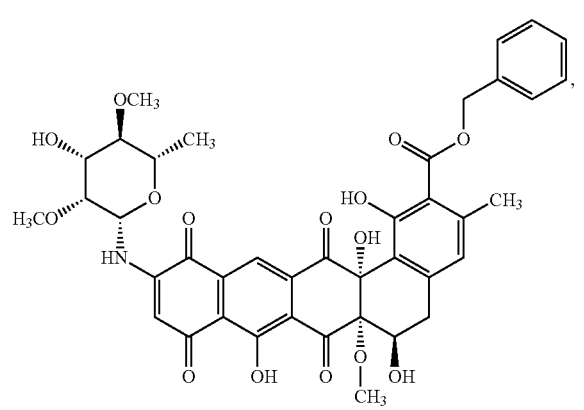
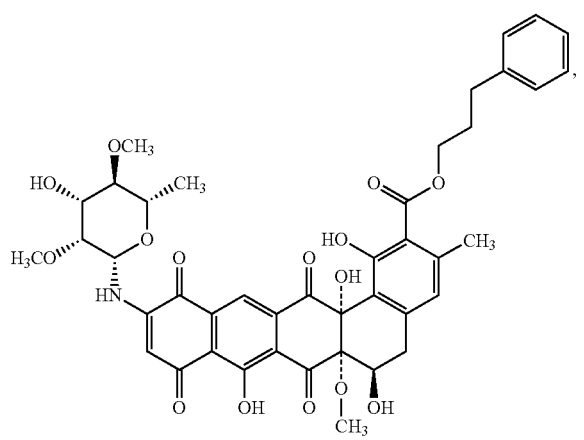
156
-continued
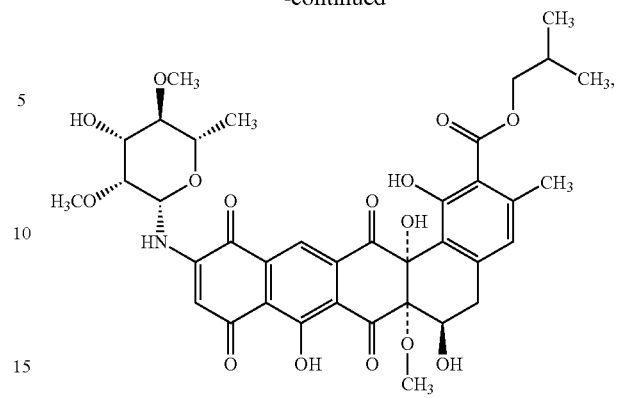
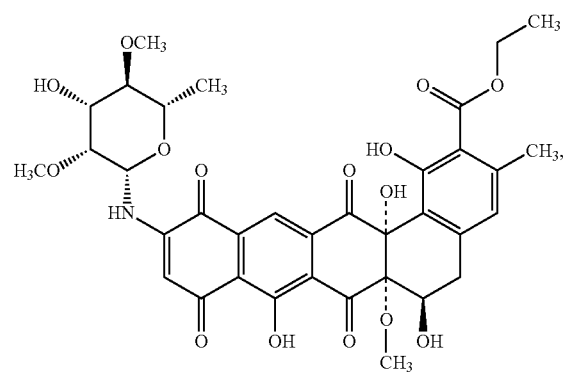
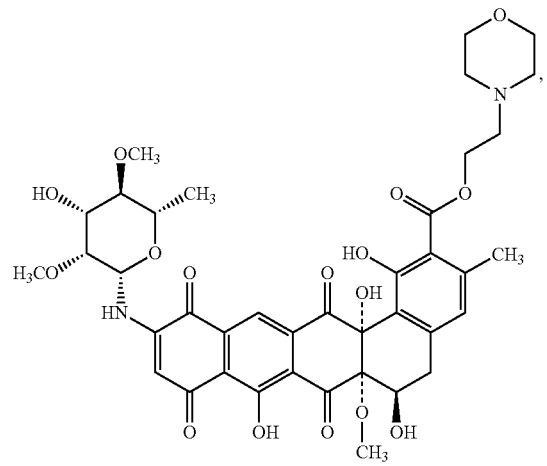
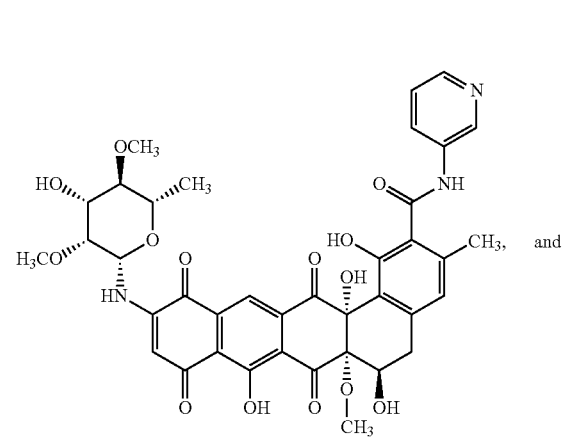
and

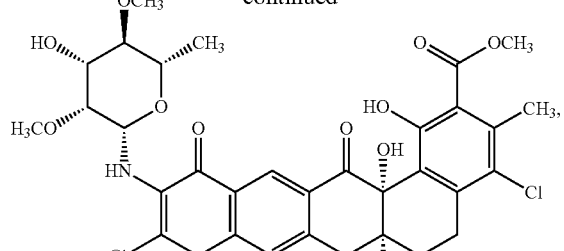
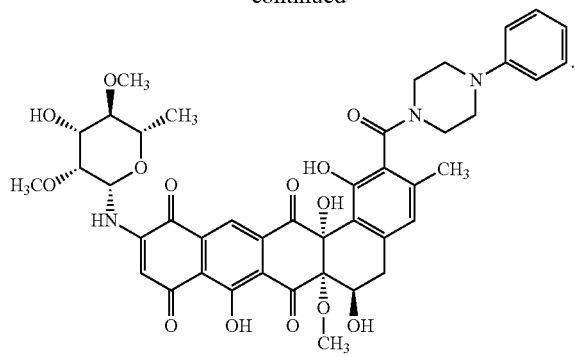
23. The therapeutic according to claim 1, wherein the structure is selected from the group consisting of:
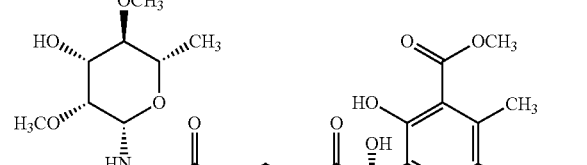
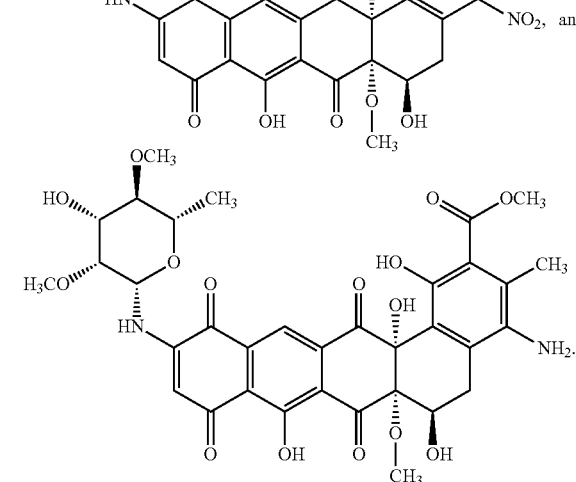
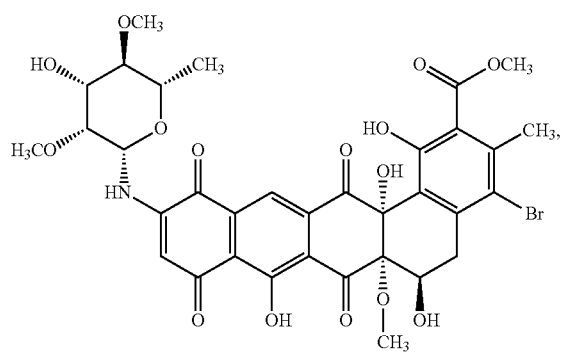
24. The therapeutic according to claim 1, wherein the structure is selected from the group consisting of:
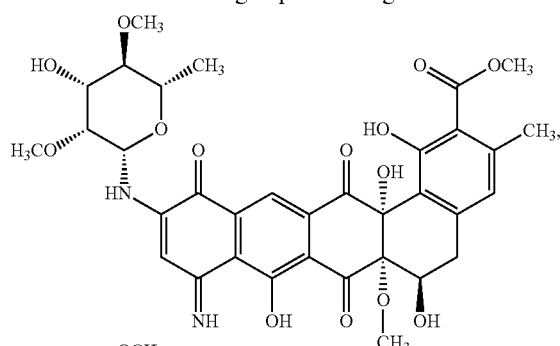
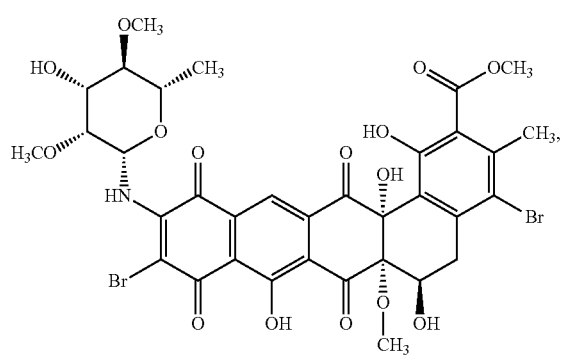
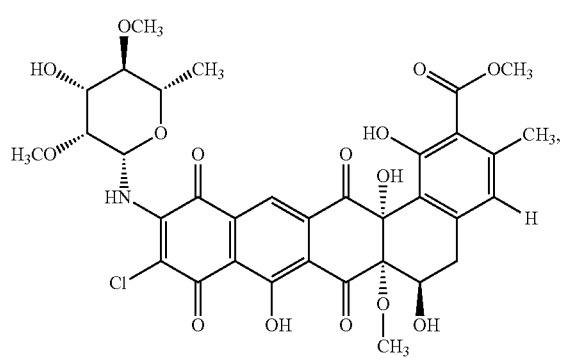
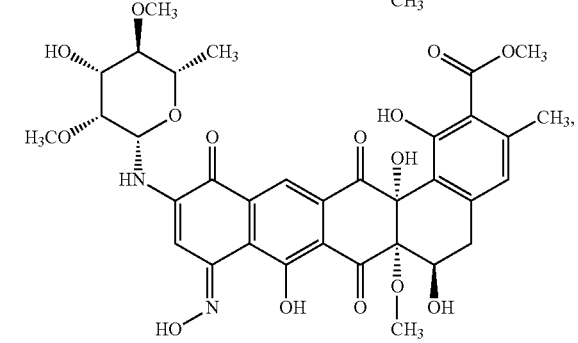

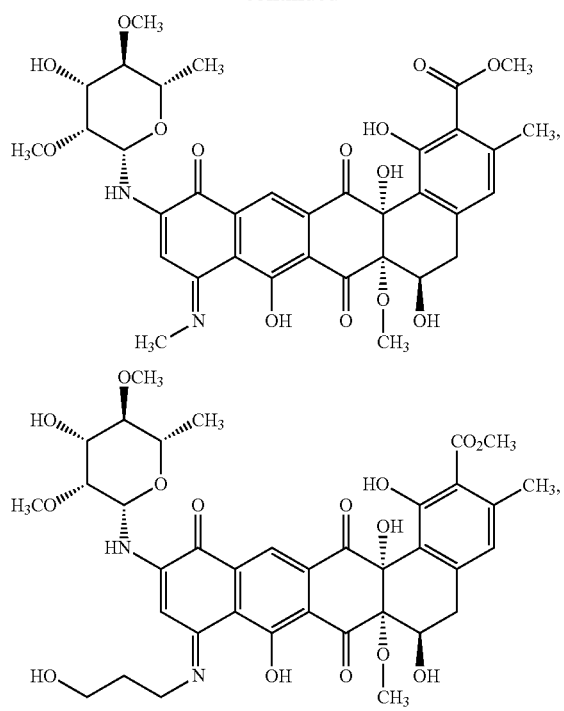
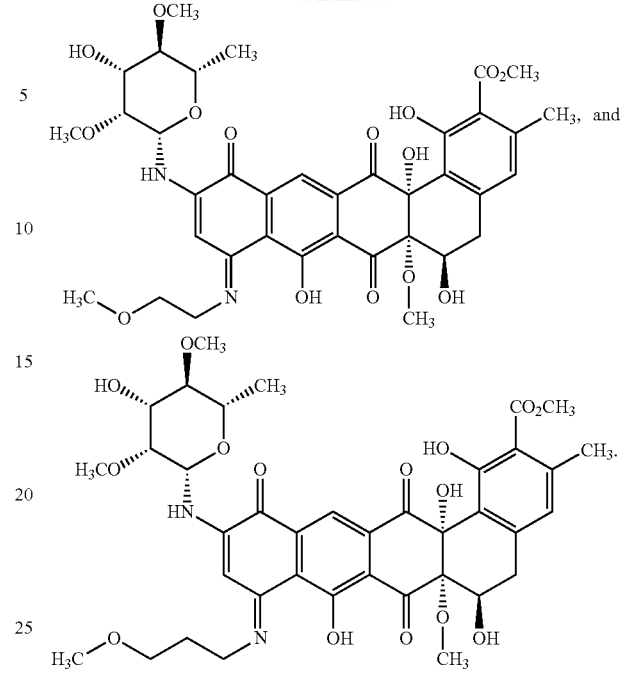
25. The therapeutic according to claim 1, wherein the structure is selected from the group consisting of:
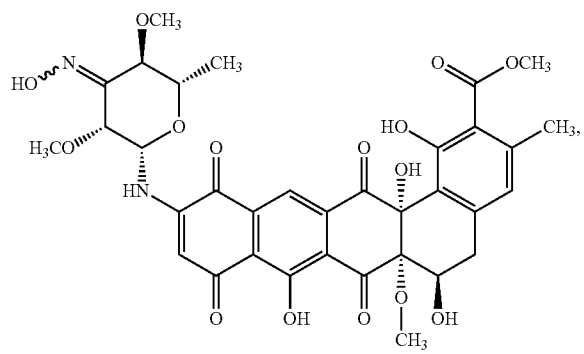
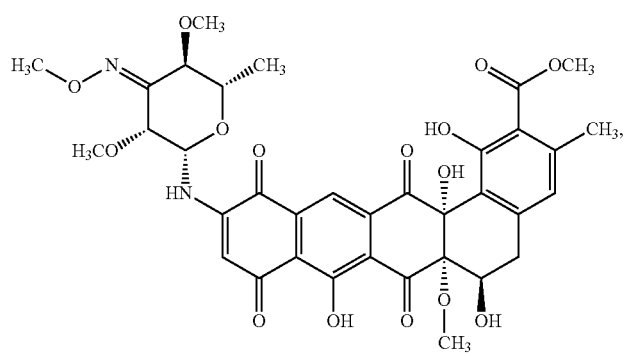

-continued
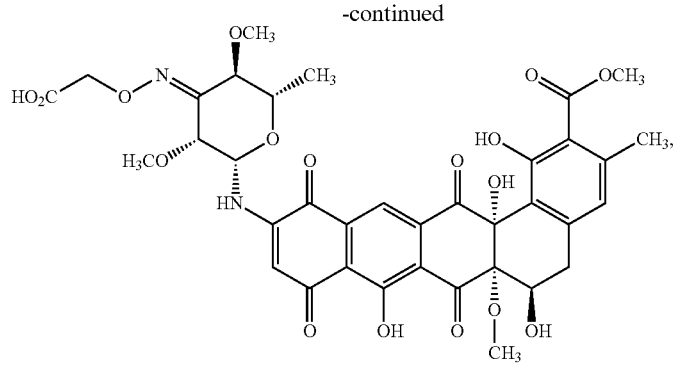
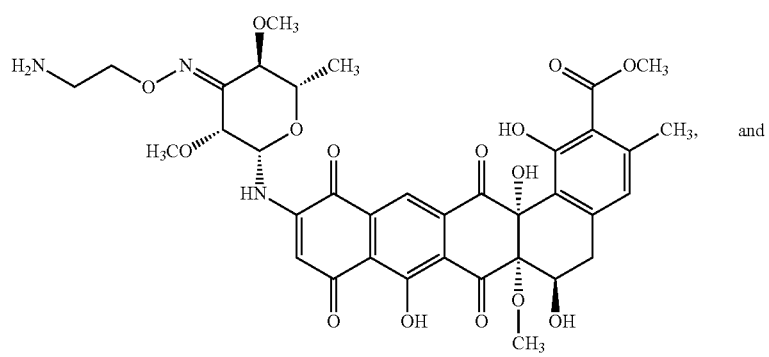
and
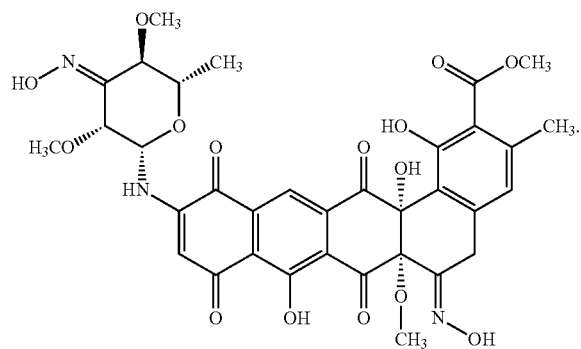 [SMILES: COC(=O)c1c(C)cc2c(c1O)[C@]1(O)C(=O)c3cc4c(c(O)c3C(=O)[C@]1(OC)/C(=N/O)C2)C(=O)C=C(N[C@H]1O[C@@H](C)[C@H](OC)/C(=N/O)[C@H]1OC)C4=O]
26. The therapeutic according to claim 1 having the formula:
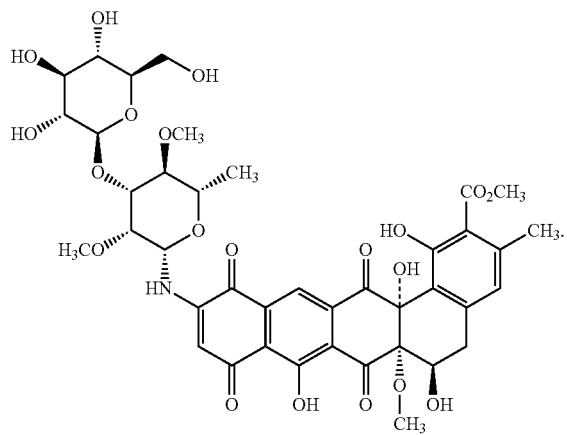 [SMILES: COC(=O)c1c(C)cc2c(c1O)[C@]1(O)C(=O)c3cc4c(c(O)c3C(=O)[C@]1(OC)[C@H](O)C2)C(=O)C=C(N[C@H]1O[C@@H](C)[C@H](OC)[C@@H](O[C@@H]2O[C@H](CO)[C@@H](O)[C@H](O)[C@H]2O)[C@H]1OC)C4=O]
27. The therapeutic according to claim 1, wherein the structure is selected from the group consisting of:
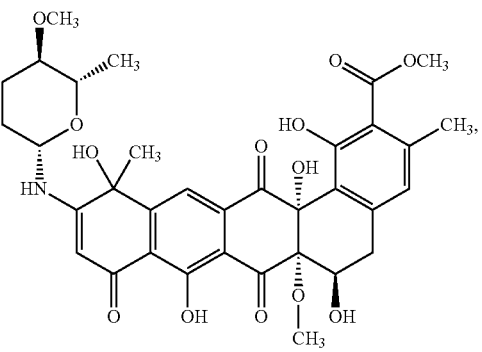

163
-continued

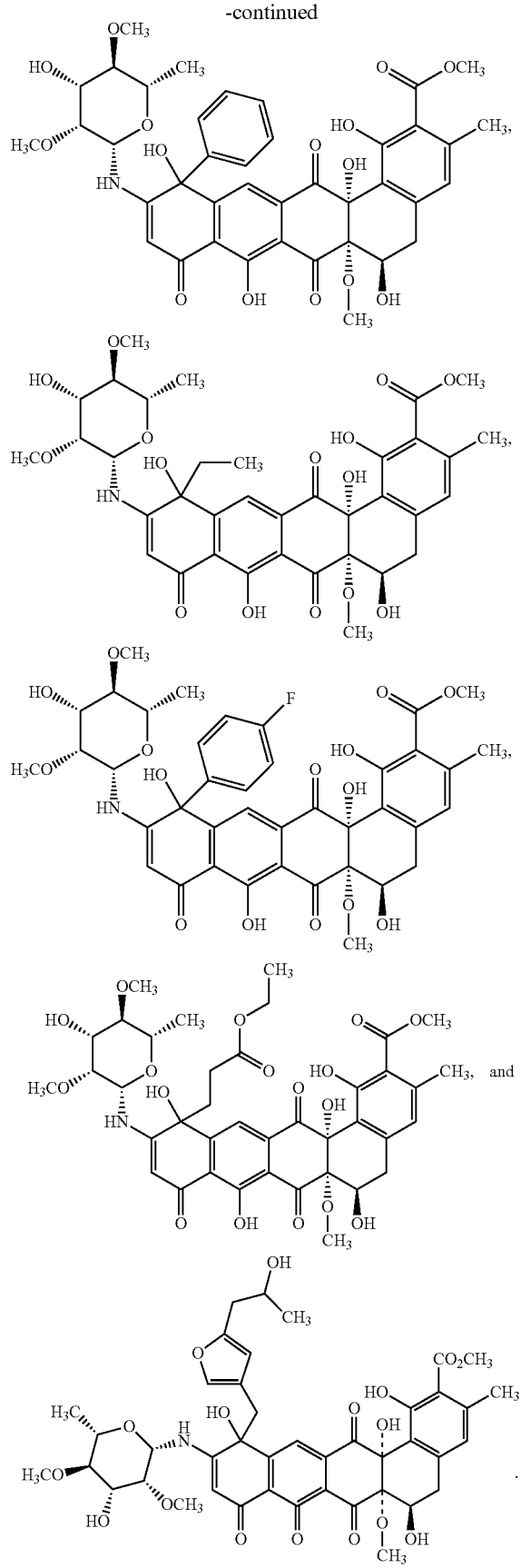

28. The therapeutic according to claim 1 having the formula:

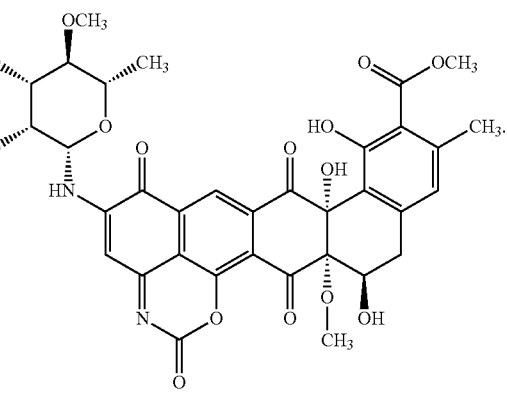

29. A pharmaceutical composition comprising a therapeutically effective amount of the therapeutic according to claim 1 and a pharmaceutically acceptable carrier.

30. A method of treating a bacterial infection comprising:
selecting a subject with a bacterial infection; and
administering to the subject a therapeutically effective amount of a therapeutic according to claim 1.

31. The method according to claim 30, wherein the subject is a human and the bacterial infection is a multi-drug resistant bacterial infection.

32. The method according to claim 31, wherein the multi-drug resistant bacterial infection is a multi-drug resistant strain of *Staphylococcus aureus, Streptococcus pneumoniae*, or *Enterococci*.

33. The method according to claim 30, wherein the bacterial infection is selected from the group consisting of epidermal infection, acne, complicated skin and soft tissue bacterial infection, and bacterial pneumonia.

34. An isolated therapeutic having a structure of formula I as follows:

formula I

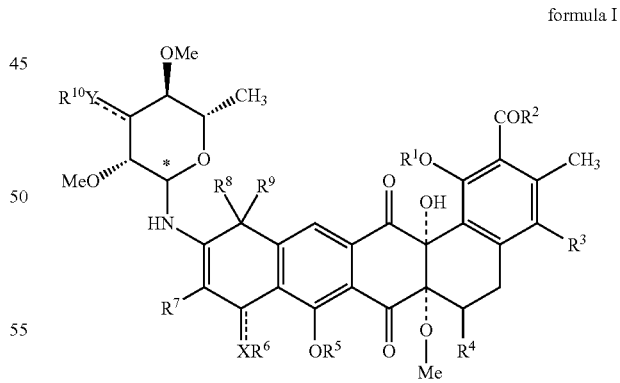

wherein:
the carbohydrate anomeric carbon designated * is in the R or S configuration;
$R^1$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_n$ $OC(O)R^{11}$, —$(CH_2)_nC(O)_2R^{11}$, —$(CH_2)_nC(O)$ $NR^{12}R^{13}$, —$(CH_2)_nOC(O)NR^{12}R^{13}$, arylalkyl, heteroarylalkyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nOC(O)R^{11}$, —$(CH_2)_nC(O)_2R^{11}$, —$(CH_2)_nC(O)NR^{12}R^{13}$, —$(CH_2)_nOC(O)NR^{12}R^{13}$, arylalkyl, and heteroarylalkyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$NO_2$, —$OR^{12}$, or —$NR^{12}R^{13}$;

$R^2$ is selected from the group consisting of H, —$OR^{12}$, —$NR^{12}R^{13}$, —$(CH_2)_nC(O)R^{11}$, —$(CH_2)_nC(O)NR^{12}R^{13}$, —$(CH_2)_nOC(O)NR^{12}R^{13}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, phenyl, benzyl, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^3$ is selected from the group consisting of H, halogen, —$OR^{12}$, —$NR^{12}R^{13}$, —$NR^{12}C(O)R^{13}$, $NR^{12}C(O)_2R^{13}$, —$NR^{12}C(O)NR^{12}R^{13}$, —$S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^4$ is selected from the group consisting of H, halogen, —$OR^{12}$, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, —$(CH_2)_nOC(O)NR^{12}R^{13}$, phenyl, benzyl, =$NOR^{14}$, =$NR^{14}$, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_3$-$C_6$ cycloalkyl, $C_4$-$C_7$ cycloalkylalkyl, phenyl, and benzyl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^5$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$, phenyl, benzyl, a benzyl ether moiety, a carbamate moiety, an =$NR^{14}$ moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)NR^{12}R^{13}$ phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

$R^6$ is optionally present and, if present, is selected from the group consisting of H, —$OR^{12}$, —$NR^{12}R^{13}$, —$(CH_2)_n(O)R^{11}$, —$(CH_2)_nC(O)NR^{12}R^{13}$, $C_1$-$C_6$ alkyl, $C_1$-$C_6$ haloalkyl, phenyl, benzyl, a benzyl ether moiety, a carbamate moiety, an =$NR^{14}$ moiety, and a carbonate moiety, wherein each of —$(CH_2)_n(O)R^{11}$, —$(CH_2)_nC(O)NR^{12}R^{13}$, $C_1$-$C_6$ alkyl, $C_1$-$C_6$ haloalkyl, phenyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

or $R^5$ and $R^6$ can combine to form a heterocycle group containing from 1 to 5 heteroatoms selected from the group consisting of oxygen, nitrogen, and sulfur and optionally substituted 1 to 3 times with halogen, oxo, cyano, $C_1$-$C_4$ alkyl, $C_1$-$C_4$ haloalkyl, or $C_1$-$C_4$ alkoxy;

$R^7$ is selected from the group consisting of H, halogen, —$OR^{12}$, —$NR^{12}R^{13}$, —$NR^{12}C(O)R^{13}$, —$NR^{12}C(O)_2R^{13}$, —$NR^{12}C(O)NR^{12}R^{13}$, —$S(O)_qR^{12}$, —CN, —$NO_2$, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, heteroaryl, a benzyl ether moiety, a carbamate moiety, an =$NR^{14}$ moiety, and a carbonate moiety, wherein each of —$(CH_2)_nC(O)R^{11}$, —$(CH_2)_nC(O)_2R^{11}$, —$(CH_2)_nC(O)NR^{12}R^{13}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, heterocyclyl, aryl, and heteroaryl is optionally substituted with from 1 to 3 substituents independently selected at each occurrence thereof from $C_1$-$C_3$ alkyl, halogen, —CN, —$OR^{12}$, —$NR^{12}R^{13}$, an amino acid group, and phenyl which is optionally substituted 1-3 times with halogen, $C_1$-$C_4$ alkyl, $C_1$-$C_4$ haloalkyl, $C_1$-$C_4$ alkoxy, —CN, —$OR^{12}$, or —$NR^{12}R^{13}$;

$R^8$ and $R^9$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, —$(CH_2)_nOC(O)NR^{12}R^{13}$, —$OR^{12}$, phenyl, benzyl, a benzyl ether moiety, a carbamate moiety, and a carbonate moiety, wherein each of $C_1$-$C_6$ alkyl, $C_3$-$C_6$ cycloalkyl, $C_4$-$C_7$ cycloalkylalkyl, —$(CH_2)_nC(O)R^{11}$, —$(CH_2)_nC(O)_2R^{11}$, —$(CH_2)_nC(O)NR^{12}R^{13}$, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^8$ and $R^9$ can combine to form an oxo, thio, imine, or an =$NR^{14}$ moiety;

$R^{10}$ is optionally present and, if present, is selected from the group consisting of H, —$OR^{12}$, $(CH_2)_nC(O)R^{11}$, —$(CH_2)_nC(O)NR^{12}R^{13}$, $C_1$-$C_6$ alkyl, $C_1$-$C_6$ haloalkyl, benzyl, a carbohydrate, a benzyl ether moiety, a carbamate moiety, an =$NR^{14}$ moiety, and a carbonate moiety, wherein each of —$(CH_2)_nC(O)R^{11}$, —$(CH_2)_nC(O)NR^{12}R^{13}$, $C_1$-$C_6$ alkyl, $C_1$-$C_6$ haloalkyl, and benzyl is optionally substituted 1 to 3 times with halogen, cyano, —$NO_2$, —$NR^{12}R^{13}$, —$OR^{12}$, $C_1$-$C_4$ alkyl, $C_1$-$C_4$ haloalkyl, $C_1$-$C_4$ alkoxy, or an amino acid group;

or $R^1$, $R^2$, $R^3$, $R^4$, $R^5$, $R^6$, $R^7$, $R^8$, $R^9$, and $R^{10}$ are each, independently, an O-glycosidic bond, an N-glycosidic bond, a C-glycosidic bond, or a peptide bond;

$R^{11}$ is H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —C(O)$R^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{12}$ and $R^{13}$ are each independently selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —(CH$_2$)$_n$NR$^{16}$R$^{17}$, —(CH$_2$)$_n$C(O)R$^{11}$, —(CH$_2$)$_n$OC(O)R$^{11}$, —(CH$_2$)$_n$C(O)$_2$R$^{11}$, —(CH$_2$)$_n$C(O)NR$^{16}$R$^{17}$, (CH$_2$)$_n$OC(O)NR$^{16}$R$^{17}$, —(CH$_2$)$_n$NR$^{16}$C(O)OR$^{17}$, —(CH$_2$)$_n$NC(O)NR$^{16}$R$^{17}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —(CH$_2$)$_n$NR$^{16}$R$^{17}$, —(CH$_2$)$_n$C(O)R$^{11}$, —(CH$_2$)$_n$OC(O)R$^{11}$, —(CH$_2$)$_n$C(O)$_2$R$^{11}$, —(CH$_2$)$_n$C(O)NR$^{16}$R$^{17}$, —(CH$_2$)$_n$OC(O)NR$^{16}$R$^{17}$, —(CH$_2$)$_n$NR$^{16}$C(O)OR$^{17}$, —(CH$_2$)$_n$NC(O)NR$^{16}$R$^{17}$, aryl, heteroaryl, arylalkyl, and heteroarylalkyl is optionally substituted 1 to 3 times with halogen, cyano, $C_1$-$C_4$ alkyl, $C_1$-$C_4$ haloalkyl, OH, $C_1$-$C_4$ alkoxy, an amino acid group, or [NR$^{11}$C(O)(CH$_2$)$_n$]$_m$NR$^{16}$R$^{17}$, which is optionally substituted 1 to 3 times with halogen, cyano, $C_1$-$C_4$ alkyl, $C_1$-$C_4$ haloalkyl, or $C_1$-$C_4$ alkoxy, aryl alkyl, wherein the $C_1$-$C_4$ alkyl and the aryl alkyl substituents are optionally substituted 1 to 3 times with halogen, alkyl, OH, NH$_2$, —CO$_2$H, —C(O)NH$_2$, —NHC(O)NH$_2$, —NHC(NH)NH$_2$, imidazole, pyrrolidine, SMe, SH, or SeH;

or $R^{12}$ and $R^{13}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

$R^{14}$ is selected from the group consisting of H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —S(O)$_q$R$^{12}$, —(CH$_2$)$_n$NR$^{12}$R$^{13}$, —(CH$_2$)$_n$C(O)R$^{11}$, —(CH$_2$)$_n$OC(O)R$^{11}$, —(CH$_2$)$_n$C(O)$_2$R$^{11}$, —(CH$_2$)$_n$C(O)NR$^{12}$R$^{13}$, —(CH$_2$)$_n$OC(O)NR$^{12}$R$^{13}$, (CH$_2$)$_n$NR$^{11}$C(O)OR$^{12}$, —(CH$_2$)$_n$NC(O)NR$^{12}$R$^{13}$, aryl, heteroaryl, arylalkyl, and heteroarylalkyl, wherein each of $C_1$-$C_6$ alkyl, $C_3$-$C_6$ cycloalkyl, $C_4$-$C_7$ cycloalkylalkyl, —(CH$_2$)$_n$C(O)R$^{11}$, —(CH$_2$)$_n$OC(O)R$^{11}$, —(CH$_2$)$_n$C(O)$_2$R$^{11}$, —(CH$_2$)$_n$NC(O)NR$^{12}$R$^{13}$, —(CH$_2$)$_n$OC(O)NR$^{12}$R$^{13}$, —(CH$_2$)$_n$NR$^{11}$C(O)OR$^2$, —(CH$_2$)$_n$NC(O)NR$^{12}$R$^{13}$, aryl, heteroaryl, arylalkyl, and heteroarylalkyl is optionally substituted with from 1 to 3 substituents independently selected at each occurrence thereof from $C_1$-$C_3$ alkyl, halogen, —CN, —OR$^{12}$, —NR$^{12}$R$^{13}$, and phenyl which is optionally substituted 1-3 times with halogen, $C_1$-$C_4$ alkyl, $C_1$-$C_4$ haloalkyl, $C_1$-$C_4$ alkoxy, —CN, —NO$_2$, —OR$^{12}$, —NR$^{12}$R$^{13}$, or an amino acid group;

$R^{15}$ is H, $C_1$-$C_4$ alkyl, arylalkyl, heteroarylalkyl $C_1$-$C_4$ haloalkyl, or phenyl, wherein each of $C_1$-$C_4$ alkyl, arylalkyl, heteroarylalkyl $C_1$-$C_4$ haloalkyl, and phenyl is optionally substituted 1 to 3 times with halogen, cyano, $C_1$-$C_4$ alkyl, $C_1$-$C_4$ haloalkyl, $C_1$-$C_4$ alkoxy, or an amino acid group;

$R^{16}$ and $R^{17}$ are each independently H, $C_1$-$C_6$ alkyl, $C_1$-$C_6$ haloalkyl, $C_1$-$C_6$ alkoxyalkyl, $C_3$-$C_6$ cycloalkyl, $C_4$-$C_7$ cycloalkylalkyl, —C(O)R$^{15}$, —C(O)OR$^{15}$, phenyl, or benzyl, wherein each of $C_1$-$C_6$ alkyl, $C_3$-$C_6$ cycloalkyl, $C_4$-$C_7$ cycloalkylalkyl, phenyl, and benzyl is optionally substituted from 1 to 3 times with a substituent selected independently at each occurrence thereof from the group consisting of halogen, cyano, $C_1$-$C_4$ alkyl, $C_1$-$C_4$ haloalkyl, $C_1$-$C_4$ alkoxy, and an amino acid group;

or $R^{16}$ and $R^{17}$ are taken together with the nitrogen to which they are attached to form a five- to seven-membered heterocyclic ring, which may be saturated or unsaturated and comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, oxo, $C_1$-$C_4$ alkyl, $C_1$-$C_4$ haloalkyl, and $C_1$-$C_4$ alkoxy;

X is O or N;

Y is O or N;

m is 0, 1, 2, or 3;

n is 0 to 5;

q is 0, 1, or 2; and

╌╌╌ represents an optional double bond;

with the provisos: (1) if $R^1$ is H, $R^2$ is OCH$_3$, $R^3$ is H, $R^4$ is OH or H, $R^5$ is H, $R^7$ is H, $R^8$ and $R^9$ are combined to form an oxo, $R^{10}$ is H, and X and Y are O, then at least one of $R^1$ to $R^{10}$ is an O-glycosidic bond, an N-glycosidic bond, a C-glycosidic bond, or a peptide bond; and (2) that X, $R^6$, $R^8$, and $R^9$ can form a dihydroquinone ring;

or a pharmaceutically acceptable salt thereof.

35. The therapeutic according to claim 34, wherein $R^1$ is selected from the group consisting of H, $C_1$-$C_6$ alkyl, —(CH$_2$)$_n$C(O)$_2$R$^{11}$, —(CH$_2$)$_n$C(O)NR$^{12}$R$^{13}$, arylalkyl, and heteroarylalkyl, wherein n is 1.

36. The therapeutic according to claim 34, wherein $R^2$ is —OR$^{14}$ or —NR$^{12}$R$^{13}$.

37. The therapeutic according to claim 34, wherein $R^3$ is selected from the group consisting of H, halogen, —NR$^{12}$R$^{13}$, and —NO$_2$.

38. The therapeutic according to claim 34, wherein $R^4$ is OH.

39. The therapeutic according to claim 34, wherein $R^4$ is =NOH.

40. The therapeutic according to claim 34, wherein $R^5$ is H or $C_1$-$C_6$ alkyl.

41. The therapeutic according to claim 34, wherein $R^6$ is selected from the group consisting of H, —OR$^{14}$, and —(CH$_2$)$_n$(O)R$^{11}$.

42. The therapeutic according to claim 34, wherein $R^7$ is H or halogen.

43. The therapeutic according to claim 34, wherein $R^8$ is $C_1$-$C_6$ alkyl or phenyl, wherein phenyl is optionally substituted from 1 to 3 times with halogen.

44. The therapeutic according to claim 34, wherein $R^9$ is OH.

45. The therapeutic according to claim 34, wherein $R^8$ and $R^9$ are combined to form an oxo group.

46. The therapeutic according to claim 34, wherein $R^{10}$ is H or —OR$^{14}$.

47. The therapeutic according to claim 34, wherein X is O.

48. The therapeutic according to claim 34, wherein X is N.

49. The therapeutic according to claim 34, wherein Y is O.

50. The therapeutic according to claim 34, wherein Y is N.

51. The therapeutic according to claim 34, wherein X is N, $R^6$ is —NR$^{12}$R$^{13}$, and $R^{12}$ is H.

52. The therapeutic according to claim 34, wherein X, $R^6$, $R^8$ and $R^9$ form a dihydroquinone ring having the formula:

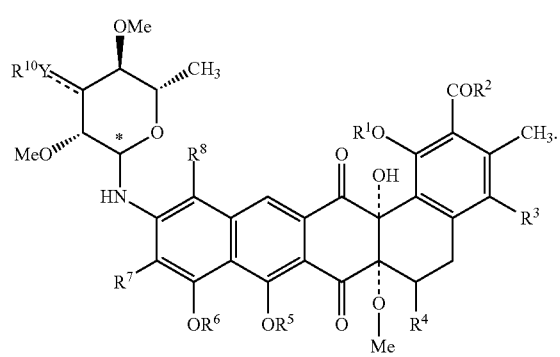
53. The therapeutic according to claim 34, wherein at least one of $R^1$ to $R^{10}$ is a benzyl ether moiety, a carbamate moiety, an $=NR^{14}$ moiety, or a carbonate moiety.
54. The therapeutic according to claim 1, wherein the structure is selected from the group consisting of:
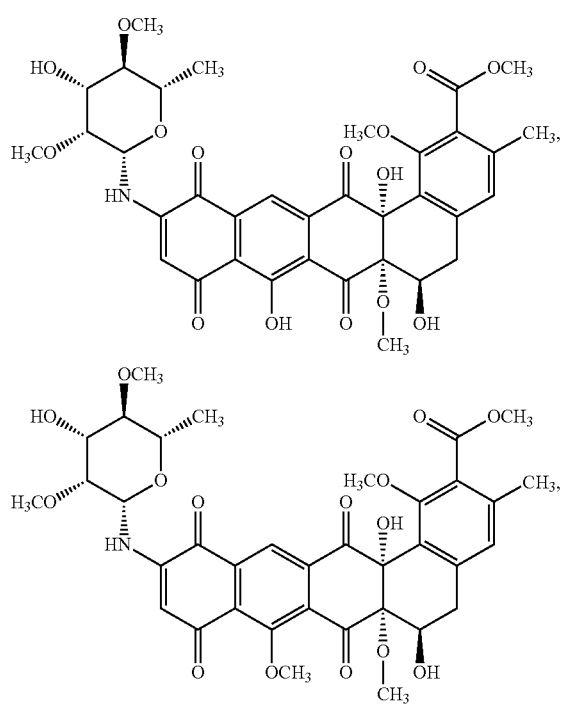
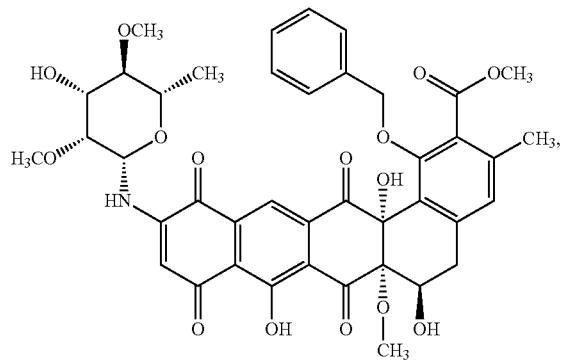
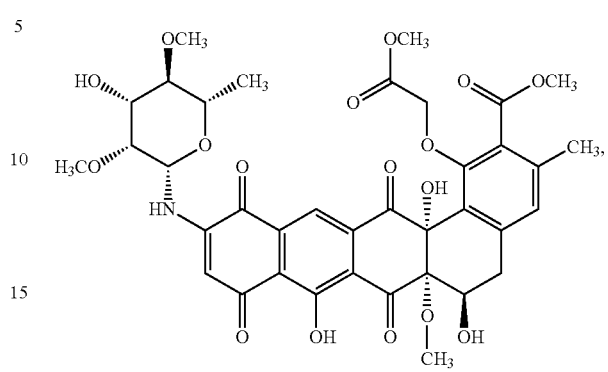
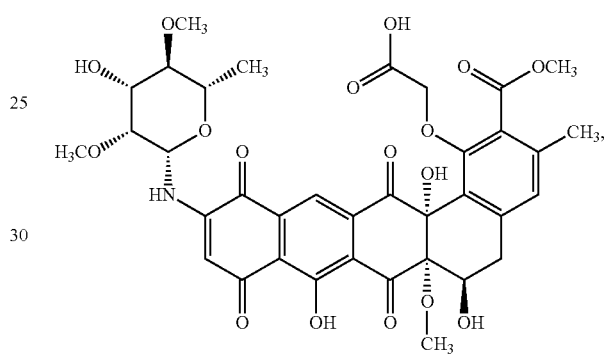
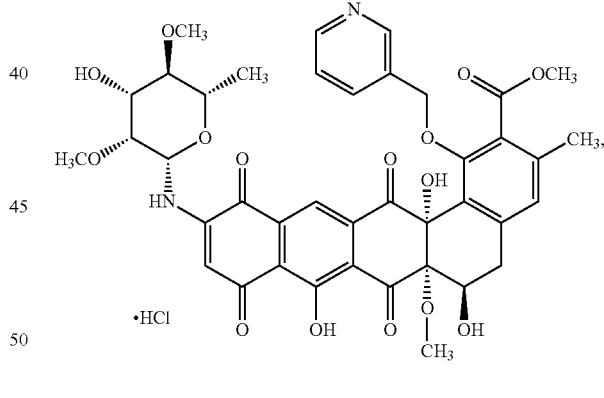
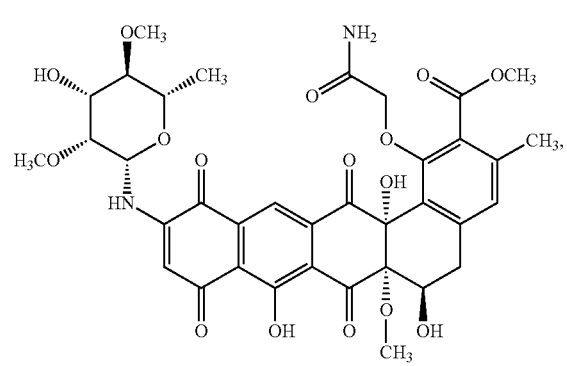

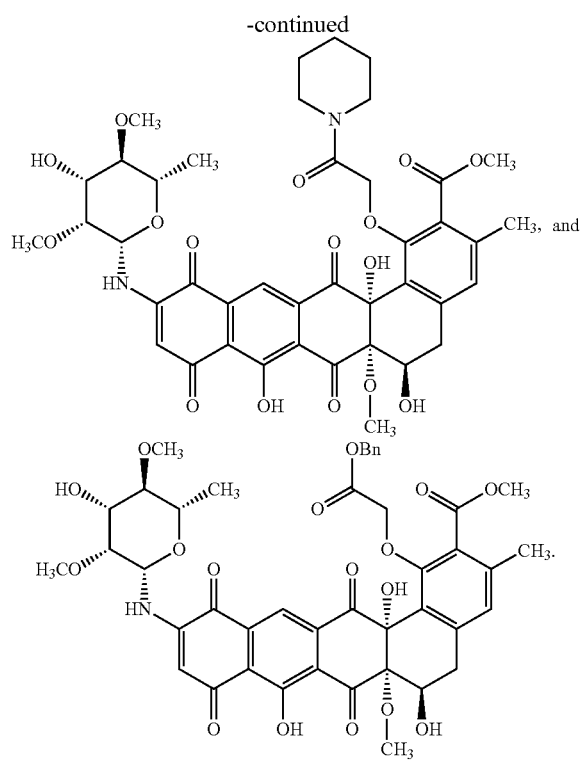
55. The therapeutic according to claim 34, wherein the structure is selected from the group consisting of:
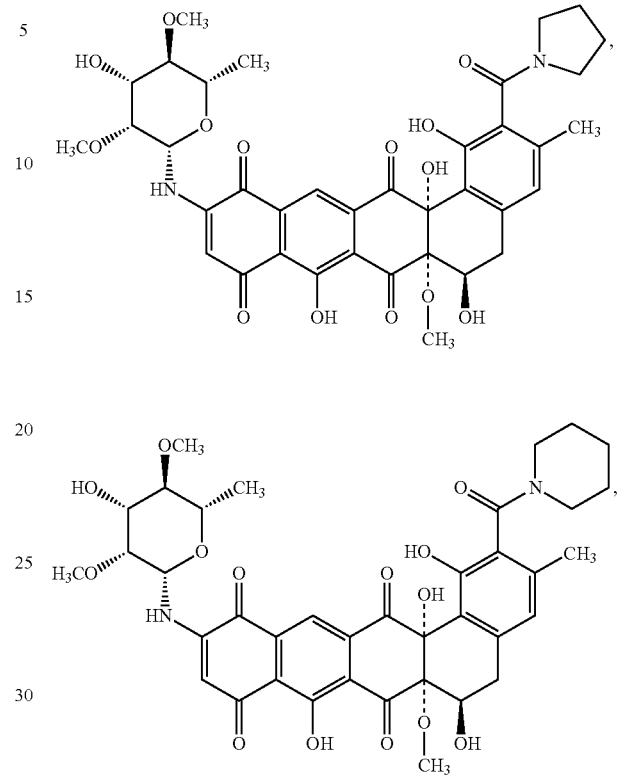
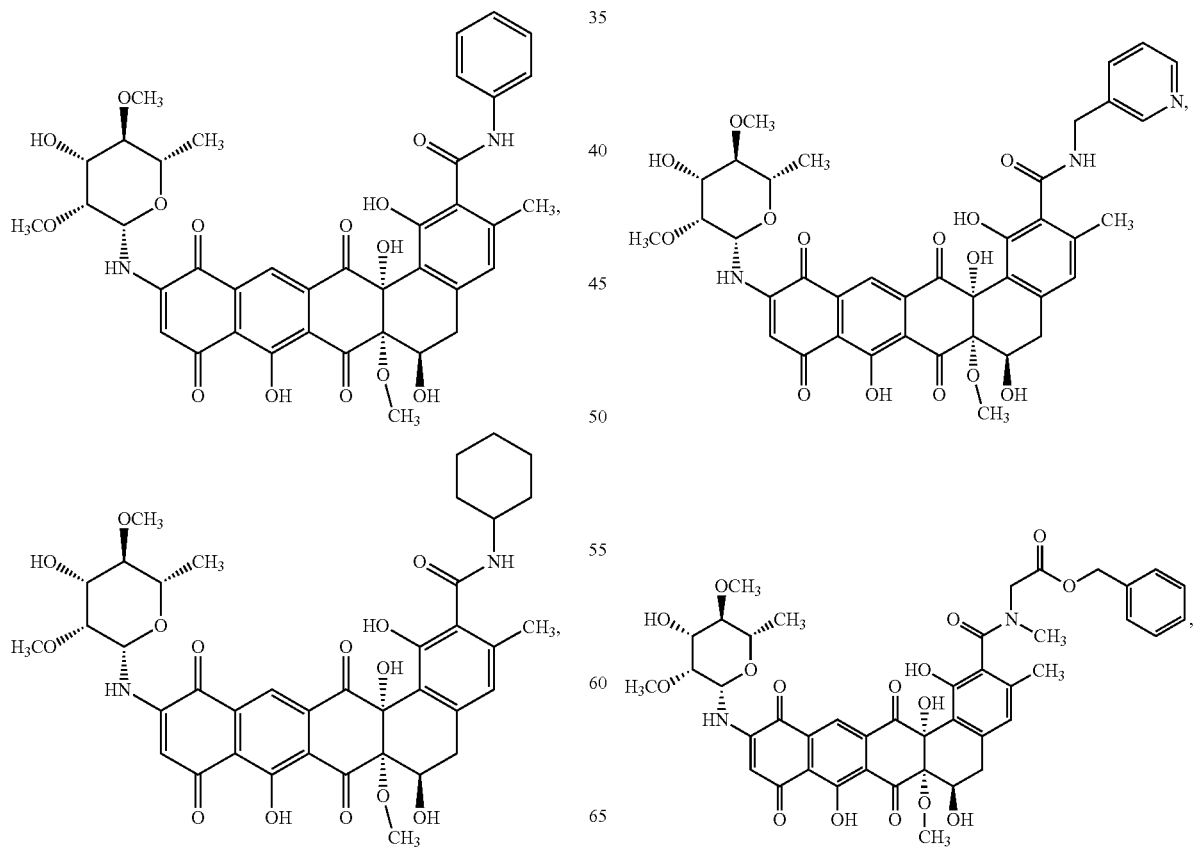

173
-continued
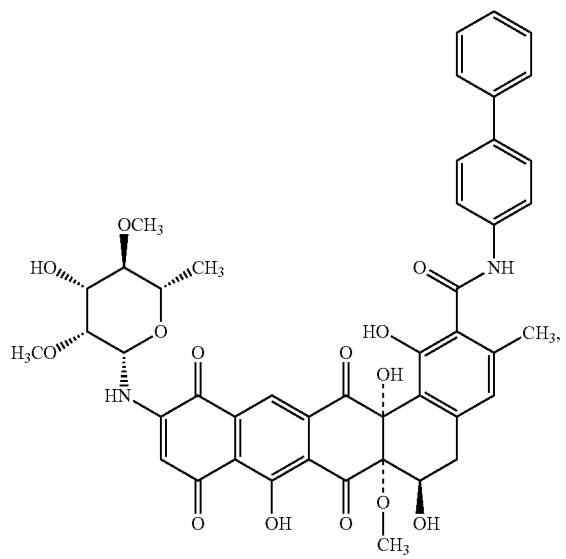
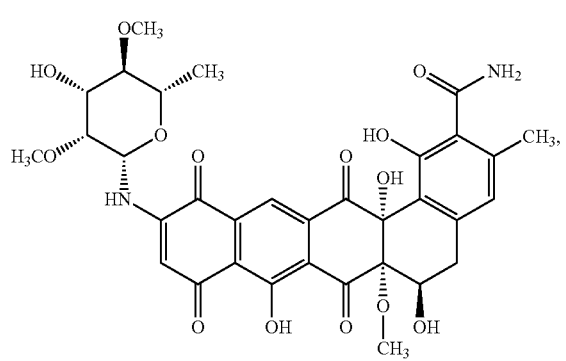
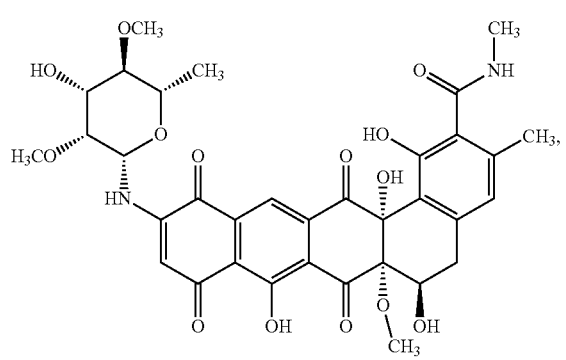
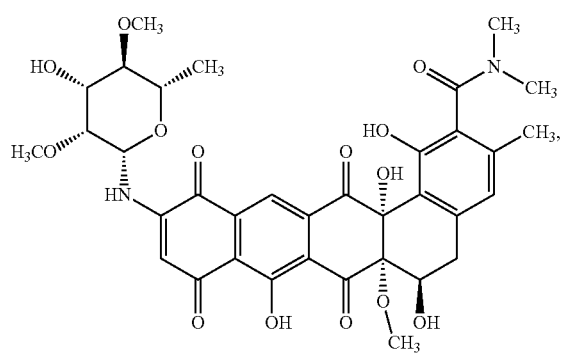
174
-continued
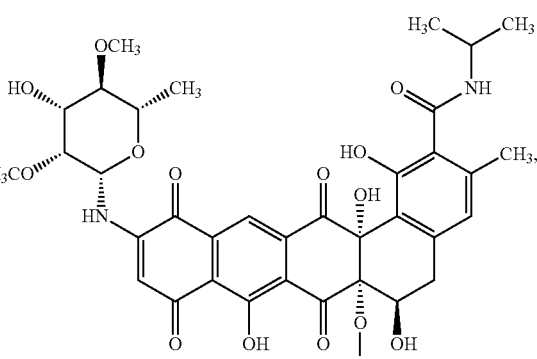
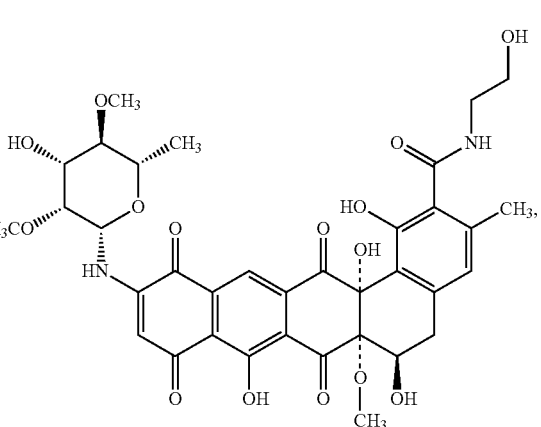
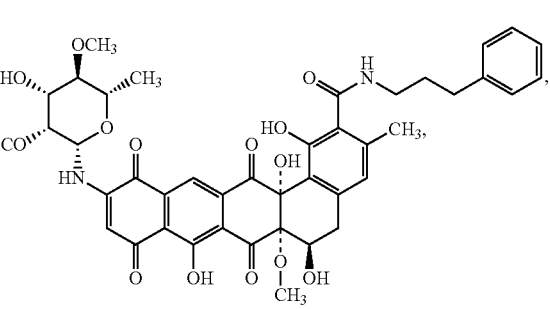
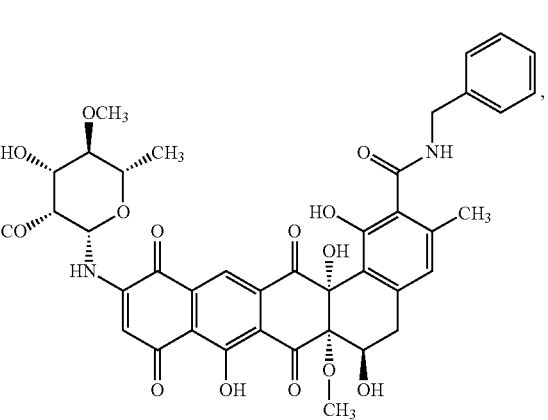

175
-continued
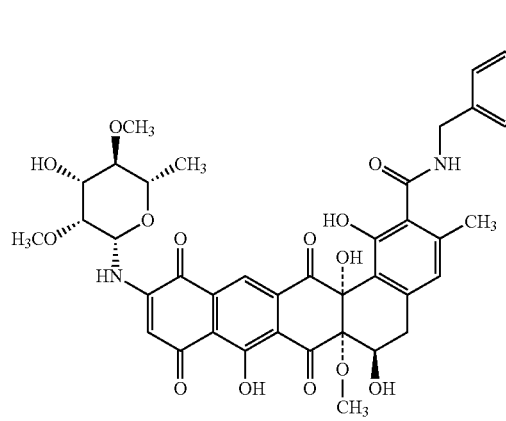
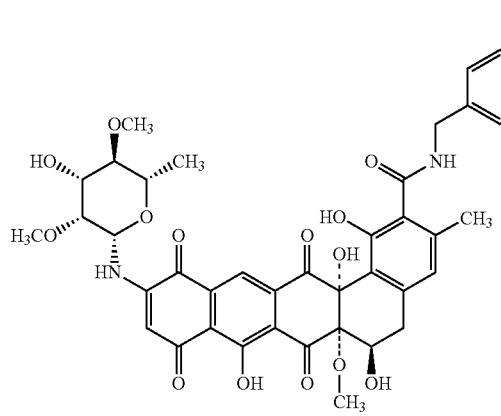
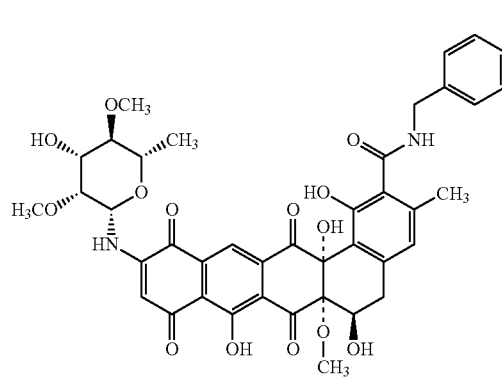
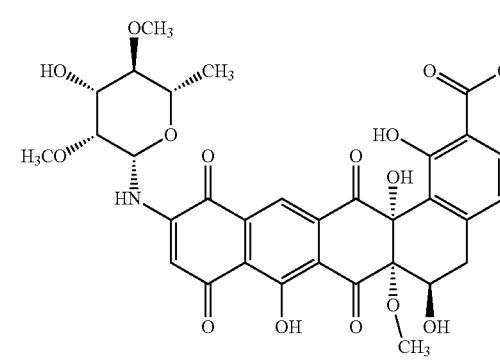
176
-continued
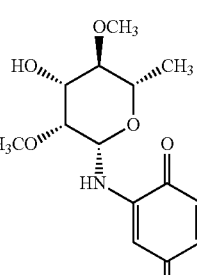
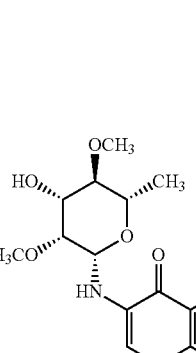
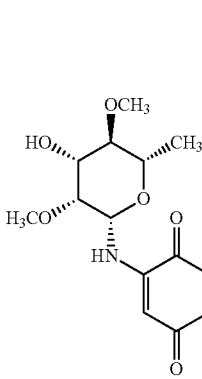
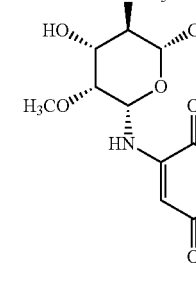

177
-continued
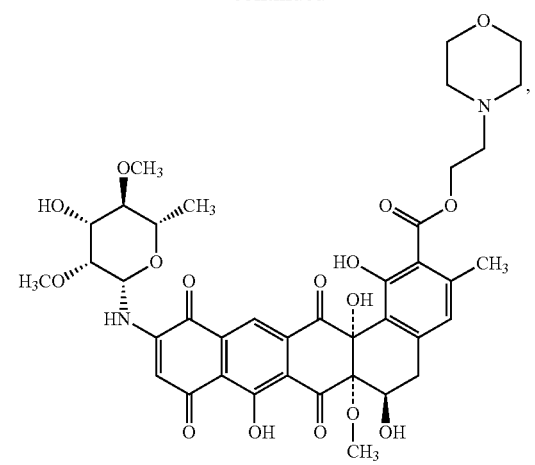
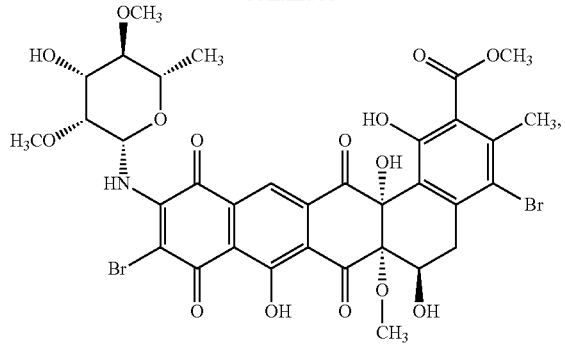
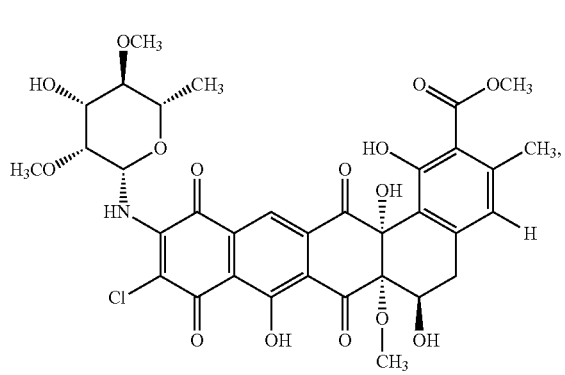
178
-continued
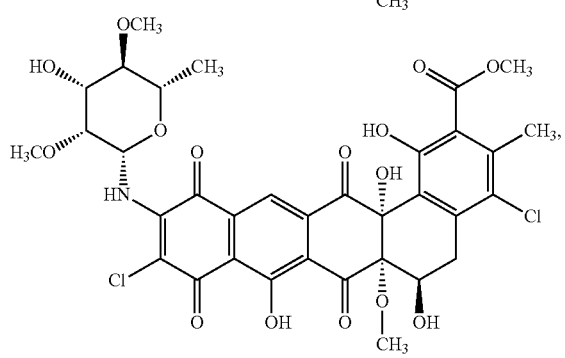
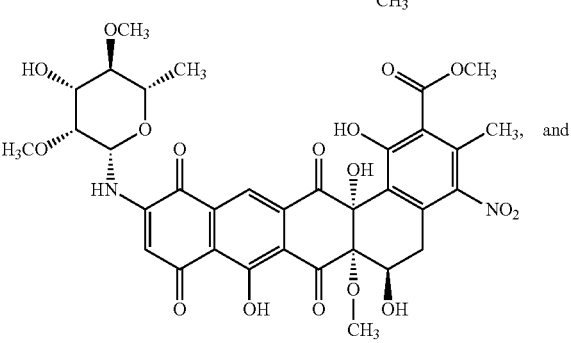
56. The therapeutic according to claim 34, wherein the structure is selected from the group consisting of:
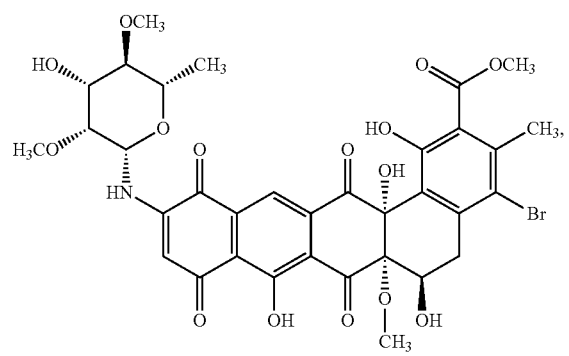
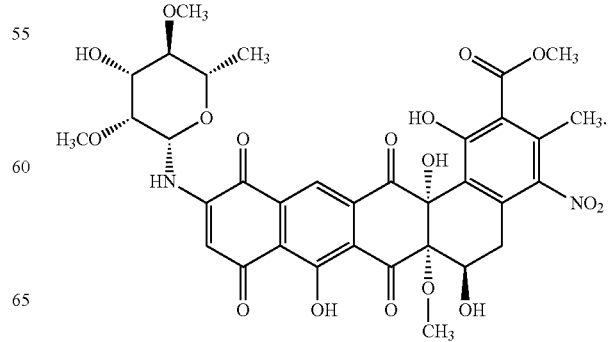

57. The therapeutic according to claim 34, wherein the structure is selected from the group consisting of:
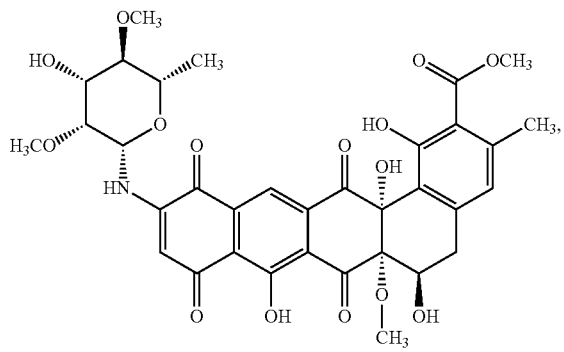
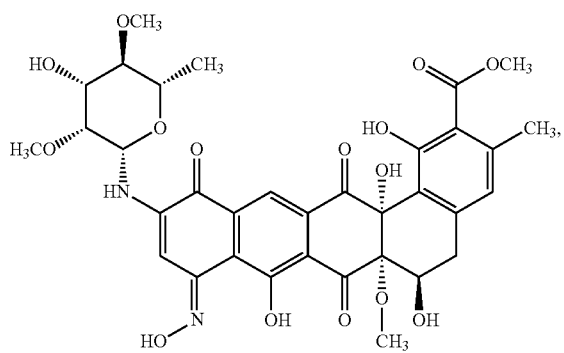
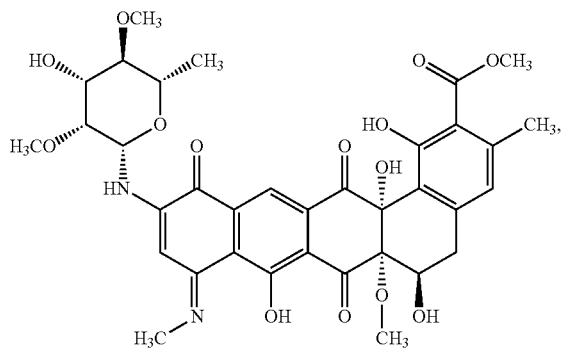
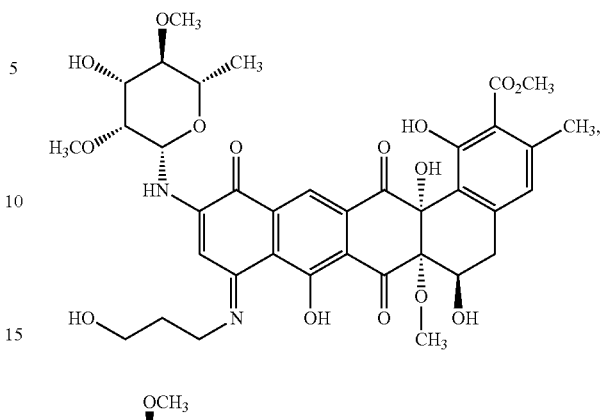
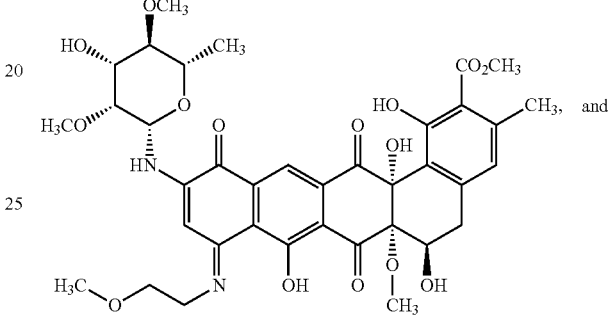
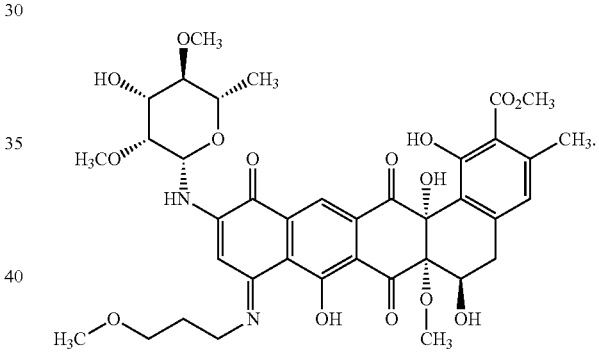
58. The therapeutic according to claim 34, wherein the structure is selected from the group consisting of:
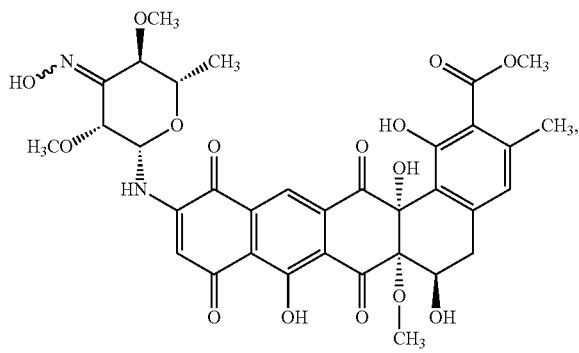

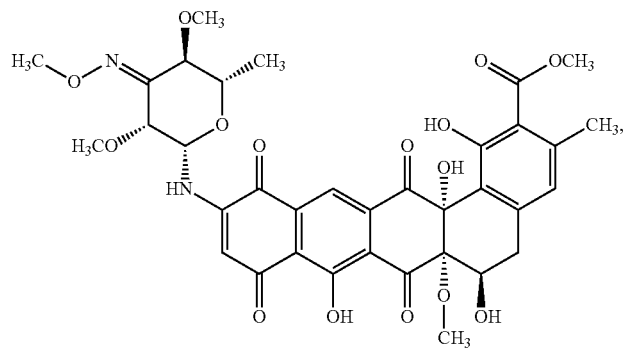
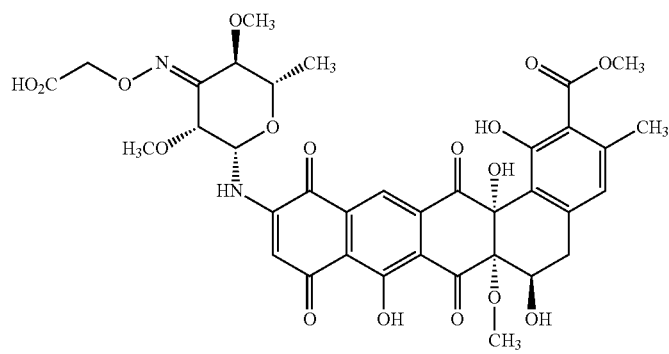
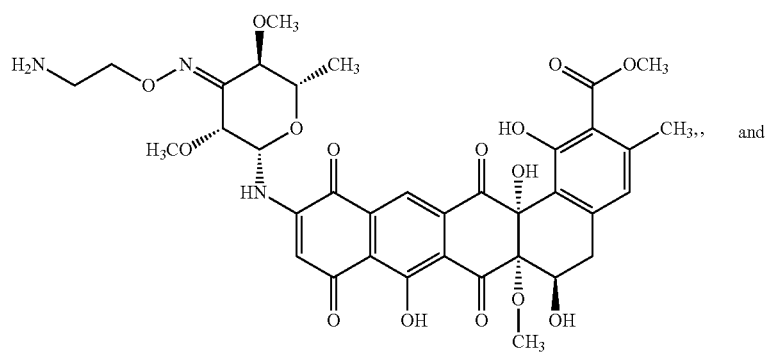
and
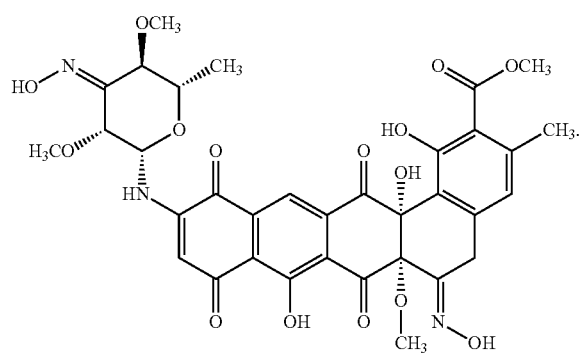 [SMILES: COC(=O)c1c(C)cc2c(c1O)[C@]1(O)C(=O)c3cc4c(c(O)c3C(=O)[C@]1(OC)/C(=N/O)C2)C(=O)C=C(N[C@H]1O[C@@H](C)[C@H](OC)/C(=N/O)[C@H]1OC)C4=O]

59. The therapeutic according to claim 34 having the formula:
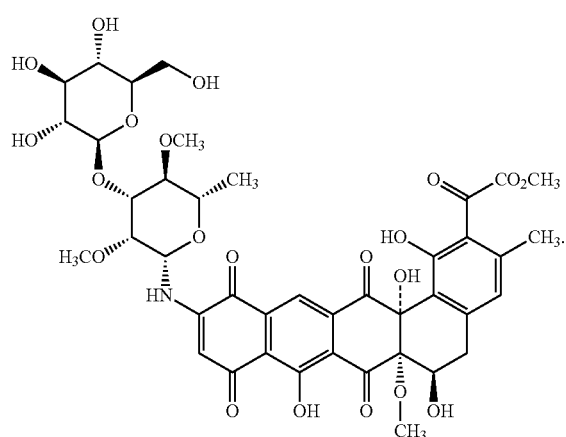
60. The therapeutic according to claim 34, wherein the structure is selected from the group consisting of:
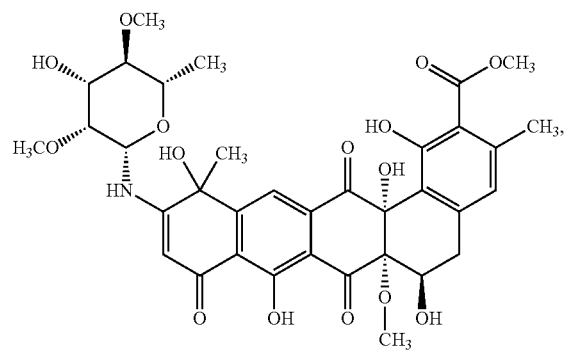
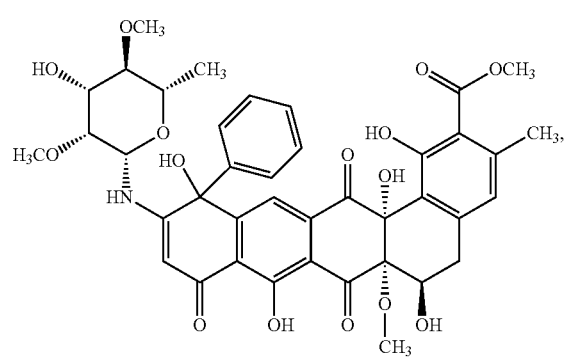
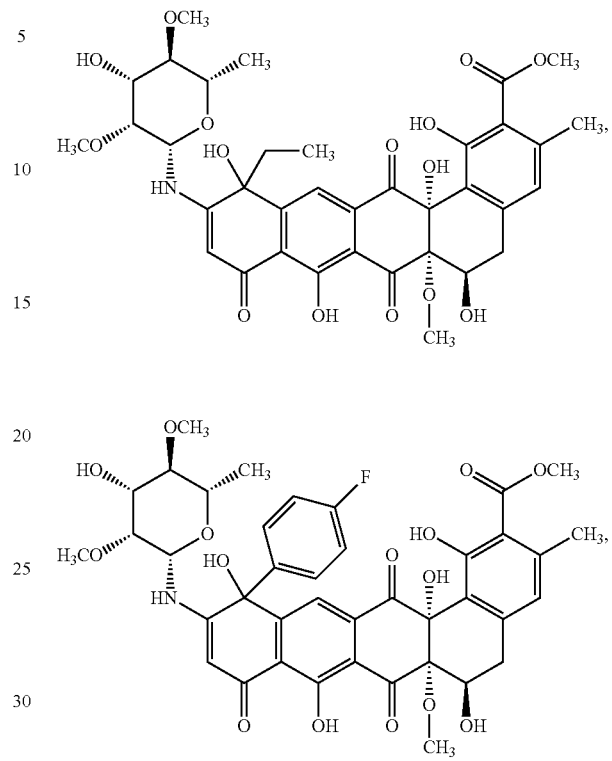
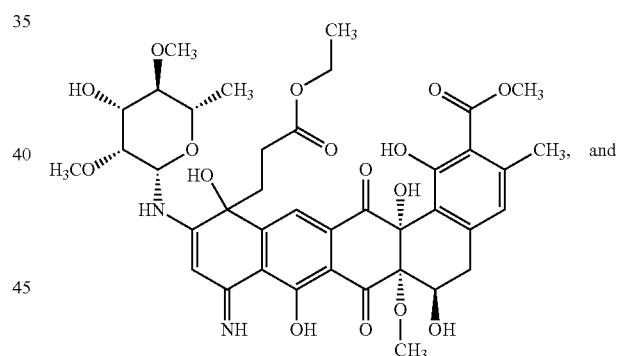
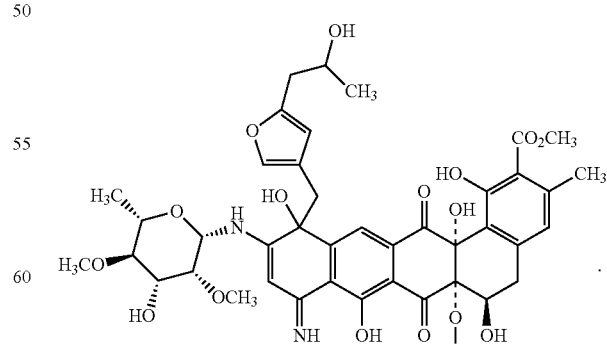
61. The therapeutic according to claim 34 having the formula:

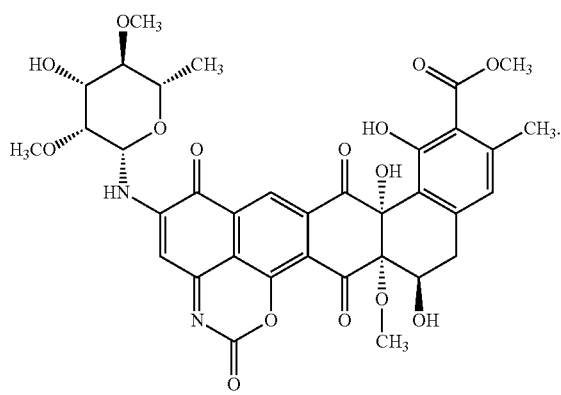 [SMILES: COC(=O)c1c(C)cc2c(c1O)[C@]1(O)C(=O)c3cc4c5c(nc(=O)oc5c3C(=O)[C@]1(OC)[C@H](O)C2)C=C(N[C@H]1O[C@@H](C)[C@H](OC)[C@@H](O)[C@H]1OC)C4=O]

62. A pharmaceutical composition comprising a therapeutically effective amount of the therapeutic according to claim 34 and a pharmaceutically acceptable carrier.

63. A method of treating a bacterial infection comprising:
selecting a subject with a bacterial infection; and
administering to the subject a therapeutically effective amount of a therapeutic according to claim 34.

64. The method according to claim 63, wherein the subject is a human and the bacterial infection is a multi-drug resistant bacterial infection.

65. The method according to claim 64, wherein the multi-drug resistant bacterial infection is a multi-drug resistant strain of *Staphylococcus aureus, Streptococcus pneumoniae*, or *Enterococci*.

66. The method according to claim 63, wherein the bacterial infection is selected from the group consisting of epidermal infection, acne, complicated skin and soft tissue bacterial infection, and bacterial pneumonia.

67. A method for making a product compound having the formula:

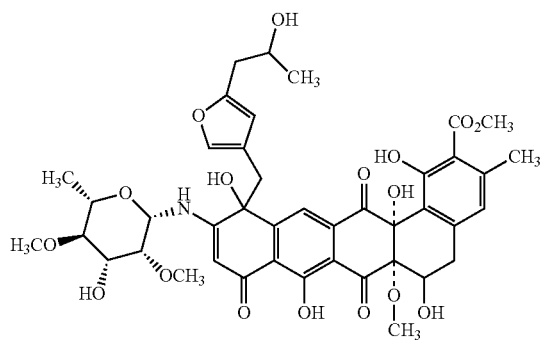 [SMILES: COC(=O)c1c(C)cc2c(c1O)[C@]1(O)C(=O)c3cc4c(c(O)c3C(=O)[C@]1(OC)C(O)C2)C(=O)C=C(N[C@H]1O[C@@H](C)[C@H](OC)[C@@H](O)[C@H]1OC)C4(O)Cc1coc(CC(C)O)c1]

said method comprising:
culturing a culture medium comprising *Streptomyces* strain AMRI-45379 under conditions effective to produce a suspension comprising the product compound, and
isolating the product compound.

* * * * *

UNITED STATES PATENT AND TRADEMARK OFFICE
CERTIFICATE OF CORRECTION

PATENT NO. : 8,754,054 B2  
APPLICATION NO. : 12/884650  
DATED : June 17, 2014  
INVENTOR(S) : Grant J. Carr et al.

Page 1 of 5

It is certified that error appears in the above-identified patent and that said Letters Patent is hereby corrected as shown below:

In the Claims

In claim 1, col. 145, line 39, delete "$NR^{12}R^{13}$" and insert in its place -- —$NR^{12}R^{13}$--.

In claim 1, col. 146, line 7, delete "—$(CH_2)_nC(O)NR^{12}R^{13}$" and insert in its place -- —$(CH_2)_nOC(O)NR^{12}R^{13}$--.

In claim 1, col. 146, line 20, delete "$(CH_2)_nC(O)R^{11}$" and insert in its place -- —$(CH_2)_nC(O)R^{11}$--.

In claim 1, col. 146, line 39, delete "$(CH_2)_nOC(O)NR^{16}R^{17}$" and insert in its place -- —$(CH_2)_nOC(O)NR^{16}R^{17}$--.

In claim 1, col. 147, line 3, delete "$(CH_2)_nNR^{11}C(O)OR^{12}$" and insert in its place -- —$(CH_2)_nNR^{11}C(O)OR^{12}$--.

In claim 27, col. 163, second structure from bottom, delete

"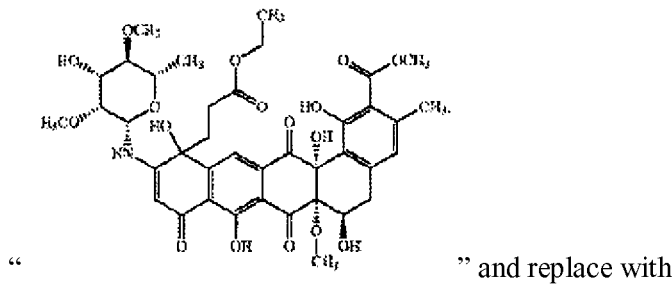" and replace with

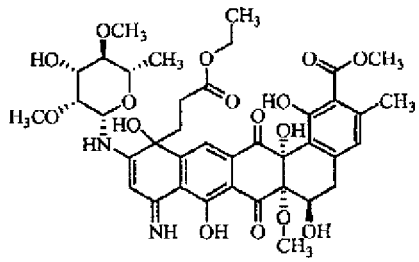 .

Signed and Sealed this  
Eighteenth Day of November, 2014

Michelle K. Lee  
*Deputy Director of the United States Patent and Trademark Office*

In claim 27, col. 163, bottom structure, delete

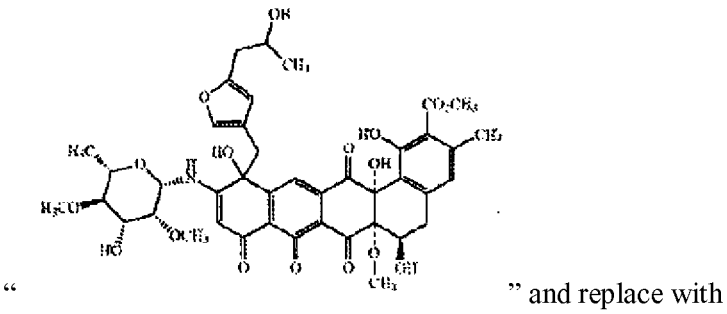

" and replace with

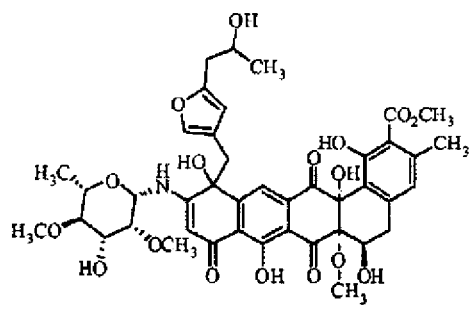

In claim 34, col. 165, line 26, delete "$NR^{12}C(O)_2R^{13}$" and insert in its place -- $—NR^{12}C(O)_2R^{13}$ --.

In claim 34, col. 165, line 67, please insert --,-- after "$—(CH_2)_nC(O)NR^{12}R^{13}$".

In claim 34, col. 166, line 56, delete "$(CH_2)_nC(O)R^{11}$" and insert in its place -- $—(CH_2)_nC(O)R^{11}$ --.

In claim 34, col. 167, line 13, delete "$(CH_2)_nOC(O)NR^{16}R^{17}$" and insert in its place -- $—(CH_2)_nOC(O)NR^{16}R^{17}$ --.

In claim 34, col. 167, line 45, delete "$(CH_2)_nNR^{11}C(O)OR^{12}$" and insert in its place -- $—(CH_2)_nNR^{11}C(O)OR^{12}$ --.

In claim 34, col. 167, lines 49-50, delete "$—(CH_2)_nNC(O)NR^{12}R^{13}$" and insert in its place -- $—(CH_2)_nC(O)NR^{12}R^{13}$ --.

In claim 34, col. 167, lines 50-51, delete "$—(CH_2)_nNR^{11}C(O)OR^2$" and insert in its place -- $—(CH_2)_nNR^{11}C(O)OR^{12}$ --.

In claim 52, col. 169, top structure, delete:

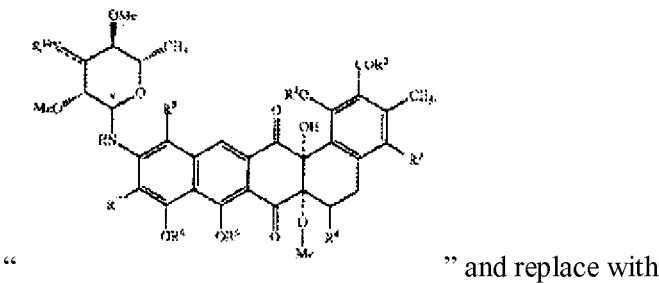

" and replace with

CERTIFICATE OF CORRECTION (continued)
U.S. Pat. No. 8,754,054 B2

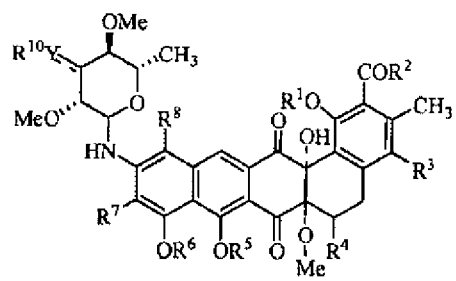

In claim 56, col. 178, bottom structure, delete

" 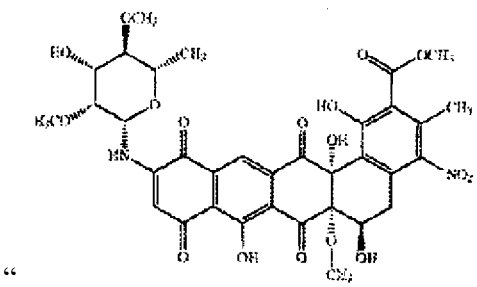 " and replace with

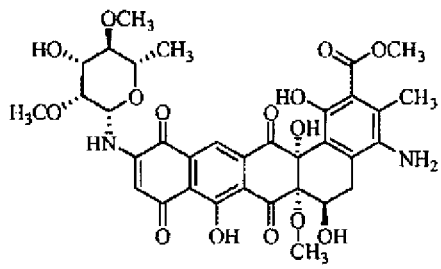

In claim 57, col. 179, top structure, delete

" 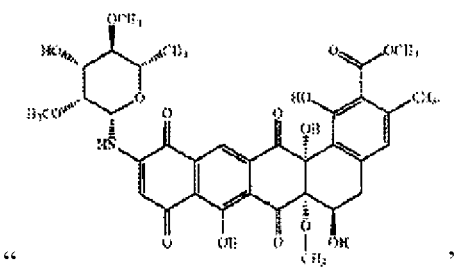 " and replace with

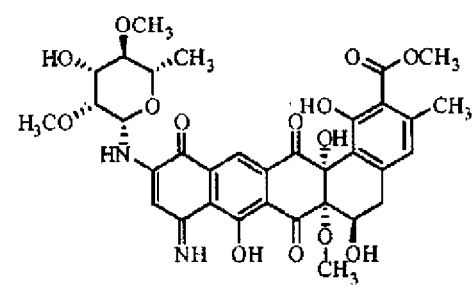

In claim 58, col. 181, please insert --,-- after the second structure from top:
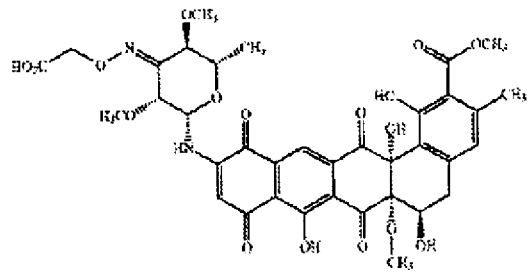
In claim 58, col. 181, please delete ",," and insert in its place --,-- after the second structure from the bottom:
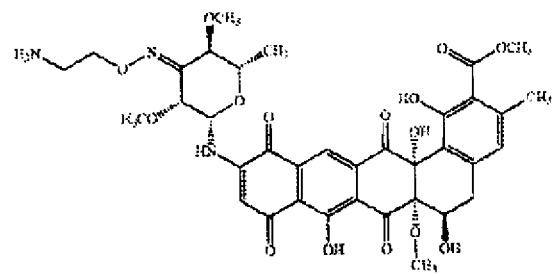
In claim 59, col. 183, top structure, delete
" 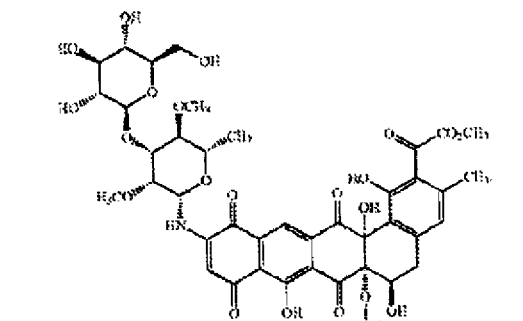 " and replace with
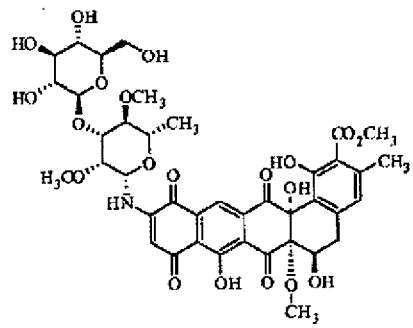

CERTIFICATE OF CORRECTION (continued)
U.S. Pat. No. 8,754,054 B2

In claim 60, col. 184, bottom structure, delete

" 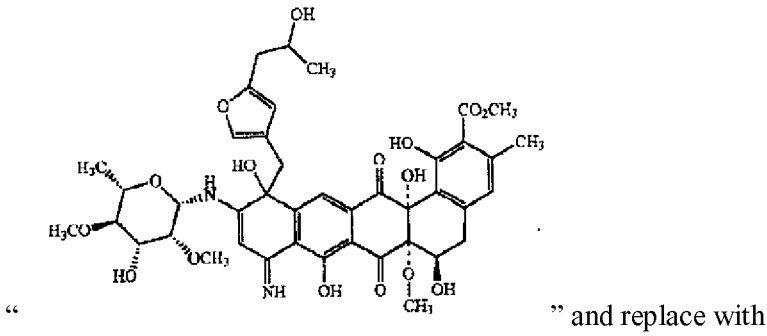 " and replace with

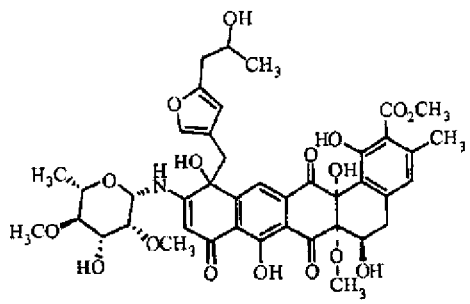 .